US012698528B2

(12) United States Patent
Bayley et al.

(10) Patent No.: US 12,698,528 B2
(45) Date of Patent: Aug. 4, 2026

(54) ASSEMBLY COMPRISING A NUCLEIC ACID SCAFFOLD, SYSTEMS, METHODS, AND USES THEREFORE

(71) Applicant: Oxford University Innovation Limited, Oxford (GB)

(72) Inventors: Hagan Bayley, Oxford (GB); Evan Spruijt, Nijmegen (NL); Anja Henning-Knechtel, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1500 days.

(21) Appl. No.: 17/260,472

(22) PCT Filed: Jul. 30, 2018

(86) PCT No.: PCT/GB2018/052170

§ 371 (c)(1),
(2) Date: Jan. 14, 2021

(87) PCT Pub. No.: WO2020/025909

PCT Pub. Date: Feb. 6, 2020

(65) Prior Publication Data

US 2022/0162692 A1 May 26, 2022

(51) Int. Cl.

| | |
|---|---|
| ***G01N 33/487*** | (2006.01) |
| ***C12Q 1/6834*** | (2018.01) |
| ***C12Q 1/6869*** | (2018.01) |
| ***C12Q 1/6874*** | (2018.01) |

(52) U.S. Cl.

CPC ......... *C12Q 1/6874* (2013.01); *C12Q 1/6834* (2013.01); *C12Q 1/6869* (2013.01); *G01N 33/48721* (2013.01)

(58) Field of Classification Search

None

See application file for complete search history.

(56) References Cited

U.S. PATENT DOCUMENTS

2013/0220809 A1* 8/2013 Gu ........................ C12Q 1/6825 204/600

FOREIGN PATENT DOCUMENTS

| | | |
|---|---|---|
| EP | 2695949 | 2/2014 |
| WO | WO 2000/028312 | 5/2000 |
| WO | WO 2005/124888 | 12/2005 |
| WO | WO 2006/100484 | 9/2006 |
| WO | WO 2008/102120 | 8/2008 |
| WO | WO 2008/102121 | 8/2008 |
| WO | WO 2009/020682 | 2/2009 |
| WO | WO 2009/035647 | 3/2009 |
| WO | WO 2009/077734 | 6/2009 |
| WO | WO 2010/086603 | 8/2010 |
| WO | WO 2011/067559 | 6/2011 |
| WO | WO 2012/005857 | 1/2012 |
| WO | WO 2013/057495 | 4/2013 |
| WO | WO 2013/098561 | 7/2013 |
| WO | WO 2013/098562 | 7/2013 |
| WO | WO 2014/013259 | 1/2014 |
| WO | WO 2014/013260 | 1/2014 |
| WO | WO 2014/013262 | 1/2014 |
| WO | WO 2014/064443 | 5/2014 |
| WO | WO 2014/064444 | 5/2014 |
| WO | WO 2015/055981 | 4/2015 |

OTHER PUBLICATIONS

Spruijt (Nature Nanotechnology vol. 13 Aug. 2018 pp. 739-745).*
Spruijt (Nature Nanotechnology vol. 13 Aug. 2018 (pre-pub online May 28, 2018) pp. 739-745).*
Henning-Knechtel (Nucleic Acids Research Oct. 27, 2017 vol. 45 No. 21 pp. 12057-12068).*
Hybripore Report Summary (Jul. 31, 2017), Horizon 2020, Cordis.*
Burns (Nano Letters 2013, 13 pp. 2351-2356).*
Howorka (Nature Nanotechnology vol. Jul. 12, 2017 (pub online Jul. 6, 2017) pp. 619-630).*
Spruijt et al., DNA scaffolds support stable and uniform peptide nanopores. Nature Nanotechnology (2018) 13:739-745.
Sakai, N., et al, Rigid-Rod Molecules in Biomembrane Models: From Hydrogen-Bonded Chains to Synthetic Multifunctional Pores. (2005) Acc Chem Res 38, 79-87.
Avan, I., et al, Peptidomimetics via modifications of amino acids and peptide bonds. (2014) Chem Soc Rev 43, 3575-3594.
Niitsu, A., et al, Membrane-spanning a-helical barrels as tractable protein-design targets. (2017) Philos Trans R Soc Lond B Biol Sci 372: Feb. 13, 2016.
Heal, J. W., et al, Applying graph theory to protein structures: an Atlas of coiled coils. (2018) Bioinformatics, 34 (19) 3316-3323.
W. C. Wimley, and S. H. White, Designing Transmembrane R-Helices That Insert Spontaneously. (2000) Biochemistry, 39 (15):4432-4442.
Baeza-Delgado, C., et al. Biological insertion of computationally designed short transmembrane segments. (2016) Scientific Reports 6, 23397.
Gonzalez-Perez et al., Biomimetic triblock copolymer membranes: from aqueous solutions to solid supports. Langmuir, 2009, 25, 1129-1138.
Colas et al., Microscopical investigations of nisin-loaded nanoliposomes prepared by Mozafari method and their bacterial targeting. (2007) Micron 38:841-847.
Ivanov A.P., et al., DNA Tunneling Detector Embedded in a Nanopore. Nano Lett. Jan. 12, 2011;11(1):279-85.
Soni G.V., et al., Synchronous optical and electrical detection of biomolecules traversing through solid-state nanopores. Rev Sci Instrum. Jan. 2010;81(1):014301.

(Continued)

*Primary Examiner* — Amanda Haney
(74) *Attorney, Agent, or Firm* — Hamilton, Brook, Smith & Reynolds, P.C.

(57) ABSTRACT

The invention provides an assembly comprising a nucleic acid scaffold and a plurality of appendages bonded to the scaffold, wherein the appendages, when bonded to the scaffold, are capable of interacting to form a pore in a layer of amphipathic molecules.

30 Claims, 62 Drawing Sheets

Specification includes a Sequence Listing.

(56)                    References Cited

OTHER PUBLICATIONS

Stoddart D., et al., Single-nucleotide discrimination in immobilized DNA oligonucleotides with a biological nanopore. Proc Natl Acad Sci, 12;106(19):7702-7.

Lieberman K.R., et al, Processive Replication of Single DNA Molecules in a Nanopore Catalyzed by phi29 DNA Polymerase. J Am Chem Soc. 2010;132(50):17961-72.

Holden et al., Functional Bionetworks from Nanoliter Water Droplets. J Am Chem Soc. Jul. 11, 2007; 129(27):8650-5.

Gilbert, R. J. C., et al. Membrane pores: from structure and assembly, to medicine and technology. Phil. Trans. R. Soc. B, 372: 20160208.

Branton, D. et al. The potential and challenges of nanopore sequencing. Nat. Biotechnol. 26, 1146-1153 (2008).

Ayub, M. & Bayley, H., Engineered transmembrane pores. Curr. Opin. Chem. Biol. 34, 117-126 (2016).

Koebnik, R., et al., Structure and function of bacterial outer membrane proteins: barrels in a nutshell. Mol. Microbiol. 37, 239-253 (2000).

Tamm, L. K., Hong, H. & Liang, B. Folding and assembly of β-barrel membrane proteins. Biochim. Biophys. Acta 1666, 250-263 (2004).

Noinaj, N., Gumbart, J. C. & Buchanan, S. K. The ebeta-barrel assembly machinery in motion. Nat. Rev. Microbiol. 15, 197-204 (2017).

Dong, C. et al. The structure of Wza the translocon for *E. coli* capsular polysaccharides defines a new class of membrane protein. Nature 444, 226-229 (2006).

Kong, L. et al. Single-molecule interrogation of a bacterial sugar transporter allows the discovery of an extracellular inhibitor. Nat. Chem. 5, 651-659 (2013).

Soskine, M. et al. An engineered ClyA nanopore detects folded target proteins by selective external association and pore entry. Nano Lett. 12, 4895-4900 (2012).

Mahendran, K. R. et al. A monodisperse transmembrane α-helical peptide barrel. Nat. Chem. 9, 411-419 (2017).

Mutter, M. & Vuilleumier, S. A chemical approach to protein design—template-assembled synthetic proteins (TASP). Angew. Chem. Int. Ed. 28, 535-554 (1989).

Futaki, S. Peptide ion channels: design and creation of function. Pept. Sci. 47, 75-81 (1998).

Bayley, H. & Jayasinghe, L. Functional engineered channels and pores (review). Mol. Membr. Biol. 21, 209-220 (2004).

Pinheiro, A. V., et al., Challenges and opportunities for structural DNA nanotechnology. Nat. Nanotech. 6, 763-772 (2011).

Wilner, O. I., et al., Self-assembly of enzymes on DNA scaffolds en route to biocatalytic cascades and the synthesis of metallic nanowires. Nano Lett. 9, 2040-2043 (2009).

Fu, J. et al. Multi-enzyme complexes on DNA scaffolds scapable of substrate channelling with an artificial lswinging arm. Nat. Nanotech. 9, 531-536 (2014).

Zhang, Y., et al., Proximity does not contribute to activity enhancement in the glucose oxidase-horseradish peroxidase cascade. Nat. Commun. 7, 13982 (2016).

Raschle, T., et al., Controlled co-reconstitution of multiple membrane proteins in lipid bilayer nanodiscs using DNA as a scaffold ACS Chem. Biol. 10, 2448-2454 (2015).

Lee, H. et al. Molecularly self-assembled nucleic acid nanoparticles for targeted in vivo siRNA delivery. Nat. Nanotech. 7, 389-393 (2012).

Douglas, S. M., et al., A logic-gated nanorobot for targeted transport of molecular payloads. Science 335, 831-834 (2012).

Langecker, M. et al. Synthetic lipid membrane channels formed by designed DNA nanostructures. Science 338, 932-936 (2012).

Burns, J. R., et al., Self-assembled DNA nanopores that span lipid bilayers. Nano Lett. 13, 2351-2356 (2013).

Karshikoff A., Nilsson, L. & Ladenstein, R. Rigidity versus flexibility the dilemma of understanding protein thermal stability. FEBS J. 282, 3899-3917 (2015).

Von Krbek, L. K. S. et al. The delicate balance of preorganisation and adaptability in multiply Bonded host-guest complexes. Chem. Eur. J. 23, 2877-2883 (2017).

Jolliffe K. A. Backbone-modified cyclic peptides: new scaffolds for supramolecular chemistry. Supramol. Chem. 17, 81-86 (2005).

Song, C. et al. Crystal structure and functional mechanism of a human antimicrobial membrane channel. Proc. Natl Acad. Sci. USA 110, 4586-4591 (2013).

Bowie, J. U. Solving the membrane protein folding problem. Nature 438, 581-589 (2005).

Krasilnikov, O. V. et al. Electrophysiological evidence for heptameric stoichiometry of ion channels formed by *Staphylococcus aureus* alpha-toxin in planar lipid bilayers. Mol. Microbiol. 37, 1372-1378 (2000).

Salay, L. C., et al., Ion channel-like activity of the antimicrobial peptide tritrpticin in planar lipid bilayers. FEBS Lett. 565, 171-175 (2004).

Paulmann, M. et al. Structure-activity analysis of the dermcidin-derived peptide DCD-1L, an anionic antimicrobial peptide present in human sweat. J. Biol. Chem. 287, 8434-8443 (2012).

Howorka, S. & Bayley, H. Probing distance and electrical potential within a protein pore with tethered DNA. Biophys. J. 83, 3202-3210 (2002).

Rothemund, P. W. K. Folding DNA to create nanoscale shapes and patterns. Nature 440, 297-302 (2006).

Soskine, M., et al., Tuning the size and properties of ClyA nanopores assisted by directed evolution. J. Am. Chem. Soc. 135, 13456-13463 (2013).

Nicol, F., Nir, S. & Szoka, F. C. Orientation of the pore-forming peptide GALA in POPC vesicles determined by a BODIPY-avidin/biotin binding assay. Biophys. J. 76, 2121-2141 (1999).

Li, W., Nicol, F. & Szoka, F. C. GALA: a designed synthetic pH-responsive amphipathic peptide with applications in drug and gene delivery. Adv. Drug Deliv. Rev. 56, 967-985 (2004).

Rausch, J. M., et al., Rational combinatorial design of pore-forming β-sheet peptides. Proc. Natl Acad. Sci. USA 102, 10511-10515 (2005).

Krauson, A. J., et al., Synthetic molecular evolution of pore-forming peptides by iterative combinatorial library screening. ACS Chem. Biol. 8, 823-831 (2013).

Gupta, K., et al., Synthetic cationic peptides have antibacterial activity against *Mycobacterium smegmatis* by forming pores in membrane and synergizing with antibiotics. Antibiotics 4, 358-378 (2015).

Thomson A. R. et al. Computational design of water-soluble α-helical barrels. Science 346, 485-488 (2014).

Yusko, E. C. et al. Real-time shape approximation and fingerprinting of single proteins using a nanopore. Nat. Nanotech. 12, 360-367 (2017).

Huang, G., et al., Electro-osmotic capture and ionic discrimination of peptide and protein biomarkers with FraC nanopores. Nat. Commun. 8, 935 (2017).

Soskine, M., et al., Single-molecule analyte recognition with ClyA nanopores equipped with internal protein adaptors. J. Am. Chem. Soc. 137, 5793-5797 (2015).

Wanunu, M. et al. Discrimination of methylcytosine from hydroxymethylcytosine in DNA molecules. J. Am. Chem. Soc. 133, 486-492 (2011).

Taylor, A. I. et al. Nanostructures from synthetic genetic polymers. Chem Bio Chem 17, 1107-1110 (2016).

Hammerstein, A. F., et al., Subunit dimers of α-hemolysin expand the engineering toolbox for protein nanopores. J. Biol. Chem. 286, 14324-14334 (2011).

Lee, J. & et al. Semisynthetic nanoreactor for reversible single-molecule covalent chemistry. ACS Nano 10, 8843-8850 (2016).

Williams, B. A. R. & Chaput, J. C. in S. L. Beaucage (ed.) Current Protocols in Nucleic Acid Chemistry (Wiley, Hoboken, 2010).

Gutsmann, T., et al., Protein reconstitution into freestanding planar lipid membranes for electrophysiological characterization. Nat. Protoc. 10, 188-198 (2015).

Šulc, P., et al., Sequence-dependent thermodynamics of a coarse-grained DNA model. J. Chem. Phys. 137, 135101 (2012).

(56) References Cited

OTHER PUBLICATIONS

Snodin, B. E. K., et al. Introducing improved structural properties and salt dependence into a coarse-grained model of DNA. J. Chem. Phys. 142, 234901 (2015).

Humphrey, W., et al., VMD: Visual molecular dynamics. J. Mol. Graph. 14, 33-38 (1996).

Pettersen, E. F., et al. UCSF Chimera—A visualization system for exploratory research and analysis. J. Comp. Chem. 25, 1605-1612 (2004).

Sobott, F., et al., Tandem Mass Spectrometer for Improved Transmission and Analysis of Large Macromolecular Assemblies. Anal. Chem. 74, 1402-1407 (2002).

Liko, I., et al., Dimer interface of bovine cytochrome c oxidase is influenced by local posttranslational modifications and lipid binding. Proc. Natl Acad. Sci. USA 113, 8230-8235 (2016).

Hernandez, H. & Robinson, C. V. Determining the stoichiometry and interactions of macromolecular assemblies from mass spectrometry. Nature Protoc. 2, 715-726 (2007).

Evans, G. W., et al., Real-time single-molecule studies of the motions of DNA polymerase fingers illuminate DNA synthesis mechanisms. Nucleic Acids Research 43, 5998-6008 (2015).

Gordon, M. P., et al., Single-molecule high-resolution imaging with photobleaching. Proc. Natl Acad. Sci. USA 101, 6462-6465 (2004).

Dave, R., et al., Mitigating Unwanted Photophysical Processes for Improved Single-Molecule Fluorescence Imaging. Biophys. J. 96, 2371-2381 (2009).

Bell N.A.W., Keyser U.F. Digitally encoded DNA nanostructures for multiplexed, single-molecule protein sensing with nanopores. Nat. Nanotechnol. 2016; 11:645-651.

Quick J., et al. Real-time, portable genome sequencing for Ebola surveillance. Nature . 2016; 530:228-232.

Litvinchuk S., et al., Synthetic pores with reactive signal amplifiers as artificial tongues. Nat. Mater. 2007; 6:576-580.

Manrao E.A., et al., Reading DNA at single-nucleotide resolution with a mutant MspA nanopore and phi29 DNA polymerase. Nat. Biotechnol. 2012; 30:349-353.

Banghart M., et al., Light-activated ion channels for remote control of neuronal firing. Nat. Neurosci. 2004; 7:1381-1386.

Rodriguez-Larrea D., Bayley H. Multistep protein unfolding during nanopore translocation. Nat. Nanotechnol. 2013; 8:288-295.

Kong J., et al., Quantifying nanomolar protein concentrations using designed DNA carriers and solid-state nanopores. Nano Lett . 2016; 16:3557-3562.

Dekker C. Solid-state nanopores. Nat. Nanotechnol. 2007; 2:209-215.

Li, J., et al., Ion-beam sculpting at nanometre length scales. Nature. 2011; 412:166-169.

Bayley H., Cremer P.S. Stochastic sensors inspired by biology. Nature. 2001; 413:226-230.

Kasianowicz J.J., et al., Characterization of individual polynucleotide molecules using a membrane channel. Proc. Natl. Acad. Sci. U.S.A. 1996; 93:13770-13773.

Majd S., et al., Applications of biological pores in nanomedicine, sensing, and nanoelectronics. Curr. Opin. Biotechnol. 2010; 21:439-476.

Fahie M.A., et al., Selective detection of protein homologues in serum using an OmpG nanopore. Anal. Chem. 2015; 87:11143-11149.

Pastoriza-Gallego M., et al., Dynamics of unfolded protein transport through an aerolysin pore. J. Am. Chem. Soc. 2011; 133:2923-2931.

Wang S., et al., Engineered nanopore of Phi29 DNA-packaging motor for real-time detection of single colon cancer specific antibody in serum. ACS Nano. 2013; 7:9814-9822.

Van Meervelt V., et al., Detection of two isomeric binding configurations in a protein-aptamer complex with a biological nanopore. ACS Nano. 2014; 8:12826-12835.

Carter J.-M., Hussain S. Robust long-read native DNA sequencing using the ONT CsgG Nanopore system. Wellcome Open Res. 2017; 2:23.

Gu L.-Q., Cheley S., Bayley H. Capture of a single molecule in a nanocavity. Science . 2001; 291:636-640.

Montenegro J., Ghadiri M.R., Granja J.R. Ion channel models based on self-assembling cyclic peptide nanotubes. Acc. Chem. Res. 2013; 46:2955-2965.

Sakai N., Mareda J., Matile S. Artificial β-Barrels. Acc. Chem. Res. 2008; 41:1354-1365.

Geng J., et al. Stochastic transport through carbon nanotubes in lipid bilayers and live cell membranes. Nature . 2014; 514:612-615.

Göpfrich K., et al., DNA-tile structures induce ionic currents through lipid membranes. Nano Lett. 2015; 15:3134-3138.

Göpfrich K., et al., Large-conductance transmembrane porin made from DNA origami. ACS Nano . 2016; 10:8207-8214.

Krishnan S., et al., Molecular transport through large-diameter DNA nanopores. Nat. Commun. 2016; 7:12787.

Plesa C., et al., Ionic permeability and mechanical properties of DNA origami nanoplates on solid-state nanopores. ACS Nano. 2014; 8:35-43.

Li C.-Y., et al., Ionic conductivity, structural deformation, and programmable anisotropy of DNA origami in electric field. ACS Nano. 2015; 9:1420-1433.

Seifert A., et al., Bilayer-spanning DNA nanopores with voltage-switching between open and closed state. ACS Nano. 2014; 9:1117-1126.

Burns J.R., et al., Lipid-bilayer-spanning DNA nanopores with a bifunctional porphyrin anchor. Angew. Chem. Int. Ed. 2013; 52:12069-12072.

Zhang F., et al., Complex wireframe DNA origami nanostructures with multi-arm junction vertices. Nat. Nanotechnol. 2015; 10:779-784.

Douglas S.M., et al., Self-assembly of DNA into nanoscale three-dimensional shapes. Nature . 2009; 459:414-418.

Saccà B., et al., Orthogonal protein decoration of DNA origami. Angew. Chem. Int. Ed. 2010; 49:9378-9383.

Yoo J., Aksimentiev A. Molecular dynamics of membrane-spanning DNA channels: conductance mechanism, electro-osmotic transport, and mechanical gating. J. Phys. Chem. Lett. 2015; 6:4680-4687.

Mantri S., et al., An engineered dimeric protein pore that spans adjacent lipid bilayers. Nat. Commun. 2013; 4:1725.

Schindelin J., et al. Fiji: an open-source platform for biological-image analysis. Nat. Methods . 2012; 9:676-682.

Horcas I., et al., WSxM: A software for scanning probe microscopy and a tool for nanotechnology. Rev. Sci. Instrum. 2007; 78:013705.

Song L.Z., et al., Structure of staphylococcal alpha-hemolysin, a heptameric transmembrane pore. Science . 1996; 274:1859-1866.

Braha O., et al., Simultaneous stochastic sensing of divalent metal ions. Nat. Biotechnol. 2000; 18:1005-1007.

Clarke J., et al., Continuous base identification for single-molecule nanopore DNA sequencing. Nat. Nanotechnol. 2009; 4:265-270.

Gu L.-Q., et al., Stochastic sensing of organic analytes by a pore-forming protein containing a molecular adapter. Nature . 1999; 398:686-690.

Harrington L., et al., Pim kinase inhibitors evaluated with a single-molecule engineered nanopore sensor. Angew. Chem. Int. Ed. 2015; 54:8154-8159.

Rosen C.B., Rodriguez-Larrea D., Bayley H. Single-molecule site-specific detection of protein phosphorylation. Nat. Biotechnol. 2014; 5:807-814.

Eddy M.T., et al., Lipid Dynamics and Protein-Lipid Interactions in 2D Crystals Formed with the b-barrel Integral Membrane Protein VDAC1. J. Am. Chem. Soc. 2012; 134:6375-6387.

Butler, T. et al., Single-molecule DNA detection with an engineered MspA protein nanopore. Proc. Natl. Acad. Sci. U.S.A., 105, 20647-20652. (2008).

Kowalczyk, S. W., et al., Modeling the conductance and DNA blockade of solid-state nanopores. Nanotechnology, 22, 315101. (2011).

Pratt, K. W., et al., Molality-based primary standards of electrolytic conductivity (IUPAC Technical Report). Pure Appl. Chem., 73, 1783-1793. (2001).

Degiacomi, M. T. and Peraro, M. D. Macromolecular Symmetric Assembly Prediction using Swarm Intellicence Dynamic Modeling. Structure, 2, 1097-1106. (2013).

(56) References Cited

OTHER PUBLICATIONS

Yamashita, D., et al., Molecular basis of transmembrane beta-barrel formation of staphylococcal pore-forming toxins. Nat. Commun., 5, 4897. (2014).
Walker, B., et al., Assembly of the oligomeric membrane pore formed by staphylococcal alpha-hemolysin examined by truncation mutagenesis. J. Biol. Chem., 267, 21782-21786. (1992).
Walkcr, B., ct al., An intcrmcdiatc in thc asscmbly of a porc-forming protcin trappcd with a genetically-engineered switch. Chem. Biol., 2, 99-105. (1995).
Stoddart, D., et al., Functional truncated membrane pores. Proc. Natl. Acad. Sci. U.S.A., 111, 2425-2430. (2014).
Bonislawski, A., DNA Scaffolds Could Enable Construction of Custom Nanopores for Protein Sequencing. Genomeweb article. (2018) Available at: https://www.genomeweb.com/proteomics-protein-research/dna-scaffolds-could-enable-construction-custom-nanopores-protein#.YCZdBjY3bIU.
Hybripore Fact Sheet, Objective, Horizon 2020, Cordis.
Spruijt et al., Nature Nanotechnology (2018) 13:739-745.
Henning-Knechtel et al., Nucleic Acids Research (2017) 45(21):12057-12068.
Hybripore Report Summary (2017), Horizon 2020, Cordis.
Presentation at Wageningen University on Feb. 1, 2018 by inventor Evan Spruijt.

* cited by examiner

Single conjugates
(kDa)
75
50
37
25
20
15
10
5
2
L 1 1 2 3 4 5 6 7 8 9 10 11 12 P L
Free peptide
Annealed hybrid rings
(kb)
10
3.0
2.0
1.5
1.0
0.7
0.5
0.4
0.3
0.2
L 0 2 4 6 8 10 11 12 L A260 (a.u.)
0.8
0.4
0
Time (min)
0 4 8 12 16
Counts (x1,000)
3 2 1 0
m/z
1,000 2,000 3,000 4,000
Counts (x1,000)
4 2
18,147 Da
m/z
12,000 14,000 16,000 18,000 20,000

(i)
50 pA
5 s
(ii)
100 pA
1 min
200 pA
0.5 s
(iii)
Normalized count
1
0
-100 0 100 200 300 400 500
I [pA]
(iv)
I [pA]
400
200
0
-200
-400
-100 -50 0 50 100
V [mV]

(i)
200 pA
20 s
(ii)
500 pA
5 s
(iii)
Normalized count
1
0
1950 2100 2250 2400 2550
I [pA]
(iv)
I [pA]
3000
2000
1000
0
-1000
-2000
-3000
-100 -50 0 50 100
V [mV]

(i)
(ii)
5.25 nm
1.46 nm
1.8 nm
Z [nm]
X [nm]

(i)
(ii)
1.9 nm
0 nm
0.95 nm
-0.32 nm
0.9 nm
Z [Å]
X [nm]

Trace of multiple insertions of hexameric template heptamer hexamers hexamers hexamers hexamers heptamer 10nm Event histogram of octamer templates heptamer Conductances (nS)

Count

Event histogram of hexamer templates heptamer hexamers

Conductance (nS)

Count

AB configuration

AD configuration

AD

*anti*-dAD
*R,R,R,R* or *M*

*ent-anti*-dAD
*S,S,S,S* or *P*

*syn*dAD
*achiral*

Top view:

SEQUENCE LISTING

```
<160> NUMBER OF SEQ ID NOS: 118

<210> SEQ ID NO 1
<211> LENGTH: 38
<212> TYPE: PRT
<213> ORGANISM: Artificial Sequence
<220> FEATURE:
<223> OTHER INFORMATION: CWza (T376R)

<400> SEQUENCE: 1

Cys Gly Gly Ala Pro Leu Val Arg Trp Asn Arg Val Ile Ser Gln Leu
1               5                   10                  15

Val Pro Thr Ile Ser Gly Val His Asp Met Thr Glu Thr Val Arg Tyr
            20                  25                  30

Ile Lys Arg Trp Pro Asn
        35


<210> SEQ ID NO 2
<211> LENGTH: 38
<212> TYPE: PRT
<213> ORGANISM: Artificial Sequence
<220> FEATURE:
<223> OTHER INFORMATION: Conjugation CWza (T376R) from paper

<400> SEQUENCE: 2

Cys Gly Gly Ala Pro Leu Val Arg Trp Asn Arg Val Ile Ser Gln Leu
1               5                   10                  15

Val Pro Thr Ile Thr Gly Val His Asp Leu Thr Glu Thr Val Arg Tyr
            20                  25                  30

Ile Lys Arg Trp Pro Asn
        35


<210> SEQ ID NO 3
<211> LENGTH: 38
<212> TYPE: PRT
<213> ORGANISM: Artificial Sequence
<220> FEATURE:
<223> OTHER INFORMATION: WzaC (T376R)

<400> SEQUENCE: 3

Ala Pro Leu Val Arg Trp Asn Arg Val Ile Ser Gln Leu Val Pro Thr
1               5                   10                  15

Ile Ser Gly Val His Asp Met Thr Glu Thr Val Arg Tyr Ile Lys Arg
            20                  25                  30

Trp Pro Asn Gly Gly Cys
        35
```

<210> SEQ ID NO 4
<211> LENGTH: 38
<212> TYPE: PRT
<213> ORGANISM: Artificial Sequence
<220> FEATURE:
<223> OTHER INFORMATION: Conjugation WzaC (T376R) from paper

<400> SEQUENCE: 4

```
Ala Pro Leu Val Arg Trp Asn Arg Val Ile Ser Gln Leu Val Pro Thr
1               5                   10                  15

Ile Thr Gly Val His Asp Leu Thr Glu Thr Val Arg Tyr Ile Lys Arg
            20                  25                  30

Trp Pro Asn Gly Gly Cys
        35
```

<210> SEQ ID NO 5
<211> LENGTH: 35
<212> TYPE: PRT
<213> ORGANISM: Artificial Sequence
<220> FEATURE:
<223> OTHER INFORMATION: Wza E.coli (R376T)

<400> SEQUENCE: 5

```
Ala Pro Leu Val Arg Trp Asn Arg Val Ile Ser Gln Leu Val Pro Thr
1               5                   10                  15

Ile Ser Gly Val His Asp Met Thr Glu Thr Val Arg Tyr Ile Lys Thr
            20                  25                  30

Trp Pro Asn
        35
```

<210> SEQ ID NO 6
<211> LENGTH: 35
<212> TYPE: PRT
<213> ORGANISM: Artificial Sequence
<220> FEATURE:
<223> OTHER INFORMATION: KRM consensus Wza (R376T)

<400> SEQUENCE: 6

```
Ala Pro Leu Val Arg Trp Asn Arg Val Ile Ser Gln Leu Val Pro Thr
1               5                   10                  15

Ile Thr Gly Val His Asp Leu Thr Glu Thr Val Arg Tyr Ile Lys Thr
            20                  25                  30

Trp Pro Asn
        35
```

<210> SEQ ID NO 7
<211> LENGTH: 35
<212> TYPE: PRT
<213> ORGANISM: Artificial Sequence
<220> FEATURE:
<223> OTHER INFORMATION: KRM consensus Wza K375C (R376T)

<400> SEQUENCE: 7

```
Ala Pro Leu Val Arg Trp Asn Arg Val Ile Ser Gln Leu Val Pro Thr
1               5                   10                  15

Ile Thr Gly Val His Asp Leu Thr Glu Thr Val Arg Tyr Ile Cys Thr
            20                  25                  30

Trp Pro Asn
        35
```

<210> SEQ ID NO 8
<211> LENGTH: 35

<212> TYPE: PRT
<213> ORGANISM: Artificial Sequence
<220> FEATURE:
<223> OTHER INFORMATION: KRM consensus Wza Y373C (R376T)

<400> SEQUENCE: 8

```
Ala Pro Leu Val Arg Trp Asn Arg Val Ile Ser Gln Leu Val Pro Thr
1               5                   10                  15

Ile Thr Gly Val His Asp Leu Thr Glu Thr Val Arg Cys Ile Lys Thr
            20                  25                  30

Trp Pro Asn
        35
```

<210> SEQ ID NO 9
<211> LENGTH: 37
<212> TYPE: PRT
<213> ORGANISM: Artificial Sequence
<220> FEATURE:
<223> OTHER INFORMATION: alpha HL-UP (111-147, T129C)

<400> SEQUENCE: 9

```
Glu Tyr Met Ser Thr Leu Thr Tyr Gly Phe Asn Gly Asn Val Thr Gly
1               5                   10                  15

Asp Asp Cys Gly Lys Ile Gly Gly Leu Ile Gly Ala Asn Val Ser Ile
            20                  25                  30

Gly His Thr Leu Lys
        35
```

<210> SEQ ID NO 10
<211> LENGTH: 37
<212> TYPE: PRT
<213> ORGANISM: Artificial Sequence
<220> FEATURE:
<223> OTHER INFORMATION: alpha HL-DOWN

<400> SEQUENCE: 10

```
Lys Ile Gly Gly Leu Ile Gly Ala Asn Val Ser Ile Gly His Thr Leu
1               5                   10                  15

Lys Gly Cys Asp Asp Gly Tyr Met Ser Thr Leu Thr Tyr Gly Phe Asn
            20                  25                  30

Gly Asn Val Thr Asp
        35
```

<210> SEQ ID NO 11
<211> LENGTH: 319
<212> TYPE: PRT
<213> ORGANISM: Artificial Sequence
<220> FEATURE:
<223> OTHER INFORMATION: alpha hemolysin protein sequence (inc leader
      sequence)

<400> SEQUENCE: 11

```
Met Lys Thr Arg Ile Val Ser Ser Val Thr Thr Thr Leu Leu Leu Gly
1               5                   10                  15

Ser Ile Leu Met Asn Pro Val Ala Gly Ala Ala Asp Ser Asp Ile Asn
            20                  25                  30

Ile Lys Thr Gly Thr Thr Asp Ile Gly Ser Asn Thr Thr Val Lys Thr
        35                  40                  45

Gly Asp Leu Val Thr Tyr Asp Lys Glu Asn Gly Met His Lys Lys Val
    50                  55                  60

Phe Tyr Ser Phe Ile Asp Asp Lys Asn His Asn Lys Lys Leu Leu Val
65                  70                  75                  80
```

```
Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
        115                 120                 125

Pro Arg Asn Ser Ile Asp Thr Lys Glu Tyr Met Ser Thr Leu Thr Tyr
    130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Thr Asp Arg Ser
    290                 295                 300

Ser Glu Arg Tyr Lys Ile Asp Trp Glu Lys Glu Glu Met Thr Asn
305                 310                 315


<210> SEQ ID NO 12
<211> LENGTH: 293
<212> TYPE: PRT
<213> ORGANISM: Artificial Sequence
<220> FEATURE:
<223> OTHER INFORMATION: alpha hemolysin mature protein sequence

<400> SEQUENCE: 12

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125
```

-continued

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 13
<211> LENGTH: 293
<212> TYPE: PRT
<213> ORGANISM: Artificial Sequence
<220> FEATURE:
<223> OTHER INFORMATION: alpha hemolysin K237C mutation

<400> SEQUENCE: 13

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

```
Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Cys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290


<210> SEQ ID NO 14
<211> LENGTH: 293
<212> TYPE: PRT
<213> ORGANISM: Artificial Sequence
<220> FEATURE:
<223> OTHER INFORMATION: alpha hemolysin N17C mutation

<400> SEQUENCE: 14

Ala Asp Ser Asp Ile Asn Ile Lys Thr Gly Thr Thr Asp Ile Gly Ser
1               5                   10                  15

Cys Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

```
Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290


<210> SEQ ID NO 15
<211> LENGTH: 43
<212> TYPE: DNA
<213> ORGANISM: Artificial Sequence
<220> FEATURE:
<223> OTHER INFORMATION: Original 12-mer scaffold (1)

<400> SEQUENCE: 15

gcctcgaatc actccactga accatcctct tgatcttgtg aac                       43


<210> SEQ ID NO 16
<211> LENGTH: 43
<212> TYPE: DNA
<213> ORGANISM: Artificial Sequence
<220> FEATURE:
<223> OTHER INFORMATION: Original 12-mer scaffold (2)

<400> SEQUENCE: 16

tgccataagt attcagtgga gcagcaacat agactctcaa caa                       43


<210> SEQ ID NO 17
<211> LENGTH: 43
<212> TYPE: DNA
<213> ORGANISM: Artificial Sequence
<220> FEATURE:
<223> OTHER INFORMATION: Original 12-mer scaffold (3)

<400> SEQUENCE: 17

gttcacaaga atcgaaacca atgttagtgt agagtgcata agc                       43


<210> SEQ ID NO 18
<211> LENGTH: 43
<212> TYPE: DNA
<213> ORGANISM: Artificial Sequence
<220> FEATURE:
<223> OTHER INFORMATION: Original 12-mer scaffold (4)

<400> SEQUENCE: 18

ccaactggga attggtttcg acaagaggat ggaacttatg gca                       43


<210> SEQ ID NO 19
<211> LENGTH: 43
<212> TYPE: DNA
<213> ORGANISM: Artificial Sequence
<220> FEATURE:
<223> OTHER INFORMATION: Original 12-mer scaffold (5)

<400> SEQUENCE: 19

gcttatgcac agagtcacag aacgggaagc agaaacgtgt gag                       43


<210> SEQ ID NO 20
<211> LENGTH: 43
<212> TYPE: DNA
<213> ORGANISM: Artificial Sequence
<220> FEATURE:
<223> OTHER INFORMATION: Original 12-mer scaffold (6)

<400> SEQUENCE: 20
```

-continued tcgagcaata atctgtgact cctacactaa caatcccagt tgg 43

<210> SEQ ID NO 21
<211> LENGTH: 43
<212> TYPE: DNA
<213> ORGANISM: Artificial Sequence
<220> FEATURE:
<223> OTHER INFORMATION: Original 12-mer scaffold (7)

<400> SEQUENCE: 21
ctcacacgtt agatacggac acttggatac ggaaaagcac ctc 43

<210> SEQ ID NO 22
<211> LENGTH: 43
<212> TYPE: DNA
<213> ORGANISM: Artificial Sequence
<220> FEATURE:
<223> OTHER INFORMATION: Original 12-mer scaffold (8)

<400> SEQUENCE: 22
cacttcactt atgtccgtat cctgcttccc gtatattgct cga 43

<210> SEQ ID NO 23
<211> LENGTH: 43
<212> TYPE: DNA
<213> ORGANISM: Artificial Sequence
<220> FEATURE:
<223> OTHER INFORMATION: Original 12-mer scaffold (9)

<400> SEQUENCE: 23
gaggtgcttt atgtcaatcg gagtagccta gcaagcctta gcc 43

<210> SEQ ID NO 24
<211> LENGTH: 43
<212> TYPE: DNA
<213> ORGANISM: Artificial Sequence
<220> FEATURE:
<223> OTHER INFORMATION: Original 12-mer scaffold (10)

<400> SEQUENCE: 24
gaaacagata accgattgac accgtatcca agaaagtgaa gtg 43

<210> SEQ ID NO 25
<211> LENGTH: 43
<212> TYPE: DNA
<213> ORGANISM: Artificial Sequence
<220> FEATURE:
<223> OTHER INFORMATION: Original 12-mer scaffold (11)

<400> SEQUENCE: 25
ggctaaggct aaatgagtac cctatgttgc tgagattcga ggc 43

<210> SEQ ID NO 26
<211> LENGTH: 43
<212> TYPE: DNA
<213> ORGANISM: Artificial Sequence
<220> FEATURE:
<223> OTHER INFORMATION: Original 12-mer scaffold (12)

<400> SEQUENCE: 26
ttgttgagag aggtactcat tgctaggcta ctatatctgt ttc 43

<210> SEQ ID NO 27
<211> LENGTH: 43
<212> TYPE: DNA

<213> ORGANISM: Artificial Sequence
<220> FEATURE:
<223> OTHER INFORMATION: 12-mer scaffold (optimised 7)

<400> SEQUENCE: 27
ctcacacgtt agatacggac acttggatag cgaaaagcac ctc 43

<210> SEQ ID NO 28
<211> LENGTH: 43
<212> TYPE: DNA
<213> ORGANISM: Artificial Sequence
<220> FEATURE:
<223> OTHER INFORMATION: 12-mer scaffold (optimised 10)

<400> SEQUENCE: 28
gaaacagata accgattgac acgctatcca agaaagtgaa gtg 43

<210> SEQ ID NO 29
<211> LENGTH: 54
<212> TYPE: DNA
<213> ORGANISM: Artificial Sequence
<220> FEATURE:
<223> OTHER INFORMATION: 12-mer scaffold with one long arm (11d)

<400> SEQUENCE: 29
ggctaaggct aaatgagtac cctatgttgc tgagattcga ggcacttact gagc 54

<210> SEQ ID NO 30
<211> LENGTH: 31
<212> TYPE: DNA
<213> ORGANISM: Artificial Sequence
<220> FEATURE:
<223> OTHER INFORMATION: 12-mer scaffold with one long arm (11f)

<400> SEQUENCE: 30
tgtttgatgt ttggtgaatg gtatttggtc g 31

<210> SEQ ID NO 31
<211> LENGTH: 42
<212> TYPE: DNA
<213> ORGANISM: Artificial Sequence
<220> FEATURE:
<223> OTHER INFORMATION: 12-mer scaffold with one long arm (11g)

<400> SEQUENCE: 31
cgaccaaata ccattcacca aacatcaaac agctcagtaa gt 42

<210> SEQ ID NO 32
<211> LENGTH: 43
<212> TYPE: DNA
<213> ORGANISM: Artificial Sequence
<220> FEATURE:
<223> OTHER INFORMATION: 14-mer scaffold (11)

<400> SEQUENCE: 32
ggctaaggct aaatgagtac ctttttctct ttacctcatc ctc 43

<210> SEQ ID NO 33
<211> LENGTH: 43
<212> TYPE: DNA
<213> ORGANISM: Artificial Sequence
<220> FEATURE:
<223> OTHER INFORMATION: 14-mer scaffold (12)

<400> SEQUENCE: 33
ttccgaacga aggtactcat tgctaggcta ctatatctgt ttc 43

-continued

<210> SEQ ID NO 34
<211> LENGTH: 43
<212> TYPE: DNA
<213> ORGANISM: Artificial Sequence
<220> FEATURE:
<223> OTHER INFORMATION: 14-mer scaffold (13)

<400> SEQUENCE: 34
gaggatgagg aaagggtggt cctatgttgc tgagattcga ggc 43

<210> SEQ ID NO 35
<211> LENGTH: 43
<212> TYPE: DNA
<213> ORGANISM: Artificial Sequence
<220> FEATURE:
<223> OTHER INFORMATION: 14-mer scaffold (14)

<400> SEQUENCE: 35
ttgttgagag agaccaccct taaagagaaa aaatcgttcg gaa 43

<210> SEQ ID NO 36
<211> LENGTH: 43
<212> TYPE: DNA
<213> ORGANISM: Artificial Sequence
<220> FEATURE:
<223> OTHER INFORMATION: 16-mer scaffold (13)

<400> SEQUENCE: 36
gaggatgagg aaacacaaca cctcctggct ataaatgcaa gat 43

<210> SEQ ID NO 37
<211> LENGTH: 43
<212> TYPE: DNA
<213> ORGANISM: Artificial Sequence
<220> FEATURE:
<223> OTHER INFORMATION: 16-mer scaffold (14)

<400> SEQUENCE: 37
cgcttagacc agtgttgtgt taaagagaaa aaatcgttcg gaa 43

<210> SEQ ID NO 38
<211> LENGTH: 43
<212> TYPE: DNA
<213> ORGANISM: Artificial Sequence
<220> FEATURE:
<223> OTHER INFORMATION: 16-mer scaffold (15)

<400> SEQUENCE: 38
atcttgcatt acatcagcat actatgttgc tgagattcga ggc 43

<210> SEQ ID NO 39
<211> LENGTH: 43
<212> TYPE: DNA
<213> ORGANISM: Artificial Sequence
<220> FEATURE:
<223> OTHER INFORMATION: 16-mer scaffold (16)

<400> SEQUENCE: 39
ttgttgagag atatgctgat gatagccagg agaggtctaa gcg 43

<210> SEQ ID NO 40
<211> LENGTH: 43
<212> TYPE: DNA
<213> ORGANISM: Artificial Sequence
<220> FEATURE:

-continued

<223> OTHER INFORMATION: 18-mer scaffold (15)

<400> SEQUENCE: 40
atcttgcatt acatcagcat attgaagaac taaacgacct gta 43

<210> SEQ ID NO 41
<211> LENGTH: 43
<212> TYPE: DNA
<213> ORGANISM: Artificial Sequence
<220> FEATURE:
<223> OTHER INFORMATION: 18-mer scaffold (16)

<400> SEQUENCE: 41
tggacttgta atatgctgat gatagccagg agaggtctaa gcg 43

<210> SEQ ID NO 42
<211> LENGTH: 43
<212> TYPE: DNA
<213> ORGANISM: Artificial Sequence
<220> FEATURE:
<223> OTHER INFORMATION: 18-mer scaffold (17)

<400> SEQUENCE: 42
tacaggtcgt aaagggtggt cctatgttgc tgagattcga ggc 43

<210> SEQ ID NO 43
<211> LENGTH: 43
<212> TYPE: DNA
<213> ORGANISM: Artificial Sequence
<220> FEATURE:
<223> OTHER INFORMATION: 18-mer scaffold (18)

<400> SEQUENCE: 43
ttgttgagag agaccaccct ttagttcttc aaatacaagt cca 43

<210> SEQ ID NO 44
<211> LENGTH: 43
<212> TYPE: DNA
<213> ORGANISM: Artificial Sequence
<220> FEATURE:
<223> OTHER INFORMATION: 20-mer scaffold (17)

<400> SEQUENCE: 44
tacaggtcgt aatccgccat caactaacta caattcattc cta 43

<210> SEQ ID NO 45
<211> LENGTH: 43
<212> TYPE: DNA
<213> ORGANISM: Artificial Sequence
<220> FEATURE:
<223> OTHER INFORMATION: 20-mer scaffold (18)

<400> SEQUENCE: 45
ctacgaaatg agatggcgga ttagttcttc aaatacaagt cca 43

<210> SEQ ID NO 46
<211> LENGTH: 43
<212> TYPE: DNA
<213> ORGANISM: Artificial Sequence
<220> FEATURE:
<223> OTHER INFORMATION: 20-mer scaffold (19)

<400> SEQUENCE: 46
taggaatgaa atggtaaagg tctatgttgc tgagattcga ggc 43

```
<210> SEQ ID NO 47
<211> LENGTH: 43
<212> TYPE: DNA
<213> ORGANISM: Artificial Sequence
<220> FEATURE:
<223> OTHER INFORMATION: 20-mer scaffold (20)

<400> SEQUENCE: 47

ttgttgagag aacctttacc atgtagttag ttacatttcg tag                    43


<210> SEQ ID NO 48
<211> LENGTH: 43
<212> TYPE: DNA
<213> ORGANISM: Artificial Sequence
<220> FEATURE:
<223> OTHER INFORMATION: 24-mer scaffold (19)

<400> SEQUENCE: 48

taggaatgaa atggtaaagg tgatgtacag ataaaacaaa caa                    43


<210> SEQ ID NO 49
<211> LENGTH: 43
<212> TYPE: DNA
<213> ORGANISM: Artificial Sequence
<220> FEATURE:
<223> OTHER INFORMATION: 24-mer scaffold (20)

<400> SEQUENCE: 49

gtagaagctg aacctttacc atgtagttag ttacatttcg tag                    43


<210> SEQ ID NO 50
<211> LENGTH: 43
<212> TYPE: DNA
<213> ORGANISM: Artificial Sequence
<220> FEATURE:
<223> OTHER INFORMATION: 24-mer scaffold (21)

<400> SEQUENCE: 50

ttgtttgttt atgagtgaga taactgtaag ggatttgaac atc                    43


<210> SEQ ID NO 51
<211> LENGTH: 43
<212> TYPE: DNA
<213> ORGANISM: Artificial Sequence
<220> FEATURE:
<223> OTHER INFORMATION: 24-mer scaffold (22)

<400> SEQUENCE: 51

agggtatcaa aatctcactc aatctgtaca tcacagcttc tac                    43


<210> SEQ ID NO 52
<211> LENGTH: 43
<212> TYPE: DNA
<213> ORGANISM: Artificial Sequence
<220> FEATURE:
<223> OTHER INFORMATION: 24-mer scaffold (23)

<400> SEQUENCE: 52

gatgttcaaa aaagggtggt cctatgttgc tgagattcga ggc                    43


<210> SEQ ID NO 53
<211> LENGTH: 43
<212> TYPE: DNA
<213> ORGANISM: Artificial Sequence
<220> FEATURE:
<223> OTHER INFORMATION: 24-mer scaffold (24)
```

<400> SEQUENCE: 53
ttgttgagag agaccaccct tcccttacag ttattgatac cct 43

<210> SEQ ID NO 54
<211> LENGTH: 54
<212> TYPE: DNA
<213> ORGANISM: Artificial Sequence
<220> FEATURE:
<223> OTHER INFORMATION: double 12-mer - figure of eight structure (11d2)

<400> SEQUENCE: 54
ggctaaggct aaatgagtac cctatgttgc tgagattcga ggcgctcagt aagt 54

<210> SEQ ID NO 55
<211> LENGTH: 18
<212> TYPE: DNA
<213> ORGANISM: Artificial Sequence
<220> FEATURE:
<223> OTHER INFORMATION: Opened Rings (11a)

<400> SEQUENCE: 55
ggctaaggct aaatgagt 18

<210> SEQ ID NO 56
<211> LENGTH: 25
<212> TYPE: DNA
<213> ORGANISM: Artificial Sequence
<220> FEATURE:
<223> OTHER INFORMATION: Opened Rings (11b)

<400> SEQUENCE: 56
accctatgtt gctgagattc gaggc 25

<210> SEQ ID NO 57
<211> LENGTH: 14
<212> TYPE: DNA
<213> ORGANISM: Artificial Sequence
<220> FEATURE:
<223> OTHER INFORMATION: Opened Rings (12a)

<400> SEQUENCE: 57
ttgttgagag aggt 14

<210> SEQ ID NO 58
<211> LENGTH: 29
<212> TYPE: DNA
<213> ORGANISM: Artificial Sequence
<220> FEATURE:
<223> OTHER INFORMATION: Opened Rings (12b)

<400> SEQUENCE: 58
actcattgct aggctactat atctgtttc 29

<210> SEQ ID NO 59
<211> LENGTH: 65
<212> TYPE: DNA
<213> ORGANISM: Artificial Sequence
<220> FEATURE:
<223> OTHER INFORMATION: Rings with docking site (11dx)

<400> SEQUENCE: 59
ggctaaggct aaatgagtac cctatgttgc tgagattcga ggcacttact gagcactatc 60
tgagc 65

-continued

<210> SEQ ID NO 60
<211> LENGTH: 19
<212> TYPE: DNA
<213> ORGANISM: Artificial Sequence
<220> FEATURE:
<223> OTHER INFORMATION: tags and tagged oligos used for binding to the docking sites (11d')

<400> SEQUENCE: 60
gctcagatag tgctcagta 19

<210> SEQ ID NO 61
<211> LENGTH: 59
<212> TYPE: DNA
<213> ORGANISM: Artificial Sequence
<220> FEATURE:
<223> OTHER INFORMATION: tags and tagged oligos used for binding to the docking sites (11d'c30)

<400> SEQUENCE: 61
cccccccccc cccccccccc cccccccccc atcccatccc gctcagatag tgctcagta 59

<210> SEQ ID NO 62
<211> LENGTH: 32
<212> TYPE: DNA
<213> ORGANISM: Artificial Sequence
<220> FEATURE:
<223> OTHER INFORMATION: tags and tagged oligos used for binding to the docking sites (11d-toe)

<400> SEQUENCE: 62
tactgagcac tatctgagcg ggatgggatg gg 32

<210> SEQ ID NO 63
<211> LENGTH: 88
<212> TYPE: DNA
<213> ORGANISM: Artificial Sequence
<220> FEATURE:
<223> OTHER INFORMATION: OC01

<400> SEQUENCE: 63
tttttgccgt atttttcctc gctttttcct cgctttttcc tcgctttttc ctcgcttttt 60
cctcgctttt tcctcgcttt ttgccgta 88

<210> SEQ ID NO 64
<211> LENGTH: 88
<212> TYPE: DNA
<213> ORGANISM: Artificial Sequence
<220> FEATURE:
<223> OTHER INFORMATION: OC02

<400> SEQUENCE: 64
tttttctcgc tttttttcctc gctttttcct cgctttttcc tcgctttttc ctcgcttttt 60
cctcgctttt tcctcgcttt ttctcgct 88

<210> SEQ ID NO 65
<211> LENGTH: 44
<212> TYPE: DNA
<213> ORGANISM: Artificial Sequence
<220> FEATURE:
<223> OTHER INFORMATION: OC03

<400> SEQUENCE: 65
tttttggtgg gtttttcctc gctttttcct cgctttttgg tggg 44

-continued

<210> SEQ ID NO 66
<211> LENGTH: 84
<212> TYPE: DNA
<213> ORGANISM: Artificial Sequence
<220> FEATURE:
<223> OTHER INFORMATION: OC04

<400> SEQUENCE: 66 tttttcctc ctttttaccc ctttttcctc gctttttacc ccttttttcct cgctttttac 60 ccctttttcc tcgctttttc accc 84

<210> SEQ ID NO 67
<211> LENGTH: 84
<212> TYPE: DNA
<213> ORGANISM: Artificial Sequence
<220> FEATURE:
<223> OTHER INFORMATION: OC05

<400> SEQUENCE: 67
tttttccact ctttttaccc ctttttcctc gctttttacc cctttttcct cgctttttac 60
ccctttttcc tcgctttttc ccgc 84

<210> SEQ ID NO 68
<211> LENGTH: 42
<212> TYPE: DNA
<213> ORGANISM: Artificial Sequence
<220> FEATURE:
<223> OTHER INFORMATION: OC06

<400> SEQUENCE: 68
tttttcacgt ctttttaccc ctttttcctc gctttttccc ct 42

<210> SEQ ID NO 69
<211> LENGTH: 84
<212> TYPE: DNA
<213> ORGANISM: Artificial Sequence
<220> FEATURE:
<223> OTHER INFORMATION: OC07

<400> SEQUENCE: 69
ttttttcctc ctttttaccc ctttttcctc gctttttacc cctttttcct cgctttttac 60
ccctttttcc tcgctttttg ccga 84

<210> SEQ ID NO 70
<211> LENGTH: 84
<212> TYPE: DNA
<213> ORGANISM: Artificial Sequence
<220> FEATURE:
<223> OTHER INFORMATION: OC08

<400> SEQUENCE: 70
tttttagccg ctttttaccc ctttttcctc gctttttacc cctttttcct cgctttttac 60
ccctttttcc tcgctttttc accc 84

<210> SEQ ID NO 71
<211> LENGTH: 63
<212> TYPE: DNA
<213> ORGANISM: Artificial Sequence
<220> FEATURE:
<223> OTHER INFORMATION: OC09

<400> SEQUENCE: 71
tttttcccac atttttaccc ctttttcctc gctttttacc cctttttcct cgctttttcc 60
cgc 63

<210> SEQ ID NO 72
<211> LENGTH: 22
<212> TYPE: DNA
<213> ORGANISM: Artificial Sequence
<220> FEATURE:
<223> OTHER INFORMATION: Cap01

<400> SEQUENCE: 72
attgacccac caaaaatacg gc 22

<210> SEQ ID NO 73
<211> LENGTH: 22
<212> TYPE: DNA
<213> ORGANISM: Artificial Sequence
<220> FEATURE:
<223> OTHER INFORMATION: Cap02

<400> SEQUENCE: 73
aagtaagcga gaaaaaccca cc 22

<210> SEQ ID NO 74
<211> LENGTH: 22
<212> TYPE: DNA
<213> ORGANISM: Artificial Sequence
<220> FEATURE:
<223> OTHER INFORMATION: Cap03

<400> SEQUENCE: 74
agatatacgg caaaaaagcg ag 22

<210> SEQ ID NO 75
<211> LENGTH: 26
<212> TYPE: DNA
<213> ORGANISM: Artificial Sequence
<220> FEATURE:
<223> OTHER INFORMATION: Cap04

<400> SEQUENCE: 75
attgaggagg aaaaaaaggg gaaaaa 26

<210> SEQ ID NO 76
<211> LENGTH: 26
<212> TYPE: DNA
<213> ORGANISM: Artificial Sequence
<220> FEATURE:
<223> OTHER INFORMATION: Cap05

<400> SEQUENCE: 76
aagtagagtg gaaaaagggt gaaaaa 26

<210> SEQ ID NO 77
<211> LENGTH: 26
<212> TYPE: DNA
<213> ORGANISM: Artificial Sequence
<220> FEATURE:
<223> OTHER INFORMATION: Cap06

<400> SEQUENCE: 77
agatagacgt gaaaaagcgg gaaaaa 26

<210> SEQ ID NO 78
<211> LENGTH: 26
<212> TYPE: DNA

<213> ORGANISM: Artificial Sequence
<220> FEATURE:
<223> OTHER INFORMATION: Cap07

<400> SEQUENCE: 78
aagtagacgt gaaaaagggt gaaaaa 26

<210> SEQ ID NO 79
<211> LENGTH: 26
<212> TYPE: DNA
<213> ORGANISM: Artificial Sequence
<220> FEATURE:
<223> OTHER INFORMATION: Cap08

<400> SEQUENCE: 79
agtatgcggc taaaaatcgg caaaaa 26

<210> SEQ ID NO 80
<211> LENGTH: 26
<212> TYPE: DNA
<213> ORGANISM: Artificial Sequence
<220> FEATURE:
<223> OTHER INFORMATION: Cap09

<400> SEQUENCE: 80
tattgtgtgg gaaaaagggt gaaaaa 26

<210> SEQ ID NO 81
<211> LENGTH: 22
<212> TYPE: DNA
<213> ORGANISM: Artificial Sequence
<220> FEATURE:
<223> OTHER INFORMATION: CapComp01

<400> SEQUENCE: 81
gccgtatttt tggtgggtca at 22

<210> SEQ ID NO 82
<211> LENGTH: 22
<212> TYPE: DNA
<213> ORGANISM: Artificial Sequence
<220> FEATURE:
<223> OTHER INFORMATION: CapComp02

<400> SEQUENCE: 82
ggtgggtttt tctcgcttac tt 22

<210> SEQ ID NO 83
<211> LENGTH: 22
<212> TYPE: DNA
<213> ORGANISM: Artificial Sequence
<220> FEATURE:
<223> OTHER INFORMATION: CapComp03

<400> SEQUENCE: 83
ctcgcttttt tgccgtatat ct 22

<210> SEQ ID NO 84
<211> LENGTH: 26
<212> TYPE: DNA
<213> ORGANISM: Artificial Sequence
<220> FEATURE:
<223> OTHER INFORMATION: CapComp04

<400> SEQUENCE: 84
tttttcccct ttttttcctc ctcaat 26

<210> SEQ ID NO 85
<211> LENGTH: 26
<212> TYPE: DNA
<213> ORGANISM: Artificial Sequence
<220> FEATURE:
<223> OTHER INFORMATION: CapComp05

<400> SEQUENCE: 85
tttttcaccc tttttccact ctactt 26

<210> SEQ ID NO 86
<211> LENGTH: 26
<212> TYPE: DNA
<213> ORGANISM: Artificial Sequence
<220> FEATURE:
<223> OTHER INFORMATION: CapComp06

<400> SEQUENCE: 86
tttttcccgc tttttcacgt ctatct 26

<210> SEQ ID NO 87
<211> LENGTH: 26
<212> TYPE: DNA
<213> ORGANISM: Artificial Sequence
<220> FEATURE:
<223> OTHER INFORMATION: CapComp07

<400> SEQUENCE: 87
tttttcaccc tttttcacgt ctactt 26

<210> SEQ ID NO 88
<211> LENGTH: 26
<212> TYPE: DNA
<213> ORGANISM: Artificial Sequence
<220> FEATURE:
<223> OTHER INFORMATION: CapComp08

<400> SEQUENCE: 88
tttttgccga tttttagccg catact 26

<210> SEQ ID NO 89
<211> LENGTH: 26
<212> TYPE: DNA
<213> ORGANISM: Artificial Sequence
<220> FEATURE:
<223> OTHER INFORMATION: CapComp09

<400> SEQUENCE: 89
tttttcaccc tttttcccac acaata 26

<210> SEQ ID NO 90
<211> LENGTH: 27
<212> TYPE: DNA
<213> ORGANISM: Artificial Sequence
<220> FEATURE:
<223> OTHER INFORMATION: IC01a

<400> SEQUENCE: 90
aaaaagcgag ttgttgttgt tgaataa 27

<210> SEQ ID NO 91
<211> LENGTH: 28
<212> TYPE: DNA
<213> ORGANISM: Artificial Sequence
<220> FEATURE:

-continued

<223> OTHER INFORMATION: IC01b

<400> SEQUENCE: 91
aaaaagcgag gttgttgttg ttgaataa 28

<210> SEQ ID NO 92
<211> LENGTH: 27
<212> TYPE: DNA
<213> ORGANISM: Artificial Sequence
<220> FEATURE:
<223> OTHER INFORMATION: IC02a

<400> SEQUENCE: 92
aaaaatacgg ttgttgttgt tgaataa 27

<210> SEQ ID NO 93
<211> LENGTH: 28
<212> TYPE: DNA
<213> ORGANISM: Artificial Sequence
<220> FEATURE:
<223> OTHER INFORMATION: IC02b

<400> SEQUENCE: 93
aaaaatacgg cttgttgttg ttgaataa 28

<210> SEQ ID NO 94
<211> LENGTH: 27
<212> TYPE: DNA
<213> ORGANISM: Artificial Sequence
<220> FEATURE:
<223> OTHER INFORMATION: IC03a

<400> SEQUENCE: 94
aaaaaagcga ttgttgttgt tgaataa 27

<210> SEQ ID NO 95
<211> LENGTH: 28
<212> TYPE: DNA
<213> ORGANISM: Artificial Sequence
<220> FEATURE:
<223> OTHER INFORMATION: IC03b

<400> SEQUENCE: 95
aaaaaagcga gttgttgttg ttgaataa 28

<210> SEQ ID NO 96
<211> LENGTH: 27
<212> TYPE: DNA
<213> ORGANISM: Artificial Sequence
<220> FEATURE:
<223> OTHER INFORMATION: IC04a

<400> SEQUENCE: 96
aaaaacccac ttgttgttgt tgaataa 27

<210> SEQ ID NO 97
<211> LENGTH: 28
<212> TYPE: DNA
<213> ORGANISM: Artificial Sequence
<220> FEATURE:
<223> OTHER INFORMATION: IC04b

<400> SEQUENCE: 97
aaaaacccac cttgttgttg ttgaataa 28

-continued

<210> SEQ ID NO 98
<211> LENGTH: 27
<212> TYPE: DNA
<213> ORGANISM: Artificial Sequence
<220> FEATURE:
<223> OTHER INFORMATION: IC05

<400> SEQUENCE: 98
aaaaaggggt ttgttgttgt tgaataa 27

<210> SEQ ID NO 99
<211> LENGTH: 28
<212> TYPE: DNA
<213> ORGANISM: Artificial Sequence
<220> FEATURE:
<223> OTHER INFORMATION: IC06a

<400> SEQUENCE: 99
aaaaagcgag gttgttgttg ttgaataa 28

<210> SEQ ID NO 100
<211> LENGTH: 27
<212> TYPE: DNA
<213> ORGANISM: Artificial Sequence
<220> FEATURE:
<223> OTHER INFORMATION: IC06b

<400> SEQUENCE: 100
aaaaagcgag ttgttgttgt tgaataa 27

<210> SEQ ID NO 101
<211> LENGTH: 28
<212> TYPE: DNA
<213> ORGANISM: Artificial Sequence
<220> FEATURE:
<223> OTHER INFORMATION: IC07a

<400> SEQUENCE: 101
aaaaaggagg attgttgttg ttgaataa 28

<210> SEQ ID NO 102
<211> LENGTH: 27
<212> TYPE: DNA
<213> ORGANISM: Artificial Sequence
<220> FEATURE:
<223> OTHER INFORMATION: IC07b

<400> SEQUENCE: 102
aaaaaggagg ttgttgttgt tgaataa 27

<210> SEQ ID NO 103
<211> LENGTH: 27
<212> TYPE: DNA
<213> ORGANISM: Artificial Sequence
<220> FEATURE:
<223> OTHER INFORMATION: IC08

<400> SEQUENCE: 103
aaaaagggtg ttgttgttgt tgaataa 27

<210> SEQ ID NO 104
<211> LENGTH: 27
<212> TYPE: DNA
<213> ORGANISM: Artificial Sequence
<220> FEATURE:
<223> OTHER INFORMATION: IC09

<400> SEQUENCE: 104
aaaaaagggg ttgttgttgt tgaataa 27

<210> SEQ ID NO 105
<211> LENGTH: 28
<212> TYPE: DNA
<213> ORGANISM: Artificial Sequence
<220> FEATURE:
<223> OTHER INFORMATION: IC010a

<400> SEQUENCE: 105
aaaaagacgt gttgttgttg ttgaataa 28

<210> SEQ ID NO 106
<211> LENGTH: 27
<212> TYPE: DNA
<213> ORGANISM: Artificial Sequence
<220> FEATURE:
<223> OTHER INFORMATION: IC010b

<400> SEQUENCE: 106
aaaaagacgt ttgttgttgt tgaataa 27

<210> SEQ ID NO 107
<211> LENGTH: 27
<212> TYPE: DNA
<213> ORGANISM: Artificial Sequence
<220> FEATURE:
<223> OTHER INFORMATION: IC011

<400> SEQUENCE: 107
aaaaagcggg ttgttgttgt tgaataa 27

<210> SEQ ID NO 108
<211> LENGTH: 28
<212> TYPE: DNA
<213> ORGANISM: Artificial Sequence
<220> FEATURE:
<223> OTHER INFORMATION: IC012a

<400> SEQUENCE: 108
aaaaagagtg gttgttgttg ttgaataa 28

<210> SEQ ID NO 109
<211> LENGTH: 27
<212> TYPE: DNA
<213> ORGANISM: Artificial Sequence
<220> FEATURE:
<223> OTHER INFORMATION: IC012b

<400> SEQUENCE: 109
aaaaagagtg ttgttgttgt tgaataa 27

<210> SEQ ID NO 110
<211> LENGTH: 27
<212> TYPE: DNA
<213> ORGANISM: Artificial Sequence
<220> FEATURE:
<223> OTHER INFORMATION: IC013

<400> SEQUENCE: 110
aaaaatcggc ttgttgttgt tgaataa 27

<210> SEQ ID NO 111
<211> LENGTH: 27

<212> TYPE: DNA
<213> ORGANISM: Artificial Sequence
<220> FEATURE:
<223> OTHER INFORMATION: IC014b

<400> SEQUENCE: 111
aaaaagcggc ttgttgttgt tgaataa 27

<210> SEQ ID NO 112
<211> LENGTH: 27
<212> TYPE: DNA
<213> ORGANISM: Artificial Sequence
<220> FEATURE:
<223> OTHER INFORMATION: IC015

<400> SEQUENCE: 112
aaaaagggtg ttgttgttgt tgaataa 27

<210> SEQ ID NO 113
<211> LENGTH: 27
<212> TYPE: DNA
<213> ORGANISM: Artificial Sequence
<220> FEATURE:
<223> OTHER INFORMATION: IC016b

<400> SEQUENCE: 113
aaaaatgtgg ttgttgttgt tgaataa 27

<210> SEQ ID NO 114
<211> LENGTH: 14
<212> TYPE: DNA
<213> ORGANISM: Artificial Sequence
<220> FEATURE:
<223> OTHER INFORMATION: ssDNA tail'

<400> SEQUENCE: 114
ttattcaaca acaa 14

<210> SEQ ID NO 115
<211> LENGTH: 7
<212> TYPE: PRT
<213> ORGANISM: Artificial Sequence
<220> FEATURE:
<223> OTHER INFORMATION: sequence of lower part of alphaHL beta-barrel
inserted into the membrane (1)

<400> SEQUENCE: 115

Gly Phe Asn Gly Asn Val Thr
1 5

<210> SEQ ID NO 116
<211> LENGTH: 8
<212> TYPE: PRT
<213> ORGANISM: Artificial Sequence
<220> FEATURE:
<223> OTHER INFORMATION: sequence of lower part of alphaHL beta-barrel
inserted into the membrane (2)

<400> SEQUENCE: 116

Gly Gly Leu Ile Gly Ala Asn Val
1 5

<210> SEQ ID NO 117
<211> LENGTH: 293
<212> TYPE: PRT
<213> ORGANISM: Artificial Sequence
<220> FEATURE:

-continued

<223> OTHER INFORMATION: alpha hemolysin (N17C, T115H) mutations

<400> SEQUENCE: 117

Ala Asp Ser Asp Ile Asn Ile Lys Thr Gly Thr Thr Asp Ile Gly Ser
1 5 10 15

Cys Thr Thr Val Lys Thr Gly Asp Leu Val Thr Tyr Asp Lys Glu Asn
20 25 30

Gly Met His Lys Lys Val Phe Tyr Ser Phe Ile Asp Asp Lys Asn His
35 40 45

Asn Lys Lys Leu Leu Val Ile Arg Thr Lys Gly Thr Ile Ala Gly Gln
50 55 60

Tyr Arg Val Tyr Ser Glu Glu Gly Ala Asn Lys Ser Gly Leu Ala Trp
65 70 75 80

Pro Ser Ala Phe Lys Val Gln Leu Gln Leu Pro Asp Asn Glu Val Ala
85 90 95

Gln Ile Ser Asp Tyr Tyr Pro Arg Asn Ser Ile Asp Thr Lys Glu Tyr
100 105 110

Met Ser His Leu Thr Tyr Gly Phe Asn Gly Asn Val Thr Gly Asp Asp
115 120 125

Thr Gly Lys Ile Gly Gly Leu Ile Gly Ala Asn Val Ser Ile Gly His
130 135 140

Thr Leu Lys Tyr Val Gln Pro Asp Phe Lys Thr Ile Leu Glu Ser Pro
145 150 155 160

Thr Asp Lys Lys Val Gly Trp Lys Val Ile Phe Asn Asn Met Val Asn
165 170 175

Gln Asn Trp Gly Pro Tyr Asp Arg Asp Ser Trp Asn Pro Val Tyr Gly
180 185 190

Asn Gln Leu Phe Met Lys Thr Arg Asn Gly Ser Met Lys Ala Ala Asp
195 200 205

Asn Phe Leu Asp Pro Asn Lys Ala Ser Ser Leu Leu Ser Ser Gly Phe
210 215 220

Ser Pro Asp Phe Ala Thr Val Ile Thr Met Asp Arg Lys Ala Ser Lys
225 230 235 240

Gln Gln Thr Asn Ile Asp Val Ile Tyr Glu Arg Val Arg Asp Asp Tyr
245 250 255

Gln Leu His Trp Thr Ser Thr Asn Trp Lys Gly Thr Asn Thr Lys Asp
260 265 270

Lys Trp Thr Asp Arg Ser Ser Glu Arg Tyr Lys Ile Asp Trp Glu Lys
275 280 285

Glu Glu Met Thr Asn
290

<210> SEQ ID NO 118
<211> LENGTH: 293
<212> TYPE: PRT
<213> ORGANISM: Artificial Sequence
<220> FEATURE:
<223> OTHER INFORMATION: alpha hemolysin (N17C, T145H) mutations

<400> SEQUENCE: 118

Ala Asp Ser Asp Ile Asn Ile Lys Thr Gly Thr Thr Asp Ile Gly Ser
1 5 10 15

Cys Thr Thr Val Lys Thr Gly Asp Leu Val Thr Tyr Asp Lys Glu Asn
20 25 30

Gly Met His Lys Lys Val Phe Tyr Ser Phe Ile Asp Asp Lys Asn His
35 40 45

-continued

```
Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

His Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

ASSEMBLY COMPRISING A NUCLEIC ACID SCAFFOLD, SYSTEMS, METHODS, AND USES THEREFORE

RELATED APPLICATIONS

This application is the U.S. National Stage of International Application No. PCT/GB2018/052170, filed Jul. 30, 2018, which designates the U.S., published in English. The entire teachings of the above application is incorporated herein by reference.

STATEMENT REGARDING PRIOR DISCLOSURES BY THE INVENTOR OR A JOINT INVENTOR

The subject application claims the benefit of PCT/GB2018/052170, filed Jul. 30, 2018. The publications of Henning-Knechtel, et al., "DNA-assisted oligomerization of pore-forming toxin monomers into precisely-controlled protein channels," *Nucleic Acids Research,* 45(21):12057-12068, Oct. 27, 2017; Spruijt, et al., "DNA scaffolds support table and uniform peptide nanopores," *Nature Nanotechnology,* 13:739-745, May 28, 2018; "HYBRIPORE Report Summary", Horizon 2020, CORDIS, Jul. 31, 2017; and Presentation at Wageningen University on Feb. 1, 2018 by inventor Evan Spruijt were published by an inventor or joint inventor of the subject application. The publications were published less than one year before the effective filing date of Jul. 30, 2018.

REFERENCE TO SEQUENCE LISTING

This application contains a Sequence Listing submitted as an electronic text file named "Sequence Listing N414111WO PJS EGH.txt", having a size in bytes of 40,611 bytes, and created on Jul. 18, 2018. The information contained in this electronic file is hereby incorporated by reference in its entirety pursuant to 37 CFR § 1.52(e)(5).

FIELD OF THE INVENTION

The invention relates to pore-forming assemblies. More particularly, an assembly wherein the formation of a membrane-spanning pore is promoted by a scaffold that pre-organises the structure. The invention also relates to methods of forming a pore, methods of detecting and/or characterising a target analyte and methods of sequencing using the assemblies of the invention.

BACKGROUND TO THE INVENTION

A pore may be characterised as an opening in or channel through a membrane. Typically, a membrane comprises a hydrophobic layer of amphipathic molecules and the pore provides a hydrophilic channel through the membrane. Thus, pores comprise amphipathic structures with hydrophobic surfaces that interact with the membrane and hydrophilic surfaces that form a hydrophilic opening in the membrane. Pores may have a wide range of channel diameters through which ions and certain molecules may pass. Many pores have a channel diameter in the nanometre range and are typically known as "nanopores". In recent years, pores and particularly nanopores have become established as versatile tools for a wide range of nanotechnological applications (1-7HK). In particular, the use of nanopores as ultra-sensitive sensor elements for rapid and label-free analysis of single molecules has garnered considerable interest.

The preparation of nanometre-scaled pores can be realised by perforating either (i) a semifluid membrane via membrane-spanning pores, or (ii) a thin solid-state film (e.g. silica, silicon nitrate or graphene) via, for instance, a focused ion or electron beam (8-11HK). Although solid-state nanopores provide a higher mechanical and chemical stability, and are less sensitive to buffer conditions, the most commonly utilized platforms for biological applications are membrane-inserted protein pores (12HK). In biology, membrane-spanning protein channels and pores play important roles in regulating transport across cell membranes and in signalling and defence mechanisms (1-3). As they are versatile and amenable to engineering, such pores have found application in single-molecule biosensors and sequencing technologies (4, 5). This is largely due to the high reproducibility of the pore structure, as well as the atomically precise positioning of chemical groups through genetic engineering, both of which cannot be achieved so far using solid-state nanopore fabrication methods. Larger protein pores are mostly β-barrels, many of which can fold spontaneously or insert into the outer membrane of Gram-negative bacteria assisted by dedicated protein machinery (6-8). Recently, a number of pores that consist of α-helical peptides, which include the polysaccharide transporter Wza and cytolysin A (ClyA), have been discovered, but their assembly is still poorly understood (9-11). Such pores could help expand the utility of biological pores in biotechnology and synthetic biology. However, an important challenge for such applications that remains is to control the geometrical and chemical properties of the sensor channels.

There remains a need in the art to provide improved means to orient and stabilise pore-forming subunits, such as peptides or proteins. This is complicated by complex requirements for the structure and assembly of the subunits to form the pore. Any such means would need to dictate the size of the desired nanopore, but must be sufficiently flexible to avoid trapping the amphipathic appendages, such as peptides or proteins, in an unwanted conformation. Moreover, any such means must not obstruct the nanopore.

It has recently been shown that cyclodextrins can be used to template peptide nanopores (12). These templates, however, cannot be used for large or heteromeric nanopores. In earlier work, four different peptide helices were tethered onto a flexible peptide backbone to form sodium channel analogues, but such peptide backbones may not be rigid enough to act as effective scaffolds for larger nanopores (13-15).

Thus, there is great potential for applications of pores in biotechnology and synthetic biology. However, there remains a need in the art to provide improved means to assemble stable and functional nanopores from pore-forming subunits.

SUMMARY OF THE INVENTION

The present inventors have surprisingly found that assembly of appendages into a configuration for formation of a pore in a layer of amphipathic molecules can be promoted by using nucleic acid scaffolds to pre-organize the structures. The inventors have found that such nucleic acid scaffolds enable the construction of uniform pores of various sizes and pores with controlled permutations around a central axis. The assemblies described herein comprise nucleic acid nanostructures that can serve as scaffolds to arrange appendages, such as peptides or polypeptides, to form uniform pores in layers of amphipathic molecules. The inventors have found that when scaffolded, appendages that do not form pores in isolation may be induced to form pores. Similarly, the nucleic acid scaffold described herein can direct the appendages to form pores with much larger diameters than naturally occurring pores. The inventors have also found that scaffolded pores have enhanced stability and improved conductance properties. The inventors have also found that the assemblies described herein allow for precise control of the arrangement of monomers within heteromeric pores. Thus, the assemblies described herein allow for the formation of larger, more uniform pores with enhanced stability and a precisely controlled structure.

The present invention provides an assembly comprising a nucleic acid scaffold and a plurality of appendages bonded to the scaffold, wherein the appendages, when bonded to the scaffold, are capable of interacting to form a pore in a layer of amphipathic molecules.

The present invention also provides an assembly comprising a nucleic acid scaffold and a plurality of appendages, wherein the appendages are bonded to the scaffold in an arrangement enabling the appendages to form a pore in a layer of amphipathic molecules.

The present invention further provides a system comprising:

(a) a layer of amphipathic molecules; and (b) an assembly comprising a nucleic acid scaffold and a plurality of appendages bonded to the scaffold, wherein the appendages form a pore in the layer of amphipathic molecules.

The invention also provides a method of forming a pore in a layer of amphipathic molecules, the method comprising applying an assembly to a layer of amphipathic molecules, which assembly comprises a nucleic acid scaffold and a plurality of appendages bonded to the scaffold, and thereby causing the appendages to interact to form a pore in the layer of amphipathic molecules.

The present invention also provides a device comprising:

(a) a layer of amphipathic molecules;

(b) an assembly comprising a nucleic acid scaffold and a plurality of appendages bonded to the scaffold, wherein the appendages form a pore in the layer of amphipathic molecules; and (c) apparatus for measuring electrical current through the pore.

The present invention also provides a system comprising:

(a) an assembly comprising a nucleic acid scaffold and a plurality of appendages bonded to the scaffold; and (b) two or more chambers, each of which is separated by a layer of amphipathic molecules;

wherein the appendages form a pore in the layer of amphipathic molecules.

The present invention further provides a method of transporting a molecule of interest across a layer of amphipathic molecules, the method comprising:

(a) contacting the molecule of interest with a pore formed by a system as defined anywhere herein;

(b) applying a potential across the layer of amphipathic molecules, thereby transporting the molecule of interest through the pore and across the layer of amphipathic molecules.

The present invention further provides a method of detecting and/or characterising a target analyte, comprising:

(a) contacting the target analyte with a pore formed in a system as defined anywhere herein or a device as defined anywhere herein; and (b) taking one or more measurements as the analyte moves with respect to the pore or of the presence of the analyte within the pore, wherein the measurements are indicative of the presence of and/or one or more characteristics of the target analyte, and thereby detecting and/or characterising the target analyte.

The present invention also provides a method of sequencing, comprising:

(a) contacting a molecule to be sequenced with a system comprising (i) an assembly comprising a nucleic acid scaffold and a plurality of appendages bonded to the scaffold, and (ii) a layer of amphipathic molecules, wherein the appendages form a pore in the layer of amphipathic molecules;

(b) applying a voltage and driving a current across the layer of amphipathic molecules;

(c) passing the molecule to be sequenced through the pore formed by the assembly; and (d) determining the sequence of the molecule based on the characteristic disruption or modulation in the electrical signal caused by each monomeric unit as it passes through the pore.

The present invention also provides a kit for characterising a target polynucleotide comprising an assembly, system or device as defined herein.

The present invention also provides a nucleic acid scaffold comprising a plurality of nucleic acids arranged to form a closed circular structure with protruding arms, wherein each nucleic acid comprises two central regions that hybridise with the central regions of other nucleic acids in the nucleic acid scaffold and two outer regions that hybridise with the outer regions of other nucleic acids in the nucleic acid scaffold.

The present invention also provides a method of making a nucleic acid scaffold comprising a plurality of nucleic acids arranged to form a closed circular structure with protruding arms, wherein the method comprises:

(i) mixing a plurality of nucleic acids, which nucleic acids each comprise two central regions that hybridise with the central regions of other nucleic acids in the nucleic acid scaffold and two outer regions that hybridise with the outer regions of other nucleic acids in the nucleic acid scaffold;

(ii) heating the mixture to a temperature above the melting temperature of the nucleic acids; and (iii) cooling the mixture to a temperature below the melting temperature of the nucleic acids.

BRIEF DESCRIPTION OF THE FIGURES

FIGS. 47 'a-*b* are schematic showing the "AB" (FIG. 47*a*)and "AD" (FIG. 47*b*)configurations of the $WT_5(T115H)_2$ αHL pores.

DESCRIPTION OF THE SEQUENCE LISTING

Figure 1A:
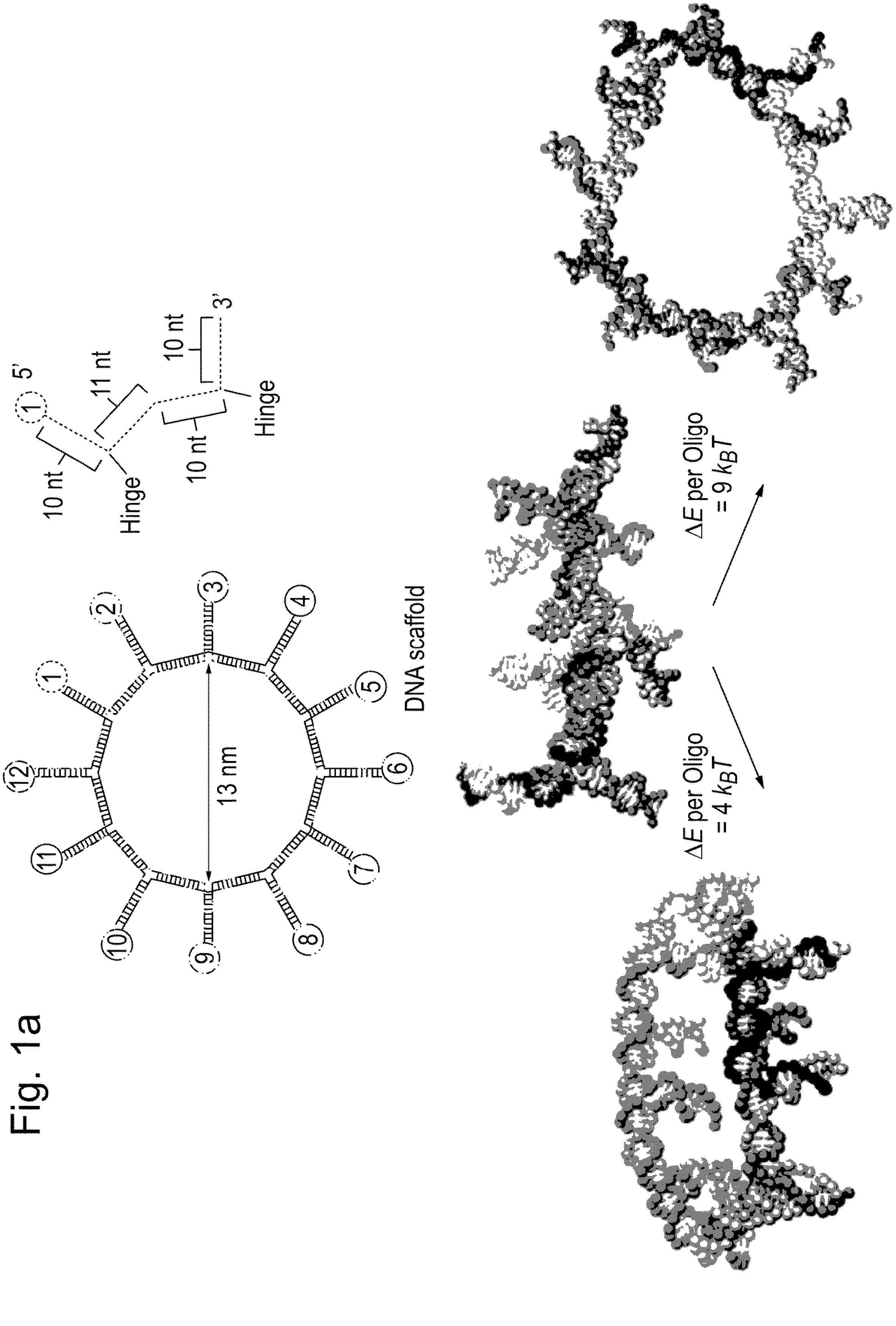
FIG. 1: Design, assembly and characterization of the DNA scaffolds for peptide nanopores. a, Schematic of the DNA scaffold with oligonucleotides numbered at their 5' ends (left) and snapshots of the scaffold from coarse-grained molecular dynamics simulations (right) without constraints (top) and with arms forced down or outward (bottom). b, Scaffold annealing was analysed in a 2.5% agarose gel, stained with SYBR Gold. The gel shows an New England Biolabs low molecular weight dsDNA ladder (L), for which the band sizes are indicated to the left of the gel, a single oligonucleotide (1), a mixture of 12 oligonucleotides without annealing (2), 11 oligonucleotides after annealing (3), 12 oligonucleotides after annealing in 100 mM potassium phosphate, pH 7.2 (4), and after annealing in 100 mM potassium phosphate, pH 7.2, with 0.5 M NaCl (5). c, Negatively stained TEM images of DNA scaffolds annealed in 100 mM Tris-HCl, pH 7.2. d, Stepwise photobleaching trace of a DNA scaffold formed from 12 Alexa-647-modified oligonucleotides. Inset: magnified view of the first 20 s. a.u., arbitrary units. e, Restriction digestion of the DNA scaffold, analysed in a 5% polyacrylamide gel and stained with SYBR Gold. The gel shows an New England Biolabs 50 bp dsDNA ladder (L), for which the band sizes are indicated to the left of the gel, a mixture of 12 oligonucleotides without annealing (1), a mixture of 11 oligonucleotides after annealing (2), closed rings formed by annealing 12 oligonucleotides (3), an annealed control construct identical to the RsaI restriction product (4) and closed rings incubated with RsaI in 100 mM potassium phosphate, pH 7.2 (5).

SEQ ID NOS: 1 and 3 show a peptide sequence derived from a consensus sequence of the D4 domain (325-359) of outer membrane protein Wza, across all organisms that have this protein. An N- or C-terminal CGG/GGC handle enables coupling of the peptide to the nucleic acid scaffold via its N- or C-terminus, respectively.

SEQ ID NOs: 2 and 4 show an alternative consensus Wza peptide sequence with an N- or C-terminal CGG/GGC handle.

SEQ ID NO: 5 shows the *E. coli* Wza peptide with a R376T substitution.

SEQ ID NO: 6 shows the alternative consensus Wza peptide sequence without the CGG/GGC handle.

SEQ ID NO: 7 shows the alternative consensus Wza peptide sequence with a K375C substitution.

SEQ ID NO: 8 shows the alternative consensus Wza peptide sequence with a Y373C substitution.

SEQ ID NOs: 9 and 10 show two peptides derived from the β-hairpin of *S. aureus* α-hemolysin (αHL) (amino acid residues 111-147 of the mature polypeptide). SEQ ID NO: 9 shows a T129C mutant that can be coupled with the trans-side loop of the β-barrel to the nucleic acid scaffold. SEQ ID NO: 10 shows another variant where the two β-strands have been exchanged, in order to flip the β-hairpins as they hang from the nucleic acid scaffold.

SEQ ID NO: 11 shows the full-length α-HL protein sequence including the signal peptide.

SEQ ID NO: 12 shows the mature α-HL protein sequence (residue numbering for αHL herein corresponds to this sequence).

SEQ ID NOs: 13 and 14 show the mature α-HL protein sequence with a K237C or a N17C mutation, respectively. The K237C or the N17C mutations provides an accessible attachment point for bonding to the nucleic acid scaffold.

SEQ ID NOs: 15-26 show the sequences of 12 nucleic acids ((1) to (12)) that can be mixed in stoichiometric amounts to assemble into a nucleic acid scaffold of the invention, as described in Example 1, having a closed circular structure with 12 protruding arms ("12-mer scaffold").

SEQ ID NOs: 27 and 28 show optimised versions of nucleic acids (7) and (10) (SEQ ID NOs: 21 and 24, respectively). SEQ ID NOs: 27 and 28 may be mixed with SEQ ID NOs: 15-20, 22, 23, 25 and 26 to form an optimised "12-mer scaffold". The optimisation prevents nucleic acids (7) and (8) (SEQ ID NO: 22) becoming trapped in a secondary minimum of hybridization between regions that are not fully complementary.

SEQ ID NOs: 29-31 show nucleic acids that can substitute nucleic acid (11) (SEQ ID NO: 25) and can be mixed with SEQ ID NOs: 15-20, 21/27, 22, 23, 24/28 and 26 to form a "12-mer scaffold" comprising one longer protruding arm.

SEQ ID NOs: 32-35 show nucleic acids that can be mixed with SEQ ID NOs: 15-20, 21/27, 22, 23 and 24/28 to form a nucleic acid scaffold of the invention, as described in Example 3, having a closed circular structure with 14 protruding arms ("14-mer scaffold").

SEQ ID NOs: 36-39 show nucleic acids that can be mixed with SEQ ID NOs: 15-20, 21/27, 22, 23, 24/28, 32 and 33 to form a nucleic acid scaffold of the invention, as described in Example 3, having a closed circular structure with 16 protruding arms ("16-mer scaffold").

SEQ ID NOs: 40-43 show nucleic acids that can be mixed with SEQ ID NOs: 15-20, 21/27, 22, 23, 24/28, 32, 33, 36 and 37 to form a nucleic acid scaffold of the invention, as described in Example 3, having a closed circular structure with 18 protruding arms ("18-mer scaffold").

SEQ ID NOs: 44-47 show nucleic acids that can be mixed with SEQ ID NOs: 15-20, 21/27, 22, 23, 24/28, 32, 33, 36, 37, 40 and 41 to form a nucleic acid scaffold of the invention, as described in Example 3, having a closed circular structure with 20 protruding arms ("20-mer scaffold").

SEQ ID NOs: 48-53 show nucleic acids that can be mixed with SEQ ID NOs: 15-20, 21/27, 22, 23, 24/28, 32, 33, 36, 37, 40, 41, 44 and 45 to form a nucleic acid scaffold of the invention, as described in Example 3, having a closed circular structure with 24 protruding arms ("24-mer scaffold").

SEQ ID NO: 54 shows a nucleic acid that can be mixed with SEQ ID NOs: 15-20, 21/27, 22, 23, 24/28, 26 and 29 to form a nucleic acid scaffold of the invention, having two closed circular structures with 12 protruding arms, joined together at one protruding arm to form a figure-of-eight shape ("double 12-mer").

SEQ ID NOs: 55-58 show nucleic acids that can be mixed with SEQ ID NOs: 15-20, 21/27, 22, 23 and 24/28 to form an "open ring" having a structure that is identical to the "12-mer scaffold" RsaI restriction product. The "open rings" were used as a control in the restriction assay shown in FIG. 1*e*.

SEQ ID NOs: 29 and 59 show nucleic acids that can be used to provide a docking moiety on the nucleic acid scaffold. A nucleic acid scaffold comprising either an "8-mer" docking site or a "19-mer" docking site can be formed by mixing SEQ ID NOs: 15-20, 21/27, 22, 23, 24/28 and 26 with either SEQ ID NO: 29 or SEQ ID NO: 59, respectively.

SEQ ID NOs: 60-62 show nucleic acids that act as "tags" and bind to the "8-mer" or "19-mer" docking sites provided by SEQ ID NOs: 29 or 59.

SEQ ID NOs: 63-71 show the "Outer Circle" nucleic acids used to form the closed circular first nucleic acid strand of a nucleic acid scaffold of the invention, as described in Example 2.

SEQ ID NOs: 72-80 show the "Cap-L" nucleic acids that are used to connect the Outer Circle nucleic acids for the first ligation step to form a long linear single-stranded DNA molecule, as described in Example 2.

SEQ ID NOs: 81-89 show the "CapComp" nucleic acids that are used to remove the "Cap-L" nucleic acids from the long linear single-stranded DNA molecule, prior to the second ligation to form the closed circular first nucleic acid strand, as described in Example 2.

SEQ ID NOs: 90-113 show the "Inner Circle" nucleic acids that are added to the closed circular first nucleic acid strand to convert it into a double-stranded nucleic acid, as described in Example 2. The "Inner Circle" nucleic acids comprise a first region that hybridises to the first nucleic acid strand and a second region that protrudes from the circular first nucleic acid strand.

SEQ ID NO: 114 shows a third nucleic acid strand (the "ssDNA tail") which can be conjugated, optionally through a linker, to each of the appendages, as described in Example 2. The third nucleic acid strand hybridises to any of SEQ ID NOs: 90-113 to bond the appendages to the nucleic acid scaffold.

SEQ ID NO: 115 and 116 show the sequence of the lower part of the αHL β-barrel that is inserted into the membrane.

SEQ ID NOs: 117 and 118 show the mature α-HL protein sequence with a N17C and either a T115H or T145H mutation, respectively. The T115H or T145H mutations introduce a histidine residue into α-HL at a position such that when the α-HL monomer is interacts with other α-HL monomers to form a pore, the histidine will be positioned in the pore channel.

DETAILED DESCRIPTION OF THE INVENTION

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, NY; Ausubel, F. M. et al. (1995 and periodic supplements; Current Protocols in Molecular Biology, ch. 9, 13, and 16, John Wiley & Sons, New York, N. Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Definitions

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

A "nucleotide" typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide. Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

The term "nucleic acid" as used herein, is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Nucleic acids may include DNA and RNA, and may be manufactured synthetically in vitro or isolated from natural sources. Nucleic acids may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Nucleic acids may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA). Sizes of nucleic acids, also referred to herein as "polynucleotides" are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called "oligonucleotides" and may comprise primers for use in manipulation of DNA such as via polymerase chain reaction (PCR).

The term "amino acid" in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

A "polypeptide" is a polymer of amino acid residues joined by peptide bonds, whether produced naturally or in vitro by synthetic means. Polypeptides of less than around 50 amino acid residues in length are typically referred to as "peptides". The term "polypeptide" as used herein denotes the product of a naturally occurring polypeptide, precursor form or proprotein. Polypeptides can also undergo maturation or post-translational modification processes that may include, but are not limited to: glycosylation, proteolytic cleavage, lipidization, signal peptide cleavage, propeptide cleavage, phosphorylation, and such like. The term "protein" is used herein to refer to a macromolecule comprising one or more polypeptide chains.

A "pore" may be defined herein as a hole or channel formed across a layer of amphipathic molecules. Typically a pore comprises a ring-shaped structure that inserts in the layer of amphipathic molecules and defines a channel through the layer. Typically the channel is hydrophilic and allows for translocation of molecules from one side of the layer of amphipathic molecules to the other. In some aspects the "pore" comprises a trans-membrane protein structure defining a channel or hole that allows the translocation of molecules and ions from one side of the layer of amphipathic molecules to the other. Such a pore may be referred to as a "biological pore". The translocation of charged molecules or ionic species through the pore may be driven by an electrical potential difference applied to either side of the pore. A "nanopore" is a biological pore in which the minimum diameter of the channel through which molecules or ions pass is in the order of nanometres ($10^{-9}$ metres).

"Hybridisation" describes the process of a portion of a single-stranded DNA, RNA or XNA nucleic acid binding or annealing to a complementary or substantially complementary portion of a second DNA, RNA or XNA nucleic acid to produce double-stranded DNA-DNA, DNA-RNA, RNA-RNA, DNA-XNA, RNA-XNA or XNA-XNA nucleic acids. Hybridisation may occur through Watson-Crick or wobble base pairing, preferably through Watson-Crick base pairing. In order for two nucleic acid sequences to hybridise they must be complementary or substantially complementary, although a certain number of mismatches are tolerated.

The term "complementary" is used to describe two nucleic acid sequences that are able to base pair, either through Watson-Crick or wobble base pairing, at nucleotide positions across the length of both sequences. The term "fully complementary" (i.e., 100% complementarity) is used to describe two nucleic acid sequences which base pair, either through Watson-Crick or wobble base pairing, at every nucleotide position across the whole length of the shorter of the two sequences (i.e., there are no mismatches). The term "substantially complementary" is used to describe two sequences which comprise less than 100% complementarity (over the length of the shorter sequence). Such fully complementary, complementary and substantially complementary sequences may hybridise or bind over any temperature or pH range. In particular, such fully complementary, complementary and substantially complementary sequences are capable of hybridising at temperatures between 18-37° C. and at physiological pH (between 5-9). Substantially complementary sequence may have a number of mismatches, but still hybridise or bind to each other. Two substantially complementary sequences may comprise 1, 2, 3, 4, 5, 6, 7, 8, 9, 10, 11, 12, 13, 14, 15, 16, 17, 18, 19 or 20 mismatches, optionally between 1-20, 2-10, 5-15, 10-20 or 8-12 mismatches, for every 20, 50 or 100 nucleotides in length of the shorter of the two sequences, optionally between 1-10 mismatches for every 20 nucleotides in length of the shorter sequence. Two substantially complementary sequences may comprise at least 1%, 2%, 3%, 4%, 5%, 10%, 15% or 20% mismatches, optionally between 1-50%, 1-40%, 1-30%, 1-20%, 1-10%, 5-10% or 1-5% mismatches, optionally between 1%-25% mismatches (as a percentage of the number of nucleotides in the shorter sequence). A mismatch may be defined as two nucleotides that do not base-pair either through Watson-Crick or wobble base pairing.

In addition as used in this specification and the appended claims, the singular forms "a", "an", and "the" include plural referents unless the content clearly dictates otherwise. Thus, for example, reference to "a nucleic acid" may include two or more nucleic acids, reference to "an appendage" may include two or more such appendages, reference to "a pore" may include two or more pores, reference to "a polypeptide" may refer to two or more polypeptides, reference to "a peptide" may include two or more peptides and the like.

"Sequence identity" between two sequences is preferably determined using pairwise global sequence alignment, wherein the alignment is calculated over the length of the sequence of described herein. Sequence identity may optionally be calculated using the Needleman-Wunsch alignment algorithm (for example as implemented through the online server EMBOSS Needle (EMBOSS: the European Molecular Biology Open Software Suite. (2000) Trends in genetics. 16(6):276-7) and applying the following parameters: Matrix: DNAfull; Gap open penalty: 10.00; Gap extension penalty: 0.5; End Gap penalty: false; End Gap open penalty: 10.00; End Gap extension penalty: 0.5. Furthermore, additional standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or align sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

The term "variant" as used in relation to nucleic acids includes substitution of any deoxyribonucleotide for the corresponding ribonucleotide (for example, a thymidine (T) nucleotide in a DNA sequence may be a uridine (U) nucleotide in a variant); substitution of any ribonucleotide for the corresponding deoxyribonucleotide; substitution of any ribonucleotide or deoxyribonucleotide for a synthetic nucleotide (XNA) (as defined herein); substitution of any ribonucleotide or deoxyribonucleotide for the corresponding modified nucleotide (as defined herein). The term "variant" includes addition or removal of 5' and 3' labels and modifiers, for example, the addition or removal of a 3' or 5' amino-C6 modifier or a fluorescent label, such as Alexa-647. The term "variant" includes the addition, deletion or substitution of 1, 2, 3, 4, 5, 6, 7, 8, 9, or 10 nucleotides, optionally the addition, deletion or substitution of up to 5 nucleotides, optionally the addition, deletion or substitution of 1-2 nucleotides, within the sequence. The term "variant" includes the addition or deletion of 1, 2, 3, 4, 5, 6, 7, 8, 9, or 10 nucleotides from the 5' and/or 3' end of the sequence, optionally the addition or deletion of up to 5 nucleotides from the 5' and/or 3' end, optionally the addition or deletion of 1-2 nucleotides from the 5' and/or 3' end. The term "variant" includes the addition or deletion of 1, 2, 3, 4, 5, 6, 7, 8, 9, or 10 nucleotides at any position(s) across the sequence, optionally the addition or deletion of up to 5 nucleotides at any position(s) across the sequence, optionally the addition or deletion of 1-2 nucleotides at any position(s) across the sequence. The added or deleted nucleotides may comprise a contiguous sequence of nucleotides or individual, separate nucleotides, or both. The term "variant" also includes sequences having at least 60%, 70%, 80%, 90%, 95%, 96%, 97%, 98% or at least 99% sequence identity, optionally at least 80%, preferably at least 95% sequence identity and most preferably at least 98% sequence identity, to the specified nucleic acid sequence.

The term "variant" as used in relation to peptides includes substitution of any amino acid(s) in the sequence. The substitutions may be conservative substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids. The term "variant" includes addition or removal of N- and/or C-terminal labels and modifiers, for example, the addition or removal of an N- and/or C-terminal fluorescent label. The term "variant" includes the addition, deletion or substitution of 1, 2, 3, 4, 5, 6, 7, 8, 9, or 10 amino acids, optionally the addition, deletion or substitution of up to 5 amino acids, typically the addition, deletion or substitution of 1-2 amino acids, within the sequence. The term "variant" includes the addition or deletion of 1, 2, 3, 4, 5, 6, 7, 8, 9, or 10 amino acids from the N- and/or C-terminus of the sequence, optionally the addition or deletion of up to 5 amino acids from the N- and/or C-terminus, typically the addition or deletion of 1-2 amino acids from the N- and/or C-terminus. The term "variant" also includes the addition, deletion or substitution of 1, 2, 3, 4, 5, 6, 7, 8, 9, or 10 amino acids, optionally 5 amino acids, typically 1-2 amino acids, at any position(s) across the sequence. The added or deleted amino acids may comprise a contiguous sequence or individual, separate amino acids, or a combination of both. The term "variant" also includes sequences having at least 60%, 70%, 80%, 90%, 95%, 96%, 97%, 98% or at least 99% sequence identity, optionally at least 95% sequence identity and typically at least 98% sequence identity, to the specified amino acid sequence. The term "variant" also includes functional fragments. For example, a variant of a peptide, polypeptide or protein capable of forming a pore in a layer of amphipathic molecules that is a fragment of said peptide, polypeptide or protein retains pore-forming activity. Fragments of peptides, polypeptides or proteins may be at least 5, 10, 15, 20, 30, 40, 50, 100, 150, 200 or at least 250 amino acids in length, optionally at least 20 amino acids in length.

Such fragments of peptides, polypeptides or proteins as defined herein may be used to form pores.

Any of the proteins, polypeptides or peptides described herein, such as those that insert in a layer of amphipathic molecules and/or form a pore as described herein, may be made synthetically or by recombinant means. For example, the protein, polypeptide or peptide may be synthesised by in vitro translation and transcription (IVTT). In particular, peptides may be chemically synthesised by methods known in the art. The amino acid sequence of the protein, polypeptide or peptide may be modified to include non-naturally occurring amino acids or to increase the stability of the protein, polypeptide or peptide. When a protein, polypeptide or peptide is produced by synthetic means, such amino acids may be introduced during production. The protein may also be altered following either synthetic or recombinant production.

Proteins, polypeptides or peptides may also be produced using D-amino acids. For instance, the protein, polypeptide or peptide may comprise a mixture of L-amino acids and D-amino acids. This is conventional in the art for producing such proteins, polypeptides or peptides. The protein, polypeptide or peptide may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins, polypeptides or peptides described herein can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein, polypeptide or peptide may be produced in a cell by in situ expression of the polypeptide from a recombinant expression vector. The expression vector optionally carries an inducible promoter to control the expression of the protein, polypeptide or peptide. These methods are described in Sambrook, J. and Russell, D. (2001). Molecular Cloning: A Laboratory Manual, 3rd Edition. Cold Spring Harbor Laboratory Press, Cold Spring Harbor, NY. Proteins, polypeptides or peptides may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

It is to be understood that different applications of the disclosed products and methods may be tailored to the specific needs in the art. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

Pore-Forming Assemblies

The present invention relates in part to assemblies that are capable of forming, or configured to form, pores in layers of amphipathic molecules. The present invention provides an assembly comprising a nucleic acid scaffold and a plurality of appendages bonded to the scaffold, wherein the appendages, when bonded to the scaffold, are capable of interacting to form a pore in a layer of amphipathic molecules. In other words, the present invention provides an assembly comprising a nucleic acid scaffold and a plurality of appendages, wherein the appendages are bonded to the scaffold in an arrangement enabling the appendages to form a pore in a layer of amphipathic molecules. The features of the assemblies of the invention are as further defined herein. Any combination of the features defined herein in the assemblies of the invention is within the scope of the invention unless otherwise stated.

Thus, the nucleic acid scaffold enables the plurality of appendages to form a pore in a layer of amphipathic molecules. In the absence of the nucleic acid scaffold, the appendages may not form a pore in a layer of amphipathic molecules. Thus, the nucleic acid scaffold may co-localise the appendages and direct the position of each appendage such that they are able to form a pore. Thus, it is typically the case that the nucleic acid scaffold stabilises the pore formed by the appendages and in the absence of the nucleic acid scaffold the appendages would not form a stable pore. The appendages when bonded to the nucleic acid scaffold are configured to form a pore and would typically not be configured to do so in the absence of the nucleic acid scaffold.

Nucleic Acid Scaffolds

The assemblies of the present invention comprise a nucleic acid scaffold which comprises one or more nucleic acids, optionally a plurality of nucleic acids. For example, a plurality of appendages may be bonded to a single polynucleotide, which may be sufficient to direct the appendages to form a pore. The single flexible polynucleotide chain may be sufficient to co-localise the appendages and stabilise the resulting pore. However, in some aspects the nucleic acid scaffold comprises a plurality of nucleic acids. In some aspects the nucleic acid scaffold comprises from about 1 to about 500; from about 2 to about 200; from about 3 to about 100; from about 5 to about 100; from about 5 to about 50; from about 5 to about 30; from about 10 to about 100; from about 10 to about 50; from about 10 to about 30; or from about 10 to about 20 nucleic acids; optionally from about 10 to about 50 nucleic acids; and typically from about 10 to about 30 nucleic acids.

The nucleic acid scaffold may comprise single-stranded or double-stranded nucleic acids, typically double-stranded nucleic acids. In some aspects the nucleic acid scaffold consists essentially of double-stranded nucleic acids. The nucleic acid scaffold comprising, or consisting essentially of, double-stranded nucleic acids will typically comprise a small number of unpaired nucleotides. Such unpaired nucleotides may be important in introducing flexibility into the nucleic acid scaffold which may be important for allowing the appendages the freedom of movement required to interact to form the pore. For example, at least 1, 2, 3, 4, 5, 6, 7, 8, 9, or 10% of the nucleotides in the nucleic acid scaffold may be unpaired or from about 1% to about 30%, from about 1% to about 20%, from about 1% to about 15%, from about 1% to about 10%, or from about 1% to about 5% of the nucleotides in the nucleic acid scaffold may be unpaired, optionally from about 1% to about 10% of the nucleotides in the nucleic acid scaffold may be unpaired. Such unpaired nucleotides may typically be found at positions between first and second regions of a nucleic acid where the first and second regions are hybridised to two different other nucleic acids.

The nucleic acid scaffold may be formed from any nucleic acids (as defined herein), including naturally occurring nucleic acids, synthetic nucleic acids or hybrid nucleic acids comprising a mixture of naturally occurring and synthetic nucleotides. In some aspects the nucleic acid scaffold comprises, or consists essentially of, DNA, RNA, XNA, or combinations thereof. In some aspects the nucleic acid scaffold comprises DNA. XNA may be useful for the formation of the nucleic acids scaffolds of the invention as it may have enhance stability as compared to DNA- or RNA-based scaffolds and may be resistant to degradation, for example by nucleases or other enzymes or by chemicals.

In some aspects the nucleic acid scaffold may be "one-dimensional", which may be understood to mean that the nucleic acid scaffold comprises a linear nucleic acid molecule. Although the skilled person would readily understand that such a linear nucleic acid molecule would be flexible and may adopt a two- or three-dimensional structure in space. In some aspects the nucleic acid scaffold may be two-dimensional or three-dimensional. For example, in some aspects the nucleic acid scaffold may comprise a planar "two-dimensional" structure, for example having essentially a circular or polygonal (e.g. essentially hexagonal, pentagonal, square, rectangular or triangular) shape. In some aspects the two-dimensional structure may comprise a planar tiled array or lattice, typically comprised of regular array of two-dimensional shapes. Although it will be understood that the "two-dimensional" structure may be flexible or comprise flexible parts that may move, extend or pivot out of the general plane adopted by the two-dimensional structure. In some aspects the nucleic acid scaffold may comprise a "three-dimensional" structure, for example, the nucleic acid scaffold may form essentially a cylindrical, cuboidal or pyramidal shape. In some aspects the three-dimensional structure may comprise a stacked tiled array or lattice. In some aspects the shape of the nucleic acid scaffold may be suitable to direct the positioning of the appendages to positions that favour the formation of a pore. For example, in some instances, the nucleic acid scaffold may comprise a tile, optionally with a hole, or a regular tiled array, optionally with a hole. Typically the hole is a central hole. In some aspects the diameter of the hole is less than, equal to or greater than the size of the pore or the diameter of the pore channel, optionally equal to or greater than the size of the pore or the diameter of the pore channel. In some aspects the nucleic acid scaffold may comprise a closed structure, for example a closed polygonal structure or a closed circular structure. In some aspects the nucleic acid scaffold may comprise a closed circular structure, optionally with a hole, or one or more closed circular structures bonded together, optionally with a hole. In some aspects the nucleic acid scaffold may comprise a closed circular structure (i.e., an annular or ring-shaped structure), wherein the diameter of the closed circular structure is less than, equal to or greater than the size of the pore or the diameter of the pore channel. In some aspects the diameter of the closed circular structure is equal to or greater than the size of the pore or the diameter of the pore channel so that the nucleic acid scaffold can stabilise the formation of the pore, but does not block the resulting pore channel.

In some aspects of the invention, the nucleic acid scaffold comprises a plurality of nucleic acids arranged to form a closed circular structure with protruding arms. Typically, the closed circular structure provides a stable scaffold structure, which may be rigid. The skilled person will appreciate, however, that a rigid closed circular structure is not "infinitely" rigid and may be capable of minor shape changes, for example from circular to more ellipsoidal. The closed circular structure also templates the positioning of the appendages for pore formation. In some aspects from about 80% to about 100%, from about 85% to about 100%, from about 90% to about 100%, from about 95% to about 100% from about 98% to about 100%, usually from about 90% to about 100%, of the nucleotides comprising the closed circular structure of nucleic acid scaffold may be hybridised (i.e., said percentages of the nucleic acids comprising the closed circular structure of nucleic acid scaffold may be double-stranded). In some aspects the diameter of the closed circular structure may be about 1-500 nm, 5-500 nm, 5-400 nm, 5-300 nm, 5-200 nm, 5-100 nm, 5-50 nm, 5-40 nm, 5-30 nm, 5-20 nm or 5-15 nm. In some aspects the diameter of the closed circular structure may be about 3-50 nm, 3-40 nm, 3-30 nm, 3-25 nm, 3-20 nm, 3-15 nm or 3-10 nm. In some aspects the diameter of the closed circular structure may be about 50-500 nm, 50-400 nm, 50-300 nm, 50-200 nm, 50-100 nm, 100-500 nm or 100-200 nm.

In terms of the circumference of the closed circular structure, this can be measured by the number of nucleotides in the circle i.e., the number of nucleotides in the closed circular structure excluding the protruding arms. Typically, the number of nucleotides in the closed circular structure is equal to or greater than 80, 90, 100, 120, 140, 160, 180, 200, 220, 240, 260, 280, 300, 350, 400, 450, 500, 550 or 600 nucleotides. The number of nucleotides in the closed circular structure may be about 40-1000, 80-1000, 100-1000, 200-1000, 40-800, 80-800, 100-800, 200-800, 40-500, 80-500, 100-500, 200-500, 40-300, 80-300, 100-300, or 200-300 nucleotides. The number of nucleotides in the closed circular structure may be about 100-1000. The number of nucleotides in the closed circular structure may be about 100-500. The number of nucleotides in the closed circular structure may be about 100-300. As the skilled person will appreciate a nucleotide may be a base or a base pair, depending on whether the nucleotide is hybridised, i.e., base paired, to another nucleotide. The circumference can also be discussed in terms of the number of nucleic acids in the circle, i.e., the number of nucleic acids in the closed circular structure excluding the protruding arms. In some aspects the closed circular structure of the nucleic acid scaffold may comprise at least 1, 2, 3, 4, 5, 6, 7, 8, 9, 10, 12, 14, 16, 18, 20, 22, 24, 26 or at least 30 nucleic acids. In some aspects the closed circular structure of the nucleic acid scaffold may comprise about 1-300, 1-200, 1-150, 1-100, 1-90, 1-80, 1-70, 1-60, 1-50, 1-40, 1-30 or about 1-20 nucleic acids, optionally about 2-200, 3-200, 5-200, 10-200, 10-150, 10-100, 10-90, 10-80, 10-70, 10-60, 10-50, 10-40 or about 10-30 nucleic acids. In some aspects the closed circular structure of the nucleic acid scaffold may comprise about 10-50 nucleic acids. In some aspects the closed circular structure of the nucleic acid scaffold may comprise about 10-100 nucleic acids.

The protruding arms are part of the nucleic acid scaffold and typically provide a more flexible part of the nucleic acid scaffold. In some aspects, unhybridised nucleotides in the nucleic scaffold may be positioned at the join between a protruding arm and the closed circular structure. These positions between the protruding arm and the closed circular structure, which typically comprise unhybridised nucleotides or bases, may be referred to as "hinge positions". Each hinge position may comprise 1, 2, 3, 4, 5, 6, 7, 8, 9, 10 unhybridised bases, optionally about 1-3 unhybridised bases, typically 1 unhybridised base. Qualitatively, nucleic acid scaffolds comprising more unhybridized bases appear more flexible, but their assembled yield is lower. The hinge positions, typically comprising unhybridised nucleotides, confer flexibility to the protruding arms. Thus, in some aspects, the protruding arms are flexible. The skilled person will appreciate that the arms themselves may be flexible or may not be flexible. For example, the arm itself may comprise, for instance, a single helical turn of double stranded DNA which would be shorter than the persistence length and therefore considered rigid. Typically, the hinge position provides flexibility for pivoting of the arm. In some aspects the protruding arms may pivot above or below the plane of the closed circular structure of the nucleic acid scaffold.

In some aspects all of the protruding arms of the nucleic acid scaffold are the same length. In some aspects the protruding arms of the nucleic acid scaffold may be different lengths. In some aspects each protruding arm may be about 1-100, 1-90, 1-80, 1-70, 1-60, 1-50, 1-40, 1-30, 1-20 or 1-15, optionally 1-50, nucleotides in length. As the skilled person will appreciate a nucleotide may be a base or a base pair, depending on whether the nucleotide is hybridised, i.e., base paired, to another nucleotide. In some aspects the length of the protruding arms will depend on the diameter or the circumference of the nucleic acid scaffold. In some aspects the protruding arms are about equal to, less than or greater than, optionally about equal to, the length of half of the diameter of the nucleic acid scaffold. In some aspects each protruding arm is positioned no more than 200, 150, 100, 90, 80, 70, 60, 50, 40, 35, 30, 25, 20, 15 or no more than 10 nucleotides, optionally no more than 50 nucleotides, and typically no more than 30 nucleotides, from the nearest other protruding arm. In some aspects each protruding arm is positioned about 5-200, 5-100, 5-90, 5-80, 5-70, 5-60, 5-50, 5-40, 5-30, 5-20, 10-200, 10-100, 10-90, 10-80, 10-70, 10-60, 10-50, 10-40, 10-30 or 10-20 nucleotides, optionally about 5-80 nucleotides, and often 5-50 nucleotides, from the nearest other protruding arm. The number of nucleotides may be understood to mean the minimum distance measured in nucleotides of the nucleic acids between the hinge region of the first protruding arm and the hinge region of the nearest other protruding arm. Where the nucleotides are hybridised to another nucleic acid the distance may also be measured in base pairs, or a combination of nucleotides (i.e., bases) and base pairs. The number of nucleotides is not necessarily nucleotides of the same nucleic acid stand, the distance in nucleotides between the hinge regions of two protruding arms may cover one or more nucleic acids.

In some aspects the nucleic acid scaffold comprises at least 1, 2, 3, 4, 5, 6, 7, 8, 9, 10, 11, 12, 14, 16, 18, 20, 22, 24, 26, 28 or at least 30 protruding arms. In some aspects the nucleic acid scaffold comprises about 3-500, 3-400, 3-300, 3-200, 3-150, 3-100, 3-90, 3-80, 3-70, 3-60, 3-50, 3-40, 3-30, 3-20, 10-500, 10-400, 10-300, 10-200, 10-150, 10-100, 10-90, 10-80, 10-70, 10-60, 10-50, 10-40, 10-30, or 10-20 protruding arms. Typically the nucleic acid scaffold may comprise about 3-100 protruding arms. The nucleic acid scaffold may comprise about 3-50 protruding arms. In some aspects each protruding arm is bonded to an appendage. In some aspects not all of the protruding arms are bonded to an appendage. In some aspects at least about 10%, 20%, 30%, 40%, 50%, 60%, 70%, 80%, 90% or at least about 100%, optionally at least about 60% of the protruding arms are bonded to an appendage. In some aspects at least about 80% of the protruding arms are bonded to an appendage. Typically, each appendage is bonded to a protruding arm via a linker and in some aspects the linker may be a flexible linker. This is discussed in more detail under the heading “Appendages” below. As also discussed in further detail under the heading “Appendages” below, the appendages may comprise, or consist essentially of, protein, polypeptide or peptide.

In the assemblies of the invention, in some aspects, each of the appendages is bonded to a protruding arm of the nucleic acid scaffold. Typically the sequence of each arm is different from the sequences of each of the other arms. The arms typically offer unique sequences to the appendages so that the appendages can be organized in a predetermined manner around the central axis of the pore. However, the skilled person would be capable of designing nucleic acid scaffolds that comprise nucleic acids that assemble to form a consistent structure, but without the sequences of each of the nucleic acids necessarily having to be unique or different from the sequences of each of the other nucleic acids. For example, the sequence of each nucleic acid may not be different from the sequences of each of the other nucleic acids. In some aspects, the sequence of each protruding arm may not be different from the sequences of each of the other protruding arms.

In the assembly, a plurality of appendages may be bonded to a single protruding arm of the nucleic acid scaffold. In some aspects, in the assembly, a single appendage is bonded to a single protruding arm of the nucleic acid scaffold. In some aspects, in the assembly, three or more protruding arms of the nucleic acid scaffold are bonded to appendages. In some aspects, in the assembly, every protruding arm of the nucleic acid scaffold is bonded to an appendage. In some aspects, in the absence of a layer of amphipathic molecules, and either with or without a plurality of appendages bonded to the scaffold, the protruding arms may be oriented such that adjacent protruding arms are positioned alternating above and below the plane of the closed circular structure. In some aspects, in the presence of a layer of amphipathic molecules, and with a plurality of appendages bonded to the scaffold, all of the protruding arms may be oriented in the same direction, either above or below the plane of the closed circular structure. In some aspects, in the presence of a layer of amphipathic molecules, and with a plurality of appendages bonded to the scaffold, all of the protruding arms bonded to an appendage may be oriented in the same direction, either above or below the plane of the closed circular structure.

One exemplary type of nucleic acid scaffold is described in Examples 1 and 3 and an alternative exemplary type of nucleic acid scaffold is described in Example 2. The Examples are not intended to be limiting. Nucleic acid scaffolds generally falling into each of the two different types are described below.

Type 1—Nucleic Acid Scaffolds. In some aspects, the nucleic acid scaffold comprises the same number of protruding arms as nucleic acids. In some aspects, the nucleic acid scaffold comprises fewer protruding arms than nucleic acids. For example, the skilled person would appreciate that by removing two outer regions, as further defined herein, from a pair of nucleic acids, which outer regions would otherwise hybridise to form a protruding arm, a scaffold may be produced having fewer protruding arms than nucleic acids. The scaffold may have one protruding arm per nucleic acid. The scaffold may have one protruding arm per two nucleic acids. In some aspects, each protruding arm comprises two different nucleic acids of the nucleic acid scaffold. In some aspects, each nucleic acid of the nucleic acid scaffold is about 5-200, 10-100, 20-100, 30-100, 40-100, 50-100, 60-100, 70-100, 80-100, 90-100, 10-50, 10-60, 20-50, 20-60, 30-50, 30-60, 40-50 or 40-60 nucleotides in length, optionally 30-60 nucleotides in length, typically between 40-50 nucleotides in length. In some aspects all of the nucleic acids in the nucleic acid scaffold are the same length. In some aspects 1, 2, 3, 4, 5, 6, 7, 8, 9 or 10 nucleic acids, optionally about 1-5 nucleic acids, in the nucleic acid scaffold are about 50-80 nucleotides in length and the remaining nucleic acids in the nucleic acid scaffold are about 30-50 nucleotides in length.

In some aspects the sequence of each nucleic acid in the nucleic acid scaffold is unique, which may be understood to mean that the sequence of each nucleic acid in the scaffold is different from the sequence of every other nucleic acid in the scaffold. This feature typically allows the nucleic acid scaffold to assemble in one favoured configuration where the maximum number of base-pairs are formed between nucleic acids in the nucleic acid scaffold. This feature may allow the nucleic acid scaffold to form a monodisperse scaffold. Thus, in some aspects, the nucleic acid scaffold self-assembles when the nucleic acids are mixed in stoichiometric (i.e., equimolar or equal) amounts. As discussed elsewhere herein, the sequence of each arm is typically different from the sequences of each of the other arms. In some aspects each nucleic acid in the nucleic acid scaffold hybridises to one or more other nucleic acids in the nucleic acid scaffold. In some aspects each nucleic acid in the nucleic acid scaffold hybridises to at least one other nucleic acid. In some aspects each nucleic acid in the nucleic acid scaffold hybridises to 1, 2, 3, 4, 5, 6, 7, 8, 9 or 10 other nucleic acids in the nucleic acid scaffold, optionally each nucleic acid in the nucleic acid scaffold hybridises to from 1 to 4 other nucleic acids in the nucleic acid scaffold. In some aspects each nucleic acid hybridises to four other nucleic acids.

In some aspects, each nucleic acid of the nucleic acid scaffold, comprises four "regions", wherein region may be understood to mean a contiguous sequence of nucleotides within a nucleic acid. In some aspects, each nucleic acid comprises two central regions that hybridise with the central regions of other nucleic acids in the nucleic acid scaffold and two outer regions that hybridise with the outer regions of other nucleic acids in the nucleic acid scaffold. The "outer regions" may be considered to mean the regions at the 5' and 3' ends of the nucleic acids. The "central regions" are positioned between the outer regions. Thus, from 5' to 3' each nucleic acid comprises a first outer region, a first central region, a second central region and a second outer region. Typically, the four regions are of essentially equal length. In some aspects each region is between 5-20, 8-16, 9-15, 10-14, 10-13, 10-12 or 10-11 nucleotides in length, optionally between 10-12 nucleotides in length. In some aspects, one outer region may be extended in length, for example, one outer region may comprise 10-20, 10-30, 10-40, 10-50, 15-30, 15-40, 15-50, 15-60, 20-30, 20-40, 20-50, 20-60, 30-40, 30-50, or 30-60 nucleotides in length, optionally 10-30 nucleotides in length. Typically 0, 1, 2, 3, 4, 5, 6, 7, 8, 9 or 10 nucleic acids, optionally 1 nucleic acid, in the nucleic acid scaffold comprise an extended outer region. In some aspects, one or more nucleic acids in the nucleic acid scaffold, optionally each nucleic acid in the nucleic acid scaffold, comprises 1-3 unhybridized bases, optionally T-bases, at the end of one of the outer regions, (i.e., extending beyond the hybridized region in the arm). Such a modification may prevent sideways stacking of multiple scaffolds via their arms. In some aspects, one or more pairs of nucleic acids, such as 1, 2, 3, 4, 5, 6, 7, 8, 9 or 10 pairs of nucleic acids, optionally 1-4 pairs, optionally one pair of nucleic acids, each comprise two central regions and only one outer region, wherein one nucleic acid in the pair has only the 3' outer region and the other nucleic acid in the pair has only the 5' outer region, such that the protruding arm that would have been formed by the pair of nucleic acids is not formed.

In some aspects, the hybridised central regions of the nucleic acids form the closed circular structure of the nucleic acid scaffold. In some aspects, the hybridised outer regions of the nucleic acids form the protruding arms of the nucleic acid scaffold. Thus, in some aspects, the nucleic acid scaffold comprises the same number of, or fewer, protruding arms as nucleic acids. For example, as described herein, the scaffold may comprise one protruding arm per two nucleic acids or one protruding arm per nucleic acid. In some aspects, the closed circular structure of the nucleic acid scaffold comprises (i.e., is formed from) the hybridised central regions of the nucleic acids of the nucleic acid scaffold and the protruding arms of the nucleic acid scaffold comprise (i.e., are formed from) the hybridised outer regions of the nucleic acids of the nucleic acid scaffold. In some aspects each nucleic acid comprises 1, 2, 3, 4, 5, 6, 7, 8, 9, 10 unhybridised bases, optionally about 1-3 unhybridised bases, typically 1 unhybridised base, between each outer region and the central regions. The unhybridised base(s) form a "hinge region" as described above. As described above, in the nucleic acid scaffold each nucleic acid may hybridise to four other nucleic acids. In such aspects, each of the four regions of the nucleic acid hybridises to a different other nucleic acid. Thus, each nucleic acid comprises a first central region that hybridises with a central region of a first nucleic acid in the nucleic acid scaffold; a second central region that hybridises with a central region of a second nucleic acid in the nucleic acid scaffold; a first outer region that hybridises with an outer region of a third nucleic acid in the nucleic acid scaffold; and a second outer region that hybridises with an outer region of a fourth nucleic acid in the nucleic acid scaffold.

In some aspects the plurality of appendages in the assembly are bonded to the outer regions of the nucleic acids, such that the appendages are bonded to the protruding arms of the nucleic acid scaffold. In some aspects at least one of, and optionally each of, the appendages is bonded to an outer region of a nucleic acid in the nucleic acid scaffold. In some aspects each of the appendages is bonded to a 5' or 3' outer region, optionally a 5' outer region, of a nucleic acid in the nucleic acid scaffold. The number of nucleic acids in the nucleic acid scaffold may be equal to, or greater than, the number of appendages in the assembly. In some aspects each 5' or each 3' outer region, optionally each 5' outer region, of each nucleic acid is bonded to an appendage. In some aspects each nucleic acid in the nucleic acid scaffold is modified, typically at the 5' or 3' end, optionally the 5' end, to facilitate bonding to an appendage. In some aspects the nucleic acid may be modified at any point along the length of the nucleic acid. Suitable modifications that allow for conjugation or bonding to an appendage are known in the art to the skilled person. In some aspects each nucleic acid comprises a 5' amino-C6 group, which allows for binding to an appendage.

Such nucleic acid scaffolds may comprise, or consist essentially of, about 8, 10, 12, 14, 16, 18, 20, 22, 24, 30, 40, 50, 60, 70, 80, 90, 100 or more nucleic acids. In some aspects, the nucleic acid scaffold comprises, or consists essentially of, 8-100, 12-100, 12-90, 12-80, 12-70, 12-60, 12-50, 12-40, 12-30, 14-100, 14-90, 14-80, 14-70, 14-60, 14-50, 14-40 or 14-30, nucleic acids. In some aspects, the nucleic acid scaffold comprises, or consists essentially of, 12, 14, 16, 18, 20 or 24 nucleic acids. In some aspects, the nucleic acid scaffold comprises, or consists essentially of, 12 nucleic acids. In some aspects, the nucleic acid scaffold comprises, or consists essentially of, 14 or more nucleic acids. In some aspects, the nucleic acid scaffold comprises, or consists essentially of, from about 14 to about 24 nucleic acids. In some aspects, the nucleic acid scaffold comprises, or consists essentially of, 14, 16, 18, 20 or 24 nucleic acids. In some aspects, the nucleic acid scaffold comprises, or consists essentially of, about 10-100, 10-80, 10-70, 10-60, 10-50, 10-40, 10-30 or 10-20 nucleic acids, optionally 10-30 nucleic acids. In some aspects the nucleic acid scaffold comprises nucleic acids comprising or consisting of the sequences of SEQ ID NOs: 15-54, or variants thereof. In some aspects the nucleic acid scaffold comprises nucleic acids comprising or consisting of the sequences of SEQ ID NOs: 15-26, or variants thereof. In such aspects the nucleic acid scaffold comprises a closed circular structure with 12 protruding arms. In some aspects the nucleic acid scaffold comprises nucleic acids comprising or consisting of the sequences of SEQ ID NOs: 15-20, 27, 22, 23, 28, 25 and 26, or variants thereof. In such aspects the nucleic acid scaffold comprises a closed circular structure with 12 protruding arms that is optimised for more efficient assembly. In some aspects the nucleic acid scaffold comprises nucleic acids comprising or consisting of the sequences of SEQ ID NOs: 15-20, 21/27, 22, 23, 24/28, 29-31 and 26, or variants thereof. In such aspects the nucleic acid scaffold comprises a closed circular structure with 12 protruding arms, wherein one protruding arm is extended in length. In some aspects the nucleic acid scaffold comprises nucleic acids comprising or consisting of the sequences of SEQ ID NOs: 15-20, 21/27, 22, 23, 24/28 and 32-35, or variants thereof. In such aspects the nucleic acid scaffold comprises a closed circular structure with 14 protruding arms. In some aspects the nucleic acid scaffold comprises nucleic acids comprising or consisting of the sequences of SEQ ID NOs: 15-20, 21/27, 22, 23, 24/28, 32, 33 and 36-39, or variants thereof. In such aspects the nucleic acid scaffold comprises a closed circular structure with 16 protruding arms. In some aspects the nucleic acid scaffold comprises nucleic acids comprising or consisting of the sequences of SEQ ID NOs: 15-20, 21/27, 22, 23, 24/28, 32, 33, 36, 37 and 40-43, or variants thereof. In such aspects the nucleic acid scaffold comprises a closed circular structure with 18 protruding arms. In some aspects the nucleic acid scaffold comprises nucleic acids comprising or consisting of the sequences of SEQ ID NOs: 15-20, 21/27, 22, 23, 24/28, 32, 33, 36, 37, 40, 41 and 44-47, or variants thereof. In such aspects the nucleic acid scaffold comprises a closed circular structure with 20 protruding arms. In some aspects the nucleic acid scaffold comprises nucleic acids comprising or consisting of the sequences of SEQ ID NOs: 15-20, 21/27, 22, 23, 24/28, 32, 33, 36, 37, 40, 41, 44, 45 and 48-53, or variants thereof. In such aspects the nucleic acid scaffold comprises a closed circular structure with 24 protruding arms. In some aspects the nucleic acid scaffold comprises nucleic acids comprising or consisting of the sequences of SEQ ID NOs: 15-20, 21/27, 22, 23, 24/28, 26, 29 and 54, or variants thereof. In such aspects the nucleic acid scaffold comprises two closed circular structures with 12 protruding arms, wherein the two structures are linked together through one of the protruding arms, forming a "figure-of-eight" shaped structure. In some aspects the nucleic acid scaffold comprises nucleic acids comprising or consisting of the sequences of SEQ ID NOs: 15-20, 21/27, 22, 23, 24/28 and 26, or variants thereof, and either SEQ ID NO: 29 or SEQ ID NO: 59, or variants thereof. In such aspects the nucleic acid scaffold comprises a closed circular structure with 12 protruding arms, wherein one of the arms has an 8 nucleotide (SEQ ID NO: 29) or 19 nucleotide (SEQ ID NO: 59) single-stranded extension or overhang.

Type 2—Nucleic Acid Scaffolds. In some alternative aspects, the nucleic acid scaffold comprises (i) a closed circular first nucleic acid strand and (ii) a plurality of second nucleic acid strands, wherein the second nucleic acids strands comprise a first region that hybridises to the first nucleic acid strand and a second region that protrudes from the circular first nucleic acid strand. The closed circular first nucleic acid strand is single-stranded. Typically, the closed circular first nucleic acid strand is formed by bonding together (e.g., by ligation) the 5' and 3' ends of a linear single-stranded nucleic acid. The length of the closed circular first nucleic acid strand dictates the diameter of the nucleic acid scaffold. The closed circular first nucleic acid strand may be about 50-500, 50-400, 50-300, 50-200, 50-100, 100-500, 100-400, 100-300, 100-200, 100-300, 200-500, 200-400, 200-300, 300-500, 300-400 or 400-500 nucleotides in length, optionally about 100-500 nucleotides in length. The closed circular first nucleic acid strand may comprise sequences having at least 70%, 75%, 80%, 85%, 90%, 95%, 96%, 97%, 98%, 99% or essentially 100% sequence identity, optionally at least 80% sequence identity, typically at least 90% sequence identity, to SEQ ID NOs: 63-71. In some aspects the closed circular first nucleic acid strand may comprise sequences having at least 70%, 75%, 80%, 85%, 90%, 95%, 96%, 97%, 98%, 99% or essentially 100% sequence identity, optionally at least 80% sequence identity, typically at least 90% sequence identity, to SEQ ID NOs: 63-65. In some aspects the closed circular first nucleic acid strand may comprise, or consist essentially of, SEQ ID NOs: 63-65, or variants thereof. In some aspects the closed circular first nucleic acid strand may comprise sequences having at least 70%, 75%, 80%, 85%, 90%, 95%, 96%, 97%, 98%, 99% or essentially 100% sequence identity, optionally at least 80% sequence identity, typically at least 90% sequence identity, to SEQ ID NOs: 66-68. In some aspects the closed circular first nucleic acid strand may comprise, or consist essentially of, SEQ ID NOs: 66-68, or variants thereof. In some aspects the closed circular first nucleic acid strand may comprise sequences having at least 70%, 75%, 80%, 85%, 90%, 95%, 96%, 97%, 98%, 99% or essentially 100% sequence identity, optionally at least 80% sequence identity, typically at least 90% sequence identity, to SEQ ID NOs: 66 and 68. In some aspects the closed circular first nucleic acid strand may comprise, or consist essentially of, SEQ ID NOs: 66 and 68, or variants thereof. In some aspects the closed circular first nucleic acid strand may comprise sequences having at least 70%, 75%, 80%, 85%, 90%, 95%, 96%, 97%, 98%, 99% or essentially 100% sequence identity, optionally at least 80% sequence identity, typically at least 90% sequence identity, to SEQ ID NOs: 68-71. In some aspects the closed circular first nucleic acid strand may comprise, or consist essentially of, SEQ ID NOs: 68-71, or variants thereof.

Each strand of the plurality of second nucleic acid strands comprises two regions, wherein region may be understood to mean a contiguous sequence of nucleotides within a nucleic acid. Typically the two regions of the second nucleic acid strands are about equal in length. In some aspects each of the second nucleic acid strands in the nucleic acid scaffold are about equal length. In some aspects the second nucleic acid strands are about 10-100, 10-90, 10-80, 10-70, 10-60, 10-50, 10-40, 10-30, 20-100, 20-90, 20-80, 20-70, 20-60, 20-50, 20-45, 20-40, 20-35, 20-30, 25-50, 25-45, 25-40, 25-35 or 25-30 nucleotides in length, optionally about 20-40 nucleotides in length. In some aspects, the first regions of each of the second nucleic acid strands hybridise to the closed circular first nucleic acid strand, thereby converting it into a double-stranded nucleic acid. Thus, in some aspects the hybridised first regions of each of the second nucleic acid strands and the closed circular first nucleic acid strand form the closed circular structure of the nucleic acid scaffold. In some aspects, there are 0, 1, 2, 3, 4, 5, 6, 7, 8, 9 or 10 unhybridised nucleotides, optionally 1-5 unhybridised nucleotides, typically 1 unhybridised nucleotide, of the closed circular first nucleic acid strand between each of the hybridised first regions of each of the second nucleic acid strands. In some aspects the plurality of second nucleic acid strands comprise, or consist essentially of, nucleic acids having sequences selected from SEQ ID NOs: 90-113, or variants thereof. In some aspects the plurality of second nucleic acid strands comprise, or consist essentially of, nucleic acids having the sequences of SEQ ID NOs: 91, 93, 95 and 97, or variants thereof. In some aspects the plurality of second nucleic acid strands comprise, or consist essentially of, nucleic acids having the sequences of SEQ ID NOs: 90, 92, 94 and 96, or variants thereof. In some aspects the plurality of second nucleic acid strands comprise, or consist essentially of, nucleic acids having the sequences of SEQ ID NOs: 98, 99, 101, 103, 104, 105, 107 and 108, or variants thereof. In some aspects the plurality of second nucleic acid strands comprise, or consist essentially of, nucleic acids having the sequences of SEQ ID NOs: 98, 100, 102, 103, 104, 106, 107 and 109, or variants thereof. In some aspects the plurality of second nucleic acid strands comprise, or consist essentially of, nucleic acids having the sequences of SEQ ID NOs: 98, 100, 102, 103, 104 and 106, or variants thereof. In some aspects the plurality of second nucleic acid strands comprise, or consist essentially of, nucleic acids having the sequences of SEQ ID NOs: 98, 100, 102, 104, 106, 107, 110, 111, 112 and 113, or variants thereof.

In some aspects the nucleic acids scaffold comprises a closed circular first nucleic acid strand that comprises, or consists essentially of, SEQ ID NOs: 63-65, or variants thereof, and a plurality of second nucleic acid strands that comprise, or consist essentially of, nucleic acids having the sequences of SEQ ID NOs: 91, 93, 95 and 97, or variants thereof. In some aspects the nucleic acids scaffold comprises a closed circular first nucleic acid strand that comprises, or consists essentially of, SEQ ID NOs: 63-65, or variants thereof, and a plurality of second nucleic acid strands that comprise, or consist essentially of, nucleic acids having the sequences of SEQ ID NOs: 90, 92, 94 and 96, or variants thereof. In some aspects the nucleic acids scaffold comprises a closed circular first nucleic acid strand that comprises, or consists essentially of, SEQ ID NOs: 66-68, or variants thereof, and a plurality of second nucleic acid strands that comprise, or consist essentially of, nucleic acids having the sequences of SEQ ID NOs: 98, 99, 101, 103, 104, 105, 107 and 108, or variants thereof. In some aspects the nucleic acids scaffold comprises a closed circular first nucleic acid strand that comprises, or consists essentially of, SEQ ID NOs: 66-68, or variants thereof, and a plurality of second nucleic acid strands that comprise, or consist essentially of, nucleic acids having the sequences of SEQ ID NOs: 98, 100, 102, 103, 104, 106, 107 and 109, or variants thereof. In some aspects the nucleic acids scaffold comprises a closed circular first nucleic acid strand that comprises, or consists essentially of, SEQ ID NOs: 66 and 68, or variants thereof, and a plurality of second nucleic acid strands that comprise, or consist essentially of, nucleic acids having the sequences of SEQ ID NOs: 98, 100, 102, 103, 104 and 106, or variants thereof. In some aspects the nucleic acids scaffold comprises a closed circular first nucleic acid strand that comprises, or consists essentially of, SEQ ID NOs: 68-71, or variants thereof, and a plurality of second nucleic acid strands that comprise, or consist essentially of, nucleic acids having the sequences of SEQ ID NOs: 98, 100, 102, 104, 106, 107, 110, 111, 112 and 113, or variants thereof.

The second region of the second nucleic acid strands protrudes from the closed circular first nucleic acid strand. In some aspects, the second regions of the second nucleic acid strands each hybridise to a third nucleic acid strand. In some aspects at least one of the second nucleic acid strands in the nucleic acid scaffold is hybridised to a third nucleic acid strand. In some aspects each of the second nucleic acid strands in the nucleic acid scaffold is hybridised to a different third nucleic acid strand. In some aspects the hybridised second regions of the second nucleic acid strands and the third nucleic acid strands form the protruding arms of the nucleic acid scaffold. In some aspects there are 1, 2, 3, 4, 5, 6, 7, 8, 9 or 10 unhybridised nucleotides, optionally about 1-5 unhybridised nucleotides, typically about 1-3 unhybridised nucleotides, between the first region of the second nucleic acid that is hybridised to the closed circular first nucleic acid strand and the second region of the second nucleic acid that is hybridised to a third nucleic acid strand. The unhybridised nucleotides can confer flexibility on the protruding arms on the nucleic acid scaffold. In some aspects, the third nucleic acid strands all have the same sequence. In some aspects, the third nucleic acid strands comprise, or consist essentially of, SEQ ID NO: 114, or a variant thereof.

In some aspects the third nucleic acid strands comprises a modification, typically a modified 5' end, that facilitates binding (i.e., attachment, or conjugation) to an appendage of the assembly. Suitable modifications for such a purpose are well-known in the art. In some aspects the third nucleic acids are 5' amine-modified. In some aspects, each of the appendages in the assembly is bonded to a third nucleic acid strand, optionally through a linker, wherein the third nucleic acid strand hybridises to the second region of a second nucleic acid strand. In some aspects all of the second regions of the second nucleic acid strands are hybridised to a third nucleic acid strand, and all of the third nucleic acid strands are bonded to an appendage. Thus, in some aspects the assembly comprises fewer appendages than nucleic acids, in contrast to assemblies comprising the Type 1 nucleic acid scaffold.

Methods of Making Type 1 Nucleic Acid Scaffolds. The present invention further provides a method of making a nucleic acid scaffold comprising a plurality of nucleic acids arranged to form a closed circular structure with protruding arms, wherein the method comprises:

(iv) mixing a plurality of nucleic acids, which nucleic acids each comprise two central regions that hybridise with the central regions of other nucleic acids in the nucleic acid scaffold and two outer regions that hybridise with the outer regions of other nucleic acids in the nucleic acid scaffold;

(v) heating the mixture to a temperature above the melting temperature of the nucleic acids; and (vi) cooling the mixture to a temperature below the melting temperature of the nucleic acids.

The nucleic acid scaffold made according to the methods of the invention may be as described anywhere herein. The nucleic acid scaffold made according to the methods of the invention may be generally considered to take the form of a "Type 1" nucleic acid scaffold as described herein. All of the features of the methods of the making the nucleic acid scaffold may be further defined as described herein.

In some aspects the plurality of nucleic acids are mixed in equal (i.e., equimolar, stoichiometric) amounts. In some aspects the sequence of each nucleic acid in the plurality of nucleic acids is unique. In some aspects, the sequence of each arm is typically different from the sequences of each of the other arms. In some aspects the plurality of nucleic acids are mixed together in solution or suspension. In some aspects the mixing is performed in phosphate buffer, Tris-HCl buffer, TAE, TBE buffer, ammonium acetate buffer or triethylammonium acetate. In some aspects the mixing is performed in 0.1 M phosphate buffer, 0.1 M Tris-HCl buffer, 1×TAE, 1×TBE buffer, 0.1 M ammonium acetate buffer or 0.1 M triethylammonium acetate. In some aspects, the mixing is performed at a pH of about 6-9, optionally 7-8.5. In some aspects the mixing is further performed in the presence of 0.3-1.5 M salt, optionally NaCl or KCl.

In some aspects the temperature above the melting temperature of the nucleic acids is at least 60° C., 65° C., 70° C., 75° C., 80° C., 85° C., 90° C., 95° C. or at least 98° C., optionally at least 90° C., typically at least 95° C. The heating step denatures the nucleic acids to convert all of the nucleic acids into single-stranded form. In some aspects the mixture may be heated to the temperature above the melting temperature of the nucleic acids for at least 30 seconds, 1, 2, 3, 4, 5, 6, 7, 8, 9 or 10 minutes, optionally at least 1 minute, typically at least 3 minutes. In some aspects the mixture is first cooled to a temperature below the melting temperature of the nucleic acids, which may be about 50° C.-70° C., 55° C.-68° C., 58° C.-68° C. or 60° C.-65° C., optionally about 60-65. In some aspects the mixture is incubated at the temperature below the melting temperature of the nucleic acids for 30 seconds, 1, 2, 3, 4, 5, 6, 7, 8, 9 or 10 minutes, optionally at least 1 minute, typically at least 3 minutes. In some aspects the mixture is first cooled to a temperature of about 65° C. for about 3 minutes. During this step the nucleic acids begin to anneal. In some aspects the mixture is secondly cooled to a temperature below the melting temperature of the nucleic acids, which may be about 0° C.-70° C., 0° C.-65° C., 4° C.-65° C., 4° C.-50° C., 4° C.-40° C., 4° C.-30° C., 4° C.-20° C., or 4° C.-10° C., optionally about 4° C.-10° C. In some aspects the second cooling may be performed over at least 1, 2, 3, 4, 5, 8, 10, 15, 18 or 20 hours, optionally at least 2 hours, typically at least 4 hours. In some aspects the mixture is secondly cooled from 65° C. to 4° C., over 2-4 hours. During this step the nucleic acids anneal in the lowest energy confirmation, where the maximum number of base-pairs (i.e., bonds) are formed.

In some aspects the yield of formation of the nucleic acid scaffold using the methods of the invention is at least 50%, 60%, 70%, 75%, 80%, 85%, 90% or 95%, optionally at least 85%. The yield of formation may be determined by performing gel electrophoresis, as described in Example 1. In some aspects, if one of the plurality of nucleic acids is omitted, such that each nucleic acid cannot hybridise to four other nucleic acids, then the yield of formation of a nucleic acid scaffold that forms a closed circular structure is less than 40%, 30%, 20% or 10%, optionally less than 30%.

Summary. The present invention provides any nucleic acid scaffold as described herein. Accordingly the present invention includes any nucleic acid scaffold described herein in isolation, i.e., outside the context of the assemblies of the invention. In one aspect, the present invention provides a nucleic acid scaffold comprising a plurality of nucleic acids arranged to form a closed circular structure with protruding arms. In some aspects, the present invention provides a nucleic acid scaffold comprising a plurality of nucleic acids arranged to form a closed circular structure with protruding arms, wherein each nucleic acid comprises two central regions that hybridise with the central regions of other nucleic acids in the nucleic acid scaffold and two outer regions that hybridise with the outer regions of other nucleic acids in the nucleic acid scaffold, as described herein.

Furthermore, the present invention provides any nucleic acid scaffold as described herein in the context of an assembly of the invention. The nucleic acid scaffold as described anywhere herein may be combined with any other features of the assemblies as described herein.

Appendages

The assemblies of the present invention comprise a nucleic acid scaffold, as defined herein, and a plurality of appendages bonded to the scaffold. When bonded to the scaffold, the appendages are capable of interacting to form a pore in a layer of amphipathic molecules. In some aspects the appendages are capable of interacting to form a pore in a layer of amphipathic molecules in the absence of the nucleic acid scaffold. In some aspects the appendages are not capable of interacting to form a pore in a layer of amphipathic molecules in the absence of the nucleic acid scaffold. In some aspects the appendages are not capable of interacting to form a stable pore, optionally a stable open pore, in a layer of amphipathic molecules in the absence of the nucleic acid scaffold. In some aspects, a stable pore, or a stable open pore, in a layer of amphipathic molecules may be understood to mean a pore that maintains a conductance level of greater than 0.4 nS at applied potentials of between −100 mV and +100 mV for at least about 1 second, 5 seconds, 10 seconds, 30 seconds, 1 minute, 5 minutes, 15 minutes, 30 minutes, 1 hour, 2 hours, 6 hours, 12 hours, 1 day, 2 days, 5 days, 10 days. In some aspects, the pore may maintain a conductance level of greater than 0.4 nS at applied potentials of between −100 mV and +100 mV for at least 5 minutes. Typically, the pore may maintain a conductance level of greater than 0.4 nS at applied potentials of between −100 mV and +100 mV for at least 1 hour. In some aspects, the pore may maintain a conductance level of greater than 0.4 nS at applied potentials of between −100 mV and +100 mV for about 5-60 minutes.

In some aspects the assembly comprises about 3-500, 3-45-, 3-400, 3-350, 3-300, 3-250, 3-200, 3-150, 3-100, 3-50, 3-40, 3-30, 3-20 or 3-10 appendages, optionally 3-300 appendages. The nucleic acid scaffold of the assemblies stabilises the configuration of the appendages and enhances pore formation. Thus, the assemblies of the invention allow for the formation of pores comprised of very large numbers of appendages as compared to, for example, naturally occurring biological pores. In some aspects the assembly may comprise 3-50, 3-40, 3-30, 3-20 or 3-10 appendages, optionally 3-20 appendages. In such aspects the appendages may form smaller pores suitable for, for example, ion or small molecule transport and polynucleotide sequencing applications. In some aspects the assembly may comprise 50-300, 50-250, 50-200, 50-150 or 50-100 appendages, optionally 50-300 appendages. In such aspects the appendages may form larger pores, suitable for, for example, complex polymers, proteins or whole enzymes to pass through.

In some aspects, each appendage is covalently bonded to the nucleic acid scaffold. In some aspects each appendage is no more than 200, 150, 100, 90, 80, 70, 60, 55, 50, 45, 40, 35, 30, 25, 20, 15 or no more than 10 bases, optionally no more than 100 bases, typically no more than 50 bases, from the nearest other appendage on the nucleic acid scaffold. In some aspects each appendage is about 10-200, 15-200, 20-150, 25-100, 30-80, 30-70, 30-60 or 30-50 bases, optionally about 25-100 bases, typically 30-60 bases, from the nearest other appendage on the nucleic acid scaffold. The number of bases may be understood to mean the minimum distance measured in bases of the nucleic acids between the point of attachment of one appendage and the point of attachment of the nearest appendage. The bases are hybridised to another nucleic acid the distance may also be measured in base pairs or a combination of bases and base pairs. The number of bases is not necessarily bases of the same nucleic acid stand, typically the distance in bases between the attachment points of the appendages will cover one or more nucleic acids.

As discussed above, the appendages are typically covalently bonded to the protruding arms of the nucleic acid scaffold. In some aspects the appendages are covalently bonded to the "outer regions" of the nucleic acids of the nucleic acid scaffold. In some alternative aspects, the appendages are covalently bonded to the third nucleic acid strands of the nucleic acid scaffold. Each appendage may be bonded to a nucleic acid of the nucleic acid scaffold at any point along the length of the nucleic acid, for example the nucleic acid may comprise a modified base at any point along its length that facilitates bonding to the appendage. Typically, each appendage is covalently bonded to either the 5'- or 3'-end, optionally the 5'-end, of a nucleic acid of a protruding arm of the nucleic acid scaffold. In some aspects suitable modifications to the appendage and the nucleic acid are made to facilitate the covalent bonding. Suitable compatible modifications are well-known in the art and may depend on the nature of the appendage. In some aspects, where the appendage is a peptide or polypeptide, a cysteine may be introduced into the peptide or polypeptide. In some aspects an appendage which is a peptide or polypeptide may be modified to introduce a Cys-Gly-Gly sequence at the N- or C-terminus. In some aspects the appendage which is a peptide or polypeptide may be modified, for example by mutation, to introduce a cysteine at an accessible location in the peptide or polypeptide. In some aspects the nucleic acid of the protruding arm of the nucleic acid scaffold is amino-modified, optionally at the 5'- or 3'-end, optionally the 5'-end. In some aspects, each appendage is covalently bonded to the nucleic acids scaffold through a flexible linker. Suitable linkers are well-known in the art and may include chemical linkers, polynucleotide linkers or peptide linkers. In some aspects the liker may be a $SM(PEG)_2$ (succinimidyl-((N-maleimidopropionamido)-diethylene glycol) ester) linker or a $(PEG)_4$-SPDP (2-Pyridyldithiol-tetraoxatetradecane-N-hydroxysuccinimide) linker. In some aspects each appendage is covalently bonded to the nucleic acids scaffold through a $SM(PEG)_2$ linker.

In some aspects at least one of, optionally at least three of, and most preferably each of, the appendages comprises a polymer, optionally an amphipathic polymer. An amphipathic polymer comprises both hydrophilic and hydrophobic (i.e., lipophilic) portions in its structure. The polymer, optionally the amphipathic polymer, may be naturally occurring or synthetic. Suitable polymers, optionally amphipathic polymers, are known in the art. In some aspects each of the appendages in the assembly comprises the same polymer, optionally amphipathic polymer. In some aspects the appendages in the assembly may comprise different polymers, optionally amphipathic polymers. In some aspects the appendages in the assembly may comprise at least 2, 3, 4, 5, 6, 7, 8, 9 or at least 10, preferably about 2-5, most preferably 2, different polymers, optionally amphipathic polymers. The polymer, which is typically an amphipathic polymer, may be any polymer that is capable of forming a pore in a layer of amphipathic molecules when bonded to a nucleic acid scaffold as described herein. There are many molecules that might be stabilized or organized as transmembrane pores by using a nucleic acid scaffold. These structures might assemble by themselves but the use of a scaffold means that weakly interacting units can be stabilized, a defined number of units can be assembled around a central axis, and heteromeric pores with different units assembled in a defined order can be made. There are numerous possibilities based on supramolecular chemistry, such as, for example, the barrel-stave structures of Matile and colleagues (Sakai, N., Mareda, J., and Matile, S. (2005) Rigid-rod molecules in biomembrane models: from hydrogen-bonded chains to synthetic multifunctional pores. Acc Chem Res 38, 79-87, incorporated herein by reference), which have poorly defined stoichiometry, and heteromers with distinct structures cannot be isolated. In some aspects the polymer, which is optionally an amphipathic polymer, may be selected from the group consisting of peptides, including stapled, branched or cyclic peptides, polypeptides, including those comprising L-amino acids, D-amino acids or any other modified amino acids, or a combination thereof, peptidomimetics (such as those disclosed in Avan, I., Hall, C. D., and Katritzky, A. R. (2014) Peptidomimetics via modifications of amino acids and peptide bonds. Chem Soc Rev 43, 3575-3594, which is incorporated herein by reference) and polynucleotides. In some aspects the polymer, which is optionally an amphipathic polymer, may be selected from the group consisting of peptides, polypeptides and polynucleotides. In some aspects the polymer, which is optionally an amphipathic polymer is a peptide, polypeptide or protein. In some aspects, at least one of, and optionally each of, the appendages comprises a peptide or a polypeptide.

In some aspects, at least one of, and optionally each of, the appendages comprises a peptide that is capable of inserting into a layer of amphipathic molecules. In some aspects, at least one of, and optionally each of, the appendages comprises a polypeptide that is capable of inserting into a layer of amphipathic molecules. Generally a peptide may be considered to comprise about 2-50 amino acids and a polypeptide may be considered to comprise more than about 50 amino acids, although the terms may be used interchangeably. Typically, it is not the full-length of the peptide or polypeptide that inserts into the layer of amphipathic molecules. Generally, the peptide or polypeptide that is capable of inserting into a layer of amphipathic molecules comprises an amphipathic portion that inserts into the layer of amphipathic molecules. In some aspects the peptide or polypeptide will comprise an amphipathic element of secondary structure that is capable of inserting into a layer of amphipathic molecules. At least one of, and optionally each of, the appendages may comprise an α-helical peptide, a β-strand, a β-hairpin, a β-ribbon or a β-sheet. For example, in some aspects, at least one of, and optionally each of, the appendages comprise a peptide or polypeptide that comprises an α-helix, a β-strand, a β-hairpin, a β-ribbon or a β-sheet that is capable of inserting into a layer of amphipathic molecules. At least one of, and optionally each of, the appendages may comprise 1, 2, 3, 4, 5, 6, 7, 8, 9, 10 or more, optionally 1-5, optionally 1 or 2, α-helices or β-strands. Where at least one of, and optionally each of, the appendages comprises one or more α-helices, the appendages may interact to form an α-helical barrel. Where at least one of, and optionally each of, the appendages comprises one or more β-strands, the appendages may interact to form a β-barrel.

In some aspects, the appendages, when bonded to the scaffold, are capable of interacting to form a complex that forms a pore in a layer of amphipathic molecules. Generally each appendage alone is not capable of forming a pore in a layer of amphipathic molecules. Typically a plurality of appendages are required to interact, typically binding to each other, to form a complex within the layer of amphipathic molecules that defines a channel (e.g., a pore) through the layer of amphipathic molecules. Thus, each appendage may be a subunit of the complex, wherein the complex forms a pore in a layer of amphipathic molecules. In some aspects the appendages may interact covalently. For example, when the appendages are in close proximity (i.e., within 1 nm, 2 nm, 3 nm, 4 nm, 5 nm, 6 nm, 7 nm, 8 nm, 9 nm, 10 nm, 15 nm or within 20 nm), reactive groups on each appendage may react to covalently bond the appendages together. In some aspects the appendages interact non-covalently, for example forming ionic, non-ionic, hydrophobic or Van der Waals interactions, forces or bonds. Generally such favourable interactions are formed when the appendages are in close proximity (i.e., within 1 nm, 2 nm, 3 nm, 4 nm, 5 nm, 6 nm, 7 nm, 8 nm, 9 nm, 10 nm, 15 nm or within 20 nm). The term "capable of interacting" may be considered to mean that two appendages are capable of forming such favourable bonds or interactions when in close proximity, which causes them to become and remain associated, or bound together. In some aspects the appendages comprise peptides or polypeptides that, when bonded to the scaffold, are capable of interacting to form a multimeric complex that forms a pore in an amphipathic bilayer. Thus, in some aspects, each appendage is a protein monomer and, when bonded to the scaffold, the protein monomers interact with each other to form a multimer or multimeric complex that is capable of forming a pore in a layer of amphipathic molecules. In some aspects the multimeric complex formed by the peptides or polypeptides comprises an α-helical peptide barrel or a β-barrel.

Typically, the multimeric complex comprises a plurality of polypeptide or peptide subunits arranged around a central axis thereby forming a protein-lined channel that extends substantially perpendicular to the layer of amphipathic molecules in which the pore is formed. In some aspects, the multimeric complex formed by the peptides or polypeptides may be homomeric or heteromeric. Thus, in some aspects each of the appendages of the assembly comprises the same peptide or polypeptide sequence. In such aspects, the multimeric complex formed by the appendages is a homomeric complex. In some aspects the appendages in the assembly may comprise different peptide or polypeptide sequences. In some aspects the appendages in the assembly may comprise at least 2, 3, 4, 5, 6, 7, 8, 9 or at least 10, optionally about 2-5, optionally 2, different peptide or polypeptide sequences. In such aspects, the multimeric complex formed by the appendages is a heteromeric complex.

The assemblies of the invention may be used to direct the formation of heteromeric pore complexes. The nucleic acid scaffold of the assembly directs the positioning of each of the appendages. Where the appendages comprise different peptides or polypeptides, these may be bonded to the nucleic acid scaffold in a predetermined pattern such that the relative location of each different peptide or polypeptide in the pore formed in a layer of amphipathic molecules may be controlled. Thus, the assembly allows for the position of each different polypeptide in the heteromeric complex to be selected.

In some aspects, at least one of, and optionally each of, the appendages comprises a peptide or polypeptide derived from a naturally occurring protein. The naturally occurring protein may be a membrane proteins, many of which comprise α-helices and/or β-strands. Typically, at least one of, and optionally each of, the appendages comprises a peptide or polypeptide derived from a natural barrel. There are many natural β-barrels, for example, porins and other proteins in the outer membrane of gram negative bacteria. There are fewer known α-helix barrels, but they include Wza and ClyA a bacterial toxin. At least one of, and optionally each of, the appendages may comprise a peptide or polypeptide derived from an antimicrobial peptide. At least one of, and optionally each of, the appendages may be derived from a designed, or synthetic α-helix barrel, such as those described in Niitsu, A., Heal, J. W., Fauland, K., Thomson, A. R., and Woolfson, D. N. (2017) Membrane-spanning alpha-helical barrels as tractable protein-design targets. Philos Trans R Soc Lond B Biol Sci 372: 20160213, which is incorporated herein by reference. In some aspects, at least one of, and optionally each of, the appendages comprises a peptide or polypeptide derived from a protein selected from the group consisting of bacterial outer membrane proteins, bacterial transporter proteins, antimicrobial peptides, bactericidal peptides, transmembrane proteins, β-barrel proteins, α-helix barrel proteins, channel proteins, ion channels, pore-forming toxins and pore forming proteins, optionally bacterial outer membrane proteins, transmembrane proteins, β-barrel proteins or α-helix barrel proteins. Typically, these natural occurring proteins comprise a plurality of monomeric subunits that assemble to form ring-like structures that insert into membranes to form pores. In some aspects, at least one of, and optionally each of, the appendages comprises a peptide or polypeptide derived from a protein selected from the group consisting of Wza, α-hemolysin, cytolysin A (ClyA), leukocidin, *Mycobacterium smegmatis* porin A (MspA), outer membrane protein phospholipase OMPLA, tachyplesin, protegrin, outer membrane porin F (OmpF), outer membrane porin G (OmpG), outer membrane phospholipase A and *Neisseria* autotransporter lipoprotein (NalP), vertebrate defensins, anthrax toxin's PA subunit, or variants thereof, or combinations thereof, optionally Wza, α-hemolysin, cytolysin A, leukocidin, *Mycobacterium smegmatis* porin A (MspA), outer membrane porin F (OmpF), outer membrane porin G (OmpG), outer membrane phospholipase A and *Neisseria* autotransporter lipoprotein (NalP), or variants thereof, or combinations thereof. In some aspects each appendage may comprise an amino acid sequence having at least 70%, 80%, 85%, 90%, 95% or substantially 100%, optionally at least 80%, most typically at least 90% sequence identity to a monomer of the protein. Alternatively, the skilled person may analyse the amino acid sequence of the protein to identify the portion of the protein that inserts into the membrane and interacts with the other subunits to form the pore. Techniques to perform such analysis are known in the art. In such aspects, each appendage may comprise an amino acid sequence having at least 70%, 80%, 85%, 90%, 95% or substantially 100%, optionally at least 80%, typically at least 90% sequence identity to the portion of the protein that inserts into the membrane and interacts with the other subunits to form the pore.

As discussed above, pore-forming peptides may be naturally occurring. Alternatively, pore-forming peptides may be designed and synthesised. Thus, in some aspects at least one of, and optionally each of, the appendages may comprise a synthetic pore-forming peptide. Methods for designing and synthesising pore-forming peptides are known in the art. Typically peptides are designed to be amphipathic and to present a continuous hydrophobic surface to the bilayer. Typically a library of such peptides may be synthesised and the peptides screened for pore-forming ability, e.g., using an anti-microbial assay. Pores formed from designed peptides, particularly a helices, are described in the following documents and at least one of, and optionally each of, the appendages may comprise a synthetic pore-forming peptide as described in any of the following documents: Niitsu, A., Heal, J. W., Fauland, K., Thomson, A. R., and Woolfson, D. N. (2017) Membrane-spanning alpha-helical barrels as tractable protein-design targets. *Philos Trans R Soc Lond B Biol Sci* 372, pii: 20160213; Heal, J. W., Bartlett, G. J., Wood, C. W., Thomson, A. R., and Woolfson, D. N. (2018) Applying graph theory to protein structures: an atlas of coiled coils. *Bioinformatics, epub* doi: 10.1093/bioinformatics/bty347; William C. Wimley, and Stephen H. White, Designing Transmembrane α-Helices That Insert Spontaneously, doi: 10.1021/bi992746j; and Carlos Baeza-Delgado, Gunnar von Heijne, Marc A. Marti-Renom and Ismael Mingarro, Biological insertion of computationally designed short transmembrane segments, doi 10.1038/srep23397, each of which is incorporated by reference herein.

In some aspects, each of the appendages may comprise a Wza peptide sequence. In some aspects, each of the appendages may comprise an α-hemolysin monomer sequence, or a functional fragment thereof. Functional fragments include fragments of the α-hemolysin monomer sequence that are able to insert into a layer of amphipathic molecules and assemble to form a pore. In some aspects each of the appendages may comprise a Wza peptide modified to comprise a Cys-Gly-Cly sequence at the N- or C-terminus. In some aspects each of the appendages may comprise an α-hemolysin monomer comprising a K237C or a N17C mutation, wherein the residue numbering corresponds to the *Staphylococcus aureus* α-hemolysin mature polypeptide. In some aspects, each of the appendages comprises a peptide comprising a sequence having at least 70%, 80%, 85%, 90%, 95%, 96%, 97%, 98%, 99% or substantially 100% sequence identity to any one of SEQ ID NOs: 1-10, or a variant thereof. In some aspects, each of the appendages comprises a peptide comprising a sequence having at least 70%, 80%, 85%, 90%, 95%, 96%, 97%, 98%, 99% or substantially 100% sequence identity to any one of SEQ ID NOs: 12-14, or a variant thereof, or a functional fragment thereof.

In some aspects the appendages are capable of interacting to form a pore in a layer of amphipathic molecules. In some instances, the appendages are capable of interacting to form a pore in a layer of amphipathic molecules having a pore channel that is hydrophilic. In some instances the appendages are capable of interacting to form a pore in a layer of amphipathic molecules, wherein the pore channel has a diameter of about 1-200 nm, 1-150 nm, 1-100 nm, 1-50 nm, 1-40 nm, 1-30 nm, 1-20 nm, 1-10 nm, 0.5-200 nm, 0.5-150 nm, 0.5-100 nm, 0.5-50 nm, 0.5-40 nm, 0.5-30 nm, 0.5-20 nm, 0.5-10 nm, 2-200 nm, 2-150 nm, 2-100 nm, 2-50 nm, 2-40 nm, 2-30 nm, 2-20 nm, 2-10 nm; 3-200 nm, 3-150 nm, 3-100 nm, 3-50 nm, 3-40 nm, 3-30 nm, 3-20 nm, or 3-10 nm, 4-200 nm, 4-150 nm, 4-100 nm, 4-50 nm, 4-40 nm, 4-30 nm, 4-20 nm, 4-10 nm, 5-200 nm, 5-150 nm, 5-100 nm, 5-50 nm, 5-40 nm, 5-30 nm, 5-20 nm, or 5-10 nm, optionally about 0.5-100 nm, 1-100 nm, 2-100 nm, 3-100 nm, 4-100 nm or 5-100 nm, typically about 1-100 nm. It will be understood by the skilled person that pore channels may not have a continuous diameter across their entire length, for example there may be numerous constrictions. Thus, the pore channel diameter as defined herein may be understood to mean the effective pore channel diameter, i.e., the minimum pore channel diameter. In other words, a molecule of interest or target analyte having a size smaller than the specified pore channel diameter would be capable of inserting into or translocating through the pore. As discussed above, one advantage of the assemblies of the invention is that they may be used to assemble pores that are much larger than naturally occurring pores. In some aspects the appendages are capable of interacting to form a pore in a layer of amphipathic molecules, having a pore channel diameter of about 1-5 nm, 1-10 nm, 1-15 nm, 1-20 nm, 1-25 nm or 1-30 nm, optionally 1-20 nm. Such pores may be suitable for transport or detection of electrons, ions or small molecules and analysis or sequencing of linear polymers such as peptides or polynucleotides. In some aspects the appendages are capable of interacting to form a pore in a layer of amphipathic molecules, having a pore channel diameter of about 30-200 nm, 30-150 nm, 30-100 nm, 40-100 nm, 50-100 nm, 60-100 nm, 70-100 nm, 80-100 nm or 90-100 nm, optionally 30-100 nm. Such pores may be suitable for transport or detection of biological macromolecules, such as folded proteins, and for the analysis of biological functions such protein conformational changes and enzyme mechanisms.

In some aspects, the assembly further comprises a second plurality of appendages bonded to the scaffold, wherein the second plurality of appendages, when bonded to the scaffold, are capable of interacting to form a second pore. In some aspects the assembly further comprises one or more further pluralities of appendages bonded to the scaffold, wherein the appendages in each further plurality, when bonded to the scaffold, are capable of interacting to form a further pore. The further pores formed by each further plurality of appendages may be formed in the same layer of amphipathic molecules or different layers of amphipathic molecules. The appendages in the second and further pluralities can be as further defined anywhere herein for the appendages in the first plurality.

Docking Moieties

In some aspects the assembly further comprises at least one docking moiety. A docking moiety may be any moiety that is capable of binding to a target analyte or molecule of interest, either covalently or non-covalently. Suitable docking moieties optionally include nucleic acid hybridisation, other forms of nucleic acid interaction such as triple helix formation; non-covalent interactions with the nucleic acid scaffold, such as intercalation and groove binding, or chemical attachment such as disulphide or azide-alkyne interactions. Other suitable docking moieties include, for example, biotin, a polynucleotide sequence, antibodies, antibody fragments, such as Fab and ScSv, antigens, polynucleotide binding proteins, poly histidine tails, GST tags, ligands, ligand-binding proteins, and aptamers. In some aspects the docking moiety is biotin or a selectable polynucleotide sequence. Biotin specifically binds to a surface coated with avidins. Selectable polynucleotide sequences specifically bind (i.e. hybridise) to homologous sequences. Typically, the docking moiety is bonded to the nucleic acid scaffold. Thus, the docking moiety functions to bind or tether the target analyte in the vicinity of the pore formed by the appendages of the assembly. In this way the target analyte may be captured for analysis. In some aspects, the docking moiety may comprise a reactive chemical group. In some aspects, the target analyte may comprise a suitable chemical group that reacts with the reactive chemical group of the docking moiety. Suitable reactive groups are known in the art. In some aspects the docking moiety may comprise, for example, maleimide groups, activated N-hydroxysuccinimide ester groups, biotin, streptavidin, antibodies, polynucleotides, proteins.

In some aspects, the docking moiety may comprise a single-stranded nucleic acid sequence. In such aspects, the docking moiety may be formed by an extension of one of the nucleic acids making up one of the protruding arms of the nucleic acids scaffold. In some aspects, the docking moiety may comprise 1, 2, 3, 4, 5, 6, 7, 8, 9 or 10 single-stranded nucleotides, or about 1-50, 1-40, 1-30, 1-20, 1-15, 1-10, 5-50, 5-40, 5-30, 5-20, 5-15 or 5-10 single-stranded nucleotides, optionally 5-20 single-stranded nucleotides. In some aspects where the docking moiety comprises a single-stranded nucleic acid sequence, the target analyte is a polynucleotide. In some aspects, a target analyte may bind to the docking moiety. In some aspects where the docking moiety comprises a single-stranded nucleic acid sequence and the target analyte is a polynucleotide, the target analyte may hybridise to the docking moiety.

In some aspects, the target analyte is capable of inserting into the pore channel. For example, a portion of the target analyte or the entire target analyte may insert into the pore channel. In such aspects the pore channel has a greater diameter than the target analyte. In some aspects the target analyte is capable of being translocated through the pore. For example, the target analyte may diffuse or be transported or translocated through the pore, either down a concentration gradient or under an applied potential. In some aspects the diameter of the pore channel along its entire length is greater than the diameter of the target analyte. In some aspects the whole target analyte may be translocated through the pore. In some aspects a portion of the target analyte may be translocated through the pore. In some aspects the target analyte may be fragmented or unfolded to be translocated through the pore.

The target analyte may be any molecule to be detected, analysed or translocated or transported through the pore. The target analyte may comprise or consist essentially of a ligand, an analyte, an ion, a small organic molecule, a protein, a peptide, a polypeptide, a protein domain, a protein fragment, a protein subunit, a chemical moiety, an antibody, and antibody fragment, an enzyme, a phosphoprotein, a glycoprotein, a lipoprotein, a lipid, a membrane lipid, a phospholipid, a carbohydrate, a simple sugar, a disaccharide, a polysaccharide, a nucleic acid, a polynucleotide, an oligonucleotide, a DNA molecule, an RNA molecule, an XNA molecule, a nucleoprotein, a small molecule, a chemical entity, an analyte, a drug, a pharmaceutical, an antibiotic, a vitamin, a banned substance, an illicit drug, a drug of addiction, a chemotherapeutic agent, a disease biomarker, a pathogen-derived molecule, such as a viral, bacterial, protozoan or fungal protein, lipid, carbohydrate or nucleic acid, or combination thereof.

Layer of Amphipathic Molecules

The assemblies of the invention form a pore in a layer of amphipathic molecules. A layer of any amphipathic molecule may be used in accordance with the invention. Suitable amphipathic molecules that form continuous layers are well-known in the art. The layer of amphipathic molecules may comprise a monolayer or a bilayer. Suitable amphipathic molecules include, for example phospholipids, which have both hydrophilic and lipophilic properties. The amphipathic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers can be engineered such that one of the monomer sub-units is hydrophobic (i.e. lipophilic), whilst the other sub-unit(s) are hydrophilic whilst in aqueous media. In this case, the block copolymer may possess amphipathic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is optionally a triblock copolymer membrane.

Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins. Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups. Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

Thus, in some aspects the layer of amphipathic molecules comprises a triblock copolymer comprising a first outer hydrophilic polymer segment, an inner hydrophobic polymer segment and a second outer hydrophilic polymer segment. In some aspects, the amphipathic molecules may for instance comprise the triblock copolymer poly(2-methyloxazoline)-block-poly(dimethylsiloxane)-block-poly(2-methyloxazoline) (PMOXA-PDMS-PMOXA), or for instance the triblock copolymer poly(2-methyloxazoline)-block-poly(ethylene)-block-poly(2-methyloxazoline) (PMOXA-PE-PMOXA). In some aspects, the amphipathic molecules may for instance comprise the triblock copolymer 6-33-6 (PMOXA-PDMS-PMOXA), 6-32-6 (PMOXA-PDMS-PMOXA), or 6-45PE-6 (PMOXA-PE-PMOXA). In some aspects, the layer of amphipathic molecules comprises poly(2-methyloxazoline)-block-poly(dimethylsiloxane)-block-poly(2-methyloxazoline) (PMOXA-PDMS-PMOXA). The layer of amphipathic molecules is optionally one of the membranes disclosed in International Application No. PCT/GB2013/052766 or PCT/GB2013/052767, which are both incorporated herein by reference.

The layer of amphipathic molecules may be a monolayer or a bilayer. The layer of amphipathic molecules is typically planar. The layer of amphipathic molecules may be curved. The layer of amphipathic molecules may be supported. The amphipathic molecules in the layer are typically naturally mobile, essentially acting as a two dimensional fluids with molecular diffusion rates of approximately $10^{-8}$ cm $s^{-1}$. This means that any pore formed within the layer of amphipathic molecules may move within layer of amphipathic molecules.

In some aspects, the layer of amphipathic molecules may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The layer of amphipathic molecules may be any lipid bilayer. Suitable lipid bilayers include, but are not limited to, a planar lipid bilayer, a supported bilayer or a liposome. The lipid bilayer is optionally a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484), all of which are hereby incorporated by reference. In some aspects the layer of amphipathic molecules comprises 1,2-diphytanoyl-sn-glycero-3-phosphocholine (DPhPC) molecules. In some aspects the layer of amphipathic molecules is a DPhPC bilayer.

Methods for forming lipid bilayers are known in the art. Lipid bilayers are commonly formed by the method of Montal and Mueller (Proc. Natl. Acad. Sci. USA., 1972; 69: 3561-3566, incorporated herein by reference). Other common methods of bilayer formation include tip-dipping, painting bilayers and patch-clamping of liposome bilayers. Liposomes can be formed by sonication, extrusion or the Mozafari method (Colas et al. (2007) Micron 38:841-847). In some aspects, the lipid bilayer is formed as described in International Application No. PCT/GB08/004127 (published as WO 2009/077734), which is incorporated herein by reference. Advantageously in this method, the lipid bilayer is formed from dried lipids. In some aspects, the lipid bilayer is formed across an opening as described in WO2009/077734 (PCT/GB08/004127), which is incorporated herein by reference.

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition optionally contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol) 2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16 -Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of a polynucleotide.

In some aspects, the layer of amphipathic molecules may comprise a plurality of amphiphilic lipids comprising a hydrophilic head group bonded to a hydrophobic tail group, optionally phospholipids. In some aspects the layer of amphipathic molecules may comprise one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In some aspects, the layer of amphipathic molecules may further comprise a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647), incorporated herein by reference. If the membrane comprises a solid state layer, the pore is typically present in the layer of amphipathic molecules, which is typically contained within the solid state layer, for instance within a hole, well, gap, channel, trench or slit within the solid state layer. The skilled person can prepare suitable solid state/amphiphilic hybrid systems. Suitable systems are disclosed in WO 2009/020682 and WO 2012/005857, which are both incorporated herein by reference. Any of the layers of amphipathic molecules discussed above may be used.

Pore Systems

As described above the present invention provides assemblies that are capable of forming pores in a layer of amphipathic molecules. The present invention further provides a system comprising: (a) a layer of amphipathic molecules; and (b) an assembly comprising a nucleic acid scaffold and a plurality of appendages bonded to the scaffold, wherein the appendages form a pore in the layer of amphipathic molecules. The features of the system, particularly the layer of amphipathic molecules and the assembly, may be as further defined anywhere herein.

In some aspects, the assembly is arranged such that the appendages are inserted into the layer of amphipathic molecules to form a pore and the nucleic acid scaffold is positioned on the layer of amphipathic molecules. In some aspects the nucleic acid scaffold does not contact or interact with the layer of amphipathic molecules. In some aspects the nucleic acid scaffold is positioned above or below the layer of amphipathic molecules. In some aspects the nucleic acid scaffold is positioned at least about 1 nm, 5 nm, 10 nm, 20 nm, 50 nm, 100 nm, 150 nm, 200 nm, 500 nm or at least 1000 nm, optionally at least 5 nm from (i.e., above/below) the layer of amphipathic molecules. In some aspects the nucleic acid scaffold contacts the layer of amphipathic molecules. In some aspects the nucleic acid scaffold is positioned parallel to the layer of amphipathic molecules.

In some aspects the appendages interact to form a pore in the layer of amphipathic molecules, as described herein. In some aspects, at least one of, optionally at least three of, and typically each of, the appendages are inserted into the layer of amphipathic molecules. As described herein appendages that are capable of inserting into a layer of amphipathic molecules are typically amphipathic. Inserting into the layer of amphipathic molecules usually requires that favourable interactions or bonds, typically non-covalent interactions or bonds, are formed between the components of the layer of amphipathic molecules and the appendages. Typically such favourable interactions include non-covalent ionic, non-ionic, hydrophobic or Van der Waals interactions. Typically the hydrophobic portions of the amphipathic appendages interact with the hydrophobic, non-polar, hydrocarbon or lipidic portions of the layer of amphipathic molecules, which are typically located in the middle of the layer of amphipathic molecules. Typically the hydrophilic portions of the amphipathic appendages interact with the hydrophilic, polar, charged or ionic portions of the layer of amphipathic molecules, which are typically located at the surfaces of the layer of amphipathic molecules.

In some aspects, at least one of, optionally at least three of, and typically each of, the appendages span the layer of amphipathic molecules. In some aspects, at least one of, optionally at least three of, and typically each of, appendages insert into and span the layer of amphipathic molecules. The appendages are typically insert perpendicular to the plane of the layer of amphipathic molecules to form the pore. Typically, the appendages are arranged in a ring-shaped structure within the layer of amphipathic molecules to form a pore. In some aspects the amphipathic appendages present a hydrophobic surface to the layer of amphipathic molecules and a hydrophilic surface away from the layer of amphipathic molecules and thereby define a hydrophilic pore channel through the membrane. In some aspects the term "pore channel" may be used to define the hole or space through the layer of amphipathic molecules formed by the insertion of the appendages into the layer of amphipathic molecules. In some aspects the pore channel is hydrophilic. The hydrophilic pore channel allows for the translocation of polar, charged or ionic molecules through the channel.

In some aspects the pore formed in the layer of amphipathic molecules has a pore channel diameter of about 1-200 nm, 1-150 nm, 1-100 nm, 1-50 nm, 1-40 nm, 1-30 nm, 1-20 nm, or 1-10 nm, optionally about 1-100 nm. As discussed above, the diameter of the pore channel may vary across its length across the layer of amphipathic molecules and therefore the pore channel diameter as defined herein may be understood to mean the effective pore channel diameter, i.e., the minimum pore channel diameter. In other words, a target analyte having a size smaller than the specified pore channel diameter would be capable of inserting into or translocating through the pore. In some aspects the pore formed in the layer of amphipathic molecules has a pore channel diameter of about 1-5 nm, 1-10 nm, 1-15 nm, 1-20 nm, 1-25 nm or 1-30 nm, optionally 1-20 nm. Such smaller pores may be suitable for detection, analysis or translocation of electrons, ions or small molecules and analysis or sequencing of linear polymers such as peptides or polynucleotides. In some aspects the pore formed in the layer of amphipathic molecules has a pore channel diameter of about 30-200 nm, 30-150 nm, 30-100 nm, 40-100 nm, 50-100 nm, 60-100 nm, 70-100 nm, 80-100 nm or 90-100 nm, optionally 30-100 nm. Such larger pores may be suitable for detection, analysis or translocation of biological macromolecules, such as folded proteins, and for the analysis of biological functions such protein conformational changes and enzyme mechanisms. The diameter of the pore can be controlled which may allow for translocation and characterization of double-stranded nucleic acids; translocation and characterization of folded proteins and protein complexes with other proteins or ligands; trapping of macromolecules and observation, for example, of conformational changes, substrate binding, or substrate turnover. Further possible applications for the pores of the invention are described in Soskine, M., Biesemans, A., and Maglia, G. (2015) Single-Molecule Analyte Recognition with ClyA Nanopores Equipped with Internal Protein Adaptors. *J Am Chem Soc* 137, 5793-5797, which is incorporated herein by reference.

In some aspects the system may comprise one layer of amphipathic molecules and one assembly as defined herein, and thus one pore. In some aspects the plurality of appendages bonded to the scaffold is a first plurality of appendages which form a first pore in the layer of amphipathic molecules, and the assembly further comprises one or more further pluralities of appendages bonded to the scaffold, wherein the appendages in each further plurality form a further pore in the layer of amphipathic molecules. Thus, a plurality of pores in the layer of amphipathic molecules may be formed. In some aspects the system may comprise one layer of amphipathic molecules and a plurality of assemblies as defined herein, and thus a plurality of pores in the layer of amphipathic molecules. In such aspects the two distinct sides of the layer of amphipathic molecules may be designated as the cis and trans sides of the membrane. In some aspects, all of the assemblies may be arranged such that the nucleic acid scaffolds are located on the same side of the layer of amphipathic molecules, which may be the cis side or the trans side. In some aspects a first plurality of assemblies may be arranged such that the nucleic acid scaffolds are located on one side (the cis side) of the layer of amphipathic molecules and a second plurality of assemblies may be arranged such that the nucleic acid scaffolds are located on the other side (the trans side) of the layer of amphipathic molecules. In some aspects the system may comprise a plurality of layers of amphipathic molecules and a plurality of assemblies as defined herein, and thus a plurality of pores in a plurality of layers of amphipathic molecules may be formed. Thus, in some aspects the system may comprise an array of layers of amphipathic molecules all comprising pores formed according to the systems of the invention.

The present invention further provides a system comprising: (a) an assembly comprising a nucleic acid scaffold and a plurality of appendages bonded to the scaffold; and (b) two or more chambers, each of which is separated by a layer of amphipathic molecules; wherein the appendages form a pore in the layer of amphipathic molecules. The features of the system, particularly the assembly and layer of amphipathic molecules, may be as further defined anywhere herein.

In some aspects a system may be prepared where the assemblies of the invention may be used to introduce pores that bring distinct chambers separated by layers of amphipathic molecules into fluid communication. In some aspects the layer of amphipathic molecules prevents fluid communication between the internal volume of the chamber and the external surroundings. In some aspects the layer of amphipathic molecules prevents fluid communication between the internal volume of the chamber and the internal volume of the adjacent chamber. In some aspects each chamber directly contacts at least one other, optionally a plurality of, chamber (s), but is not in fluid communication with any other chamber. In some aspects each chamber may be formed from a layer of amphipathic molecules. For example, in some aspects, each chamber may be a liposome. In some aspects each chamber may be formed from a solid material. Suitable solid materials are well-known in the art and include, for example, plastics and metals. In some aspects each chamber may be formed from a solid state layer, as described herein. As described herein, solid state layers can be formed from both organic and inorganic materials including, but not limited to, microelectronic materials, insulating materials such as Si3N4, Al2O3, and SiO, organic and inorganic polymers such as polyamide, plastics such as Teflon® or elastomers such as two-component addition-cure silicone rubber, and glasses. In such aspects where the chamber is made from a solid material or a solid state material, a layer of amphipathic molecules is comprised within the material, for instance within a hole, gap, channel, or slit within the solid state layer. In some aspects the chambers may be arranged to form an array. In some aspects the chambers may be arranged to form a synthetic signalling system. In some aspects, where the chambers may be arranged to form a synthetic signalling system, a predetermined signal may induce an assembly to form a pore in the layer of amphipathic molecules. Such signals may include, for example, a change in applied voltage, a change in ion concentration, a protein-protein interaction or a change in the concentration of an analyte.

The present invention also provides a system comprising (a) a layer of amphipathic molecules; and (b) an assembly comprising a nucleic acid scaffold and a plurality of appendages bonded to the scaffold, wherein the appendages form a pore in the layer of amphipathic molecules, optionally as further defined anywhere herein, wherein the pore is capable of binding one or more d-block metal atoms within the pore channel. In some aspects the system comprises one or more d-block metal atoms bound to the pore within the pore channel. In some aspects the system comprises 1, 2, 3, 4, 5, 6, 7, 8, 9, 10 or more d-block metal atoms bound to the pore within the pore channel. In some aspects the system comprises one, or most optionally two, d-block metal atoms bound to the pore within the pore channel. As will be appreciated by the skilled person, the term d-block metal, as used herein, refers to any metal in the d-block of the periodic table, i.e., any metal in any one of groups 3-12 of periodic table. In some aspects, the d-block metal is a transition metal. In some aspects, the d-block metal is a noble metal. In some aspects the d-block metal atoms are metals from any of groups 3-12, 4-12, 5-12, 6-12, 7-12, 8-12, 9-12 or 10-12, optionally metals from any of groups 9-12, typically metal from any of groups 10, 11 or 12. In some aspects the d-block metal atoms are metals from group 10, 11 or 12 of the periodic table. In some aspects the d-block metal atoms are selected from the group consisting of gold, silver, platinum, palladium, cadmium, copper zinc and nickel. In some aspects the d-block metal atoms are selected from the group consisting of gold, cadmium, zinc and nickel. In some aspects the d-block metal atoms are gold atoms.

In some aspects, the pore comprises one or more d-block metal-binding moieties bonded to one or more appendages in the pore. Suitable moieties for binding d-block metals will be well-known to the person skilled in the art. In some aspects the one or more d-block metal-binding moieties protrude into the pore channel. In some aspects, the appendages are polypeptides or peptides and the d-block metal-binding moiety comprises an amino acid side chain. In some aspects, the appendages are polypeptides or peptides and the d-block metal-binding moiety comprises a basic amino acid side chain. In some aspects, the appendages are polypeptides or peptides and the d-block metal-binding moiety comprises an aspartic acid, glutamic acid, lysine, arginine, histidine, serine, threonine, cysteine, tyrosine, asparagine or glutamine side chain. In some aspects where the appendages are polypeptides or peptides, the d-block metal-binding moiety comprises an aspartic acid, glutamic acid, lysine, arginine or histidine side chain. In some aspects where the appendages are polypeptides or peptides, the d-block metal-binding moiety comprises a lysine, arginine or histidine side chain. In some aspects where the appendages are polypeptides or peptides, the d-block metal-binding moiety comprises a histidine side chain.

In some aspects one or more appendages comprise one or more d-block metal-binding moieties. In some aspects, 1, 2, 3, 4, 5, 6, 7, 8, 9, 10 or more appendages comprise one or more d-block metal-binding moieties. In some aspects each of the appendages comprise one or more d-block metal-binding moieties. In some aspects two of the appendages comprise one or more d-block metal-binding moieties. In some aspects each appendage comprising one or more d-block metal-binding moieties comprises one d-block metal-binding moiety. In some aspects each appendage comprising one or more d-block metal-binding moieties comprises 1, 2, 3, 4, 5, 6, 7, 8, 9, 10 or more d-block metal-binding moieties. In some aspects each appendage comprising one or more d-block metal-binding moieties comprises two d-block metal-binding moieties. In some aspects, two of the appendages each comprise one d-block metal-binding moiety.

Typically, the d-block metal-binding moieties protrude into the pore channel, which is typically hydrophilic. The nucleic acid scaffolds in the systems of the invention may be used to direct the positioning of the appendages that comprise the d-block metal-binding moieties. In this manner the relative positions of the d-block metal-binding moieties may be selected, for example to orient the d-block metal-binding moieties at a predetermined distance from each other. In some aspects, the d-block metal-binding moieties will be positioned at about the same distance along the length of the pore channel through the layer of amphipathic molecules.

In some aspects where the appendages are polypeptides or peptides, mutations may be introduced into one or more appendages to direct the position of the amino acid side chain that functions as a d-block metal-binding moiety. In some aspects, one or more appendages in the pore that are polypeptides or peptides may comprise a histidine mutation. In some aspects, the one or more appendages comprise α-hemolysin pore-forming peptide and comprise a T145H or a T115H mutation, optionally a T115H mutation, wherein the residue numbering corresponds to that of SEQ ID NO: 12. In some aspects, the α-hemolysin pore-forming peptide may comprise or consist essentially of a sequence having at least 80%, 85%, 90%, 95%, 96%, 97%, 98%, 99% or 100%, optionally at least 80%, typically at least 90% sequence identity to any one of SEQ ID NOs: 9, 10, 12 13, 117 or 118 or variants thereof. In some aspects, the residue numbering for the T145H mutation or the T115H mutation corresponds to that of SEQ ID NO: 12. In some aspects, the pore may be a heptameric pore. In some aspects the pore may be a heteromeric pore. In some aspects the pore may comprise two α-hemolysin pore-forming peptides comprising a T145H or a T115H mutation, optionally a T115H mutation, and 5 α-hemolysin pore-forming peptides that do not comprise a T145H or T115H mutation.

Methods of Forming Pores

The assemblies of the invention are capable of forming pores in a layer of amphipathic molecules. The systems of the invention comprise an assembly forming a pore in a layer of amphipathic molecules. The invention further provides a method of forming a pore in a layer of amphipathic molecules, the method comprising applying an assembly to a layer of amphipathic molecules, which assembly comprises a nucleic acid scaffold and a plurality of appendages bonded to the scaffold, and thereby causing the appendages to interact to form a pore in the layer of amphipathic molecules. The features of the method, particularly the pore, the layer of amphipathic molecules and the assembly, may be as further defined anywhere herein.

In some aspects "applying" the assembly to a layer of amphipathic molecules comprises contacting the layer of amphipathic molecules with the assembly. As described herein, the nucleic acid scaffold of the assembly co-localises the pore-forming appendages of the assembly and positions the appendages in a favourable orientation for insertion into the layer of amphipathic molecules. Therefore, in some aspects spontaneous insertion of the appendages into the layer of amphipathic molecules will occur. This is typically driven by the formation of favourable non-covalent interactions or bonds between the appendages and the layer of amphipathic molecules, as described herein. In some aspects an applied potential of about −100 mV and −150 mV results in the formation of an open pore. An "open pore" may be defined as a pore having a pore channel with a diameter as defined herein. The open pore typically has a high conductance, for example an open pore may have a mean conductance at −50 mV applied potential of at least 1.2 nS, although it will be appreciated that the pore conductance varies with pore diameter. In some aspects formation of the pore proceeds via an intermediate state having a lower conductance than the open pore. For example, in some aspects where the open pore has a conductance of at least 1.2 nS, the intermediate state may have a conductance of less than 0.8 nS.

In some aspects, the method further comprises forming the assembly by attaching a plurality of appendages to a nucleic acid or to a plurality of nucleic acids. In some aspects, the method comprises forming the assembly by (i) attaching a plurality of appendages to a plurality of nucleic acids, and (ii) forming the scaffold with the plurality of nucleic acids. As described above, the appendages are typically covalently bonded to a nucleic acid of the nucleic acid scaffold, optionally through a flexible linker. Suitable methods for bonding an appendage to a nucleic acid are known in the art and described in detail in the Examples. In some aspects, in a first step, the plurality of appendages are bonded to the plurality of nucleic acids. In some aspects, in a second step, the nucleic acid scaffold is assembled from a plurality of nucleic acids comprising a plurality nucleic acids that are bonded to the appendages. Methods of assembling suitable nucleic acid scaffolds are known to the skilled person or are described in the Examples. Different numbers of appendages may be included in the assembly by changing the number of nucleic acids that are bonded to appendages.

In some aspects, the appendages are attached to the nucleic acid scaffold in an arrangement that enables the appendages to form the pore in the layer of amphipathic molecules. As described herein, the appendages may be bonded to the nucleic acid scaffold at selected predetermined positions, such that the nucleic acid scaffold determines the arrangement of the appendages within the pore. For example the appendages may be bonded at selected positions on the nucleic acid scaffold so that different appendages are arranged in a predetermined repeating pattern in the pore. For example, two different types of appendages, that may be referred to as "A" and "B", may be bonded to the scaffold such that they are arranged in the pore in a selected or pre-determined repeating pattern, such as any one of $[AB]_x$, $[BA]_x$, $[ABA]_x$, $[BAB]_x$, $[ABB]_x$, $[AAB]_x$, $[BAA]_x$, $[BBA]_x$, or combination thereof, or any other alternative arrangements. This is particularly useful for heteromeric pores. This is particularly useful for heteromeric pores formed from polypeptide subunits where particular polypeptide subunits may only interact with certain other polypeptide subunits in the pore.

Devices

The present invention further provides a device comprising:

(a) a layer of amphipathic molecules;
(b) an assembly comprising a nucleic acid scaffold and a plurality of appendages bonded to the scaffold, wherein the appendages form a pore in the layer of amphipathic molecules; and
(c) apparatus for making measurements, optionally electrical measurements, typically measurement of electrical current through the pore.

The features of the device, particularly the layer of amphipathic molecules and the assembly, may be as further defined anywhere herein.

As described herein, the layer of amphipathic molecules may comprise a triblock copolymer comprising a first outer hydrophilic polymer segment, an inner hydrophobic polymer segment and a second outer hydrophilic polymer segment. The layer of amphipathic molecules may comprise poly(2-methyloxazoline)-block-poly(dimethylsiloxane)-block-poly(2-methyloxazoline) (PMOXA-PDMS-PMOXA). In some aspects, the layer of amphipathic molecules may comprise a plurality of amphiphilic lipids comprising a hydrophilic head group bonded to a hydrophobic tail group, optionally phospholipids. In some aspects, the layer of amphipathic molecules may be a bilayer, optionally a lipid bilayer. In some aspects, at least one of, optionally at least three of, and typically each of, the appendages are inserted into the layer of amphipathic molecules. In some aspects, at least one of, optionally at least three of, and typically each of, the appendages span the layer of amphipathic molecules.

In some aspects the device may comprise one layer of amphipathic molecules and one assembly as defined herein, and therefore one pore. In some aspects, the plurality of appendages bonded to the scaffold is a first plurality of appendages which form a first pore in the layer of amphipathic molecules, and the assembly further comprises one or more further pluralities of appendages bonded to the scaffold, wherein the appendages in each further plurality form a further pore in the layer of amphipathic molecules. Thus, a plurality of pores in the layer of amphipathic molecules may be formed. In some aspects the device may comprise one layer of amphipathic molecules and a plurality of assemblies as defined herein, and thus a plurality of pores in the layer of amphipathic molecules. In such aspects the two distinct sides of the layer of amphipathic molecules may be designated as the cis and trans sides of the layer. In some aspects, all of the assemblies may be arranged such that the nucleic acid scaffolds are located on the same side of the layer of amphipathic molecules, which may be the cis side or the trans side. In some aspects a first plurality of assemblies may be arranged such that the nucleic acid scaffolds are located on one side (the cis side) of the layer of amphipathic molecules and a second plurality of assemblies may be arranged such that the nucleic acid scaffolds are located on the other side (the trans side) of the layer of amphipathic molecules. In some aspects the device may comprise a plurality of layers of amphipathic molecules and a plurality of assemblies as defined herein, and thus a plurality of pores in a plurality of layers of amphipathic molecules may be formed. Thus, in some aspects the device may comprise an array of layers of amphipathic molecules all comprising pores formed according to the systems of the invention.

In some aspects, the assembly may interact with at least one other assembly. In some aspects, the assembly may interact with at least 1, 2, 3, 4, 5, 6, 7, 8, 9 or at least 10 other assemblies. In some aspects, the assembly may interact with about 1-50, 1-30, 1-25, 1-20, 1-15, 1-12, 1-10, 1-8, 1-5 or 1-3 other assemblies, optionally about 1-10 other assemblies. In some aspects, the interaction between the assemblies may be mediated by the nucleic acid scaffold. Thus, in some aspects, the nucleic acid scaffold of an assembly may interact with the nucleic acid scaffold of at least one other assembly. In some aspects, the nucleic acid scaffold of an assembly may interact with at least 1, 2, 3, 4, 5, 6, 7, 8, 9 or at least 10 other nucleic acid scaffold of other assemblies. In some aspects, the nucleic acid scaffold of the assembly may interact with about 1-50, 1-30, 1-25, 1-20, 1-15, 1-12, 1-10, 1-8, 1-5 or 1-3 other nucleic acid scaffolds of other assemblies, optionally about 1-10 other nucleic acid scaffolds of other assemblies. For example, as the skilled person will appreciate, a nucleic acid within the nucleic acid scaffold may be extended to provide a single-stranded sequence that may hybridise to a complementary single-stranded sequence on another nucleic acid scaffold. In some aspects, the interactions may be covalent or non-covalent. In some aspects the interactions may comprise hybridisation between at least two nucleic acid sequences. In some aspects, the interactions may be mediated by any of the docking moieties described herein, wherein interacting assemblies comprise complementary docking moieties. In some aspects, the assemblies may interact to form an array or matrix, optionally a regular array or matrix, of assemblies. In some aspects, the assemblies may interact to form a two-dimensional or three-dimensional array or matrix, optionally a two-dimensional or three-dimensional regular array or matrix, of assemblies.

The device may comprise a chamber comprising an aqueous solution and a barrier that separates the chamber into two sections. The barrier typically has an aperture which comprises within it the layer of amphipathic molecules within which the pore is formed. Alternatively, the barrier may comprise a layer of amphipathic molecules in which the pore is formed and/or is present. Typically, the device comprises an apparatus for measuring electrical current through the pore. In some aspects the device is a biosensor. In some aspects the device is configured to detect a target analyte, as defined herein. In some aspects, the device may be configured to detect a target analyte entering or translocating through the pore channel. In some aspects, the device may be configured to analyse one or more characteristics of a target analyte. The device of the invention may be adapted or configured for use in any of the methods described herein. Thus, features of the methods described herein may equally apply to the devices of the invention.

The device may comprise apparatus such as that described in International Application No. PCT/GB08/000562 (WO 2008/102120), incorporated herein by reference. A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85, incorporated herein by reference), and FET measurements (International Application WO 2005/124888, incorporated herein by reference). Optical measurements may be combined with electrical measurements (Soni G V et al., Rev Sci Instrum. 2010 January; 81(1):014301, incorporated herein by reference). The measurement may be a transmembrane current measurement such as measurement of ionic current flowing through the pore. The apparatus for making electrical measurements may comprise standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312, all incorporated herein by reference. Alternatively, the apparatus for making electrical measurements may comprise a multi-channel system, for example as described in International Application WO 2009/077734 and International Application WO 2011/067559, incorporated herein by reference. The apparatus may also comprise an electrical circuit capable of applying a potential and measuring an electrical signal across the layer of amphipathic molecules and pore. The apparatus may comprise a patch clamp or a voltage clamp, optionally a voltage clamp. Suitable conditions in which to operate suitable apparatus for measuring ionic currents through a pore in a layer of amphipathic molecules are known in the art and described in the Examples.

Methods

In some aspects the pore-forming assemblies and systems and devices of the invention comprising a pore may be useful for detecting a target analyte, optionally in a sample. In some aspects the pore-forming assemblies and systems and devices of the invention comprising a pore may be useful for characterising or analysing one or more characteristics of a target analyte, optionally in a sample. In some aspects the pore-forming assemblies and systems and devices of the invention comprising a pore may be useful for characterising or analysing one or more characteristics of a target polynucleotide. In some aspects the pore-forming assemblies and systems and devices of the invention comprising a pore may be useful for sequencing a target polynucleotide. In some aspects the pore-forming assemblies and systems and devices of the invention comprising a pore may be useful in constructing synthetic or artificial signalling networks. Such signalling networks may comprise translocating target molecules, or molecules of interest, as described herein, across a layer of amphipathic molecules, for example, in response to a stimulus or to induce an effect.

Methods of Transporting Molecules

In some aspects, the present invention provides a method of transporting a molecule of interest across a layer of amphipathic molecules, the method comprising contacting the molecule of interest (or target analyte) with a pore formed by a system as defined anywhere herein; wherein the molecule of interest moves through the pore and across the layer of amphipathic molecules.

The present invention further provides a method of transporting a molecule of interest across a layer of amphipathic molecules, the method comprising:

(a) contacting the molecule of interest (or target analyte) with a pore formed by a system as defined anywhere herein; and (b) applying a potential across the layer of amphipathic molecules, thereby transporting the molecule of interest through the pore and across the layer of amphipathic molecules. The features of the method, particularly the molecule of interest (which may be defined equivalently to the target analyte), the system and the layer of amphipathic molecules, may be as further defined herein.

In some aspects any molecule of interest may be transported across the layer of amphipathic molecules according to the methods of the invention. In some aspects the molecule of interest must be smaller in size than the diameter of the pore. In some aspects, the molecule of interest may comprise, or consist essentially of, a ligand, an analyte, an ion, a small organic molecule, a protein, a peptide, a polypeptide, a protein domain, a protein fragment, a protein subunit, a chemical moiety, an antibody, and antibody fragment, an enzyme, a phosphoprotein, a glycoprotein, a lipoprotein, a lipid, a membrane lipid, a phospholipid, a carbohydrate, a simple sugar, a disaccharide, a polysaccharide, a nucleic acid, a polynucleotide, an oligonucleotide, a DNA molecule, an RNA molecule, an XNA molecule, a nucleoprotein, a small molecule, a chemical entity, an analyte, a drug, a pharmaceutical, an antibiotic, a vitamin, a banned substance, an illicit drug, a drug of addiction, a chemotherapeutic agent, a disease biomarker, a pathogen-derived molecule, such as a viral, bacterial, protozoan or fungal protein, lipid, carbohydrate or nucleic acid, or combination thereof. In some aspects, the molecule of interest is selected from the group consisting of an electron, a proton, an ion, a metal ion, a coordination complex comprising a metal ion and one or more ligands attached thereto, an inorganic salt, a small molecule, a polymer, an amino acid, a peptide, a polypeptide, a protein, a nucleotide, a polynucleotide, an oligonucleotide, a dye, a bleach, a fluorescent molecule, a drug, a pharmaceutical, and combinations thereof. In some aspects, the molecule of interest is selected from the group consisting of an ion, a metal ion, a coordination complex comprising a metal ion and one or more ligands attached thereto, an inorganic salt, a small molecule, a polymer, an amino acid, a peptide, a polypeptide, a protein, a nucleotide, a polynucleotide, an oligonucleotide, a dye, a bleach, a fluorescent molecule, a drug, a pharmaceutical, and combinations thereof.

The contacting may be preceded by placing the molecule in the vicinity of the pore and the molecule may then contact the pore, for example, the molecule may enter the pore by diffusion or the action of an electrokinetic force. In some aspects, the potential applied across the layer of amphipathic molecules is selected from the group consisting of electrical potential, electrochemical potential, chemical potential, solute potential, pressure potential, an analyte concentration gradient, a pressure gradient, an electroosmotic potential and combinations thereof. Electroosmosis is another possible driving force. The potential applied may depend on certain characteristic of the molecule of interest and the skilled person would be capable of selecting a suitable potential to apply. For example, an electrical potential or electrochemical potential would only be suitable for translocating charged molecules through the pore.

Methods of Detecting and/or Characterising a Target Analyte

In present invention provides a method of detecting and/or characterising a target analyte, comprising:

(a) contacting the target analyte with a pore formed in a system as defined anywhere herein; and (b) taking one or more measurements (i) as the analyte moves with respect to the pore, or (ii) of the presence of the analyte within the pore, wherein the measurements are indicative of the presence of and/or one or more characteristics of the target analyte, and thereby detecting and/or characterising the target analyte.

In some aspects, step (b) comprises measuring the current passing through the pore as the analyte moves with respect to the pore wherein the current is indicative of the presence of and/or one or more characteristics of the analyte and thereby detecting and/or characterising the analyte. As used anywhere herein, contacting may be preceded by placing the target analyte in the vicinity of the pore, and then the target analyte may contact the pore, for example the target analyte may enter the pore by diffusion or the action of an electrokinetic force.

In some aspects any target analyte may be detected or characterised according to the method of the invention. In some aspects the target analyte must be smaller in size than the diameter of the pore. In some aspects the target analyte must be capable of entering or translocating through the pore. In some aspects, the target analyte may comprise, or consist essentially of, a ligand, an analyte, an ion, a small organic molecule, a protein, a peptide, a polypeptide, a protein domain, a protein fragment, a protein subunit, a chemical moiety, an antibody, and antibody fragment, an enzyme, a phosphoprotein, a glycoprotein, a lipoprotein, a lipid, a membrane lipid, a phospholipid, a carbohydrate, a simple sugar, a disaccharide, a polysaccharide, a nucleic acid, a polynucleotide, an oligonucleotide, a DNA molecule, an RNA molecule, an XNA molecule, a nucleoprotein, a small molecule, a chemical entity, an analyte, a drug, a pharmaceutical, an antibiotic, a vitamin, a banned substance, an illicit drug, a drug of addiction, a chemotherapeutic agent, a disease biomarker, a pathogen-derived molecule, such as a viral, bacterial, protozoan or fungal protein, lipid, carbohydrate or nucleic acid, or combination thereof. In some aspects, the target analyte is a metal ion, an inorganic salt, a polymer, an amino acid, a peptide, a polypeptide, a protein, a nucleotide, a polynucleotide, an oligonucleotide, a dye, a bleach, a pharmaceutical, a drug, a diagnostic agent, a recreational drug, an explosive or an environmental pollutant. The analyte is optionally an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The protein can be an enzyme, an antibody, a hormone, a growth factor or a growth regulatory protein, such as a cytokine. The cytokine may be selected from interleukins, optionally IFN-1, IL-1, IL-2, IL-4, IL-5, IL-6, IL-10, IL-12 and IL-13, interferons, optionally IL-g, and other cytokines such as TNF-a. The protein may be a bacterial protein, a fungal protein, a virus protein or a parasite-derived protein.

The target analyte is optionally a nucleotide, an oligonucleotide or a polynucleotide. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers. The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. In some aspects, the target analyte is a polynucleotide, optionally a DNA or RNA polynucleotide.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The method is for detecting and/or characterising at least one target analyte. The method may comprise detecting and/or characterising two or more target analytes. The method may comprise detecting and/or characterising any number of target analytes, such as 2, 5, 10, 15, 20, 30, 40, 50, 100 or more target analytes. The method may concern characterising two or more analytes of the same type, such as two or more proteins, two or more nucleotides or two or more pharmaceuticals. Alternatively, the method may concern characterising two or more analytes of different types, such as one or more proteins, one or more nucleotides and one or more pharmaceuticals.

The target analyte, which is optionally a polynucleotide, is typically present in any suitable sample. The method may be carried out on a sample that is known to contain or suspected to contain the target analyte, which may be a polynucleotide. Alternatively, the method may be carried out on a sample to test whether the sample contains the target analyte, which may be a polynucleotide. Alternatively, the method may be carried out on a sample to confirm the presence or identity of a target analyte, which may be a polynucleotide, whose presence in the sample is known or expected.

The sample may be a biological sample. The method may be carried out in vitro using a sample obtained from or extracted from any organism or microorganism. The organism or microorganism is typically archaeal, prokaryotic or eukaryotic. The method may be carried out in vitro on a sample obtained from or extracted from any virus. In some aspects, the method may be carried out in vitro using a sample obtained from or extracted from a mammal, optionally a human. The sample may optionally be a fluid sample. In some aspects, the sample may comprise a body fluid of a human, optionally a patient. In some aspects, the sample may be urine, lymph, saliva, mucus or amniotic fluid but is optionally blood, plasma or serum. In some aspects, the sample is human in origin, but alternatively it may be from another mammalian animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton. In some aspects, the sample may be a non-biological sample. The non-biological sample is optionally a fluid sample. Examples of non-biological samples include surgical fluids, water such as drinking water, sea water or river water, and reagents for laboratory tests. The sample is typically processed prior to being used in the method, for example by centrifugation or by passage through a membrane that filters out unwanted molecules or cells, such as red blood cells. The sample may be analysed immediately upon being taken. Alternatively, the sample may be stored prior to use, optionally below −70° C.

In some aspects, the method comprises detecting a target analyte. In some aspects, the method comprises characterising a target analyte. In some aspects, the method comprises detecting and characterising a target analyte. In some aspects detecting a target analyte comprises confirming the presence of a pre-selected analyte. In some aspects detecting a target analyte comprises identifying the analyte. In some aspects detecting a target analyte comprises confirming the presence of or identifying a related analyte, such as a metabolite or intermediate, which may indicate the presence of the target analyte. In some aspects, characterising a target analyte comprises measuring one or more characteristics of the target analyte. In some aspects, characterising a target analyte comprises measuring at least one characteristic of the target analyte. In some aspects, characterising a target analyte comprises measuring one, two, three, four, five or more characteristics of the polynucleotide. In some aspects, characterising a target analyte comprises measuring a plurality of characteristics of the target analyte. The characteristics may comprise, charge, size, sequence, length, composition, identity, or any other suitable characteristics.

In some aspects the target analyte is a polynucleotide and the method may comprise measuring one, two, three, four, five or more characteristics of the polynucleotide. The one or more characteristics are optionally selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as (i), (ii), (iii), (iv), (v), (i,ii), (i,iii), (i,iv), (i,v), (ii,iii), (ii,iv), (ii,v), (iii,iv), (iii,v), (iv,v), (i,ii,iii), (i,ii,iv), (i,ii,v), (i,iii,iv), (i,iii,v), (i,iv,v), (ii,iii,iv), (ii,iii,v), (ii,iv,v), (iii,iv,v), (i,ii,iii,iv), (i,ii,iii,v), (i,ii,iv,v), (i,iii,iv,v), (ii,iii,iv,v) or (i,ii,iii,iv,v). Different combinations of (i) to (v) may be measured for the first polynucleotide analysed compared with the second or any subsequent polynucleotide analysed, including any of those combinations listed above.

In some aspects the target analyte may be a protein. In some aspects the pores formed by the assemblies of the invention and in the systems of the invention are large pores, typically larger than naturally occurring pores. Such large pores may be suitable for analysing biological macromolecules such as proteins and even multimeric protein complexes. Thus, the methods of charactering a target analyte described herein may also be applied, wherein the target analyse is a protein, to characterise protein shape, protein-protein interactions, protein conformational changes and enzyme mechanisms. In some aspects the protein target analyte may move with respect to the pore, optionally under the control of an applied potential as described herein. For example, the protein may translocate through the pore channel. Typically, changes in electrical current may be measured where the protein undergoes a conformational change or a change in shape during translocation through the pore.

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85, incorporated by reference), and FET measurements (International Application WO 2005/124888, incorporated by reference). Optical measurements may be combined with electrical measurements (Soni G V et al., Rev Sci Instrum. 2010 January; 81(1):014301, incorporated by reference). The measurement may be a transmembrane current measurement such as measurement of ionic current flowing through the pore. Electrical measurements may be made using standard single channel recording equipment as described in Stoddart D et al., Proc Natl Acad Sci, 12; 106(19):7702-7, Lieberman K R et al, J Am Chem Soc. 2010; 132(50):17961-72, and International Application WO 2000/28312, all of which are incorporated by reference. Alternatively, electrical measurements may be made using a multi-channel system, for example as described in International Application WO 2009/077734 and International Application WO 2011/067559, both incorporated by reference.

The method is optionally carried out with a potential applied across the layer of amphipathic molecules. The applied potential may be a voltage potential. Alternatively, the applied potential may be a chemical potential. An example of this is using a salt gradient across the layer of amphipathic molecules. A salt gradient is disclosed in Holden et al., J Am Chem Soc. 2007 Jul. 11; 129(27):8650-5, incorporated by reference. In some instances, the current passing through the pore as a polynucleotide moves with respect to the pore is used to estimate or determine the sequence of the polynucleotide. This is strand sequencing. The method may involve measuring the current passing through the pore as the target analyte, which may be a polynucleotide, moves with respect to the pore. Therefore the apparatus used in the method may also comprise an electrical circuit capable of applying a potential and measuring an electrical signal across the membrane and pore. The methods may be carried out using a patch clamp or a voltage clamp. The methods optionally involve the use of a voltage clamp.

The method of the invention may involve the measuring of a current passing through the pore as the target analyte, which may be a polynucleotide, moves with respect to the pore.

Suitable conditions for measuring ionic currents through transmembrane protein pores are known in the art and described in the Examples. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is optionally in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is optionally in the range 100 mV to 240 mV and typically in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. In some aspects KCl, NaCl and a mixture of potassium ferrocyanide and potassium ferricyanide are used. The charge carriers may be asymmetric across the layer of amphipathic molecules. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is optionally from 150 mM to 1 M. The method is optionally carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a target analyte, which may be a nucleotide, to be identified against the background of normal current fluctuations.

The method is typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is optionally about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

As discussed above, in some aspects the target analyte is a polynucleotide. Thus, the present invention provides a method for characterising a target polynucleotide, wherein the method comprises:

a) contacting the polynucleotide with a pore formed in a system as defined herein, such that the polynucleotide moves with respect to the pore; and b) taking one or more measurements as the polynucleotide moves with respect to the pore, wherein the measurements are indicative of one or more characteristics of the polynucleotide, and thereby characterising the target polynucleotide. Wherein any of the features of the method may be as further defined anywhere herein. As described herein, in some aspects, the one or more characteristics are selected from (i) the length of the polynucleotide, (ii) the identity of the polynucleotide, (iii) the sequence of the polynucleotide, (iv) the secondary structure of the polynucleotide and (v) whether or not the polynucleotide is modified. In some aspects the polynucleotide may bind to a docking moiety on the assembly of the system forming the pore. In some aspects the polynucleotide moves with respect to the pore under the control of an applied potential, optionally an electrical potential.

In some aspects, step a) of the method further comprises contacting the polynucleotide with a polynucleotide binding protein such that the protein controls the movement of the polynucleotide through the pore. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement. The polynucleotide binding protein is optionally derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme.

The enzyme may be any of those disclosed in International Application No. PCT/GB10/000133 (published as WO 2010/086603), incorporated herein by reference. Suitable enzymes are polymerases, exonucleases, helicases and topoisomerases, such as gyrases. Suitable enzymes include, but are not limited to, exonuclease I from *E. coli*, exonuclease III enzyme from *E. coli*, RecJ from *T. thermophilus* and bacteriophage lambda exonuclease, TatD exonuclease and variants thereof. The enzyme is most optionally derived from a helicase, such as Hel308 Mbu, Hel308 Csy, Hel308 Tga, Hel308 Mhu, TraI Eco, XPD Mbu or a variant thereof. Any suitable helicase may be used. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736, which are all incorporated herein by reference.

Additionally, the present invention provides a method of sequencing, comprising:

(a) contacting a molecule to be sequenced with a system comprising (i) an assembly comprising a nucleic acid scaffold and a plurality of appendages bonded to the scaffold, and (ii) a layer of amphipathic molecules, wherein the appendages form a pore in the layer of amphipathic molecules;
(b) applying a voltage and driving a current across the layer of amphipathic molecules;
(c) passing the molecule to be sequenced through the pore formed by the assembly; and
(d) determining the sequence of the molecule based on the characteristic disruption or modulation in the electrical signal caused by each monomeric unit as it passes through the pore.

Any of the features of the method of sequencing of the invention may be as further defined herein. The method of sequencing has many similarities to the method of detecting and/or characterising a target analyte, which is optionally a polynucleotide. Thus many of the features of the methods of sequencing may be as further defined for the methods of detecting and/or characterising a target analyte.

In some aspects the molecule to be sequenced is a polynucleotide or a polypeptide, optionally a polynucleotide. In some aspects, an electrical current is passed across the layer of amphipathic molecules. In some aspects an applied potential, optionally an electrical potential, is passed across the layer of amphipathic molecules. The molecule to be sequenced may be passed through the pore by the applied current or potential, optionally an electrical potential. In some aspects, a protein may control the movement of the molecule to be sequenced through the pore. In some aspects such a protein may bind to the molecule to be sequenced and move or translocate the molecule to be sequenced, to processively pass the molecule to be sequenced through the pore. In some aspects, where the molecule to be sequenced is a polynucleotide, a polynucleotide binding protein may control the movement of the polynucleotide through the pore, as described herein.

In some aspects, the molecule to be sequenced is a polymer comprising monomeric units, wherein each type of monomeric unit is chemical different. In such instances, as each monomeric unit passes through the pore it will disrupt the electrical signal in a unique manner. The disruption or modulation in the electrical signal caused by each monomeric unit as it passes through the pore may be measured and the characteristic disruption or modulation of each type of monomeric unit allows for the monomeric unit to be identified. In some aspects, the monomeric unit is a nucleotide. Each of the different nucleotides, adenine (A), guanine (G), cytosine (C), thymine (T) and uracil (U) provide a different characteristic disruption or modulation in the electrical signal, which allows for the polynucleotide to be sequenced. In some aspects, the monomeric unit is an amino acid. Each of the different amino acids, Alanine (Ala), Arginine (Arg/R), Asparagine (Asn/N), L-Aspartic acid (Asp/D), L-Cysteine (Cys/C), L-Glutamic acid (Glu/E), L-Glutamine (Gln/Q), Glycine (Gly/G), L-Histidine (His/H), L-Isoleucine (Ile/I), L-Leucine (Leu/L), L-Lysine (Lys/K), L-Methionine (Met/M), L-Phenylalanine (Phe/F), L-Proline (Pro/P), L-Serine (Ser/S), L-Threonine (Thr/T), L-Tryptophan (Trp/W), L-Tyrosine (Tyr/Y), L-Valine (Val/V), L-Selenocysteine (Sec/U), L-Pyrrolysine (Pyl/O), provide a different characteristic disruption or modulation in the electrical signal, which allows for the polypeptide to be sequenced.

Methods of Performing Reactions

The present invention further provides a method of performing an organic reaction in a pore, the method comprising contacting a system of the invention, optionally as further defined anywhere herein, with the reactant or reactants necessary for the organic reaction. In some aspects, the system comprises (a) a layer of amphipathic molecules; and (b) an assembly comprising a nucleic acid scaffold and a plurality of appendages bonded to the scaffold, wherein the appendages form a pore in the layer of amphipathic molecules, optionally which system is as further defined anywhere herein. In some aspects the system comprises (a) a layer of amphipathic molecules; and (b) an assembly comprising a nucleic acid scaffold and a plurality of appendages bonded to the scaffold, wherein the appendages form a pore in the layer of amphipathic molecules, wherein the pore is capable of binding one or more d-block metal atoms within the pore channel, optionally which system is as further defined anywhere herein.

The organic reaction may be any reaction that is capable of taking place within the pore channel formed by the pore in the system of the invention. The diameter of the pore channel will typically effect the reactions that may occur in the pore channel. The reactants must be able to enter into, and optionally translocate through, the pore. In some aspects the reactions are small molecule organic reactions. In some aspects the pore may be considered to catalyse the organic reaction. In some aspects one or more d-block metal atoms, as further defined herein, are bound to the pore and catalyse the organic reaction. Therefore, in some aspects the organic reaction may be any organic reaction that may be catalysed by d-block metal atoms. In some aspects the organic reaction maybe a polymerisation reaction, a conjugation reaction, a dimerization reaction, a synthesis reaction or a decomposition reaction. In some aspects the organic reaction is a dimerization reaction, optionally wherein the organic reaction is dimerization of 2,6-anthracene dicarboxylic acid.

In some aspects one reactant may be necessary for the reaction. In some aspects two reactants may be necessary for the reaction. In some aspects 1, 2, 3, 4, 5, 6, 7, 8, 9, 10 or more reactants may be necessary for the reaction. The skilled person would be capable of identifying the particular reactants that are necessary for a particular reaction.

Kits

The present invention further provides a kit for characterising a target polynucleotide comprising an assembly, a system or a device of the invention. Any of the features or components of the assemblies, systems or devices of the invention may be as further defined herein. The kit of the invention may additionally comprise one or more other reagents or instruments which enable any of the aspects or methods mentioned herein to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

Example 1

This Example shows that a ring-shaped DNA scaffold that is not anchored to the lipid bilayer (23, 24) can bring together a defined number of 38 amino acid amphiphilic peptides. The peptide we used (CGG-cWza[T376R], the Wza peptide hereafter) is a variant of the D4 domain of the *Escherichia coli* polysaccharide transporter Wza (9, 10), which is an octameric protein. The scaffolded Wza peptides formed conducting nanopores of which octamers are stable and of uniform conductance. Scaffolds with more than eight peptides yielded nanopores with the same conductance as octamers. When the scaffold was removed after bilayer insertion, the pores were lost within minutes, indicating the importance of the scaffold for the stability of these specific nanopores. Finally, the scaffold can add functionality to the peptide nanopores by acting as a docking site for tagged oligonucleotides near the nanopore entrance.

Materials and Methods

Materials. Oligonucleotides were purchased from Biomers or Sigma Aldrich as HPLC-purified dried samples. All Wza peptides were purchased from Peptide Protein Research Ltd at >95% purity (HPLC) as lyophilized powders. Precast gels were purchased from Bio-Rad, lipids from Avanti Polar Lipids and all other chemicals from Sigma Aldrich, unless otherwise stated.

Peptide-oligonucleotide conjugation. The preparation of peptide-oligonucleotide conjugates was based, in part, on a published procedure (49). Briefly, 10 nmol (20 μl, 500 μM) of 5'-amino-C6-functionalized oligonucleotide was mixed with 60 μl of 100 mM potassium phosphate, pH 7.2, and 500 nmol of a bifunctional linker, and incubated for 2 h at room temperature. For uncleavable peptide-oligonucleotide conjugates, 21 μl of 10 mg $ml^{-1}$ $SMPEG_2$ (Thermo Fisher) in dimethylsulfoxide (DMSO) was used.

For cleavable conjugates, 6 μl of 50 mg $ml^{-1}$ 2-pyridyldithiotetraoxatetradecane-N-hydroxysuccinimide (Thermo Fisher) in DMSO was used. After incubation, 100 mM potassium phosphate was added to the reaction mixture to reach a total volume of 140 μl. Removal of the excess reagent and transfer into 100 mM potassium phosphate, pH 7.2, was done by three desalting steps with PD SpinTrap G25 columns (GE Healthcare). ESI-MS revealed a linker attachment yield of >90% after this step, with about 10% hydrolysis of the maleimide group in the case of $SMPEG_2$.

Meanwhile, the Wza peptide (CGG-cWza[T376R] or cWza[T376R]-GGC) was dissolved in 100 mM potassium phosphate, pH 7.2, with 0.01% (w/w) n-dodecyl-β-d-maltoside (DDM (Thermo Fisher)) to a typical concentration of 0.15 mg $ml^{-1}$. The dissolved peptide was reduced by incubation with immobilized-TCEP disulfide-reducing agarose gel beads (Pierce/Thermo Fisher). After removal of the beads, the concentration of the reduced peptide was measured with a NanoDrop spectrometer. Reduced peptide (20 nmol) was added to the triply desalted oligonucleotide-linker solution, and the reaction mixture was incubated at room temperature for 12 h.

The conjugates were purified by HPLC (Agilent Infinity 1260 series) by using a C18 column (4.6×150 mm), with 10 mM tetraethylammonium bromide in MilliQ water, pH 8.5, as the binding buffer (A), and acetonitrile for elution (buffer B). Oligonucleotides were bound to the column in 96% A, and eluted by using a gradient from 4% to 65% B over 10 min at 1 ml $min^{-1}$. Unmodified oligonucleotides were eluted at 30% B, and Wza-peptide-modified oligonucleotides at 45% B. The peptide-modified oligonucleotides were lyophilized, dissolved in 50 μl of 100 mM potassium phosphate, pH 7.2, diluted to 5 μM and stored at −80° C. until use.

Annealing of the DNA scaffold with attached Wza peptides. Equal amounts of the 12 oligonucleotides (SEQ ID NOs: 15-20, 22, 23, 25-28) were mixed at an total strand concentration of 200 nM in a total volume of 50 μl that contained 100 mM potassium phosphate, pH 7.2, 0.5 M NaCl and 0.02% w/w DDM, for the peptide-modified oligonucleotides. The oligonucleotides were then annealed in a Veriti Thermal Cycler (Applied Biosystems) by heating the sample for 3 min at 95° C., cooling to 65° C. in 3 min and finally cooling to 4° C. in 4 h. The samples were stored at 4° C. for up to one week until use.

Electrical recordings. A planar lipid bilayer of DPhPC was formed across an aperture of 100 μm diameter in a Teflon film sandwiched between two polycarbonate half cells with a compartment volume of 0.5 ml. The Teflon film was pre-painted with a solution of hexadecane in n-pentane (1% w/w). The assembled chamber was placed in a Faraday cage on an antivibration table. An electrical circuit was then formed by a pair of Ag/AgCl electrodes, each set in 1.5% agarose in 3 M KCl, connected to an Axopatch 200B amplifier and a Digidata 1440AA/D converter. The electrode in the cis compartment was grounded, whereas the electrode in the trans compartment was used as the working electrode. The compartments were filled with electrolyte solution (10 mM HEPES, pH 7.4, 1 M KCl) and DPhPC in n-pentane (3 μl, 5 mg $ml^{-1}$) was added to each side. After evaporation of the n-pentane, bilayers were formed by using the Montal-Mueller technique (50). Peptide-bearing DNA scaffolds (1-4 nM) or scaffold-free peptides (150-400 nM) were added to the cis compartment and the insertion of pores into the bilayer was observed under an applied potential of −100 or −150 mV. Data were recorded using pClamp 10.3 (Molecular Devices) with a low-pass filter frequency of 2 kHz and a sampling frequency of 10 kHz, unless stated otherwise. The data were analysed and prepared for presentation with Clampfit.

Coarse-grained molecular dynamics simulations (oxDNA2). All coarse-grained molecular dynamics simulations were performed by using the oxDNA2 simulation code, available from http://dna.physics.ox.ac.uk (S1, S2). We used a periodic cubic box of 150 units (128 nm). To generate the input configurations, the single-stranded oligos were hybridized using temporary harmonic traps between complementary bases. The resulting configuration was used as input in a constraint-free virtual-move Monte Carlo simulation with a total of $2\times10^7$ steps, until the free energy no longer decreased. End configurations of that simulation were used as input in subsequent molecular dynamics simulations with and without constraints. All simulations were performed at 25° C. and at an ionic strength of 0.5 M.

To probe the flexibility of the scaffold, an external force was applied to all terminal 3' and 5' nucleotides in the direction perpendicular to the plane of the ring. To maintain a zero net force, the same external force was applied in the opposite direction to all hinge nucleotides (FIG. 1*a*). Alternatively, a radial force was applied to push all arms outward, implemented as sets of harmonic traps between terminal 5' nucleotides of every pair of arms at opposite ring positions with an equilibrium separation of 19.5 nm. The applied forces were increased linearly from 0 to their final value during a 1.5 μs loading stage and kept constant afterwards.

Configurations were visualised using VMD (S3) and Chimera (UCSF) (S4). An atomic model of the scaffold was made from coarse-grained configurations by using a Python script kindly provided by Dr Lorenzo Rovigatti (S5). The base order, which is 3'→5' in the oxDNA files, was inverted using a custom-written Matlab script to comply with the 5'→3' PDB convention, and missing P—O bonds were added using the PyMol bond tool.

Transmission electron microscopy. Samples for TEM were annealed at a strand concentration of 100 nM in 100 mM Tris.HCl buffer, pH 7.5, without added salt. The annealed mixture was 50-100 times diluted in 100 mM Tris.HCl buffer, applied to freshly glow-discharged 400-mesh carbon-coated copper grids (TAAB) and stained with 2 mM uranyl acetate. EM images were made with a Fei Tecnai 12 Transmission Electron Microscope equipped with a 4 Megapixel Gatan Ultrascan 1000 CCD camera.

Mass spectrometry of intact DNA scaffolds. DNA rings for native mass spectrometry were annealed by mixing 12 oligonucleotides in equal amounts at a strand concentration of 500 nM in 10 aliquots of 100 μL in 100 mM NH4Ac, pH 7.5 and 0.5 M NaCl. The aliquots were combined and purified by five subsequent filter and dilution steps with 1 M ammonium acetate pH 7.5 in Amicon Ultra spin filters with a cutoff molecular weight of 100,000 Da. After the last dilution the DNA rings were concentrated in the same spin filters to final scaffold concentration of 14 μM. Spectra were acquired on a Synapt1 mass spectrometer (Waters) modified for high masses (S6, S7) using gold-coated glass capillaries prepared in-house (S8). Optimized instrument parameters were as follows: capillary voltage 1.8 kV, cone voltage 200 V, extractor 5 V, source backing pressure 7-10 mbar, and a collision cell pressure of 10 psi. Collision cell energy was 30-80 V. Spectra were processed and assigned using MassLynx software.

Stepwise photobleaching. Alexa-647 labeled oligos were prepared by incubating 1 nmol of each 5' amino-C6 modified oligo in 100 mM potassium phosphate, pH 7.2, with 50 nmol of Alexa-647 NHS ester (50 mg/mL in DMSO) in a total volume of 20 μL at room temperature for 2 h. Labeled oligos were purified by HPLC (Agilent Infinity 1260 series) on a C18 column (4.6×150 mm) by using 10 mM tetraethylammonium bromide (TEAB) in MilliQ water, pH 8.5, as the binding buffer (A), and in acetonitrile for elution (B). Labeled oligos were eluted by using a shallow gradient of 5% to 35% B over 30 min at 1 mL/min, as monitored by the absorbance at 260 and 636 nm. The Alexa-modified fractions were lyophilized, dissolved in 20 μL 100 mM potassium phosphate, pH 7.2, and diluted to 500 nM. The purity of the labeled oligos was checked by HPLC and from the ratio of the absorbance at 260 and 647 nm (see Table 1 for details).

The purified Alexa-647 labeled oligos were assembled into ring-shaped scaffolds for use in stepwise photobleaching experiments following the same procedure as for unlabelled oligos. A biotin group, attached to the 3' end of one of the Alexa-647 labeled oligos, was used to anchor the rings to streptavidin-modified glass slides. Control samples with no biotinylated oligos were prepared to check for nonspecific adsorption to the glass slides. For annealing, twelve Alexa-647 labeled oligos or twelve Alexa-647 labeled oligos, of which one contained a 3' biotin, were mixed in equal amounts at a strand concentration of 40 nM in a total volume of 30 μL, containing 100 mM Tris.HCl, pH 7.5 and 0.5 M NaCl. The oligos were then annealed in a Veriti Thermal Cycler (Applied Biosystems) by heating the sample for 3 min at 95° C., cooling to 65° C. in 3 min and finally cooling to 4° C. in 4 h. The samples were used immediately after annealing.

Single-molecule photobleaching steps were counted with total internal reflection fluorescence (TIRF) microscopy, using excitation at 633 nm. DNA scaffolds with single biotin anchors were diluted to 0.5 pM in degassed TBSG (100 mM Tris.HCl pH 7.5, 0.5 M NaCl and 0.8% (w/v) D-glucose). These scaffolds were immobilized on streptavidin-modified glass slides that prepared as described elsewhere (S9), after checking for nonspecific adsorption of a 0.5 pM solution of non-biotinylated scaffolds, and imaged in the presence of an oxygen radical scavenging system (S10, S11). Images were corrected for drift and single-molecule fluorescence intensities were obtained from circular Gaussian fits to the spots. Full photobleaching traces shorter than 3 second and steps that deviated by more than 50% from the average photobleaching step size were excluded from the analysis.

Synthesis and purification of oligo-tagged PEG-5k probes. Oligonucleotide-tagged PEG-5k probes were prepared as follows. Amino-C3 modified 11c' (8-mer) or 11d' (19-mer) (100 nmol) was reacted with 500 nmol dibenzocyclooctyne-sulfo-N-hydroxysuccinimidyl ester in 250 μL 100 mM potassium phosphate, pH 7.2. Without purification, the product was reacted with 10 μmol PEG-5k-azide (100 mg/mL) in 100 mM potassium phosphate, pH 7.2. The adduct was purified by electrophoresis in a 10% acrylamide gel. The PEG-5k modified oligo was extracted from the appropriate gel band, subjected to buffer exchange and then concentrated by using Amicon 3k spin filters. The final oligo concentration was determined from the absorbance at 260 nm.

DNA Sequences

Basic Ring-Shaped Scaffold

The oligonucleotide sequences of this design are as follows:

(1) (SEQ ID NO: 15):
5' [AmC6]-GCCTCGAATCACTCCACTGAACCATCCTCTTGATCTTGTG
AAC 3'

(2) (SEQ ID NO: 16):
5' [AmC6]-TGCCATAAGTATTCAGTGGAGCAGCAACATAGACTCTCAA
CAA 3'

(3) (SEQ ID NO: 17):
5' [AmC6]-GTTCACAAGAATCGAAACCAATGTTAGTGTAGAGTGCATA
AGC 3'

(4) (SEQ ID NO: 18):
5' [AmC6]-CCAACTGGGAATTGGTTTCGACAAGAGGATGGAACTTATG
GCA 3'

(5) (SEQ ID NO: 19):
5' [AmC6]-GCTTATGCACAGAGTCACAGAACGGGAAGCAGAAACGTGT
GAG 3'

(6) (SEQ ID NO: 20):
5' [AmC6]-TCGAGCAATAATCTGTGACTCCTACACTAACAATCCCAGT
TGG 3'

(7) (SEQ ID NO: 27):
5' [AmC6]-CTCACACGTTAGATACGGACACTTGGATAGCGAAAAGCAC

-continued

CTC 3'

(8) (SEQ ID NO: 22):
5' [AmC6]-CACTTCACTTATGTCCGTATCCTGCTTCCCGTATATTGCT
CGA 3'

(9) (SEQ ID NO: 23):
5' [AmC6]-GAGGTGCTTTATGTCAATCGGAGTAGCCTAGCAAGCCTTA
GCC 3'

(10) (SEQ ID NO: 28):
5' [AmC6]-GAAACAGATAACCGATTGACACGCTATCCAAGAAAGTGAA
GTG 3'

(11) (SEQ ID NO: 25):
5' [AmC6]-GGCTAAGGCTAAATGAGTACCCTATGTTGCTGAGATTCGA
GGC 3'

(12) (SEQ ID NO: 26):
5' [AmC6]-TTGTTGAGAGAGGTACTCATTGCTAGGCTACTATATCTGT
TTC 3'

Figure 10:
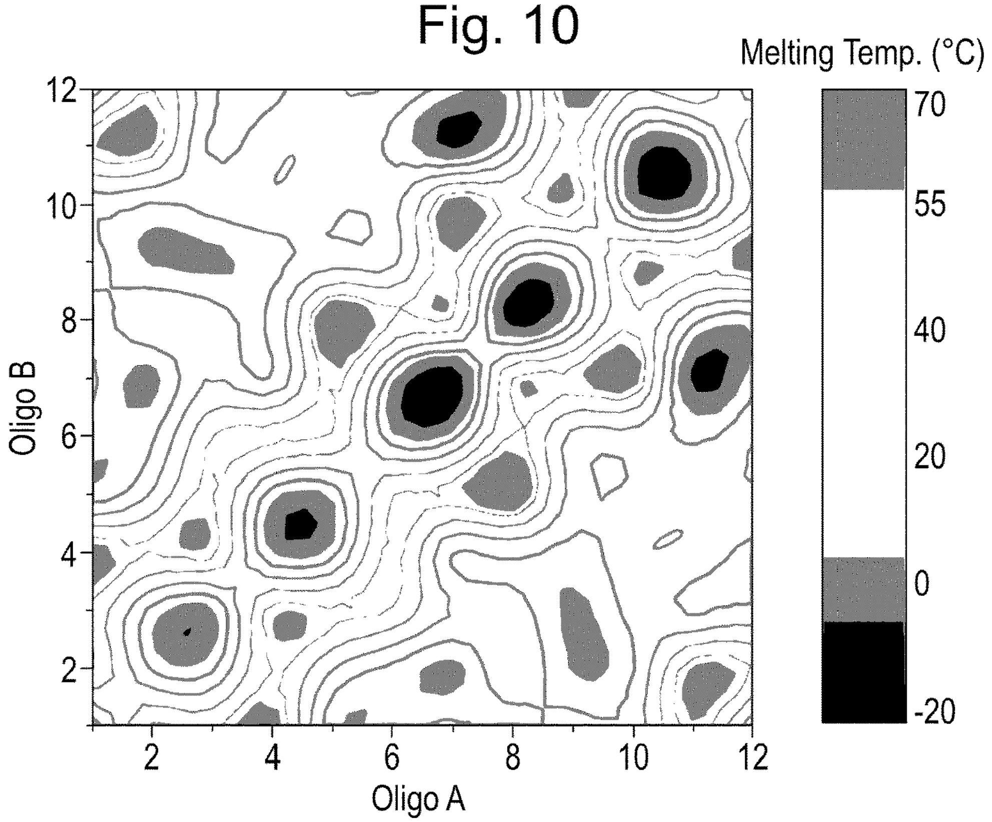
FIG. 10: 2D melting diagram of oligonucleotide duplexes, predicted using the DinaMelt webserver.
Figure 11A:
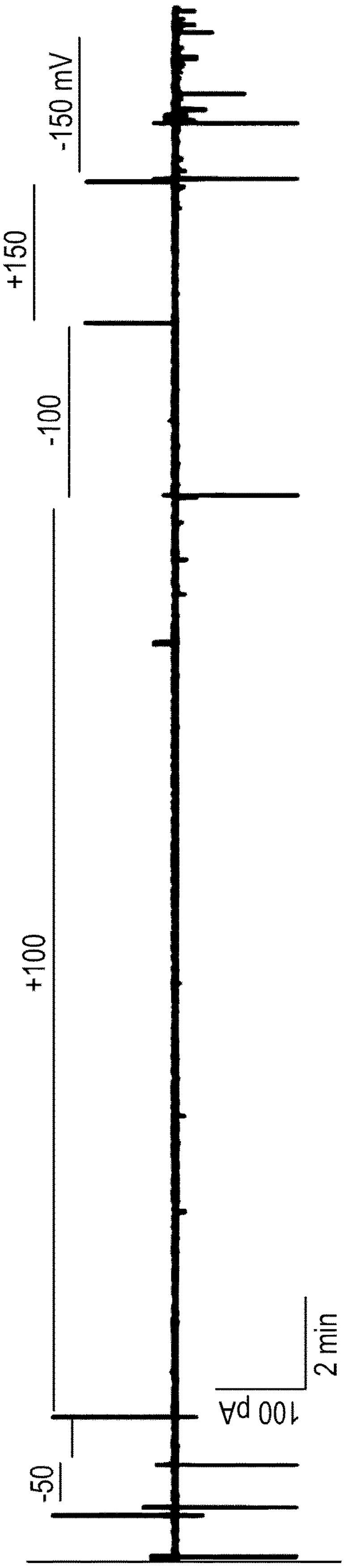
FIG. 11: A. Electrical recording of naked DNA scaffold at 100 nM. The applied potential is indicated at the top of the trace. B. Electrical recording of events elicited by free CGG-cWza[T376R] peptides (250 nM). The applied potential is indicated at the top of the trace. The I-V profile of these events resembles that of the L state of scaffolded Wza nanopores (Fig. S12), but their mean lifetime is of the order of seconds (Fig. S13), whereas scaffolded Wza nanopores are stable for at least an hour (Fig. S6). A transition to a higher conductance state has not been observed for these unscaffolded peptides. C. Electrical recording of events elicited by free cWza[T376R]-GGC peptides (400 nM). The applied potential is indicated at the top of the trace. The mean conductance of these events is smaller than either the L- or H-state of scaffolded Wza nanopores, and their mean lifetime is shorter than a second at any applied potential. D. Electrical recording of events elicited by free oligol-Wza conjugates (400 nM). The applied potential is indicated at the top of the trace. The I-V profile of these events resembles that of the L state of scaffolded Wza nanopores (Fig. S12), but their mean lifetime is of the order of seconds (Fig. S13), whereas scaffolded Wza nanopores are stable for at least an hour (Fig. S6). A transition to a higher conductance state has not been observed for these unscaffolded peptides. E. Electrical recording of events elicited by free *E. coli* Wza D4[R376T] peptides (250 nM). The applied potential is indicated at the top of the trace. These peptides differ from the Wza peptides used for scaffolding: they have only one cationic residue near the C-terminus instead of two, which seems to enhance their stability. The IV profile of these events is shown in Fig. S12 and resembles that of the L-state of scaffolded Wza nanopores at negative applied potentials. Their mean lifetime at positive applied potentials is of the order of seconds, whereas scaffolded Wza nanopores are stable for at least an hour (Fig. S6). A transition to a higher conductance state has not been observed for these unscaffolded peptides.
Figure 11B:
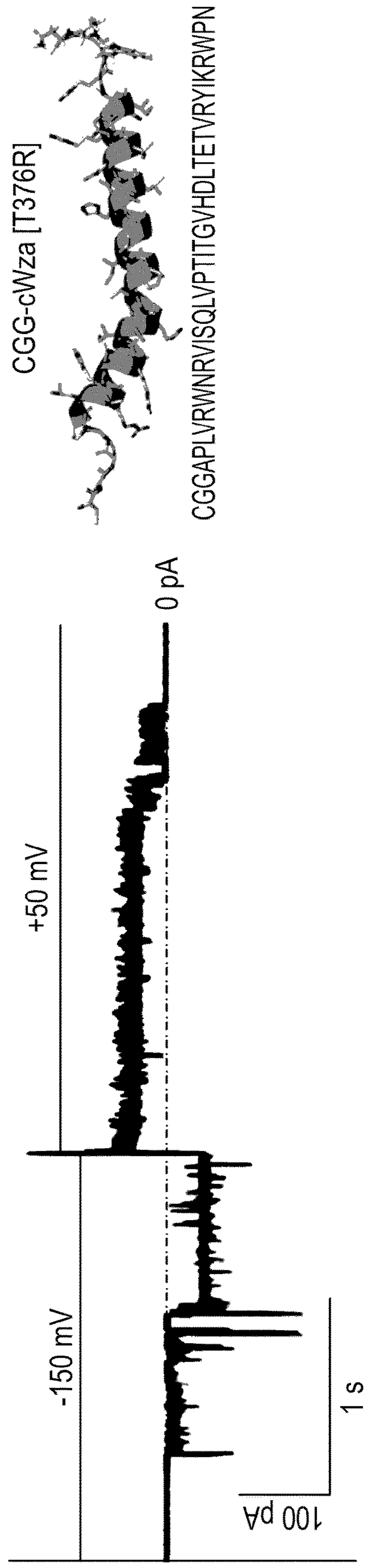
Figure 11C:
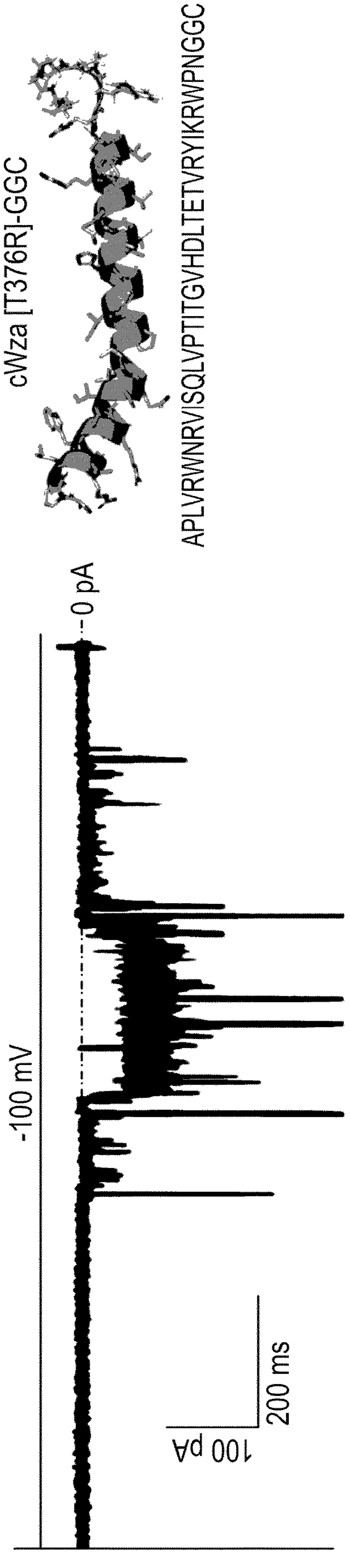
Figure 11D:
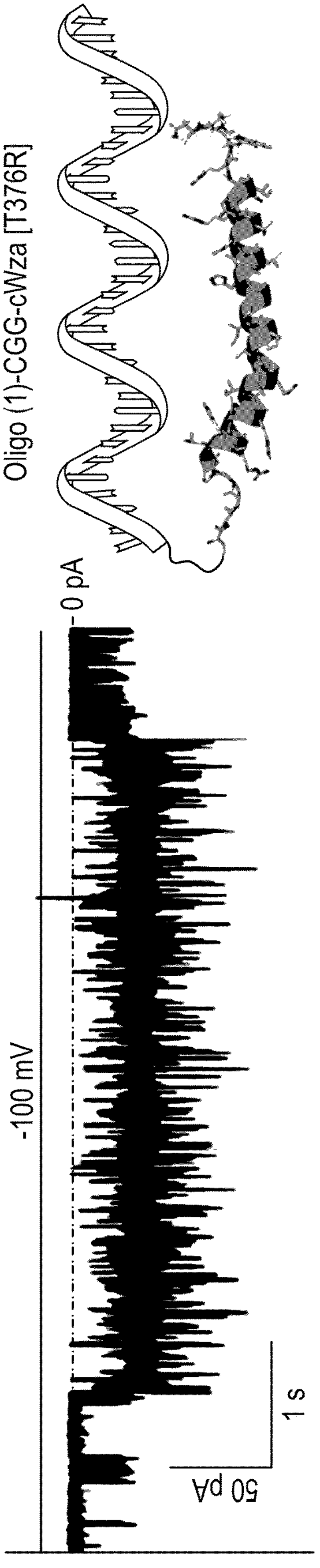
Figure 11E:
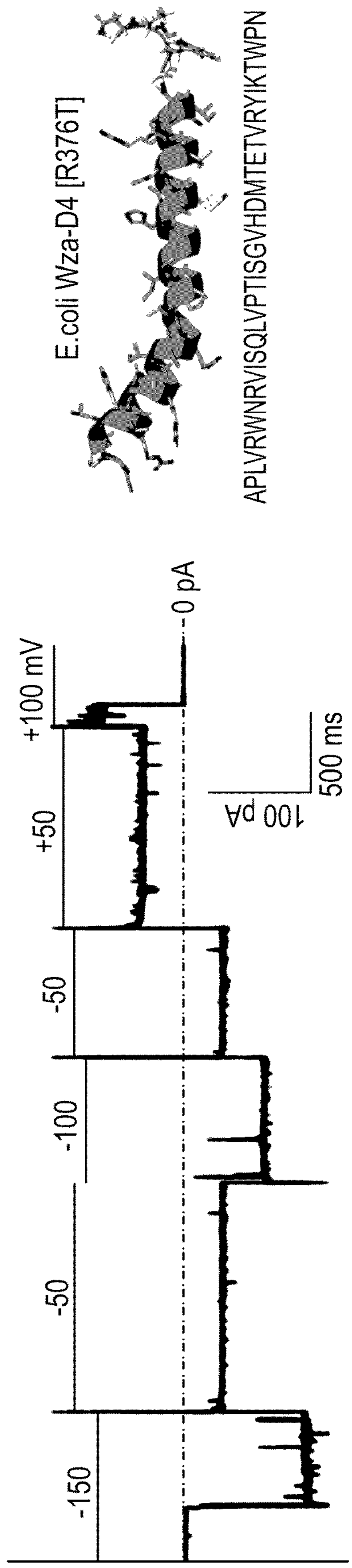
Figure 12A:
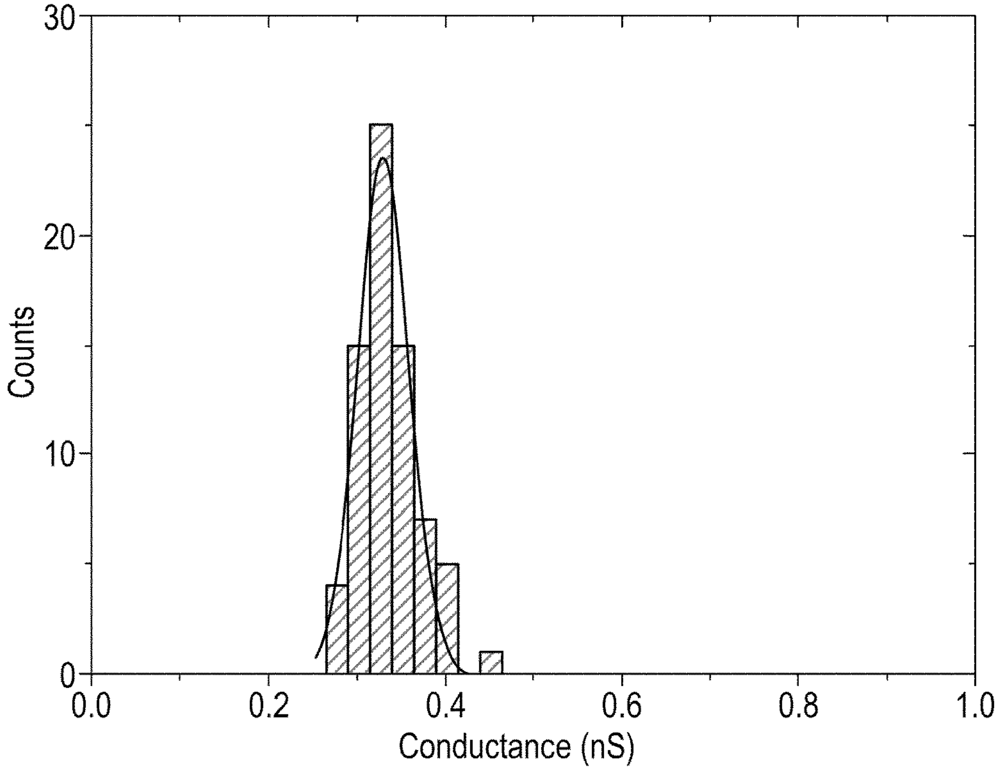
FIG. 12: Event histograms of the mean conductance of events elicited by (a) free CGG-cWza[T376R] peptides at +50 mV (72 events in 3 experiments) and (b) oligo(1)-Wza conjugates at −50 mV (118 events in 2 experiments).
Figure 12B:
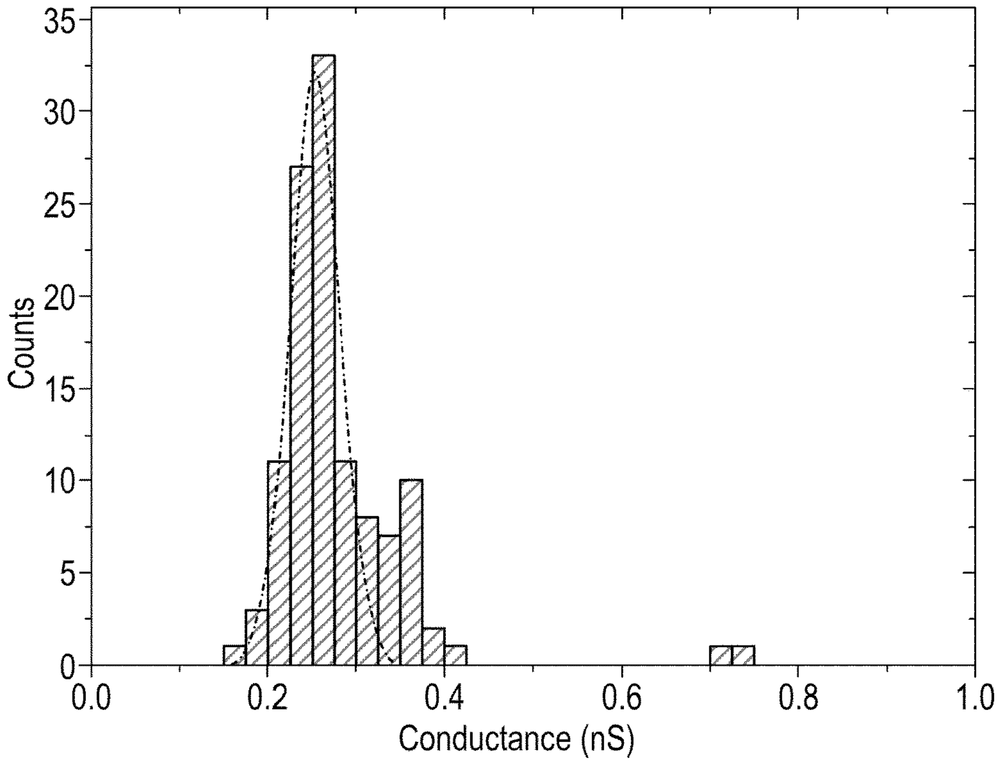

All oligos used for conjugation were modified with a 5' amino-C6 group. All oligos contain two adenosine hinge bases (at positions 11 and 33) included to increase the flexibility of the arms. The oligo sequences were optimized to give low melting temperatures for all non-complementary strands as shown in FIG. 10.

Opened Rings

Figure 1B:
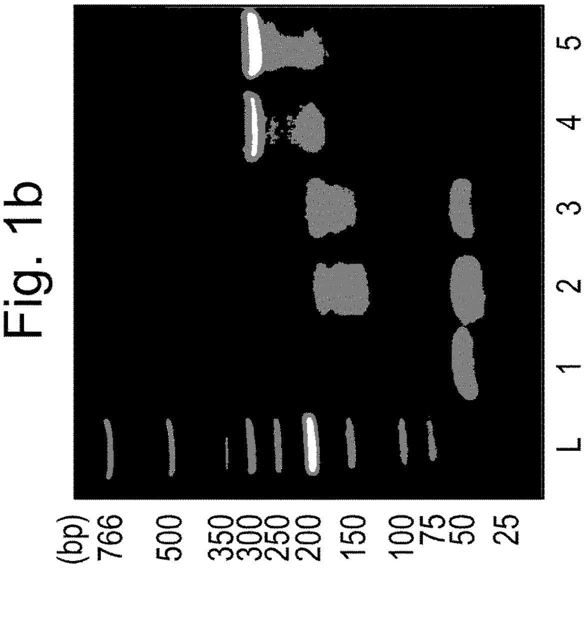
Figure 1C:
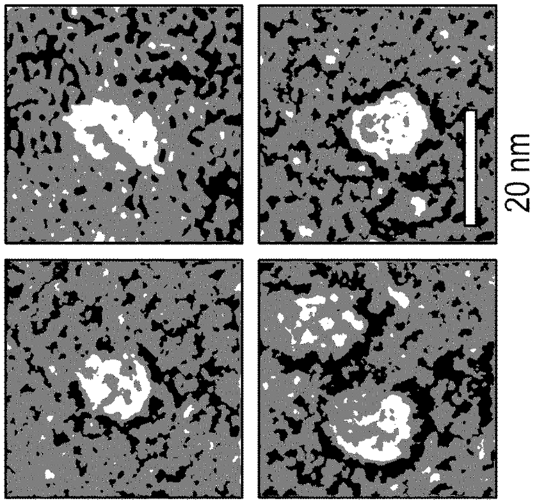
Figure 1D:
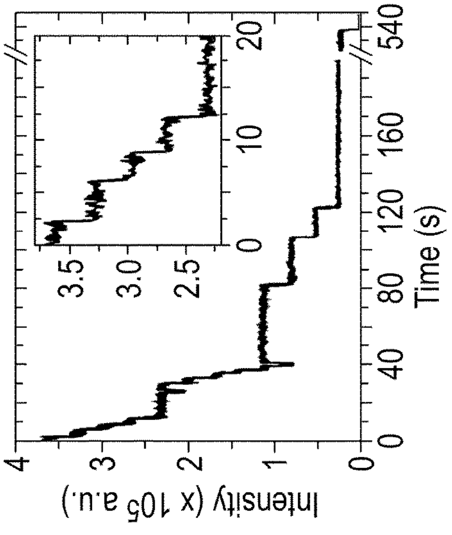
Figure 1E:
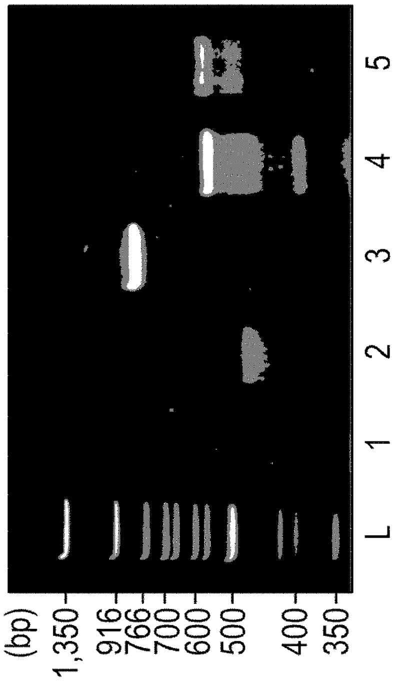

The opened rings used in the restriction assay in FIG. 1*e* were prepared from strands 1-10 of the basic ring, complemented with 11a/b and 12a/b below. These constructs are designed to be identical to the restriction product of the closed ring (oligos 1-12) with RsaI and were used as a control in FIG. 1*e*.

(11a) (SEQ ID NO: 55)
5' GGCTAAGGCTAAATGAGT 3'

(11b) (SEQ ID NO: 56)
5' ACCCTATGTTGCTGAGATTCGAGGC 3'

(12a) (SEQ ID NO: 57)
5' TTGTTGAGAGAGGT 3'

(12b) (SEQ ID NO: 58)
5' ACTCATTGCTAGGCTACTATATCTGTTTC 3'

Rings with Docking Site

Rings with docking sites used in the experiments in FIG. 4 were prepared from strands 1-10 and 12 of the basic ring, complemented with an elongated oligo-11c (8-mer) or oligo 11d (19-mer):

(11c) (SEQ ID NO: 29)
5' GGCTAAGGCTAAATGAGTACCCTATGTTGCTGAGATTCGAGGCACTT
ACTGAGC 3'

(11d) (SEQ ID NO: 59)
5' GGCTAAGGCTAAATGAGTACCCTATGTTGCTGAGATTCGAGGCACTT
ACTGAGCACTATCTGAGC 3'

The tags and tagged oligos used for binding to the docking sites are:

```
(11c'):
5' [AmC3]-GCTCAGTA 3'

(11d') (SEQ ID NO: 60):
5' [AmC3]-GCTCAGATAGTGCTCAGTA 3'

(11d'c30) (SEQ ID NO: 61):
5' C30ATCCCATCCCGCTCAGATAGTGCTCAGTA 3'

(11d-toe) (SEQ ID NO: 62):
5' TACTGAGCACTATCTGAGCGGGATGGGATGGG 3'
```

Rings with Biotin Handles

Rings with one or two biotin handles for stepwise photobleaching experiments were prepared from 5' Alexa-647 labelled strands 1,2,4-9,11 and 12 of the basic ring, and 5'-Alexa-647, 3'-biotin modified strands 3 and 9. The biotinylated strands were synthesized from:

```
(3Bio) (SEQ ID NO: 17):
5' [AmC6]-GTTCACAAGAATCGAAACCAATGTTAGTGTAGAGTGCATA

AGC-[Bio] 3'
```

-continued

```
(9Bio) (SEQ ID NO: 23):
5' [AmC6]-GAGGTGCTTTATGTCAATCGGAGTAGCCTAGCAAGCCTTA

GCC-[Bio] 3'
```

Peptide sequences. The peptide sequences used in this work are (cysteines used for conjugation to the DNA are highlighted in red):

CGG-cWza[T376R] (SEQ ID NO: 2):
$NH_2$-CGGAPLVRWNRVISQLVPTITGVHDLTETVRYIKRWPN-COOH cWza-GGC[T376R] (SEQ ID NO: 4):
$NH_2$,-APLVRWNRVISQLVPTITGVHDLTETVRYIKRWPNGGC-COOH (*E. coli*) Wza-D4-R376T (SEQ ID NO: 5):
$NH_2$- APLVRWNRVISQLVPTISGVHDMTETVRYIKTWPN-COOH All peptides were purchased from Peptide Protein Research Ltd (Fareham, UK), as HPLC purified (>95%) lyophilized powders. The molecular masses were verified by MALDI mass spectrometry and the peptides were used without further purification.

Purification of Peptide-Oligo Conjugates

TABLE 1

Characterization of peptide-oligo conjugates and Alexa-labeled oligos.

| Name | Length (nt) | Concentration (ng/uL) | Mass theor. (g/mol) | Mass exper. (g/mol) | Delta Mass (ppm) | Yield (%) | Purity (%) |
|---|---|---|---|---|---|---|---|
| 1-PEG2-Mal-CWza | 43 | 806 | 17870.4 | 17871.4 | 58 | 15.5 | 98.6 |
| 2-PEG2-Mal-CWza | 43 | 924 | 18049.2 | 18048.2 | −53 | 17.5 | 99.7 |
| 3-PEG2-Mal-CWza | 43 | 1048 | 18144.2 | 18144.37 | 7 | 19.7 | 99.2 |
| 4-PEG2-Mal-CWza | 43 | 1150 | 18192.2 | 18192.0 | −9 | 21.5 | 99.3 |
| 5-PEG2-Mal-CWza | 43 | 1095 | 18220.2 | 18220.8 | 35 | 20.5 | 99.6 |
| 6-PEG2-Mal-CWza | 43 | 1031 | 17967.2 | 17966.3 | −48 | 19.6 | 99.6 |
| 7-PEG2-Mal-CWza | 43 | 340 | 18026.2 | 18026.5 | 19 | 6.4 | 100 |
| 8-PEG2-Mal-CWza | 43 | 1336 | 17858.2 | 17858.9 | 41 | 25.6 | 99.6 |
| 9-PEG2-Mal-CWza | 43 | 1113 | 18095.2 | 18095.3 | 7 | 21.0 | 99.5 |
| 10-PEG2-Mal-CWza | 43 | 1039 | 18147.2 | 18146.8 | −20 | 19.5 | 100 |
| 11-PEG2-Mal-CWza | 43 | 1143 | 18159.2 | 18159.7 | 29 | 21.4 | 99.4 |
| 12-PEG2-Mal-CWza | 43 | 1270 | 18081.2 | 18081.3 | 7 | 24.0 | 99.7 |
| 1-PEG2-Mal-WzaC | 43 | 792.6 | 17870.4 | 17871.6 | 69 | 30.4 | 98.7 |
| 2-PEG2-Mal-WzaC | 43 | 515.2 | 18049.2 | 18049.1 | −4 | 19.5 | 96.6 |
| 3-PEG2-Mal-WzaC | 43 | 480.8 | 18144.2 | 18144.3 | 7 | 18.1 | 98.0 |
| 4-PEG2-Mal-WzaC | 43 | 431.8 | 18192.2 | 18191.9 | −15 | 16.2 | 97.6 |
| 5-PEG2-Mal-WzaC | 43 | 473.1 | 18220.2 | 18219.8 | −20 | 17.7 | 98.8 |
| 6-PEG2-Mal-WzaC | 43 | 518.8 | 17967.2 | 17968.3 | 63 | 19.8 | 98.5 |
| 7-PEG2-Mal-WzaC | 43 | 486.6 | 18026.2 | 18026.6 | 24 | 18.4 | 97.9 |
| 8-PEG2-Mal-WzaC | 43 | 397.8 | 17858.2 | 17858.4 | 13 | 15.3 | 97.0 |
| 9-PEG2-Mal-WzaC | 43 | 278.1 | 18095.2 | 18096.2 | 57 | 10.5 | 98.0 |
| 10-PEG2-Mal-WzaC | 43 | 433.1 | 18147.2 | 18147.6 | 24 | 16.3 | 97.9 |
| 11-PEG2-Mal-WzaC | 43 | 396.8 | 18159.2 | 18158.3 | −48 | 14.9 | 97.9 |
| 12-PEG2-Mal-WzaC | 43 | 468.2 | 18081.2 | 18080.2 | −53 | 17.7 | 98.9 |

| Name | Length (nt) | Concentration (ng/uL) | Mass theor. (g/mol) | Mass exper. (g/mol) | Delta Mass (ppm) | Yield (%) | Purity (%) |
|---|---|---|---|---|---|---|---|
| 1-PEG4-SS-CWza | 43 | 273.8 | 17893.5 | 17894.6 | 62 | 21.0 | 96.4 |
| 2-PEG4-SS-CWza | 43 | 361.9 | 18072.3 | 18072.6 | 17 | 27.4 | 94.0 |
| 3-PEG4-SS-CWza | 43 | 357.9 | 18167.3 | 18165.9 | −77 | 26.9 | 96.0 |
| 4-PEG4-SS-CWza | 43 | 261.6 | 18215.3 | 18213.6 | −93 | 19.6 | 94.5 |
| 5-PEG4-SS-CWza | 43 | 295.9 | 18243.3 | 18245.0 | 93 | 22.1 | 96.7 |
| 6-PEG4-SS-CWza | 43 | 340.7 | 17990.3 | 17990.9 | 34 | 25.9 | 92.7 |
| 7-PEG4-SS-CWza | 43 | 277.5 | 18049.3 | 18049.5 | 11 | 21.0 | 95.6 |
| 8-PEG4-SS-CWza | 43 | 376 | 17881.3 | 17883.3 | 112 | 28.9 | 95.5 |
| 9-PEG4-SS-CWza | 43 | 299 | 18118.3 | 18118.2 | −5 | 22.6 | 95.6 |
| 10-PEG4-SS-CWza | 43 | 352.8 | 18170.3 | 18169.9 | −22 | 26.5 | 92.9 |
| 11-PEG4-SS-CWza | 43 | 386 | 18182.3 | 18183.3 | 55 | 29.0 | 96.5 |
| 12-PEG4-SS-CWza | 43 | 146.3 | 18104.3 | 18102.5 | −99 | 5.5 | 97.3 |

TABLE 1-continued

Characterization of peptide-oligo conjugates and Alexa-labeled oligos.

| Name | Length (nt) | A260 (—) | Conc. DNA (ng/μL) | Conc. DNA (μM) | A647 (—) | Conc. Alexa647 (μM) | Labeling eff. (%) |
|---|---|---|---|---|---|---|---|
| 1-[5'-Alexa647] | 43 | 1.265 | 42.2 | 3.24 | 0.856 | 3.17 | 98 |
| 2-[5'-Alexa647] | 43 | 0.709 | 23.6 | 1.79 | 0.427 | 1.58 | 88 |
| 3-[5'-Alexa647] | 43 | 0.244 | 8.1 | 0.61 | 0.156 | 0.58 | 95 |
| 3-[5'-Alexa647][3'-Biotin] | 43 | 0.376 | 12.5 | 0.94 | 0.242 | 0.90 | 95 |
| 4-[5'-Alexa647] | 43 | 0.500 | 16.7 | 1.25 | 0.382 | 1.41 | 113 |
| 5-[5'-Alexa647] | 43 | 0.359 | 12.0 | 0.89 | 0.254 | 0.94 | 105 |
| 6-[5'-Alexa647] | 43 | 0.616 | 20.5 | 1.56 | 0.427 | 1.58 | 101 |
| 7-[5'-Alexa647] | 43 | 0.715 | 23.8 | 1.81 | 0.480 | 1.78 | 98 |
| 8-[5'-Alexa647] | 43 | 0.950 | 31.7 | 2.43 | 0.644 | 2.39 | 98 |
| 9-[5'-Alexa647] | 43 | 0.468 | 15.6 | 1.18 | 0.308 | 1.14 | 97 |
| 9-[5'-Alexa647][3'-Biotin] | 43 | 0.457 | 15.2 | 1.15 | 0.368 | 1.36 | 119 |
| 10-[5'-Alexa647] | 43 | 0.906 | 30.2 | 2.27 | 0.593 | 2.20 | 97 |

Electrical Recordings

Structural Details of Wza Peptide-Bearing DNA Scaffolds

TABLE 2

Configurational details and experimental information of DNA scaffolds bearing Wza peptides used in electrical recordings. The number of Wza peptides was varied from 1 to 12.

| # peptides per scaffold | Arms* | # experiments | # pores | Conductance ** (nS) | Outliers *** (nS) |
|---|---|---|---|---|---|
| 1 | 1 | | | | |
| 2 | 1, 7 | 3 | 0 | | |
| 3 | 2, 6, 10 | 2 | 0 | | |
| 4 | 1, 4, 7, 10 (2, 5, 8, 11) | 5 | 0 | | |
| 5 | 2, 4, 6, 9, 11 (1, 3, 5, 8, 10) | 6 | 1 | | 0.46 |
| 6 | 1, 3, 5, 7, 9, 11 (2, 4, 6, 8, 10, 12) | 23 | 4 | | 0.53, 0.52, 0.53, 0.49 |
| 7 | 1, 3, 4, 5, 7, 9, 11 (2, 4, 6, 8, 10, 11, 12) | 13 | 2 | | 1.28, 1.27 |
| 8 | 2, 3, 5, 6, 8, 9, 11, 12 | 163 | 124 | 1.46 ± 0.06 | |
| 9 | 1, 2, 3, 5, 6, 7, 9, 10, 11 | 11 | 8 | 1.46 ± 0.07 | 1.71, 1.84 |
| 10 | 1-5, 7-11 | 28 | 19 | 1.47 ± 0.06 | 1.96 |
| 11 | 1-11 | 14 | 8 | 1.50 ± 0.05 | |
| 12 | 1-12 | 27 | 21 | 1.48 ± 0.07 | |

* In most experiments the modified arms were selected to be as much as possible radially symmetric and the numbers in this column indicate the typical choice of modified arm numbers (alternative configurations in brackets). Control experiments with more asymmetric distributions of modified arms were carried out as well for the scaffolds with 8 peptides (arms 1-8 and arms 1-4, 7-10), but we did not observe any differences in the conductance or rectification of the current compared to the scaffolds with symmetrically distributed arms.

** Only stable pores (>1 min) are included in the averages. Both conjugates with fixed and cleavable scaffolds are included in the averages.

*** Individual nanopores are counted as outliers when the measured conductance is more than 3σ separated from the average conductance value for the octamers.

Ring-Shaped DNA Scaffold from Short Oligonucleotides

We designed a DNA ring with 12 arms as a scaffold for pore-forming peptides. The ring is composed of 12 unique 43-mer oligonucleotides and has a diameter of 13.6 nm (FIG. 1*a*). Each oligonucleotide consists of four segments: the two central segments cover two helical turns and hybridize to form the ring, whereas the two outer segments contribute to each of two arms. Single unhybridized bases form hinges that separate the central segments in the ring from the outer segments and give flexibility to the arms.

The balance between rigidity and flexibility is of critical importance for a supramolecular scaffold (25-28). Therefore, we performed coarse-grained molecular dynamics simulations of the scaffold in a solution of 0.5 M ionic strength at 25° C., in both the presence and absence of an external force. The scaffold is very stable with an average of 243 out of 246 base pairs (bp) formed. The ring-shaped backbone remains closed, whereas the unconstrained arms pivot around their attachment points, with a preference for alternating orientations of odd and even arms above and below the ring. When a constant force of more than 9 pN in a direction perpendicular to the plane of the ring is applied to the arms, all of them become oriented in the same direction (FIG. 1*a*). The free energy of the resulting structure is higher than the unconstrained structure by 4 kBT per oligonucleotide, but such a small energy difference is easily compensated for by a favourable interaction energy between residues on adjacent peptide α-helices attached to the arms, or between those peptides and a lipid bilayer, both of which can reach 3 kBT per residue (29).

Figure 6A:
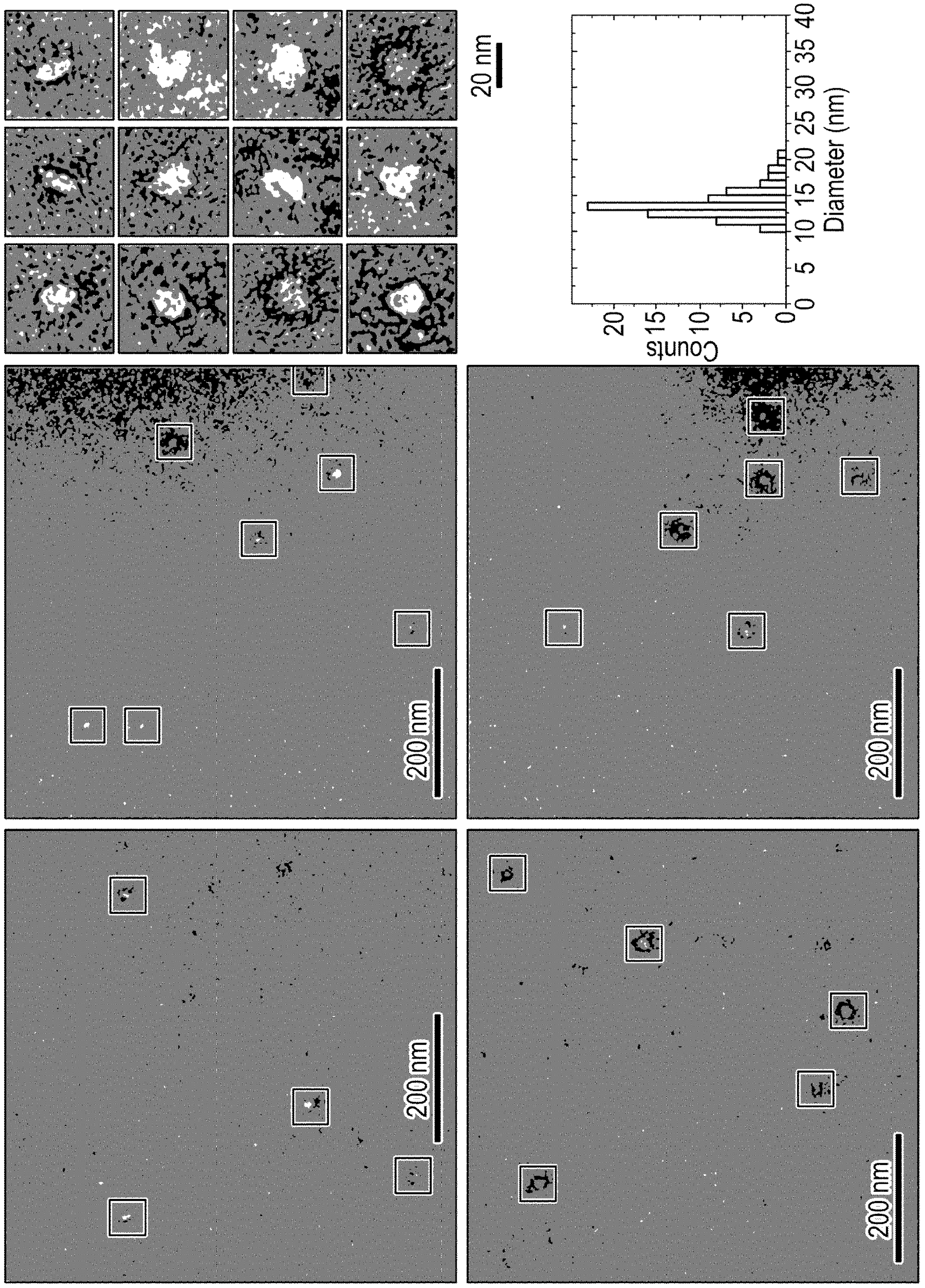
FIG. 6: a, TEM images of DNA scaffold rings (see FIG. 1*b* for an acrylamide gel analysis), a composite of single rings (top right), and a histogram of ring diameters (bottom right). Scale bars: left and middle 200 nm, right 20 nm. The diameter of the rings is 13.8 f 2.0 nm (expected: 13.0 nm). b, TEM images of RsaI digested DNA scaffold rings (see FIG. 1*e* for an acrylamide gel analysis), and a composite of individual structures. Scale bars: left and middle 200 nm, right 20 nm. The contour length of the individual digested rings is 44±6 nm (expected: 41 nm).
Figure 6B:
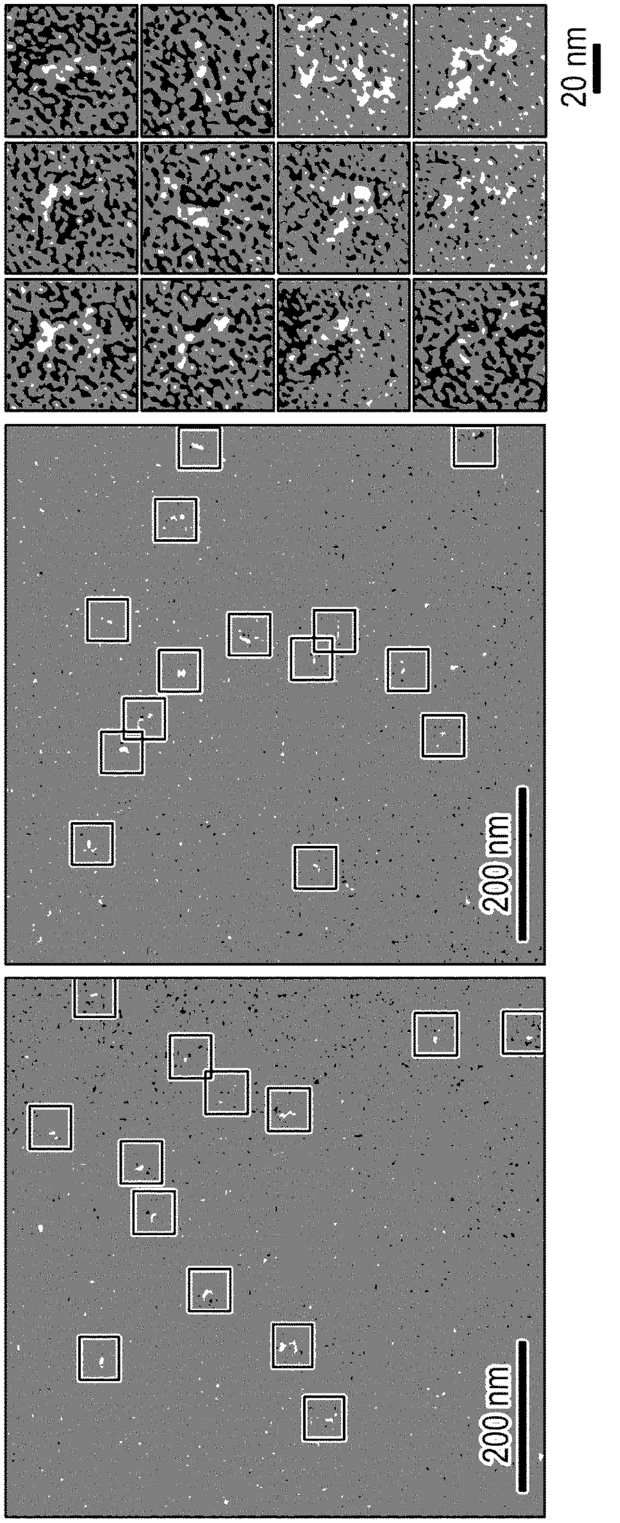
Figure 7:
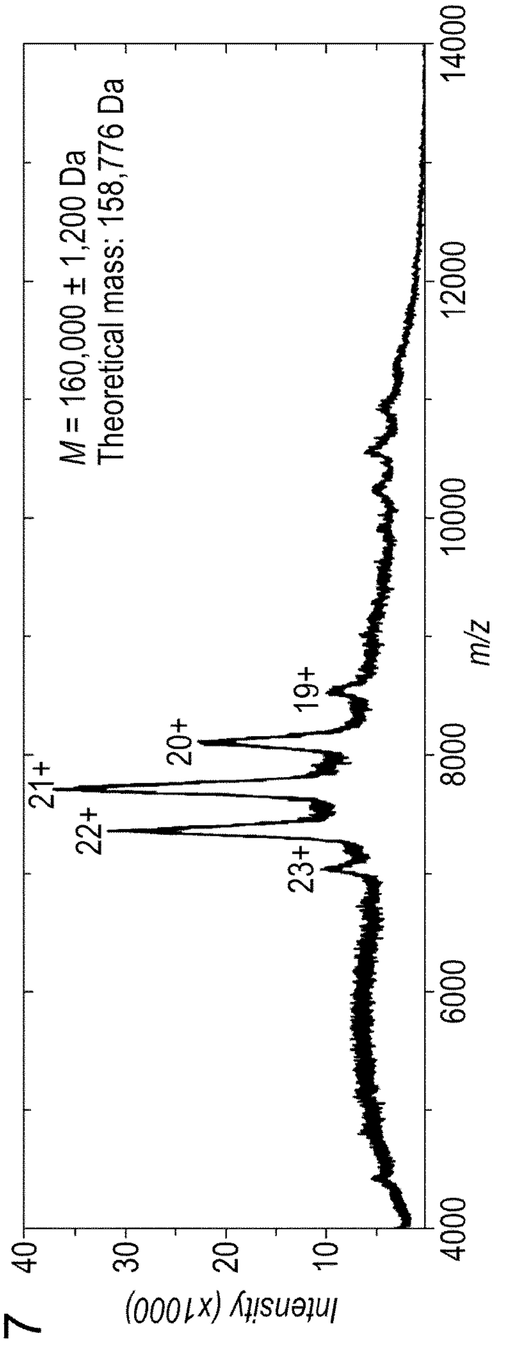
FIG. 7: Native mass spectrometry of DNA scaffold rings. The theoretical mass is calculated as the sum of the theoretical masses of the twelve individual oligos without 5' amino-C6 group.
Figure 8:
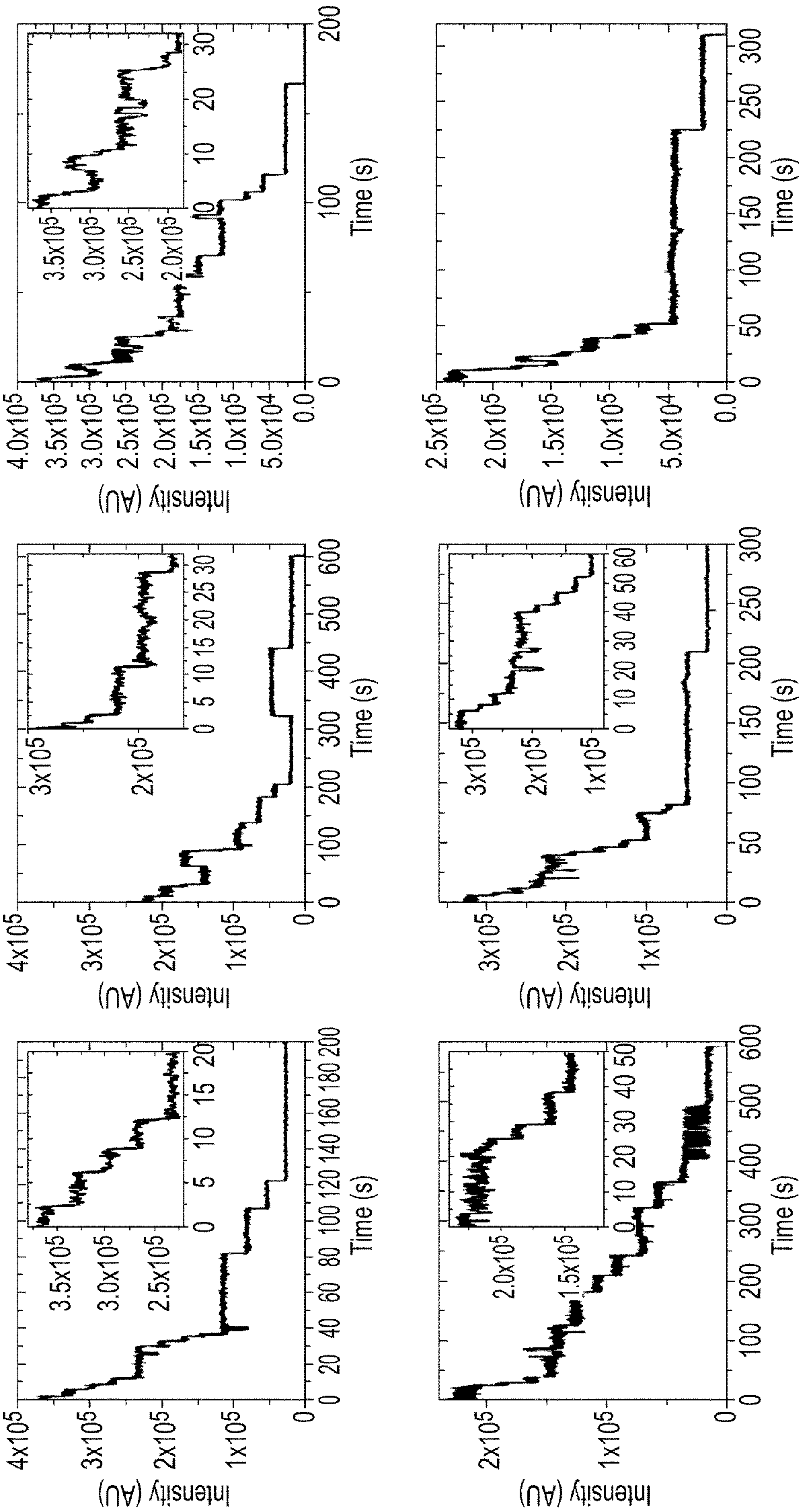
FIG. 8: Additional traces of the stepwise photobleaching of a single DNA scaffolds with 12 Alexa-647-modified oligos, attached to the surface via a single biotin-streptavidin bond. Insets show a zoomed-in view of the initial part of the traces.
Figure 9:
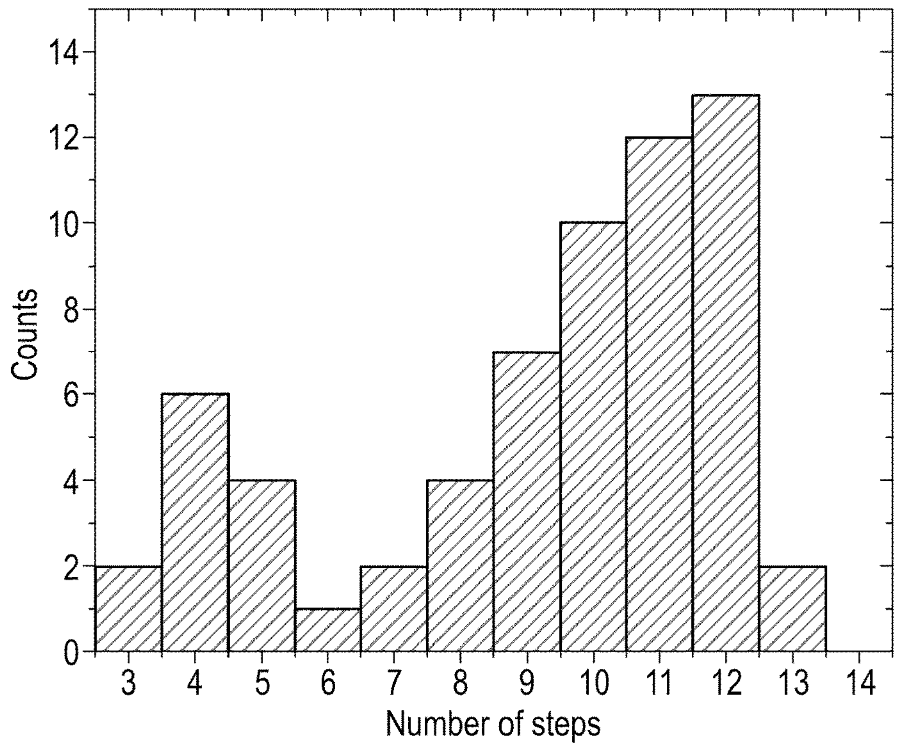
FIG. 9: Distribution of the number of photobleaching steps for DNA scaffolded with 12 Alexa-647-modified oligos.

The DNA scaffold was assembled by mixing equal amounts of all 12 oligonucleotides in potassium phosphate-buffered saline, heating the mixture and cooling it to room temperature over 4 h. Above 0.5 M of monovalent salt, the scaffold formed with a yield of 90%, as estimated by gel electrophoresis (FIG. 1*b*). In transmission electron microscopy (TEM) images on negatively stained samples, the scaffolds were recognizable as ring-shaped objects with a diameter of 13.8±2.0 nm, in the expected range, but the individual arms could not be distinguished (FIG. 1*c* and FIG. 6*a*). Class averaging of individual objects did not improve the resolution, probably because the scaffold is too flexible. Instead, we verified the scaffold stoichiometry by native mass spectrometry and stepwise photobleaching experiments. The mass of the intact scaffold is in agreement with the predicted combined mass of the 12 oligonucleotides (FIG. 7). Accordingly, photobleaching of scaffolds formed by 12 Alexa-647-modified oligonucleotides proceeded in a maximum of 12 steps (FIG. 1*d* and FIGS. 8 and 9). Finally, digestion with the restriction enzyme RsaI was used to establish that the scaffold is circular. Our design contains a single RsaI recognition site in the ring between arms 11 and 12. Incubation of the scaffold with RsaI resulted in opening of the ring to yield a linear fragment with 12 side chains that migrated faster in a polyacrylamide gel than the undigested scaffold and at the same rate as a control DNA construct designed to be identical to the restriction product (FIG. 1*e* and FIG. 6*b*).

Scaffolding Yields Stable Wza Peptide Nanopores

Figure 2A:
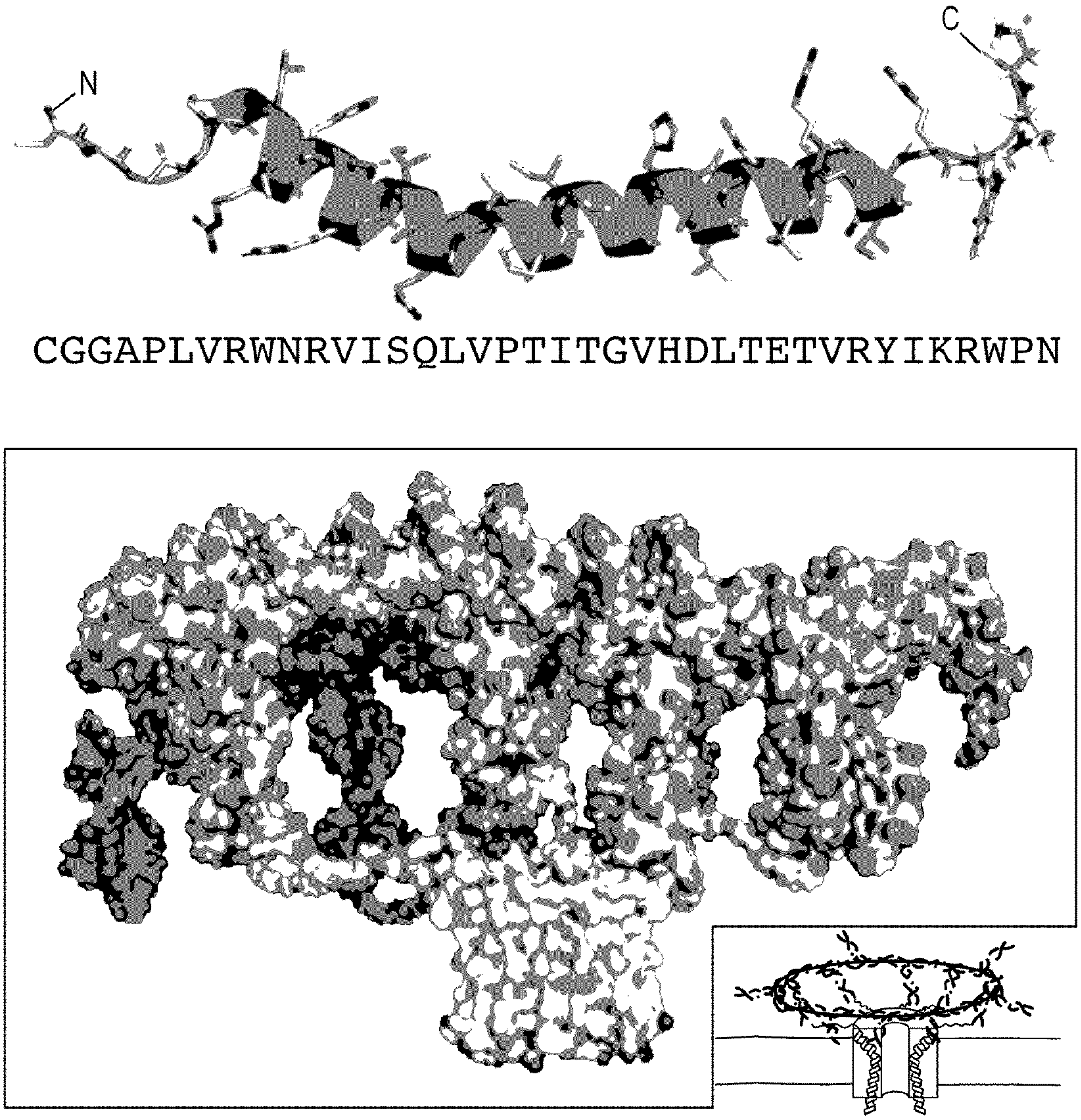
FIG. 2: Attachment of the Wza peptides to oligonucleotides and annealing of peptide-bearing DNA scaffolds. a, Sequence and structural model of the Wza peptide (top, based on the X-ray structure of Wza, Protein Data Bank ID 2J58) and a full-atom representation (bottom) of eight Wza peptides attached to the DNA scaffold from FIG. 1*a*. b, HPLC trace, ESI mass spectrum and maximum entropy deconvolution of the mass spectrum for the purified conjugate of the Wza peptide and oligonucleotide no. 1. The deconvoluted spectrum shows a single peak with the expected mass of 18,147 Da. c, Polyacrylamide gel analysis of the purified peptide-oligonucleotide conjugates before and after annealing into rings. The top gel shows the individual peptide-oligonucleotide conjugates (1-12) run in an AnykD SDS-polyacrylamide gel together with a Bio-Rad Precision Plus Dual Xtra protein marker (L), for which the band sizes are indicated to the left of the gel, and free Wza peptide (P). The gel was stained with InstantBlue. The bottom gel shows annealed DNA rings, with an increasing number of attached peptides (0 to 12), run in a 5% polyacrylamide gel without SDS, together with a NEB 2-log dsDNA ladder (L), for which the band sizes are indicated to the left of the gel. The gel was stained with SYBR Gold and the DNA detected by fluorescence.

We tested the scaffolding capabilities of the DNA ring by attaching peptides with a propensity to form pores to the arms. The selected peptide Wza (CGG-cWza[T376R], FIG. 2*a*) is a variant of the consensus sequence of the Wza D4 domain (cWza) that does not form stable open pores by itself, because it contains two cationic residues near the C terminus (K375/R376) and lacks a stabilizing mutation, such as Y373C, near the C-terminal entrance of the pore (12). Without scaffolding, this peptide produces only short-lived, noisy channels in planar lipid bilayers with an average open lifetime of 3.0 s at +150 mV and a unitary conductance of 0.32 nS (FIGS. 11B-E and 12-14).

Figure 2C:
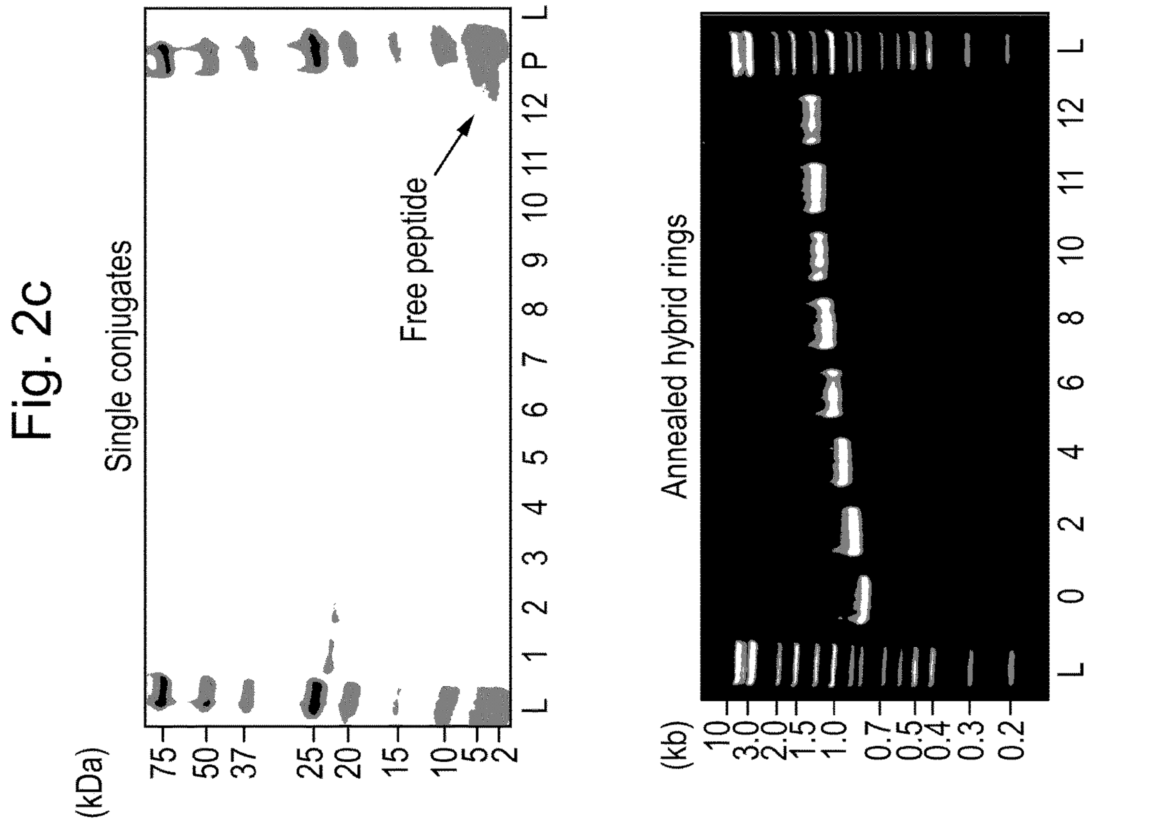
Figure 2B:
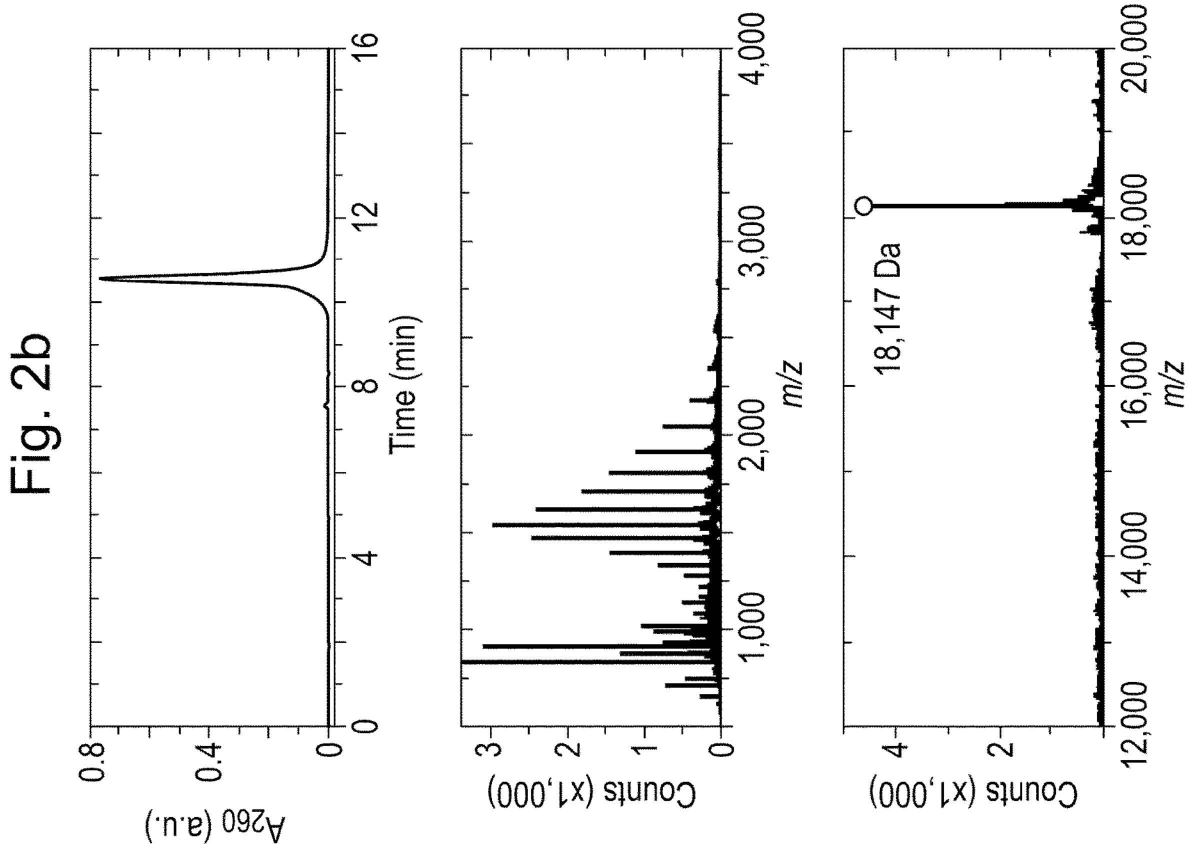

The peptide was attached to each of the 5'-amino-modified oligonucleotides at the N-terminal Cys-Gly-Gly handle through a flexible linker (SMPEG2 (succinimidyl-((N-maleimidopropionamido)-dieth-ylene glycol) ester). The 12 peptide-oligonucleotide conjugates were individually purified by HPLC, lyophilized and analysed by electrospray ionization mass spectrometry (ESI-MS) (FIG. 2*b* and Table 1). We assembled DNA rings with various numbers of attached peptides at predefined positions (Table 2 for a detailed list) around the ring by combining the desired peptide-conjugated oligonucleotides with unmodified oligonucleotides while keeping the total number of oligonucleotides fixed at 12. Attached peptides decrease the electrophoretic mobility of both the oligonucleotides before annealing and the DNA rings after annealing and the number of attached peptides is readily estimated from the position of the band of the hybrid DNA-peptide ring in a polyacrylamide gel (FIG. 2*c*).

Figure 3A:
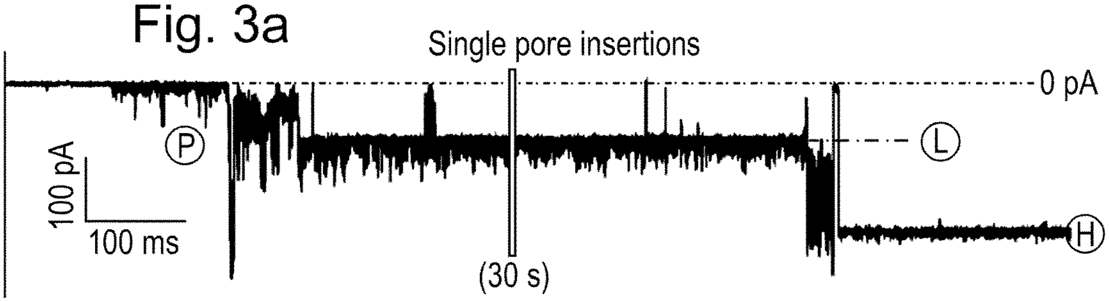
FIG. 3: Electrical properties of DNA-scaffolded octameric Wza peptide nanopores. α-d, Electrical recordings of the insertion of Wza peptide nanopores formed from DNA scaffolds that bear eight Wza peptides into planar DPhPC lipid bilayers. Insertions may occur via a P state and an intermediate L state, recorded at −150 mV (a), without an intermediate state, recorded at −120 mV (b) or without reaching a uniform intermediate conductance level, recorded at −150 mV (c). Switching between the intermediate L state and the open pore H state may occur briefly after insertion, recorded at −120 mV (d). e, Event histogram of the electrical conductance values of 124 DNA-scaffolded octameric Wza peptide nanopores, recorded at −50 mV. f, Electrical recording of single-stranded DNA-streptavidin blocking (B) (poly $(dC)_{50}$-biotin:streptavidin=1:3, 200 nM) and being released from a single DNA-scaffolded octameric Wza peptide nanopore (21 blockades were observed with three nanopores). g, Averaged current-voltage (I-V) characteristics of five different DNA-scaffolded octameric Wza peptide nanopores in their L and H states. The error bars indicate one standard deviation.
Figure 3B:
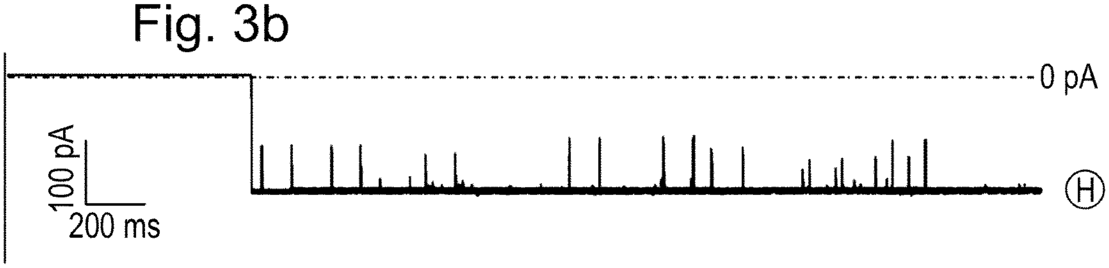
Figure 3C:
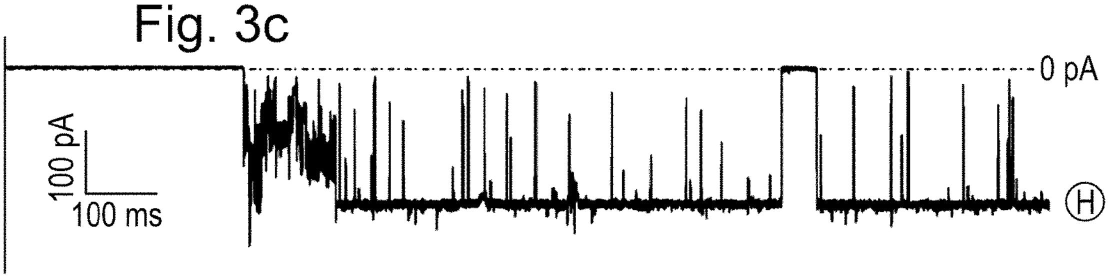
Figure 3D:
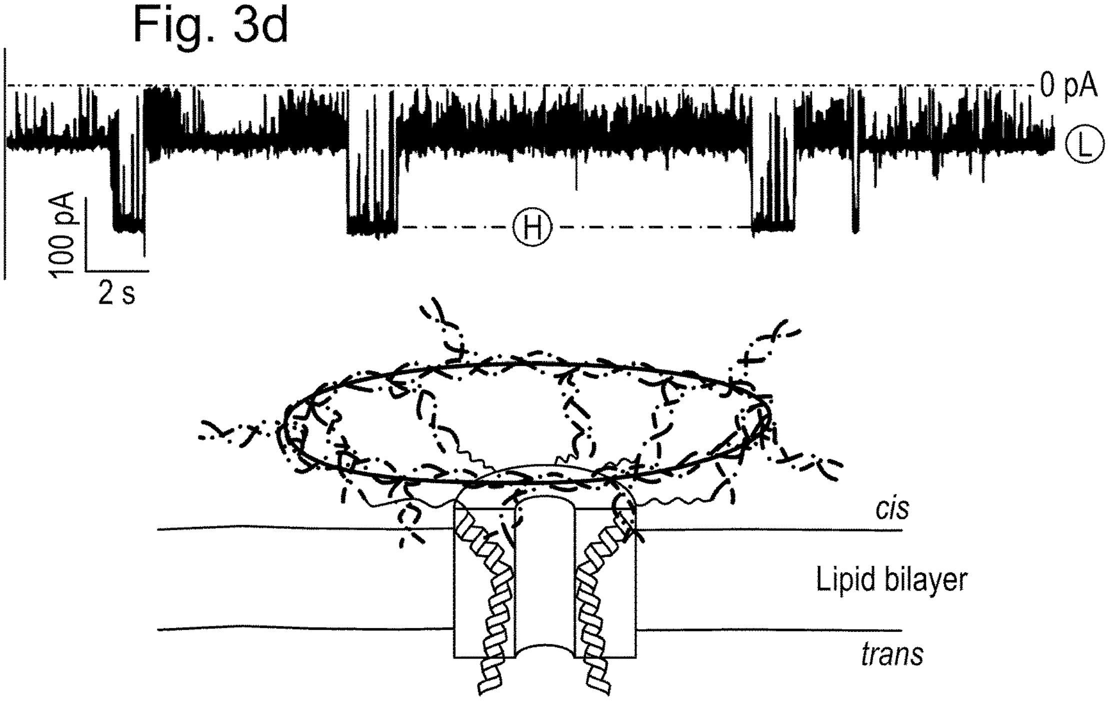
Figure 3E:
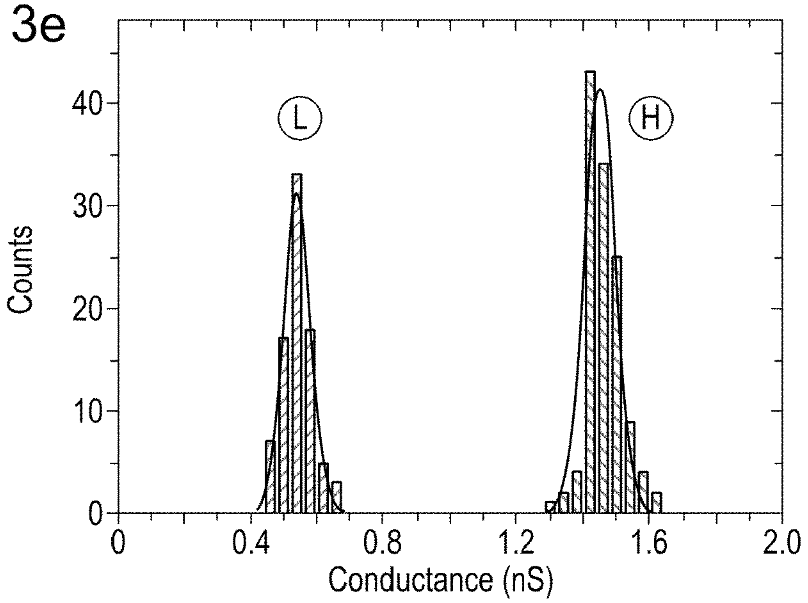
Figure 15:
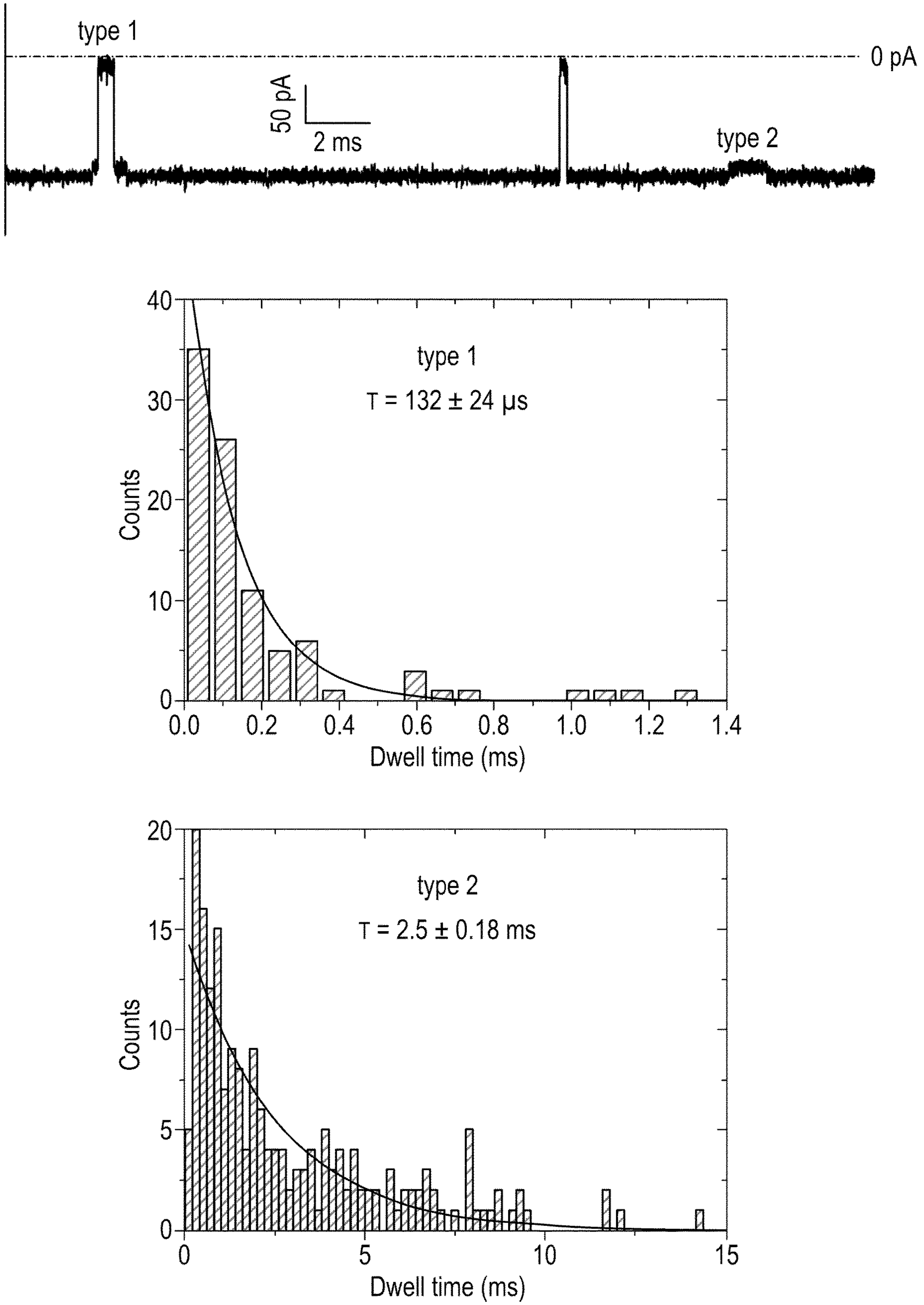
FIG. 15: Top: segment of electrical recording from H-state of a scaffolded Wza octamer sampled at −100 mV and 50 kHz (filtered at 10 kHz), showing two types of subconductance: transient pore closing (type 1) and an openpore subconductance (type 2). These two types of subconductance are observed in all scaffolded H-state Wza nanopores. Bottom: dwell time analysis of transient pore closing (type 1) and an open-pore subconductance state (type 2).
Figure 16:
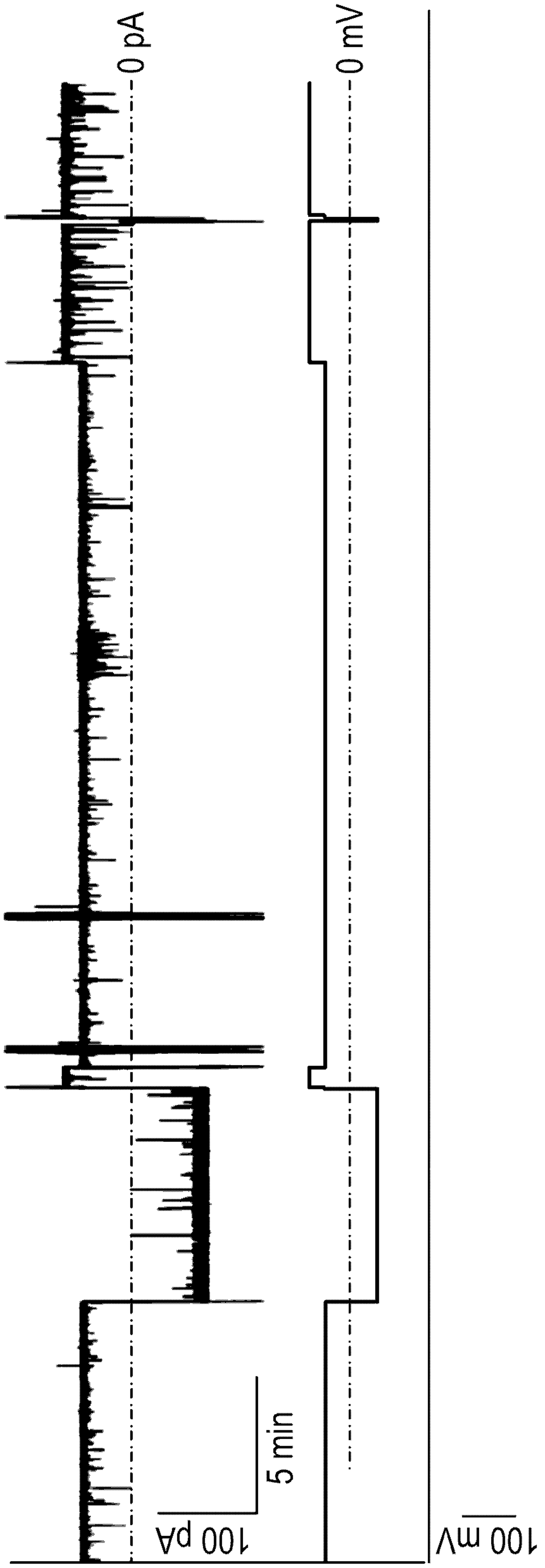
FIG. 16: Prolonged recording of a pore from scaffolded Wza peptides in H-state (1 h total).

The pore-forming properties of the scaffolded Wza peptide were examined by electrical recording in planar lipid bilayers (FIG. 3*a-d*). When eight peptides (Table 2 gives configurational details) were attached to the scaffold we observed spontaneous insertion into 1,2-diphytanoyl-sn-glycero-3-phospho-choline (DPhPC) bilayers and the formation of stable open pores at a scaffold concentration of 4 nM and an applied potential between −100 mV and −150 mV. In 72% of the cases, pore formation occurred in two steps: first, a noisy low-conductance state (L, 0.54±0.03 nS at −50 mV) was observed, which then opened after several tens of seconds to a higher conductance state (H, 1.46±0.06 nS at −50 mV), characterized by a much lower noise (FIG. 3*a*). These insertions were sometimes preceded by a precursor (P) state that we identified from bursts of transient spikes, similar to previous observations with the cWza consensus sequence (12), and we occasionally observed switching between L and H for a brief period immediately after insertion. In the remaining 28% of cases, pore formation occurred either directly to the H state (FIG. 3*b*) or after a noisy transition without reaching a stable intermediate conductance level (FIG. 3*c*). In all cases, the high conductance level eventually reached was the same, as judged from the low current noise, identical sub-conductance states and transient closures (FIG. 15), and the narrowly distributed mean conductance of 1.46±0.06 nS (FIG. 3*e*), which is comparable to the variation found in natural protein nanopores, such as α-haemolysin (30). Once a high conductance state was reached, the scaffolded pores were stable and could be kept in an open state for at least an hour at applied potentials between −100 mV and +100 mV (FIG. 16).

Figure 3F:
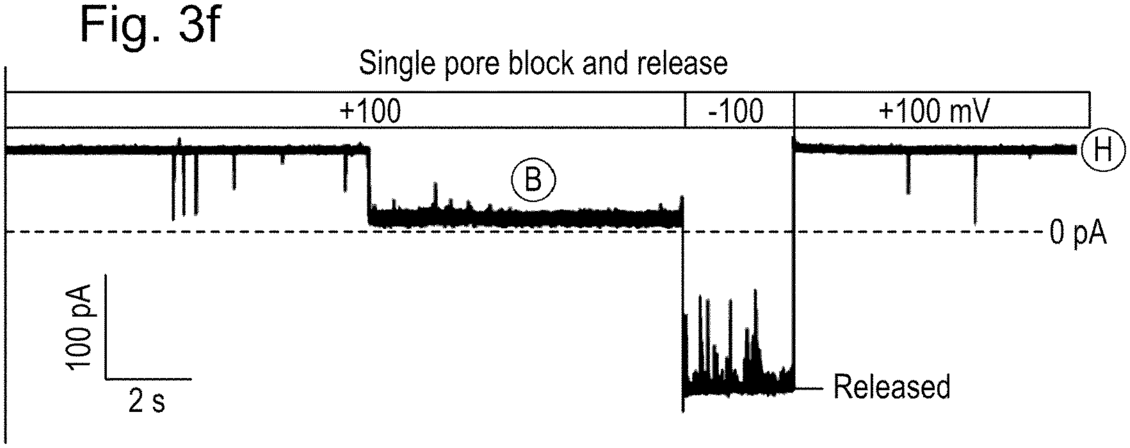
Figure 13:
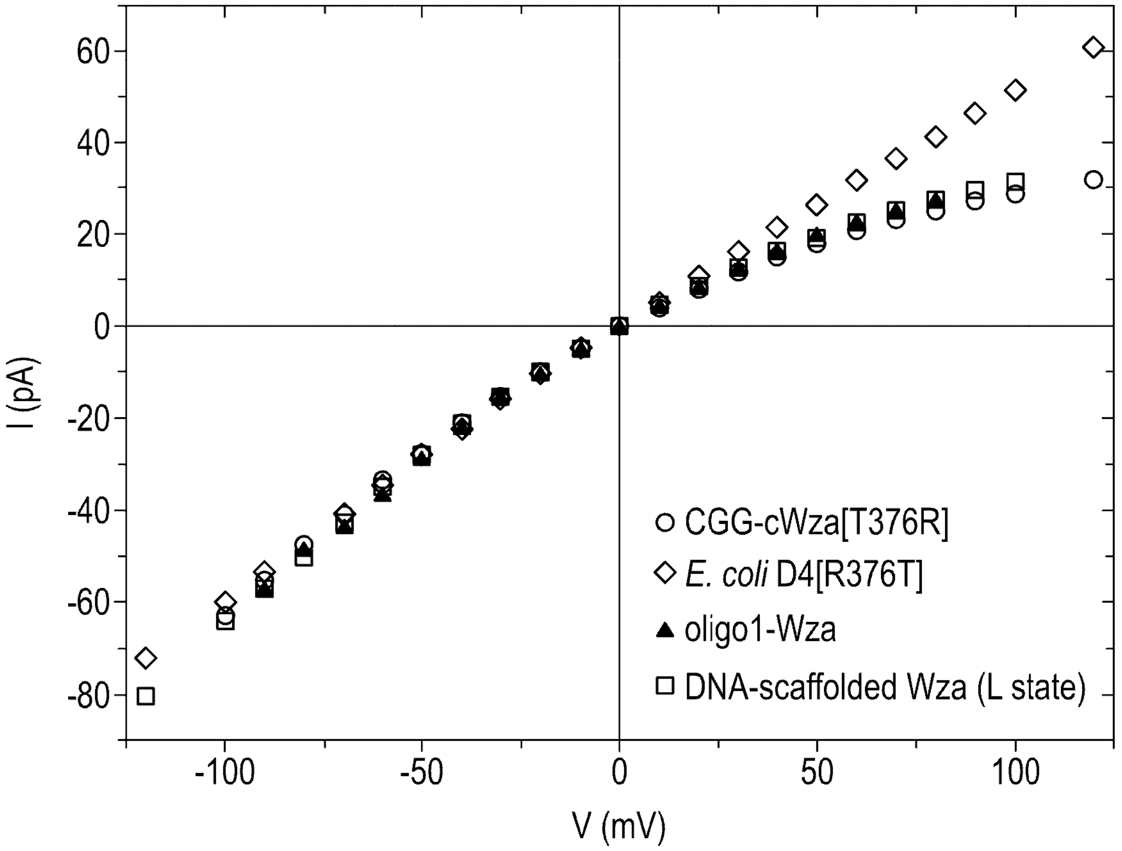
FIG. 13: I-V profiles of nanopores formed from free peptides, free oligo-Wza conjugates and the intermediate L-state of DNA-scaffolded Wza peptides. Characteristic I-V curves of both the L and H-state are shown in FIG. 3*f*.
Figure 14A:
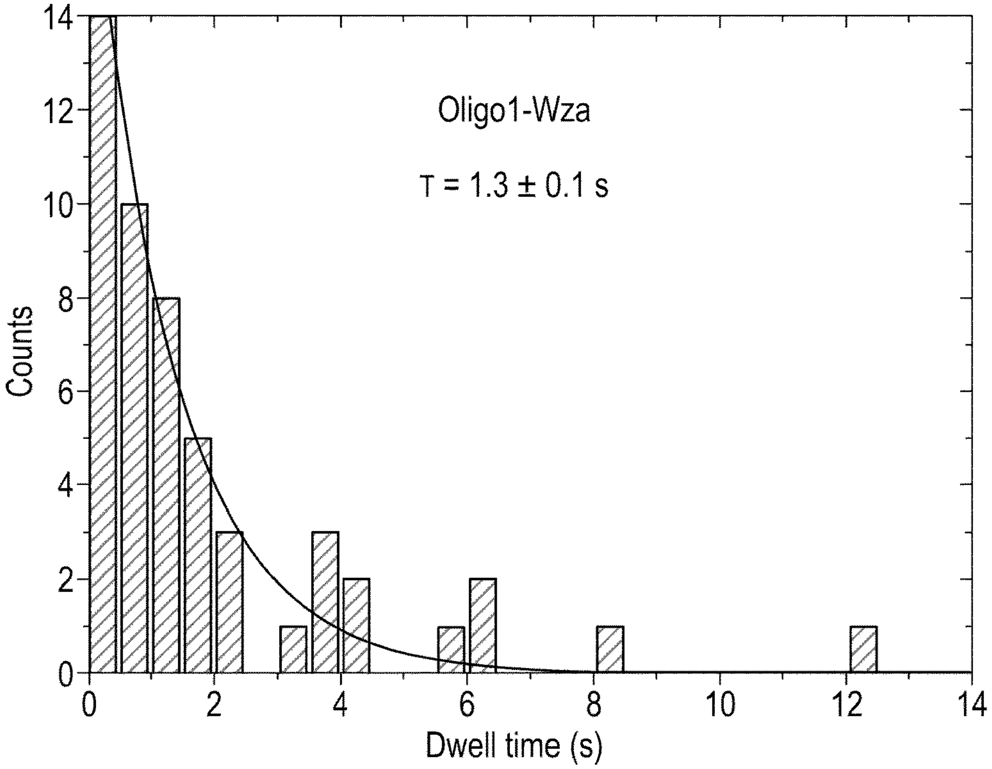
FIG. 14: Lifetime of pores formed from free oligol-Wza conjugates (−150 mV) and from free Wza peptides (+150 mV).
Figure 14B:
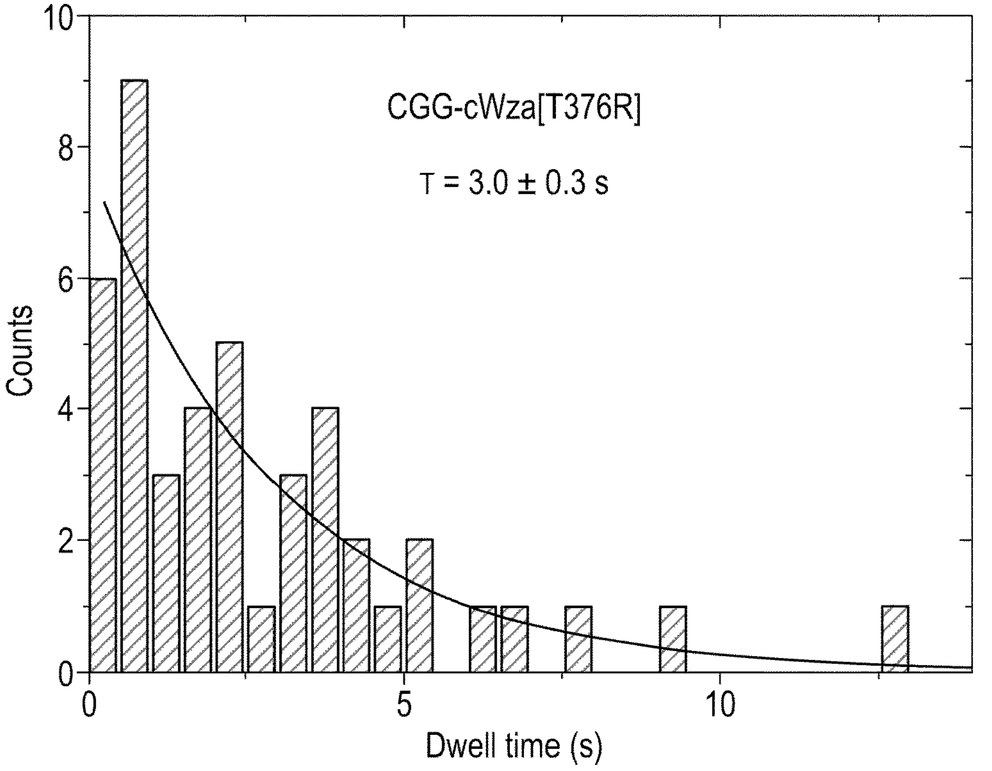

The two observed levels (L and H) are different conductance states of the same pore. This is supported by the observed switching between the two levels (FIG. 3*d*), the fact that the ratio of the two conductance levels (2.7 (FIG. 3*e*)) is not an integer and the observed single-step blockades (residual current 11±4%) of the H state by a streptavidin-bound biotinylated oligonucleotide (FIG. 3*f*). Though the two levels are states of the same pore, the current noise differs significantly between them. In the L state, the coefficient of variation (CV) of the current is 11% (at −150 mV, filtered at 2 kHz), whereas it is only 3.1% in the H state, which suggests that the H state is a more static configuration. The H state has a remarkably low noise compared to most nanopores formed from peptides (31, 32), but it is more noisy than some well-known natural protein nanopores, such as α-haemolysin (CV<1% when filtered at 2 kHz). The scaffolded pores show significant rectification of the ionic current in both states (FIG. 3*g*), with $-I_{+50}/I_{-50}=1.51$ for the L state and 1.42 for the H state, which is most probably caused by the two cationic residues (K375/R376) near the C-terminal pore entrance (FIG. 13 gives data on mutant peptides). A more extensive study of different mutants is required to confirm this.

Figure 17:
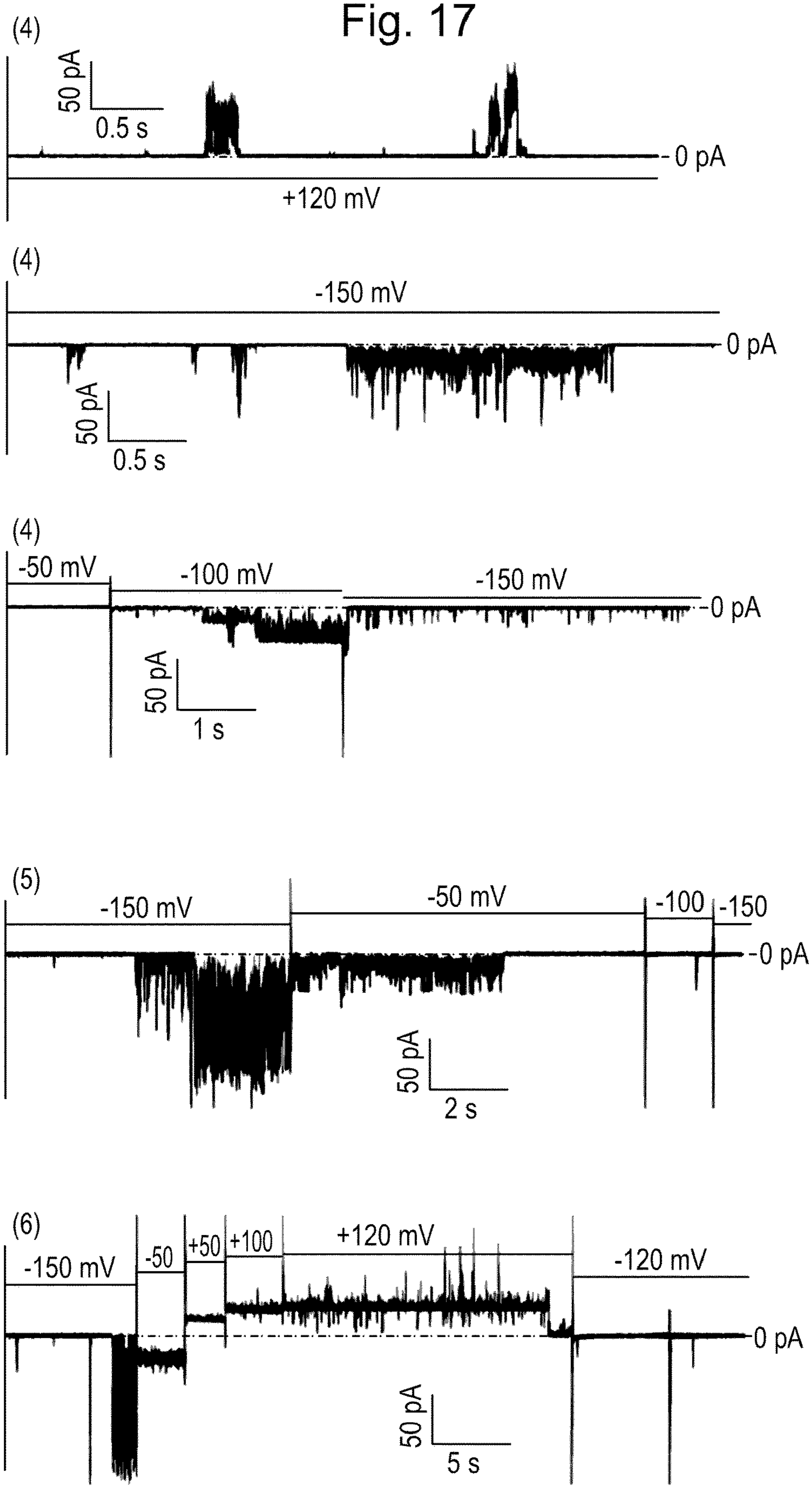
FIG. 17: Electrical recordings of the insertion of unstable pores from scaffolds with fewer than 8 Wza peptides. The number of scaffolded Wza peptides is indicated by the numbers above each trace. The potential applied initially was +120 mV (top trace), and −150 mV (all other traces). The current signals were filtered at 2 kHz.

To examine the possibility of scaffolding larger peptide nanopores, we annealed DNA rings with between 0 and 12 peptides and investigated their pore-forming properties in planar lipid bilayers (Table 2 gives configurational details). We found that all the scaffolds that carry at least eight peptides led to the insertion of pores, as shown in FIG. 3*a-e* with the same unitary conductance and rectification as the ring with eight peptides. We observed some rare double and triple insertions (in 3% of experiments) of two or three pores attached to separate DNA scaffolds, which can be recognized by conductance values that are two or three times higher than the unitary conductance. Experiments with scaffolds bearing fewer than eight peptides showed a range of lower conductance levels, none of which were stable for more than one minute (FIG. 17 and Table 2).

Figure 18:
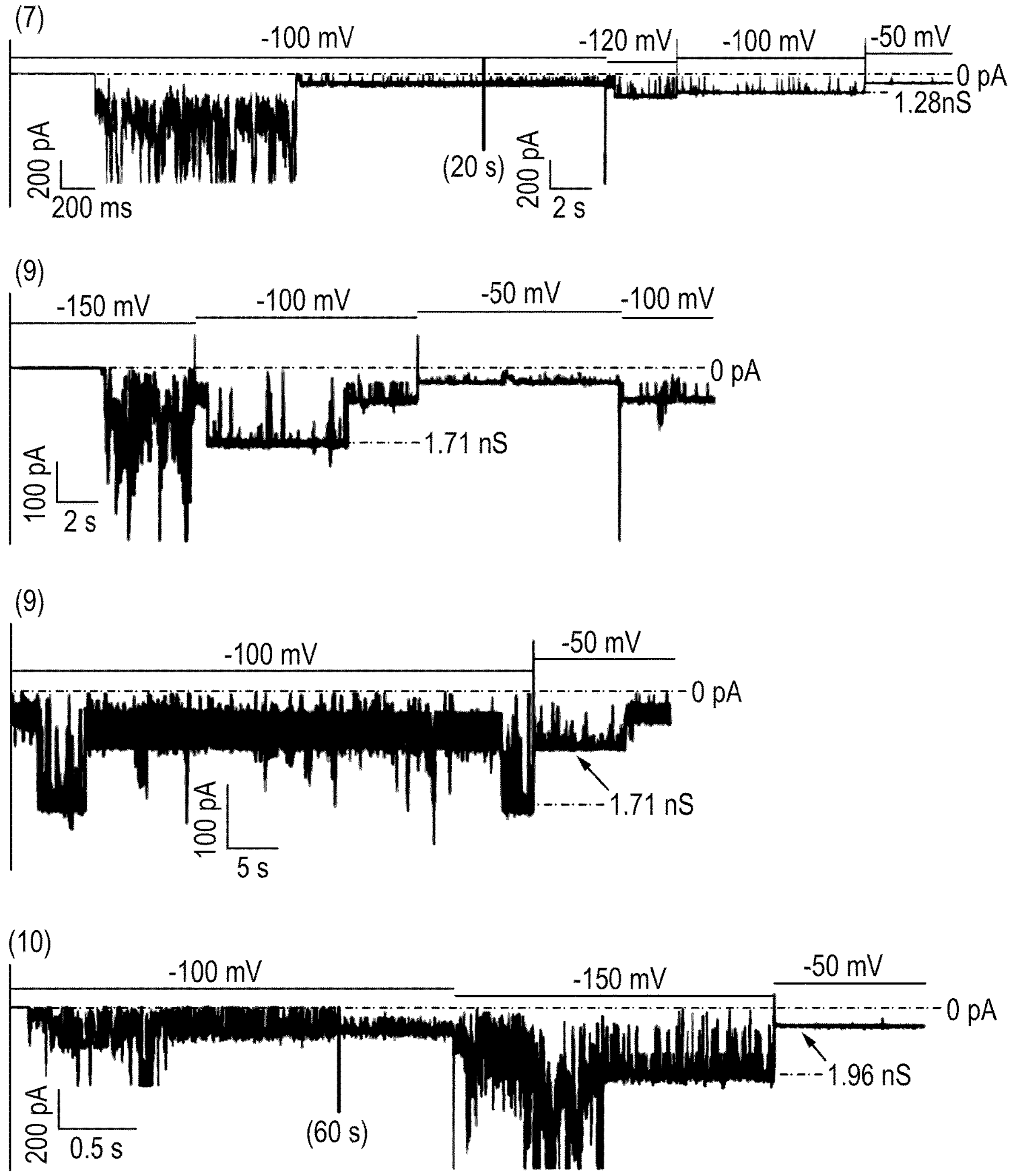
FIG. 18: Electrical recordings displaying the insertion of pores with smaller or larger conductances than the 1.46±0.06 usually observed for octamers. Top: a scaffold with 7 peptides, middle: a scaffold with 9 peptides, bottom: a scaffold with 10 peptides. In all cases, these pores are lost or return to an L-state within minutes. The current signals were filtered at 2 kHz.

In isolated cases, we observed the insertion of unstable pores with a greater conductance than that of the H state, but not corresponding to H+L or H+H (FIG. 18 and Table 2). These unstable higher conductance states most probably originate from the formation of pores with nine or ten α-helices that return to a more stable octameric L or H configuration by expelling the supernumerary peptide chain (s). This suggests that rearrangements of the peptides after nanopore insertion are possible and that Wza peptide octamers are not in a kinetically trapped state. In short, this Wza peptide variant has a clear propensity for assembly in planar lipid bilayers, but only the octameric assembly can form open pores that remain stable for extended periods.

Loss of Wza Peptide Pores from Bilayers on Scaffold Removal

Figure 4A:
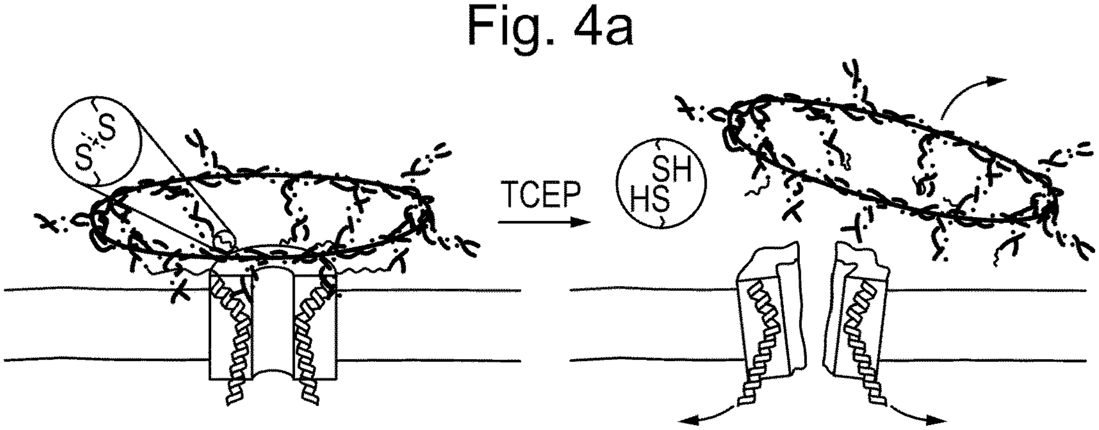
FIG. 4: The DNA scaffold stabilizes Wza peptide nanopores. a, Schematic illustration of the scaffold removal experiment. b, Electrical recording of the insertion of a Wza peptide nanopore formed from a DNA scaffold that bears eight Wza peptides attached through cleavable disulfide linkers. The nanopore inserts through various P and L states before reaching the stable open-pore H state (top). The H-state is stable at −100 mV when the scaffold is attached (bottom). c, Two exemplary electrical recordings of the loss of Wza peptide nanopores at −100 mV after the DNA scaffold is cleaved off by the addition of 10 mM TCEP (five nanopores were tested). d, Current-voltage curves obtained from single Wza peptide nanopores with a fixed scaffold (average of three nanopores) and with a cleavable scaffold before cleavage (average of three nanopores) and one experiment in which the scaffold was removed from a Wza peptide pore by TCEP while the pore was kept at an applied potential of +20 mV to prevent loss. The current-voltage curve was recorded 13 min after TCEP addition.
Figure 4B:
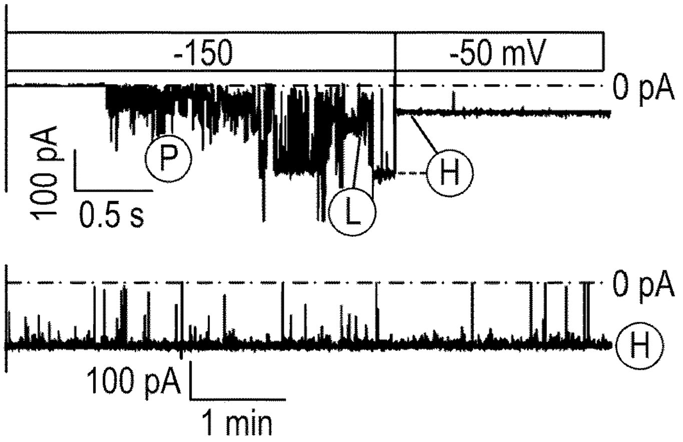

To highlight the importance of the DNA scaffold for nanopore stability, we prepared cleavable conjugates of the Wza peptide with all 12 oligonucleotides (FIG. 4*a* and Table 1). After assembly, the scaffolded Wza peptides could be inserted into planar lipid bilayers in the same way as the uncleavable constructs (FIG. 4*b*). As long as the peptides were attached to the scaffold, the pore was stable and its conductance remained constant and electrically indistinguishable from that of Wza peptide pores on the uncleavable scaffold.

Figure 4C:
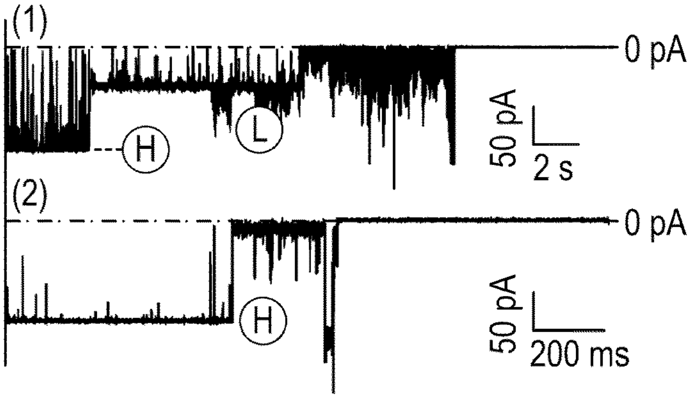
Figure 4D:
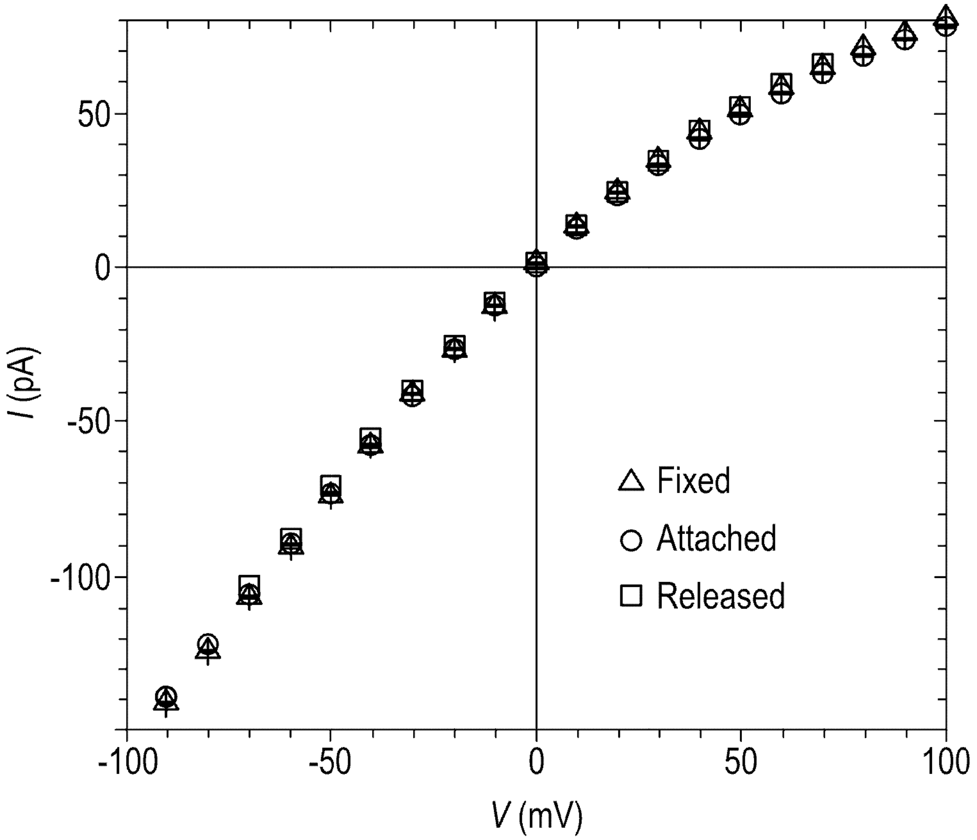

We then investigated the stability of open octameric Wza peptide nanopores after the separation of the scaffold by treatment with 10 mM tris(2-carboxyethyl)phosphine (TCEP) in the cis compartment. Within two minutes, we observed a complete loss of the pores, either through an intermediate L state or through an unknown intermediate state that is almost fully closed (FIG. 4*c*). After the pore was lost, we observed no reinsertion, which confirms our previous observation that this free Wza peptide variant does not form stable nanopores in planar lipid bilayers. In one experiment, we managed to keep a Wza peptide nanopore open by applying a low potential of +20 mV after the scaffold was cleaved. When the conductance of this unscaffolded pore was carefully examined, we found that it exhibited almost the same the conductance as scaffolded pores, with only a slightly less pronounced rectification (FIG. 4*d*). When the applied potential was stepped to −90 mV, this unscaffolded pore was quickly lost via the L state.

The Scaffold as a Docking Site

Figure 5A:
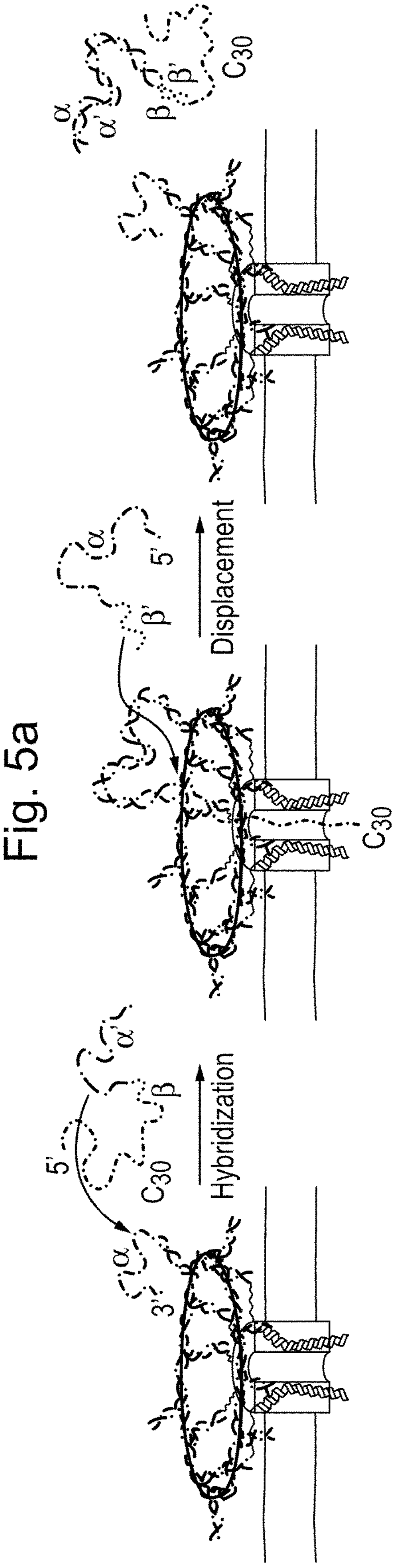
FIG. 5: The DNA scaffold is a versatile docking site for tagged oligonucleotides. a, Schematic illustration of the docking and displacement of tagged oligonucleotides. b, Electrical recording at +100 mV of the binding (B) and dissociation of PEG-5k attached to an α'-oligonucleotide octamer (see a, 53 blockades were observed with four nanopores). c, Electrical recording of the binding and permanent blockade by PEG-5k attached to a 19-mer α'-oligonucleotide (two nanopores). d, Three exemplary electrical recordings of the blockade (B) and release from the nanopore of a poly$(dC)_{30}$ bound to the scaffold's α-handle via an α'β-sequence (28 blockades with three nanopores). e, Electrical recording of the sustained H state of a scaffolded Wza peptide nanopore after removal of the bound poly$(dC)_{30}$ by a toehold-mediated strand displacement with a 32-mer αβ'-oligonucleotide at +120 mV.

Our DNA nanostructures are suited as docking stations for incoming target molecules that are linked to complementary oligonucleotides. This was investigated by using three example probes and a scaffold in which one of the arms was extended by up to 22 nucleotides to generate a docking site of adjustable affinity (FIG. 5*a*).

Figure 5D:
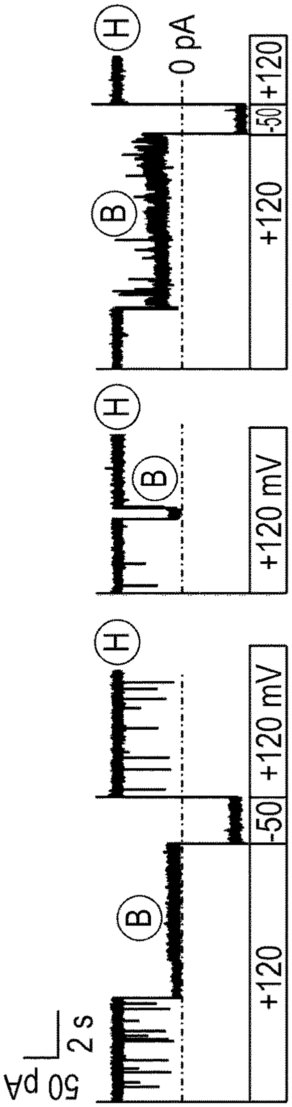
Figure 5E:
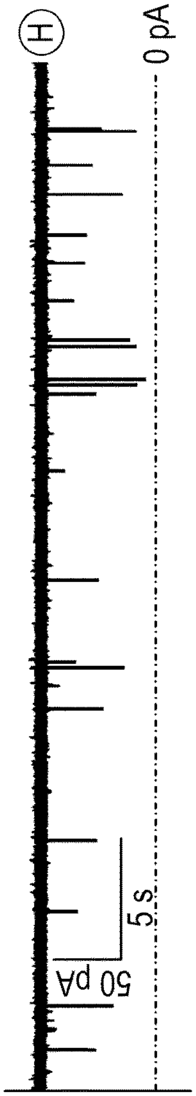
Figure 5B:
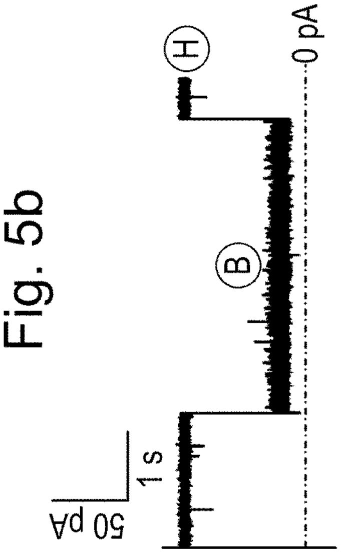
Figure 19:
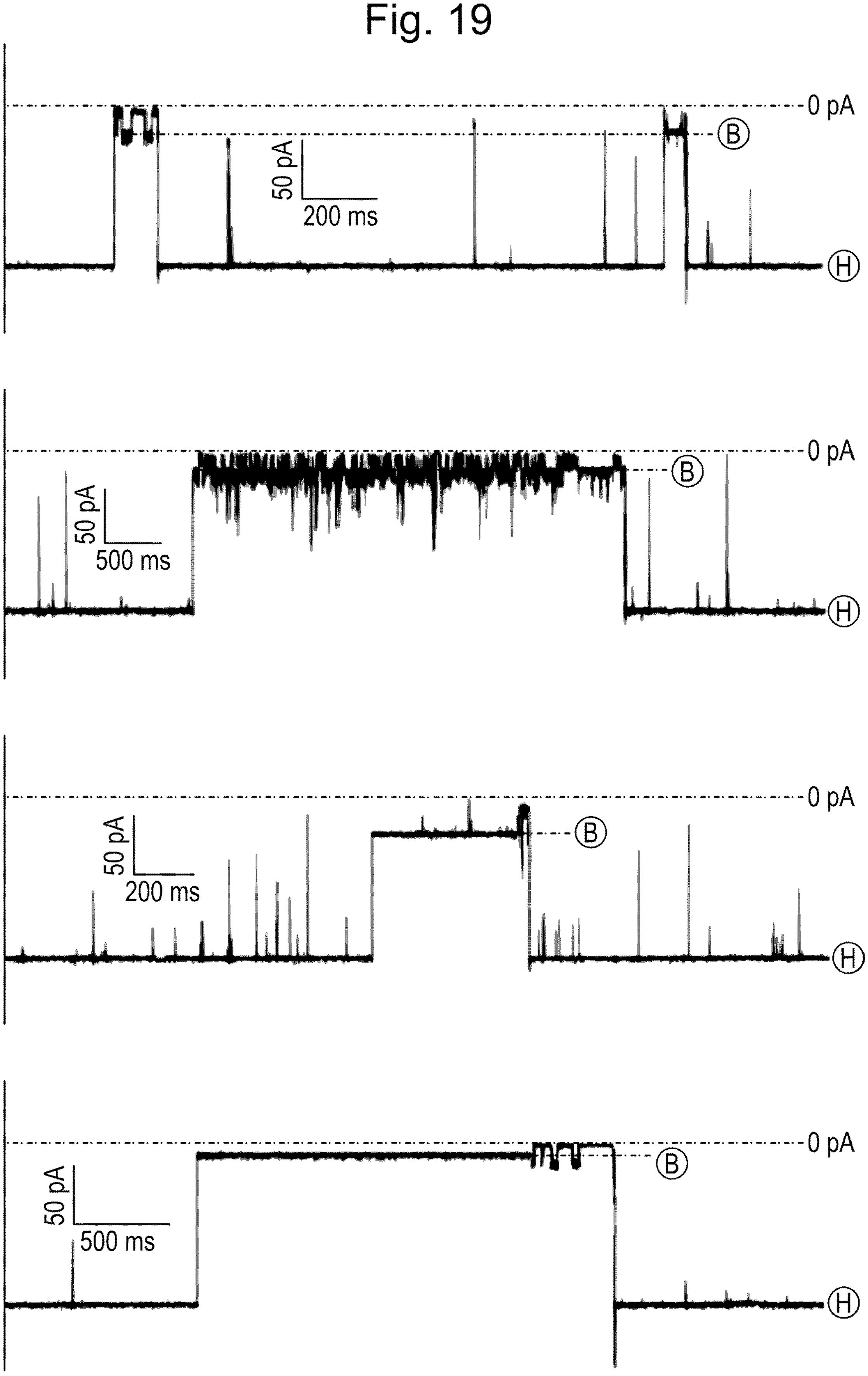
FIG. 19: Electrical recordings showing reversible oligo-PEG binding (B) at −100 mV. In some cases, the conductance in the bound state fluctuates between two or more levels. The average current during a blockade (see for example the second trace) was used to calculate the residual current.
Figure 20:
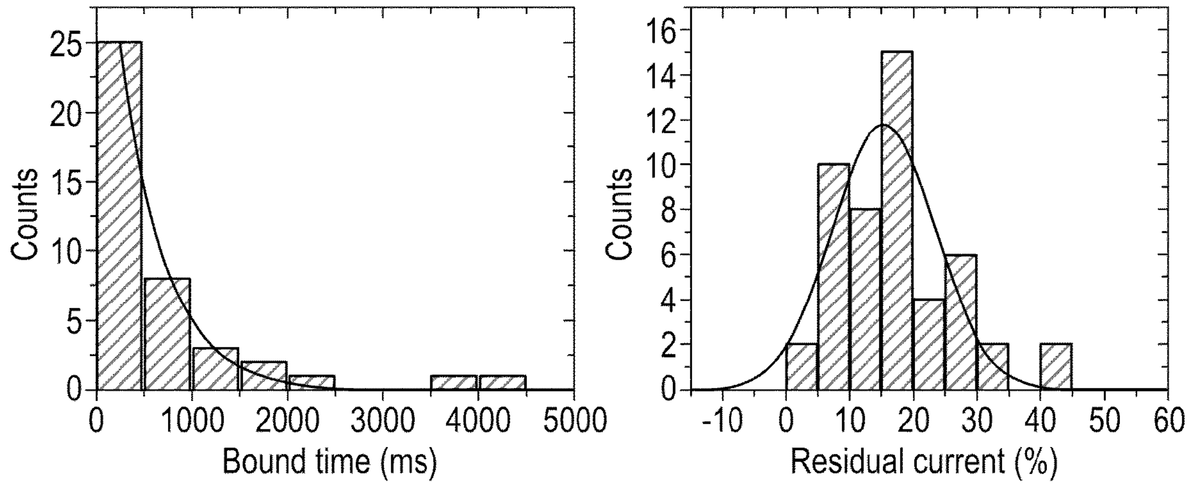
FIG. 20: Lifetimes of states with oligo-PEG bound at −100 mV and event histogram of the residual current during blockades.

The scaffold with eight covalently attached Wza peptides and a single docking site of unhybridized bases was assembled and added to a planar lipid bilayer. After the insertion of a single peptide nanopore and perfusion of the chamber, tagged probes were added to the cis side of the bilayer. When a PEG-5k polymer was bound to an eight-nucleotide tag, we observed reversible binding, as evidenced by transient current blockades with a mean duration of 466±14 ms and an average residual current of 15±1.2% (FIGS. 5*b*, 19 and 20 and Table 3). The short octamer duplexes have a limited lifetime, previously found to range from 0.1-1.0 s, depending on the sequence of the oligonucleotide (33).

TABLE 3

Oligo-PEG binding characteristics.

| # oligolength | # events | V (mV) | Bound time (ms) | Residual current (%) |
|---|---|---|---|---|
| 8 | 53 | −100 | 466 ± 14 | 15.3 ± 1.2 |
| 19 | 2 experiments (irreversible binding) | −100 | Bound state observed for 5 and 12 min, resp., followed by bilayer disruption. | 11.4 ± 2.0<br>24.2 ± 1.7<br>(average of trace) |

Figure 5C:
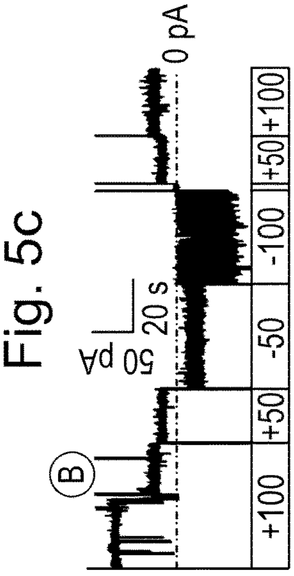

PEG binding can be made essentially irreversible with a longer hybridization sequence of 19 nucleotides. In this case, instead of transient blocking events, we observed permanent blockades with a residual current of 18% that could not be reversed by varying the applied potential between −100 and +100 mV (FIG. 5*c*). Eventually, these measurements concluded by loss of the pore, for example, by rupture of the bilayer.

Figure 3G:
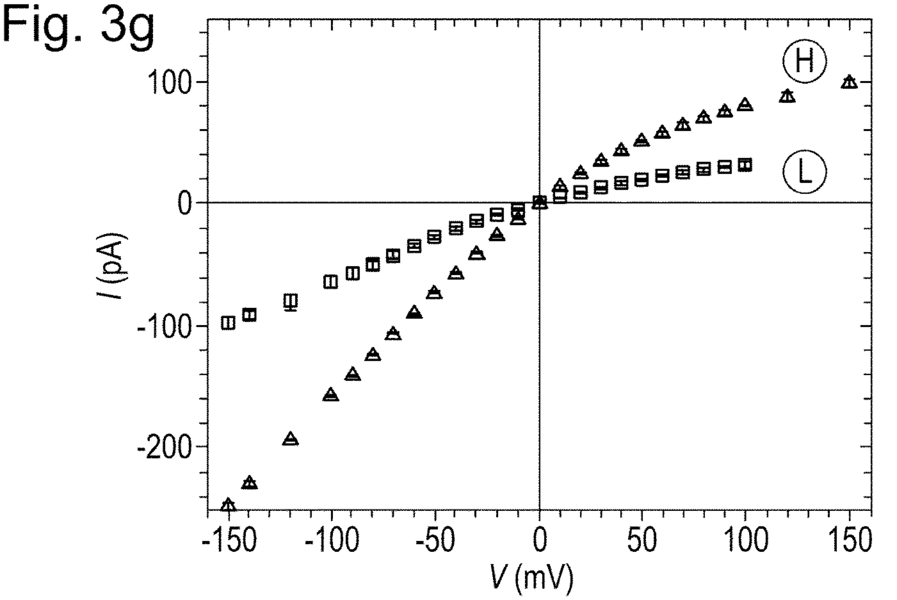

When a $C_{30}$ oligonucleotide tag was attached to the same 19-mer handle, the blocking characteristics changed. As the C30 end entered the pore, the current was reduced to 12±5% (FIG. 3*g*). The tagged oligonucleotide could not translocate through the pore because it was hybridized to the scaffold, and hence the blockade persisted in most cases (FIG. 5*d*). Reversal of the applied potential resulted in the release of oligonucleotide from the constriction and unblocking of the pore. The C30-tagged oligonucleotide could be removed fully from the scaffold through toehold-mediated strand displacement, in which a second oligonucleotide was hybridized to a toe-hold region (β (FIG. 5*a*)) between the C30 and the hybridized handle. We observed no more blocking events after the addition of a 1.5-fold excess of the displacement strand (α β'), which established that the docking site on the scaffold had been freed (FIG. 5*e*).

Pre-Organization of Pore-Forming Peptides on DNA Scaffolds.

Synthetic supramolecular scaffolds have not been used previously to guide the assembly of transmembrane peptide assemblies. In our ring-shaped DNA scaffold, all the oligonucleotides were modified with peptides and purified before assembly, which provides confidence in the final stoichiometry of the scaffolded nanostructure. The inevitable non-quantitative nature of conjugation reactions on preformed scaffolds and the presence of excess free oligonucleotides or peptide is of no concern then here. By choosing a scaffold that closes only when all the constituent short oligonucleotides are present, instead of hybridizing multiple short oligonucleotides to a long scaffold strand, as is common for DNA origami (34), we avoided the possibility that a fraction of short oligonucleotides could inadvertently be excluded from the scaffold. The implementation of our strategy indeed showed that the number of scaffolded peptides in the construct can be tuned precisely without compromising the scaffold integrity (FIG. 2*c*), though this does not imply that all scaffolded constructs are able to form functional nanopores with the same number of peptides as templated. Based on the measured purities of the individual conjugates (Table 1), we infer that 96% of the scaffolds that were designed to bear eight peptides actually hold the anticipated number of eight peptides.

The DNA scaffold lowered the concentration of peptides required for pore formation significantly by pre-concentrating the peptides on the scaffold: 150-400 nM Wza peptide was added for control experiments (FIGS. 11B-E and 12-14), whereas only 5-40 nM of Wza peptides was used when they were attached to DNA scaffolds (FIGS. 3-5). However, despite the pre-concentration of up to 12 peptides on a single scaffold, we observed the insertion of nanopores of the same conductance for all scaffolds with at least eight peptides (Table 2), which suggests that the α-helices that compose the Wza D4 domain preferentially form octameric barrels, possibly because the D4 domain has evolved so that the octameric configuration is of the lowest free energy. We therefore suppose that it is not possible to force another stoichiometry on Wza peptides simply by bringing them together on the DNA scaffold used here. However, it might be possible to change the stoichiometry of nanopores made of more promiscuous peptides, or proteins that are known to form multiple species naturally, such as ClyA (35). To change the preferential stoichiometry of a homomeric nanopore, such as Wza, a more rigid scaffold that fits only one state could be used (12), but this will come at the expense of scaffold versatility: a specific scaffold may be required for every peptide and every stoichiometry.

Figure 21:
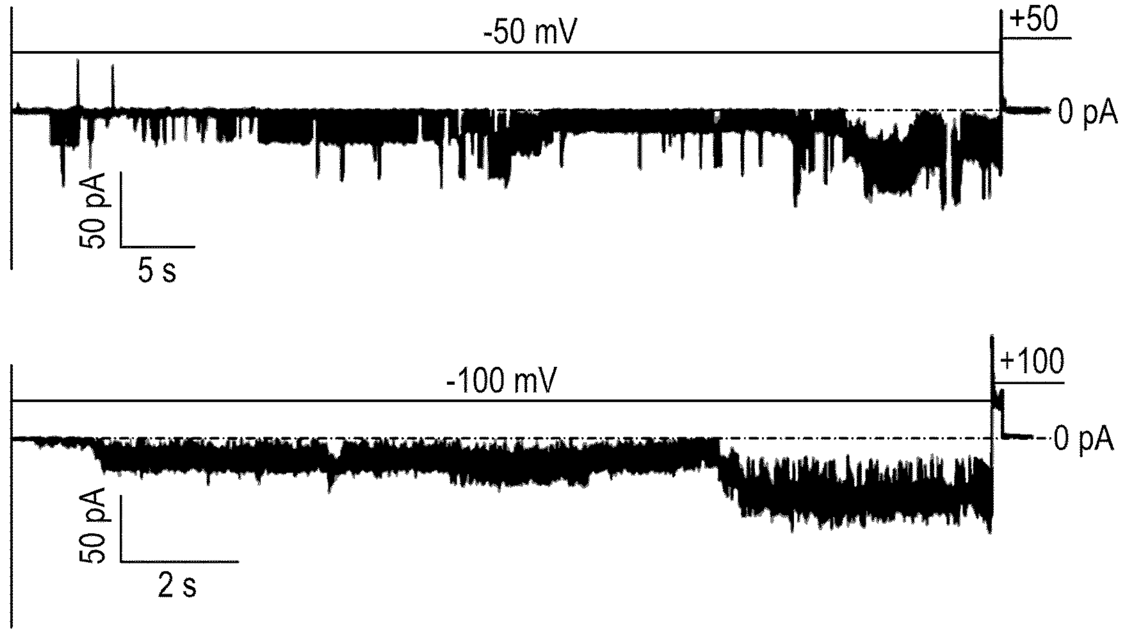
FIG. 21: Electrical recordings of pores formed by Wza peptides scaffolded through their C termini. Eight peptides were attached to the scaffold. The current signals were filtered at 2 kHz.

Our demonstration that DNA scaffolds can be used to pre-concentrate peptides and stabilize their assemblies to form membrane-spanning pores is of importance in several areas. For many synthetic peptides designed to form transmembrane channels and pores, it is difficult to obtain a crystal structure to determine the stoichiometry, pin down the transmembrane region and discern the orientation within the membrane (12, 36-40). The present approach is a direct means to control the stoichiometry, or at least its upper limit, and the direction of the insertion of candidate peptides into bilayers, provided the DNA scaffold does not restrict their assembly. For example, we also attached the Wza peptides through their C termini to the DNA scaffold, which leaves the N termini free. In this case, we did not observe insertions even at a tenfold higher concentration than that used for the N-terminus-attached Wza peptides (FIG. 21), which confirms that Wza typically requires a free C terminus for the insertion into planar lipid bilayers (9, 10, 12).

Conclusions

DNA rings can serve as scaffolds to template the formation of amphiphilic α-helical Wza peptides into stable octameric nanopores of uniform conductance. The inventors have shown that the scaffold is important for the stability of the pores tested and can be used to bind a variety of tagged oligonucleotides (with or without cargoes) after bilayer insertion. To enable the formation of uniform nanopores with various numbers of subunits, our scaffolds might also be used to direct the assembly of more promiscuous peptides, either designed de novo (41) or derived from antimicrobial peptides (28). The ability to form uniform large nanopores would open an immense range of possibilities, from the detection and fingerprinting of proteins in complex mixtures (42, 43) to single-molecule studies of enzymes (44) and the mapping of epigenetic markers on long strands of double-stranded DNA (dsDNA) (45). DNA scaffolds could be used further to form well-defined assemblies of multiple membrane proteins and pores (20), each held on a different arm or on separate, linked scaffolds. To prevent degradation of these scaffolds in living cells, synthetic analogues of DNA, such as xeno nucleic acid (46), could be used. Finally, the control over the relative position of each oligonucleotide in our scaffold will allow the assembly of well-known nanopores, such as α-haemolysin, with specified permutations of the subunits around a central axis as a first step towards creating advanced artificial enzymes (47, 48).

REFERENCES

1. Luckey, M. Membrane Structural Biology 2nd edn (Cambridge Univ. Press, Cambridge, 2014).
2. Zheng, J. & Trudeau M. C. (eds) Handbook of Ion Channels (CRC Press, Boca Raton, 2015).
3. Gilbert, R. J. C., Bayley, H. & Anderluh, G. Membrane pores: from structure and assembly, to medicine and technology. Phil. Trans. Roy. Soc. Lond. 372, 20160208 (2017).
4. Branton, D. et al. The epotential and challenges of nanopore sequencing. Nat. Biotechnol. 26, 1146-1153 (2008).
5. Ayub, M. & Bayley, H. Engineered transmembrane pores. Curr. Opin. Chem. Biol. 34, 117-126 (2016).
6. Koebnik, R., Locher, K. P. & van Gelder, P. Structure and function of bacterial outer membrane proteins: barrels in a nutshell. Mol. Microbiol. 37, 239-253 (2000).
7. Tamm, L. K., Hong, H. & Liang, B. Folding and assembly of O-barrel membrane proteins. Biochim. Biophys. Acta 1666, 250-263 (2004).
8. Noinaj, N., Gumbart, J. C. & Buchanan, S. K. The ebeta-barrel assembly machinery in motion. Nat. Rev. Microbiol. 15, 197-204 (2017).
9. Dong, C. et al. Wza the translocon for *E. coli* capsular polysaccharides defines a new class of membrane protein. Nature 444, 226-229 (2006).
10. Kong, L. et al. Single-molecule interrogation of a bacterial sugar transporter allows the discovery of an extracellular inhibitor. Nat. Chem. 5, 651-659 (2013).
11. Soskine, M. et al. An engineered ClyA nanopore detects folded target proteins by selective external association and pore entry. Nano Lett. 12, 4895-4900 (2012).
12. Mahendran, K. R. et al. A monodisperse transmembrane α-helical peptide barrel. Nat.

Chem. 9, 411-419 (2017).

13. Mutter, M. & Vuilleumier, S. A chemical approach to protein design—template-assembled synthetic proteins (TASP). Angew. Chem. Int. Ed. 28, 535-554 (1989).
14. Futaki, S. Peptide ion channels: design and creation of function. Pept. Sci. 47, 75-81 (1998).
15. Bayley, H. & Jayasinghe, L. Functional engineered channels and pores (review). Mol. Membr. Biol. 21, 209-220 (2004).
16. Pinheiro, A. V., Han, D., Shih, W. M. & Yan, H. Challenges and opportunities for structural DNA nanotechnology. Nat. Nanotech. 6, 763-772 (2011).
17. Wilner, O. I., Shimron, S., Weizmann, Y., Wang, Z.-G. & Willner, I. Self-assembly of enzymes on DNA scaffolds en route to biocatalytic cascades and the synthesis of metallic nanowires. Nano Lett. 9, 2040-2043 (2009).
18. Fu, J. et al. Multi-enzyme complexes on DNA scaffolds scapable of substrate channeling with an artificial lswinging arm. Nat. Nanotech. 9, 531-536 (2014).
19. Zhang, Y., Tsitkov, S. & Hess, H. Proximity does not contribute to activity enhancement in the glucose oxidase-horseradish peroxidase cascade. Nat. Commun. 7, 13982 (2016).
20. Raschle, T., Lin, C., Jungmann, R., Shih, W. M. & Wagner, G. Controlled co-reconstitution of multiple membrane proteins in lipid bilayer nanodiscs using DNA as a scaffold ACS Chem. Biol. 10, 2448-2454 (2015).
21. Lee, H. et al. Molecularly self-assembled nucleic acid nanoparticles for targeted in vivo siRNA delivery. Nat. Nanotech. 7, 389-393 (2012).
22. Douglas, S. M., Bachelet, I. & Church, G. M. A logic-gated nanorobot for targeted transport of molecular payloads. Science 335, 831-834 (2012).
23. Langecker, M. et al. Synthetic lipid membrane channels formed by designed DNA nanostructures. Science 338, 932-936 (2012).
24. Burns, J. R., Stulz, E. & Howorka, S. Self-assembled DNA nanopores that span lipid bilayers. Nano Lett. 13, 2351-2356 (2013).
25. Karshikoff A., Nilsson, L. & Ladenstein, R. Rigidity versus flexibility the dilemma of understanding protein thermal stability. FEBS J. 282, 3899-3917 (2015).
26. von Krbek, L. K. S. et al. The delicate balance of preorganisation and adaptability in multiply Bonded host-guest complexes. Chem. Eur. J. 23, 2877-2883 (2017).
27. Jolliffe K. A. Backbone-modified cyclic peptides: new scaffolds for supramolecular chemistry. Supramol. Chem. 17, 81-86 (2005).
28. Song, C. et al. Crystal structure and functional mechanism of a human antimicrobial membrane channel. Proc. Natl Acad. Sci. USA 110, 4586-4591 (2013).
29. Bowie, J. U. Solving the membrane protein folding problem. Nature 438, 581-589 (2005).
30. Krasilnikov, O. V. et al. Electrophysiological evidence for heptameric stoichiometry of ion channels formed by *Staphylococcus aureus* alpha-toxin in planar lipid bilayers.

Mol. Microbiol. 37, 1372-1378 (2000).

31. Salay, L. C., Procopio, J., Oliveira, E., Nakaie, C. R. & Schreier, S. Ion channel-like activity of the antimicrobial peptide tritrpticin in planar lipid bilayers. FEBS Lett. 565, 171-175 (2004).

32. Paulmann, M. et al. Structure-activity analysis of the dermcidin-derived peptide DCD-1L, an anionic antimicrobial peptide present in human sweat. J. Biol. Chem. 287, 8434-8443 (2012).
33. Howorka, S. & Bayley, H. Probing distance and electrical potential within a protein pore with tethered DNA. Biophys. J. 83, 3202-3210 (2002).
34. Rothemund, P. W. K. Folding DNA to create nanoscale shapes and patterns. Nature 440, 297-302 (2006).
35. Soskine, M., Biesemans, A., De Maeyer, M. & Maglia, G. Tuning the size and properties of ClyA nanopores assisted by directed evolution. J. Am. Chem. Soc. 135, 13456-13463 (2013).
36. Nicol, F., Nir, S. & Szoka, F. C. Orientation of the pore-forming peptide GALA in POPC vesicles determined by a BODIPY-avidin/biotin binding assay. Biophys. J. 76, 2121-2141 (1999).
37. Li, W., Nicol, F. & Szoka, F. C. GALA: a designed synthetic pH-responsive amphipathic peptide with applications in drug and gene delivery. Adv. Drug Deliv. Rev. 56, 967-985 (2004).
38. Rausch, J. M., Marks, J. R. & Wimley, W. C. Rational combinatorial design of pore-forming O-sheet peptides. Proc. Natl Acad. Sci. USA 102, 10511-10515 (2005).
39. Krauson, A. J., He, J., Wimley, A. W., Hoffmann A. R. & Wimley, W. C. Synthetic molecular evolution of pore-forming peptides by iterative combinatorial library screening. ACS Chem. Biol. 8, 823-831 (2013).
40. Gupta, K., Singh, S. & van Hoek, L. M. Short, synthetic cationic peptides have antibacterial activity against *Mycobacterium smegmatis* by forming pores in membrane and synergizing with antibiotics. Antibiotics 4, 358-378 (2015).
41. Thomson A. R. et al. Computational design of water-soluble α-helical barrels. Science 346, 485 (2014).
42. Yusko, E. C. et al. Real-time shape approximation and fingerprinting of single proteins using a nanopore. Nat. Nanotech. 12, 360-367 (2017).
43. Huang, G., Willems, K., Soskine, M., Wloka, C. & Maglia, G. Electro-osmotic capture and ionic discrimination of peptide and protein biomarkers with FraC nanopores. Nat. Commun. 8, 935 (2017).
44. Soskine, M., Biesemans, A. & Maglia, G. Single-molecule analyte recognition with ClyA nanopores equipped with internal protein adaptors. J. Am. Chem. Soc. 137, 5793-5797 (2015).
45. Wanunu, M. et al. Discrimination of methylcytosine from hydroxymethylcytosine in DNA molecules. J. Am. Chem. Soc. 133, 486-492 (2011).
46. Taylor, A. I. et al. Nanostructures from synthetic genetic polymers. ChemBioChem 17, 1107-1110 (2016).
47. Hammerstein, A. F., Jayasinghe, L. & Bayley, H. Subunit dimers of α-hemolysin expand the engineering toolbox for protein nanopores. J. Biol. Chem. 286, 14324-14334 (2011).
48. Lee, J. & et al. Semisynthetic nanoreactor for reversible single-molecule covalent chemistry. ACS Nano 10, 8843-8850 (2016).
49. Williams, B. A. R. & Chaput, J. C. in S. L. Beaucage (ed.) Current Protocols in Nucleic Acid Chemistry (Wiley, Hoboken, 2010).
50. Gutsmann, T., Heimburg, T., Keyser, U., Mahendran, K. R. & Winterhalter, M. Protein reconstitution into free-standing planar lipid membranes for electrophysiological characterization. Nat. Protoc. 10, 188-198 (2015).

S1. Šulc, P., Romano, F., Ouldridge, T. E., Rovigatti, L., Doye, J. P. K. & Louis, A. A. Sequence-dependent thermodynamics of a coarse-grained DNA model. J. Chem. Phys. 137, 135101 (2012).
S2. Snodin, B. E. K., Randisi, F., Mosayebi, M., Šulc, P., Schreck, J. S., Romano, F., et al. Introducing improved structural properties and salt dependence into a coarse-grained model of DNA. J. Chem. Phys. 142, 234901 (2015).
S3. Humphrey, W., Dalke, A. & Schulten, K. VMD: Visual molecular dynamics. J. Mol. Graph. 14, 33-38 (1996).
S4. Pettersen, E. F., Goddard, T. D., Huang, C. C., Couch, G. S., Greenblatt, D. M., Meng, E. C., et al. UCSF Chimera-A visualization system for exploratory research and analysis. J. Comp. Chem. 25, 1605-1612 (2004).
S5. Rovigatti, L. Utility to convert coarse-grained representation into all-atom representation. [posted 15 Aug. 2016]; Available from: https://sourceforge.net/p/oxdna/discussion/features/thread/lfcbb235/#121c
S6. Sobott, F., Hernández, H., McCammon, M. G., Tito, M. A. & Robinson, C. V. A Tandem Mass Spectrometer for Improved Transmission and Analysis of Large Macromolecular Assemblies. Anal. Chem. 74, 1402-1407 (2002).
S7. Liko, I., Degiacomi, M. T., Mohammed, S., Yoshikawa, S., Schmidt, C. & Robinson, C. V. Dimer interface of bovine cytochrome c oxidase is influenced by local post-translational modifications and lipid binding. Proc. Natl Acad. Sci. USA 113, 8230-8235 (2016).
S8. Hernandez, H. & Robinson, C. V. Determining the stoichiometry and interactions of macromolecular assemblies from mass spectrometry. Nature Protoc. 2, 715-726 (2007).
S9. Evans, G. W., Hohlbein, J., Craggs, T., Aigrain, L. & Kapanidis, A. N. Real-time single-molecule studies of the motions of DNA polymerase fingers illuminate DNA synthesis mechanisms. Nucleic Acids Research 43, 5998-6008 (2015).
S10. Gordon, M. P., Ha, T. & Selvin, P. R. Single-molecule high-resolution imaging with photobleaching. Proc. Natl Acad. Sci. USA 101, 6462-6465 (2004).
S11. Dave, R., Terry, D. S., Munro, J. B. & Blanchard, S. C. Mitigating Unwanted Photophysical Processes for Improved Single-Molecule Fluorescence Imaging. Biophys. J. 96, 2371-2381 (2009).

Example 2

This Example shows that the drawbacks of both protein- and DNA-based nanopores can be largely mitigated by merging them into novel, functional hybrid pores. This principle is demonstrated by templating alpha-hemolysin (αHL) monomers on well-defined DNA nanostructures into artificial pores.

The DNA nanostructures in this study are based on a single-stranded circular DNA molecule whose dimensions match those of the targeted pore. Various binding sites along the DNA template allow for the attachment of multiple α-hemolysin monomers. Using atomic force and electron microscopy, along with electrophoretic mobility assays, the well-defined dimensional scalability of the DNA/protein hybrid nanopores was verified. Electrical recordings in planar lipid bilayers corroborated the stepwise insertion of these constructs via stable and size-dependent current levels.

Materials and Methods

Materials. HPLC-purified DNA oligonucleotides were purchased from biomers.net as lyophilized powder.

Unmodified and phosphorylated oligonucleotides were dissolved in ddH2O at a concentration of 100 μM. The amino-modified oligonucleotide (ssDNA tail') was resuspended in 0.1 M phosphate buffer (pH 7.85) to a concentration of 800 PM. The lipid used in this study was 1,2-diphytanoyl-sn-glycero-3-phosphocholine (DPhPC) (Avanti Polar Lipids). The lipid was dissolved in hexadecane (Sigma-Aldrich).

Ammonium acetate, calcium chloride, ethylenediaminetetraacetic acid, imidazole, InstantBlue™—Protein Stain for PAGE, magnesium acetate, magnesium chloride, pentane, potassium chloride, tris(2-carboxyethyl)phosphine (TCEP), sodium chloride, sodium phosphate dibasic, sodium phosphate monobasic, sodium dodecyl sulfate (SDS), Tris-acetate-EDTA (TAE) buffer, glycine, triton X-100 and Trizma base were all purchased from Sigma-Aldrich. Any kDTM Mini-Protean® TGX precast protein gel and Precision Plus Protein™ Standards were from Bio-Rad Laboratories, Inc. λ-DNA, Quick Ligation Reaction Buffer and Quick T4 DNA Ligase were procured from New England Biolabs Inc. N-ε-maleimidocaproyl-oxysulfosuccinimide ester (Sulfo-EMCS) and SYBR Gold Nucleic Acid Gel Stain were obtained from Thermo Fisher Scientific. Poly-methylmethacrylate (PMMA 495 a5) was purchased from MicroChem. All chemicals were used as received without further purification.

Potassium chloride buffers (0.05-1.5 M KCl, 25 mM Tris, 50-400 μM EDTA, pH 7.99-8.0), and TEM buffer, were prepared and membrane-filtered (0.2 μm cellulose acetate, Nalgene) prior to use.

αHL monomer engineering and synthesis. Introduction of the K237C mutation into the αHL gene and protein expression was done as previously described (38). The vector also encoded a D8H6 tag at the C-terminus that was used for purification by $Ni^{2+}$-NTA chromatography. The αHL proteins were eluted using a buffer (50 mMTris, 0.5 MNaCl, 250 mMimidazole, 0.1% v/v Triton X-100, pH 8.0) that was supplemented with 1 mM tris(2-carboxyethyl)phosphine (TCEP), pH 8.0) in order to prevent the formation of disulphide bonds between the proteins. To verify the expression of K237C-αHLmutants, eluates in Laemmli buffer were run at 200 V for 40 min in an 'Any kD' precast protein gel in TGS (25 mMTris-HCl, 192 mM glycine, 0.1% w/v SDS) running buffer. The concentration of the eluates was determined photometrically using a NanoDrop Spectrophotometer (ThermoScientific)).

Preparation of ssDNA-modified αHL monomers. 650 μM amine-modified oligonucleotide ('the ssDNA tail') was treated with 12 mM N-ε-maleimidocaproyl-oxysulfosuccinimide ester (Sulfo-EMCS) in a 50 μl final volume (0.1M phosphate buffer (pH 7.85)) for 45 min at 35° C. on a shaker. During the preceding process, monomeric K237C-αHL mutants were separated from αHL heptamers by centrifugation through a 100-kDa MWCO filter device (Amicon, MerckMillipore, USA) for 30 min at 4° C. (0.2 M phosphate buffer (pH 6.6)). The reducing agent TCEP was then removed from the eluate containing the 30-kDa αHL monomers using a 10-kDaMWCO filter unit Amicon, Merck Millipore, USA) per the manufacturer's instructions. To exchange the buffer, the centrifugation was repeated twice with the addition of 200 μl 0.2M phosphate buffer (pH 6.6). At the same time, excess of Sulfo-EMCS was removed by two-timeMicroSpinG-25 column (IllustraGE healthcare Life Science, UK) filtration The purified SulfoEMCS modified oligonucleotide and monomeric K237C-αHL mutants were mixed at a ratio of 10:1 on a shaker for 1.5 h at 30° C., then for 20 min at 25° C. Finally, the proteins were separated from unbound DNA molecules, and the buffer exchanged to a 1×TEM buffer (5 mMTris, 1 mM EDTA, 12.5 mM $Mg(CH_3COO)_2$, pH8.05), by filtration using a10-kDa MWCO filter device Amicon, Merck Millipore, USA). To verify the oligonucleotide-protein conjugation, the sample was mixed at a 1:1 ratio with Laemmli buffer and run for 40 min at 200V in an 'Any kD' precast protein gel in TGS running buffer.

Preparation of circular DNA structures. Circular DNA structures with 12, 20 or 26 binding domains were prepared similarly. The procedure involved the step-wise ligation of shorter DNA oligonucleotides to a closed circular single-stranded DNA, and the subsequent addition of oligonucleotides that hold the complementary sequence to both: one helical turn of the ssDNA circle at its 5' end and the 'ssDNA tail' element. The respective oligonucleotide sequence for the ligation of the single-stranded DNA circle (Outer Circle, Cap and CapComp) and for its transition into its double-stranded form (Inner Circle) are given in Table 4.

First, 2.75 μM of each Outer Circle strand was mixed with a 3-fold molar excess of each Cap-L strand in 1× Quick Ligation Reaction Buffer, incubated for 20 min at room temperature on a shaker before 1 μl of Quick T4 DNA Ligase was added. The mixture was kept on a shaker for 2 h at 25° C. In order to remove the Cap-L strands, 33 μM of the Cap-L complementary strands CapComp were added. The mixture was heated to 80° C. for 5 min and then slowly cooled down to room temperature. The reaction mixture was electrophoretically separated on a non-denaturing polyacrylamide gel (120 V, 70 minutes) in 0.5× Tris-acetate-EDTA (TAE) buffer. SYBR Gold Nucleic Acid Gel Stain was used to stain the gel. The band representing the correctly ligated Outer Circle oligonucleotides was excised and homogenized in 300 μl diffusion buffer (0.5 M $NH_4C_2H_3O_2$, 10 mM $Mg(C_2H_3O_2)_2$). After incubation on a shaker at room temperature overnight, the gel debris was removed by filtration for 30 min at 10 000 g in a Proteus Clarification Mini Spin Column (Generon) and the DNA recovered by ethanol precipitation. The recovered linear single-stranded DNA molecule was circularized by adding 3-fold molar excess of the corresponding Cap-C strand in 1× Quick Ligation Reaction Buffer. 1 μl Quick T4 DNA Ligase was added after 20 min and the reaction kept at room temperature for 2 h. The Cap-C complementary CapComp oligonucleotide was added, heated to 80° C. for 5 min, followed by slowly cooling down of the solution. The ssDNA circle was purified by polyacrylamide gel electrophoresis (PAGE) as previously described. After separation of the gel debris, the corresponding Inner Circle strands were added at a ratio of 1:5 per binding side along the circular DNA scaffold strand in a 1×TEM buffer. The reaction was incubated on a shaker for 3 h at room temperature and, then, the excess of Inner Circle strands was removed by filtration through a 30-kDa MWCO filter device (Amicon, Merck Millipore, USA) using 1×TEM buffer. The DNA nanostructures were analyzed by native gel electrophoresis in a 0.5×TAE buffer at 120 V for 70 min. Unless otherwise stated, a 10% non-denaturing polyacrylamide gel was used. For verification of complete double-stranded DNA nanostructures the gel and buffer was supplemented with 6 mM $MgCl_2$.

Conjugation of the circular DNA structure and αHL monomers. The DNA-tail'-modified K237C-αHL mutants were passed through a 100-kDa MWCO filter device, and then mixed with the DNA circles in 1×TEM buffer at a DNA tail to DNA tail' ratio of 1:5. The mixture was placed on a shaker at room temperature for 15 min, and then incubated at 4° C. overnight. Excess αHL monomers were removed by filtration of the mixture using a100-kDa MWCO filter device (Amicon, Merck Millipore).

Liposome preparation. 1 mg/ml DPhPC solution was dried down from chloroform/methanol (9:1 v/v) under a nitrogen stream in a round glass vial, and kept in a desiccator for 3-4 h. The lipid film was hydrated with 1×TEM buffer to give a 1 mg/ml total lipid solution. The resulting dispersion was vortexed and then extruded 21 times through two 100 nm polycarbonate filters using a mini-extruder apparatus (Avanti Polar Lipids) to produce large unilamellar DPhPC liposomes.

Transmission electronmicroscopy (TEM). DNA/αHL constructs were mixed with DPhPC liposomes at a lipid to protein ratio of 1:1, and the mixture was shaken at room temperature for 15 min and further incubated overnight at 4° C. 5 μl droplet of the solution was pipetted onto a freshly glow-discharged copper/formvar/carbon grid (400 mesh, 3.05 mm diameter; Plano GmbH). After 5 min, the droplet was wicked away and the grid gently washed with double distilled water. Then, 5 μl of 2% (w/v) uranyl acetate was applied to the grid for 5 min and wicked away. Images of the DNA/αHL constructs inserted into the liposomes were acquired on a FEI Talos F200X TEM equipped with a Ceta 16M camera operated at an accelerating voltage of 200 kV. Analysis of the images was done using the Fiji image processing software (39).

Atomic force microscopy (AFM). The samples were prepared for AFM images on a freshly cleaved mica surface that was pre-treated with 5 mM MgCl2 for 2 min before rinsing with distilled water and drying under a nitrogen stream. 5 μl of the DNA nanostructure sample was applied and the excess solution wicked away after 2 min. The sample was then washed twice with 70 μl distilled water and dried under a nitrogen stream. Finally, the assembled circular DNA structures were imaged on an Agilent 5500 AFM with a MacMode III module (Keysight Technologies). AFM images were taken with NSC 15 AFM tips (Mikromasch) in tapping mode in air, and the images were analysed with WSxM 5.0 software (Nanotec, Inc.) (40). All images were processed prior to analysis by applying simple flattening with offset as subtract type Single-channel electrical recording. Electrical recordings were performed on a PLB formed across a 125-μm aperture in a 25-μm-thick Teflon film (Goodfellow) separating two Delrin chambers, at 21.0±2.0° C. The aperture was first treated with 1 μl hexadecane in pentane (1:100, v/v) on each side. After the pentane had evaporated, 0.5 mLbuffer solution (25 mM Tris, 50 μM EDTA, pH 7.99, supplemented with 0.1 M KCl unless stated otherwise) was added to each compartment such that the aperture was below the buffer level. A drop of DPhPC in pentane (10 mg/ml) was added on the buffer surface of each chamber. A lipid bilayer was formed across the Teflon aperture by lowering and raising the buffer level of the aperture in each compartment. Ag/AgCl electrodes were used for application of a bias potential (given as $V_{trans}-V_{cis}$) and electrical current measurements. The electrodes were connected to the headstage of a patch-clamp amplifier (Axopatch 200B, Molecular Devices) operating in voltage-clamp mode. Current signals were low-pass-filtered 80 dB/decade) with a corner frequency of 2 kHz, and sampled at 10 kHz with a Digidata 1440A digitizer (Axon Instruments). After the bilayer was stable for 10 min, 0.5-1 μl of the purified DNA αHL hybrid structure (typically 10 ng/μl) was added to the cis chamber. A potential of +100 mV (unless otherwise stated) was applied to assist the bilayer insertion and opening of the construct. Data were collected from freshly prepared DNA/protein hybrid structures: three independent assemblies for the $[21^{+}]_{12}$-DNA/$\alpha HL_{12}$, $[21^{-}]_{20}$-DNA/$\alpha HL_{20}$ and $[11^{-}]_{20}$-DNA/$\alpha HL_{20}$ constructs; five independent assembly reactions for the $[11^{+}]_{20}$-DNA/$\alpha HL_{20}$ and $[21^{+}]_{20}$-DNA/$\alpha HL_{20}$ constructs; four independent assemblies for $[21^{+}]_{26}$-DNA/$\alpha HL_{26}$ constructs. In order to block the ion current flow through the pore, 0.5 μl of a 15.6 nM λ-DNA solution was added to either the cis- or trans-side of an icosameric αHL pore that was stably inserted for at least 15 minutes. Data analysis was performed with the pClamp 9.2 software suite (Molecular Devices).

Statistical analysis. Unless otherwise indicated, all presented data is mean±S.D.

Modular Construction Principles for DNA/αHL Hybrid Structures

Figure 22A:
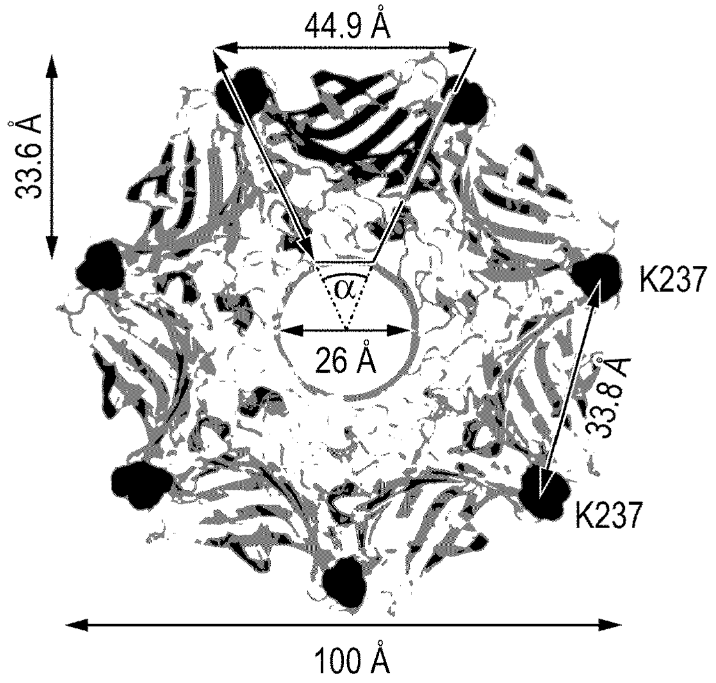
FIG. 22: Design of the DNA/αHL$_{20}$ hybrid pore. Top view of (A), the overall structure of the wild-type αHL pore, and (B), the β-sandwich domain of a single protomer. The residue K237 is highlighted in blue. The protein pore can be simplified as a ring of 7 triangles with an angle, α, of ~51.43°. The positions for possible monomer-monomer interactions within the cap domain in the region are highlighted in orange. (C) Comparison of the dimensions of a 220-bp long DNA ring (green, magenta) and the circular arrangement of 20 αHL monomers (blue). (D) Illustration of the assembly of the DNA/αHL hybrid structure. The DNA ring is composed of a closed single strand (the 'scaffold strand', green) that includes segments complementary to the 5' end of the DNA protruding strands. K237C-αHL mutants that are modified with an oligonucleotide which is complementary to the 3' end of these DNA strands can be arranged along the resulting DNA structure. (E) Schematic representation of the nucleic acid modification of a single αHL cys-mutant through a chemical crosslinker. (F) SDS-polyacrylamide gel showing unheated samples of unmodified (lane 2) and ssDNA-modified (lanes 3 and 4) K237C-αHL mutants. Lane 1 contains a protein standard; lanes 3 and 4 represent two different reactions under the same conditions. (G) Design of the repetitive sequence segments of the DNA template based on either 11 bp per one helical turn (i,ii), or 21 bp per two helical turns (iii, iv). (H) AFM images of DNA structures based on 21 bp per helical turn. Scale bars=27 nm. (I) $MgCl_2$-supplemented native PAGE analysis of 210-bp-DNA template assemblies. Lane 1: linear ssDNA strand; lane 2: circularized ssDNA strand; lane 3: dsDNA $[21^+]_{20}$-circle; lane 4: dsDNA $[21^-]_{20}$-circle.
Figure 22B:
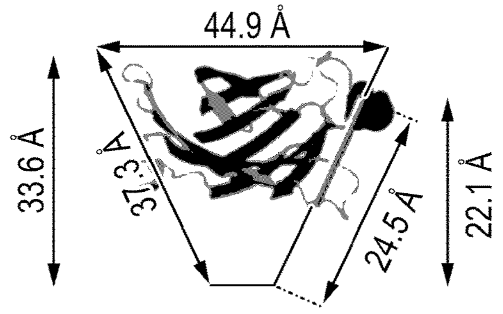
Figure 22C:
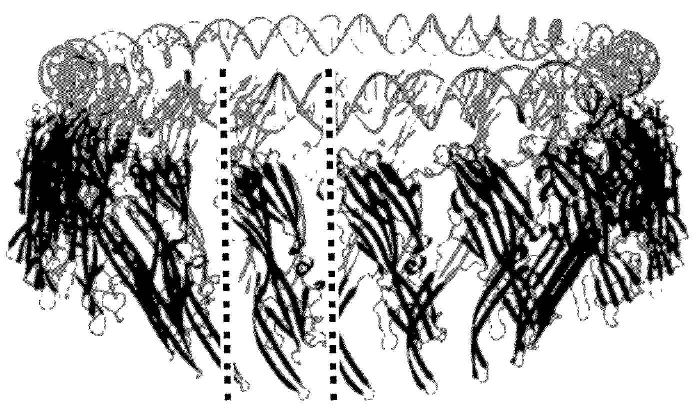
Figure 28:
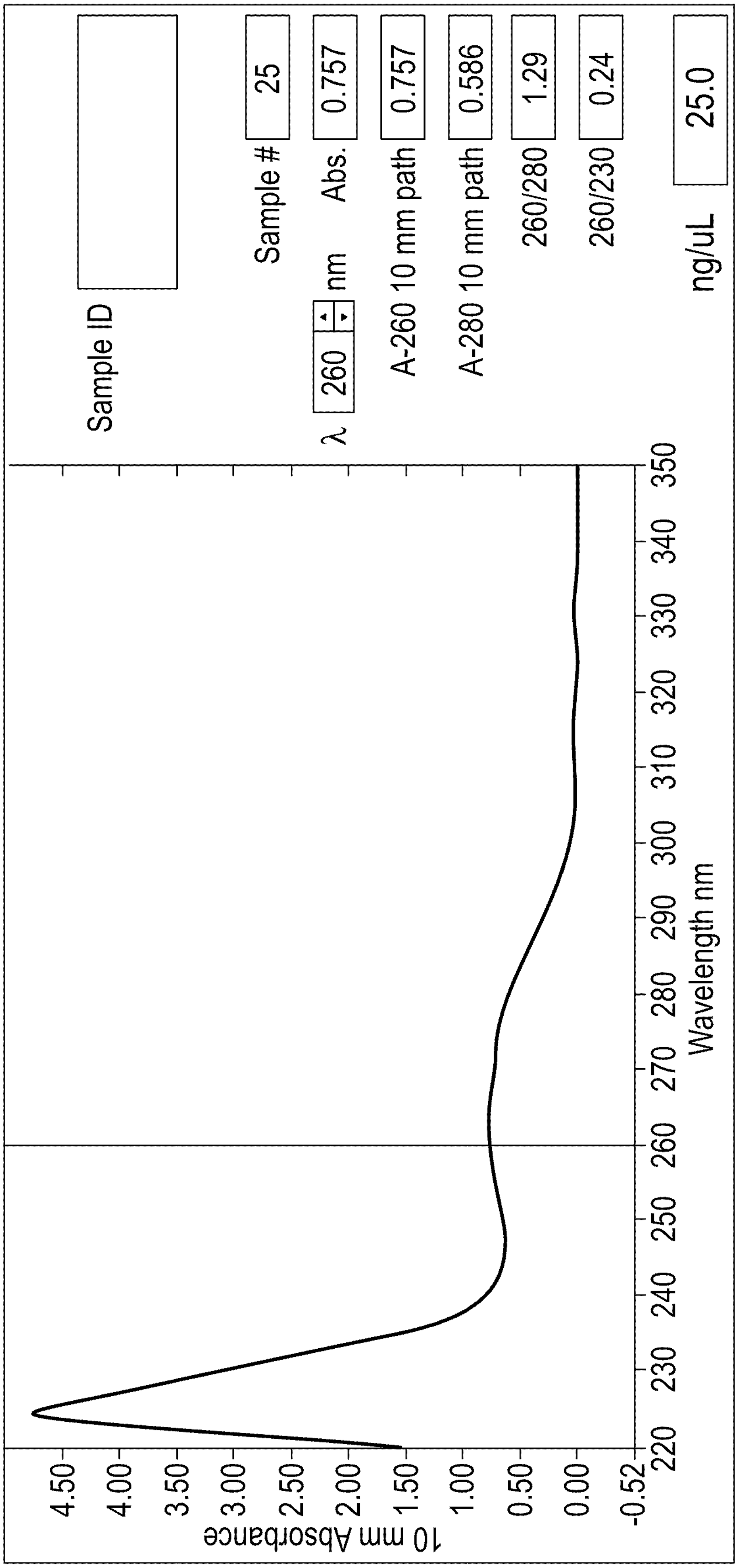
FIG. 28: Typical 260 and 280 nm absorbance of DNA-modified K237C-αHL mutants using a NanoDrop spectrophotometer. The sample was filtered to remove unbound oligonucleotides. Using an extinction coefficient of ε1%=11 (1), the calculated concentration of αHL monomers was 16.1 μM. The calculated DNA concentration of 5.93 μM was determined using the ssDNA-specific conversion factor of 33 μg/OD260. Thus, the ratio of DNA to protein was 1:2.7. Unmodified αHL monomers were removed after the conjugation with the DNA templates. Gel electrophoretic separation of the sample is shown in Figure if (lane 3).

The well-characterized, mushroom-shaped αHL occurs naturally as a homoheptamer (41), and is one of the most commonly studied proteins in nanopore sensing (11,42-46). αHL's 293-amino acid (aa) long protomer can be regarded in plan view as a trapezoid (FIGS. 22A and B). The residue K237 at the top of the protomer is separated by 33.8 Å from the same residue in the adjacent protomer. Since this length is very similar to the 34 Å helical pitch of B-DNA (47), we designed a circular DNA template that has a single strand of DNA protruding from every helical turn (FIGS. 22C and D). The sequence of this strand was optimized to be free of any hairpin structure. Therefore, the strand provides an accessible attachment point for 37.8 kDa K237C-αHL mutants that were chemically cross-linked at C237 to a complementary amide-modified oligonucleotide (FIGS. 22E and F; FIG. 28). The three nucleotides of the protruding strand nearest to the circular DNA remained unpaired to provide sufficient flexibility for the monomer arrangement without risking entanglement. To facilitate the circular shape of the DNA nanostructure, its design was based on sequences with a reported intrinsic curvature, i.e. five base pairs (bp)-long A-tracts in each helical turn (48-49).

Concept for the Circular DNA Structure Assembly

Figure 23A:
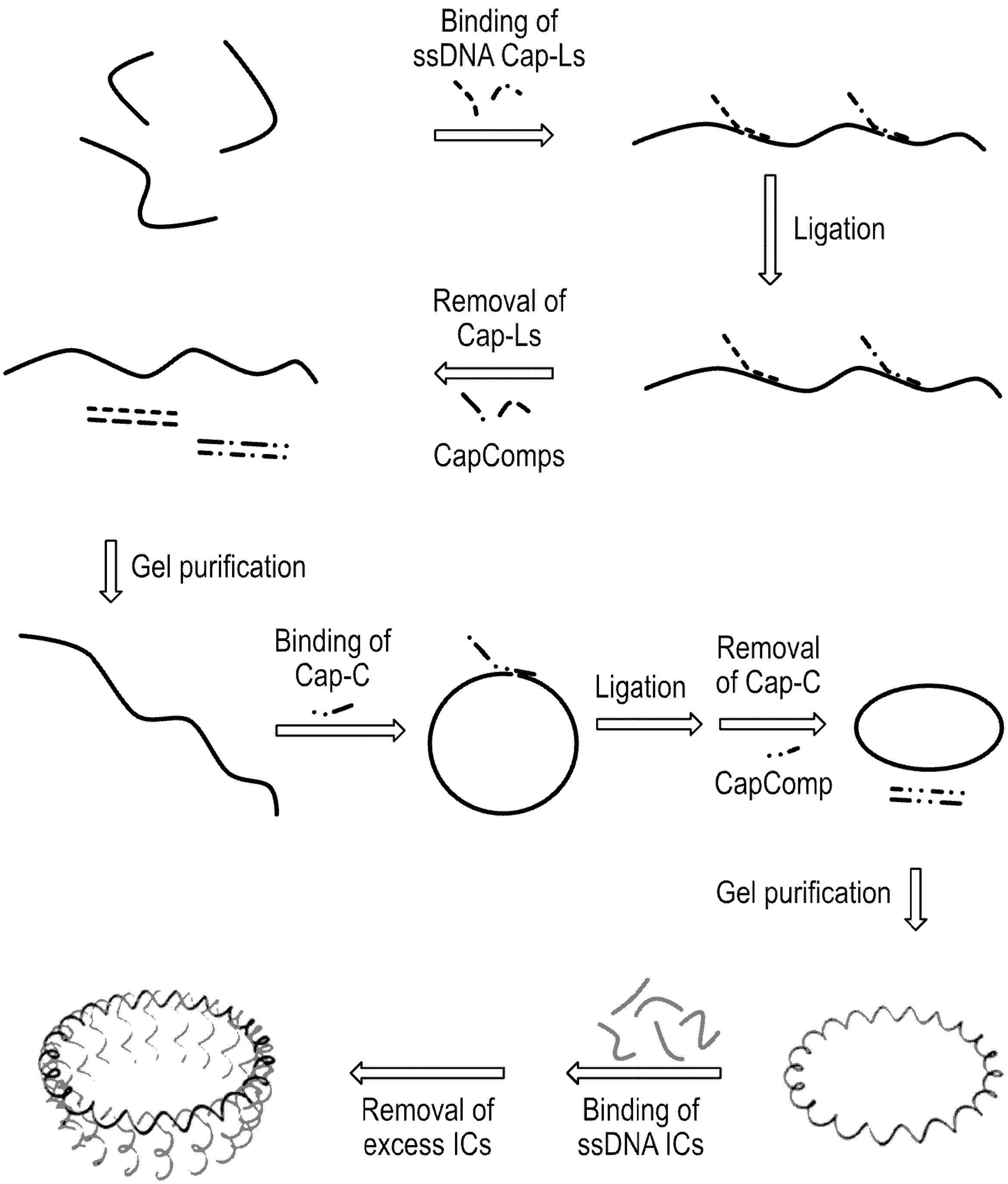
FIG. 23: Preparation of the circular DNA template with 20 segment elements. (A) Schematical representation of the two-step ligation of several Outer Circle oligonucleotides (highlighted in green) into a single-stranded DNA circle. The addition of the Inner Circle oligonucleotides (ICs) results in the completion of the dsDNA nanostructure. (B) Native PAGE analysis of the ligation of the Outer Circle oligonucleotides. Lane 1: sequence OC01; lane 2: sequence OC02; lane 3: sequence OC03; lane 4: ligation of OC01 and OC02; lane 5: ligation of OC02 and OC03; lane 6: ligation of OC01 and OC03; lane 7: ligation of OC01, OC02 and OC03. (C) Native PAGE analysis of ligated and non-ligated Outer Circle oligonucleotides under different conditions for the binding of the Cap oligonucleotides. Annealing of the Cap sequences by heating-cooling treatment (lanes 1-4) or at room temperature (lanes 5-8). Resulting products were ligated for samples in lanes 1, 2, 5, 6. Caps were removed for lanes 1, 3, 5, 7.
Figure 23B:
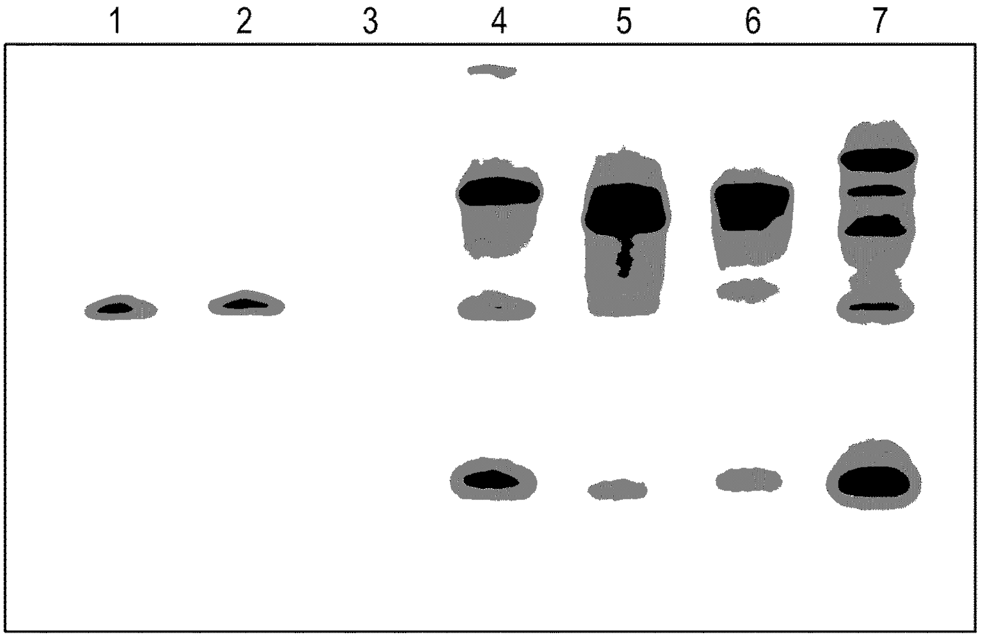
Figure 31A:
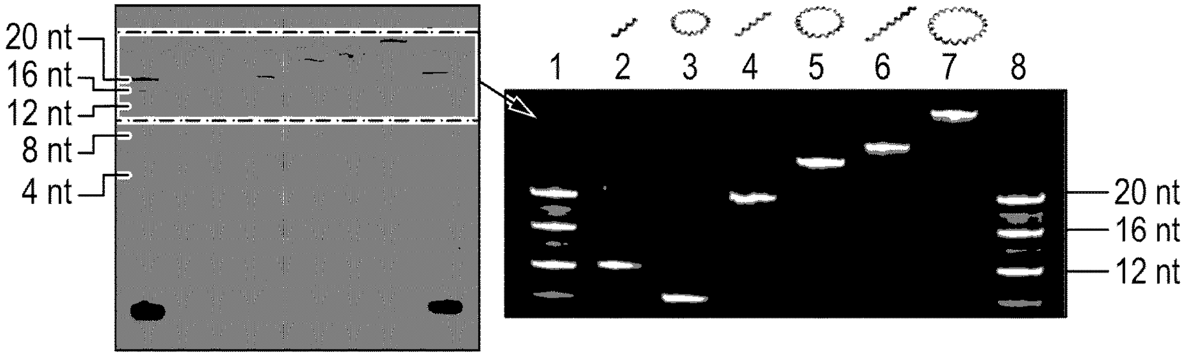
FIG. 31: Native PAGE analysis of $[21^+]_{12}$-, $[21^+]_{20}$-, and $[21^+]_{26}$-DNA assemblies. a, Comparison of linear and circularized ssDNA scaffold strands with 12, 20, and 26 domains. Lanes 1 and 8: ligation of 3 oligonucleotides to the linear 210-nt long ssDNA strand; lane 2: linear 126-nt ssDNA long strand; lane 3: circularized 126-nt long ssDNA strand; lane 4: linear 210-nt long ssDNA; lane 5: circularized 210-nt long ssDNA; lane 6: linear 273-nt long ssDNA; lane 5: circularized 273-nt long ssDNA. Note that the circular ssDNA strand with 12 segments (lane 3) runs before the linear strand since its compact shape enables it to pass the pores of the gel more easily. The two gels represent 10% PAGE gels that were run under the same conditions, but for different durations. b, Comparison of single-stranded and double-stranded circular $[21^+]_j$-DNA templates. Lane 1: circularized 126-nt long ssDNA strand; lane 2: circularized 210-nt long ssDNA; lane 3: circularized 273-nt long ssDNA; lane 4: circularized 126-nt long dsDNA strand; lane 5: circularized 210-nt long dsDNA; lane 6: circularized 273-nt long dsDNA. The $[21^+]_{12}$-DNA structure runs in a 10% PAGE gel (supplemented with 6 mM MgCl2) as a smear; running it in a 15%-Mg2+ PAGE gel results in a sharp band with a lower mobility than the 126-nt long ssDNA scaffold, as shown in the inset.

In order to prepare well-defined annular DNA nanostructures (FIG. 31), we used a design that is based on a circular single-stranded (ss) scaffold (called Outer Circle) with a diameter that matches the targeted DNA/αHL hybrid pore. This Outer Circle comprises appropriate segments in the form of one or two helical turns. The segments guide the arrangement of several, shorter DNA oligonucleotides (called Inner Circle) that, in turn, hold each of the complementary sequences to the oligonucleotide-modified αHL monomer. As schematically illustrated in FIG. 23A, the preparation of the Outer Circle involves a two-step ligation. The first ligation chemically links shorter oligonucleotides into a long linear single-stranded DNA molecule. This step is necessary due to the oligonucleotide-length limitations of chemical oligonucleotide synthesis. The second ligation joins both ends of the linear DNA molecule into a circle. In detail, the sequences for the Outer Circles for the first ligation are connected through CapL oligonucleotides that bind specifically to the two sequence domains at the 5' and 3' end of two Outer Circle oligonucleotides. A third sequence domain at the 5' end of the Cap-L strand remains unbound. After ligation, the Cap-L strands are removed through strand displacement by the addition of their fully complementary oligonucleotide called CapComp. The resulting linear ss-DNA strand is PAGE purified. For instance, for a linear twenty segment-long Outer Circle strand, the upper band of the gel was cut out (lane 7 of the PAGE assay in FIG. 23B). The connection of the Outer Circle oligonucleotides through Cap sequences can be performed at room temperature.

Figure 23C:
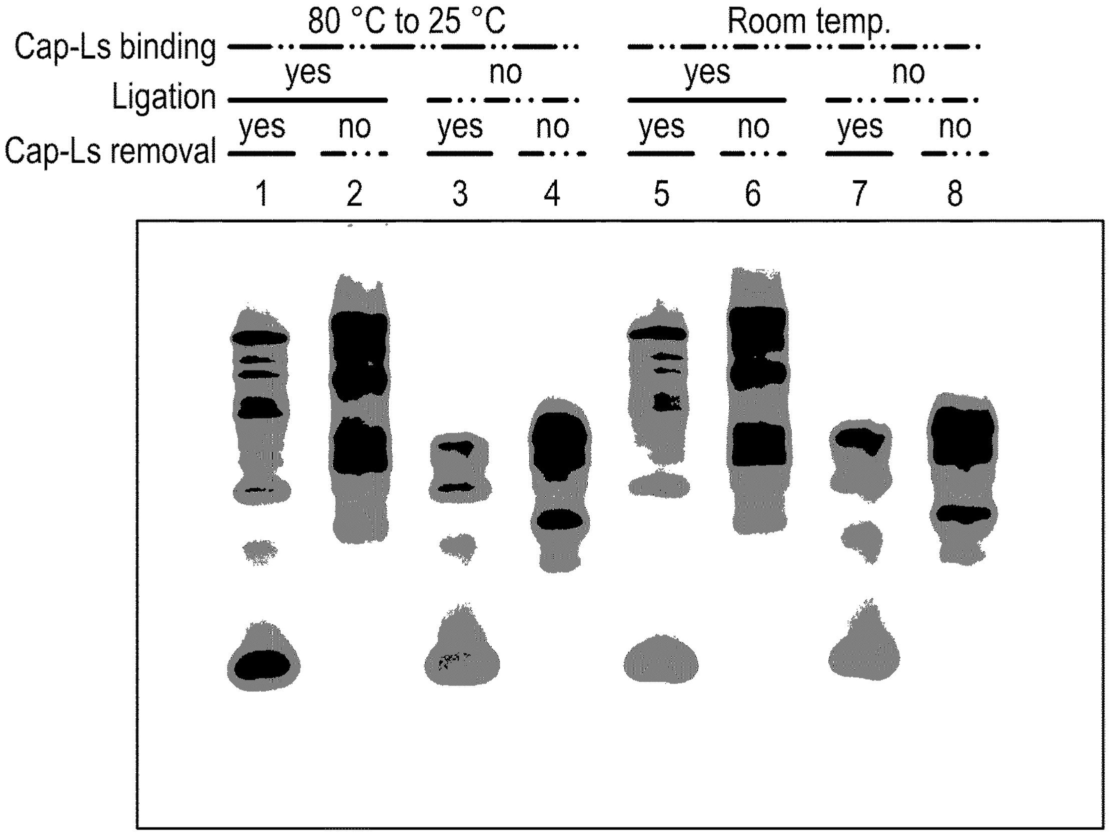
Figure 31B:
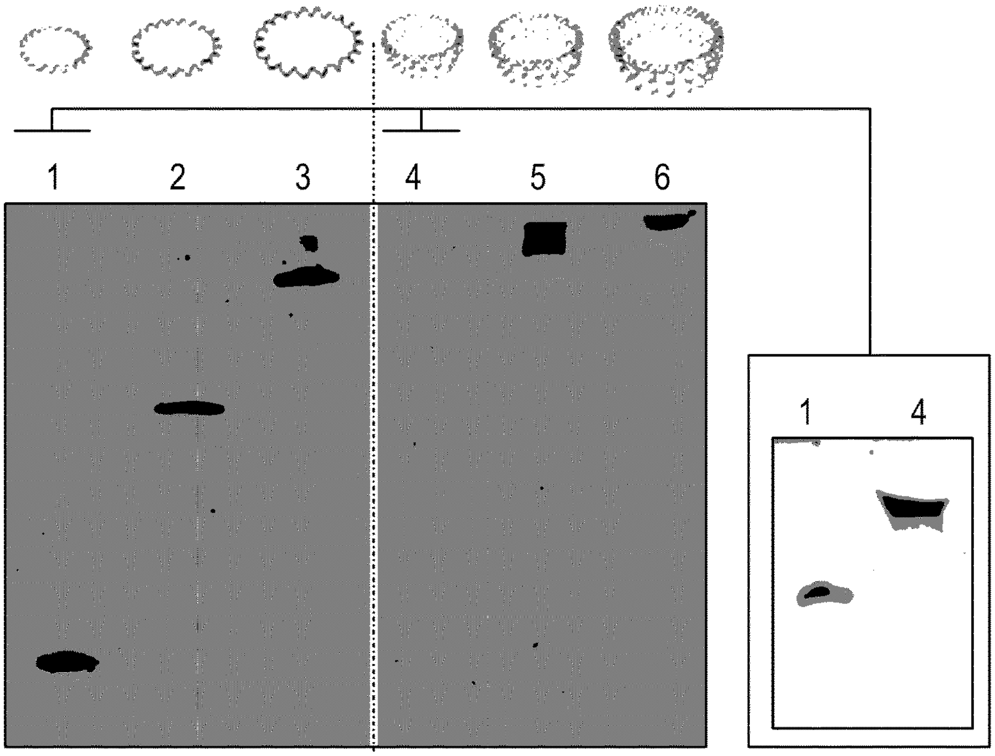

Annealing by heating to 80° C. and slowly cooling down to 25° C. resulted in a similar yield of the linearized ssDNA template (FIG. 23C). The purified Outer Circle strand is closed into a ssDNA circle by adding a Cap-C oligonucleotide with a sequence that is complementary to both ends of the linear ssDNA molecule. Finally, the Cap-C is removed through strand displacement. After PAGE purification the circular ssDNA template is converted into its double-stranded (ds) form by the addition of the corresponding Inner Circle oligonucleotides (FIG. 23A; FIG. 31B).

Formation of a Homo-Oligomeric αHL Icosamer

Figures 22D, 22E, 22F, 22G, 22H, 22I:
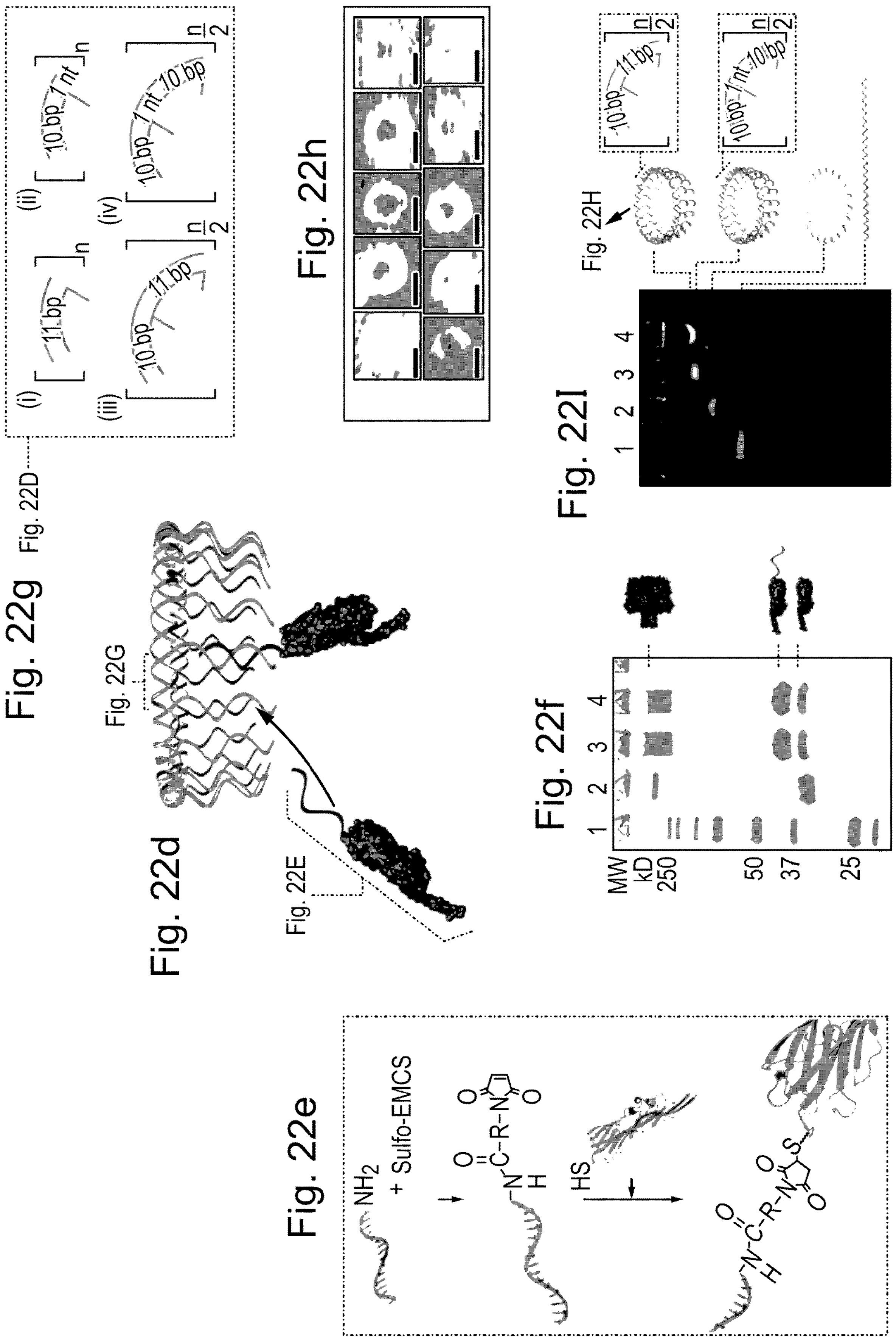
Figure 24A:
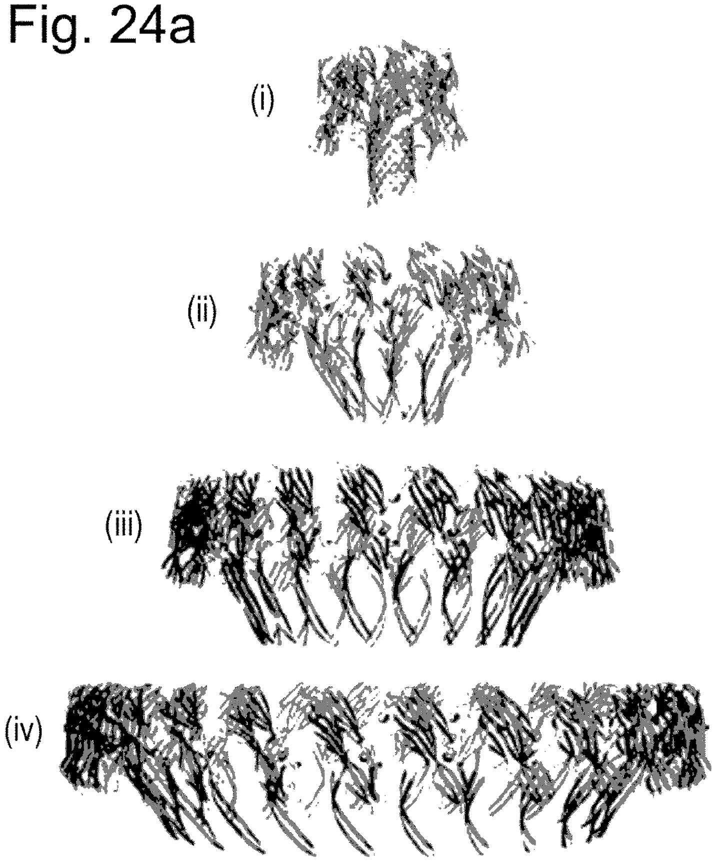
FIG. 24: Different stoichiometries of the DNA/αHL hybrid pores investigated in this study. (A) Comparison of the dimensions of a (i) heptameric, (ii) dodecameric, (iii) icosameric and (iv) hexacosameric αHL pore based on a monomer width of 33.8 Å. (B) Example TEM micrographs of liposomes-adhered DNA-modified K237C-αHL mutants in (i) the absence of a DNA structure, or assembled along a circular DNA with (ii) 12, (iii) 20, and (iv) 26, sequence segments. Scale bar in (i) is 10 nm and applies to all images. (C) Conductance dependence on pore stoichiometry of DNA-modified K237C-αHL mutants. (D) Conductance histogram for the different DNA/αHL hybrid pores.
Figure 24B:
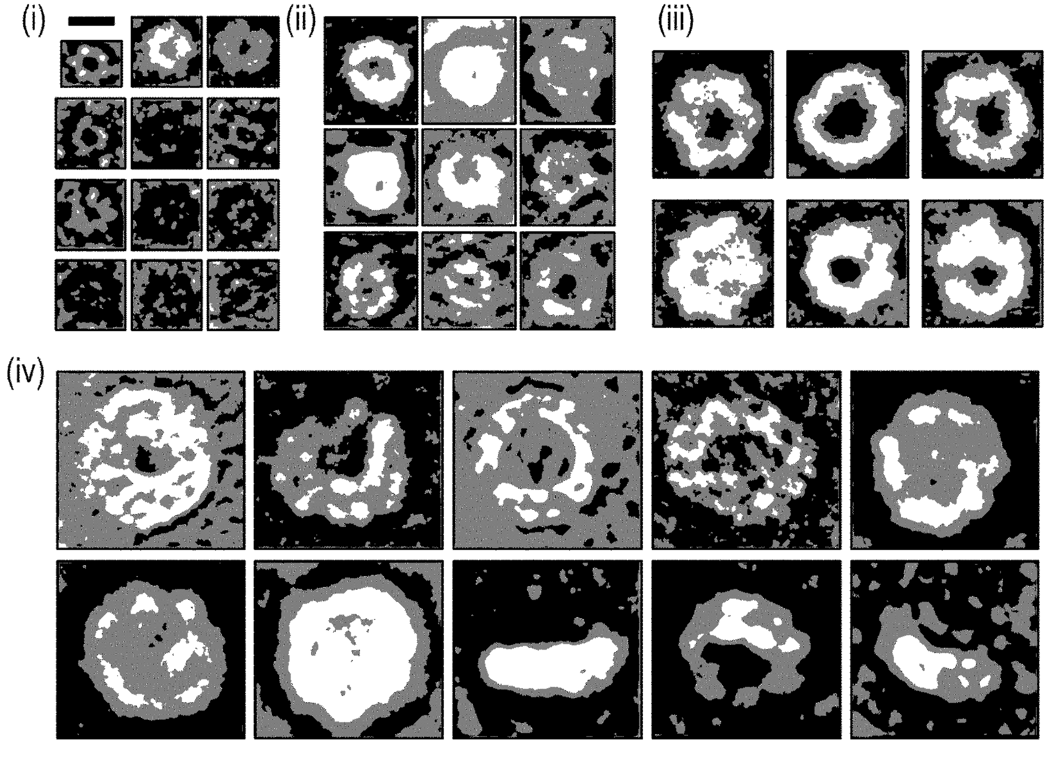
Figure 29A:
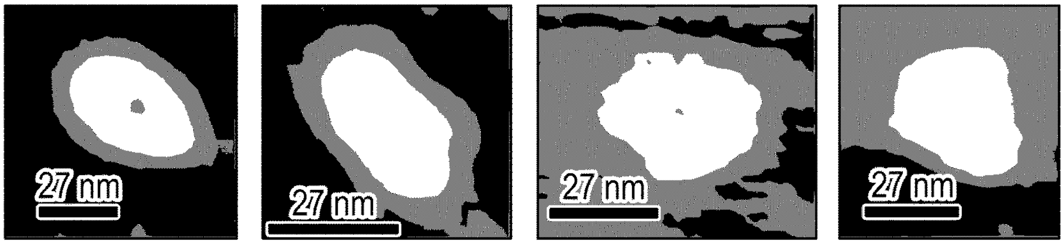
FIG. 29: 220-bp-DNA template assemblies. a, AFM images of DNA structures based on 11 bp per helical turn. Scale bars=27 nm. b, MgCl2-supplemented native PAGE analysis of 220-bp-DNA template assemblies. Lane 1: ligation of 3 oligonucleotides to the linear ssDNA strand; lane 2: circularized ssDNA strand; lane 3: dsDNA $[11^+]_{20}$-circle; lane 4: dsDNA $[11^-]_{20}$-circle.
Figure 29B:
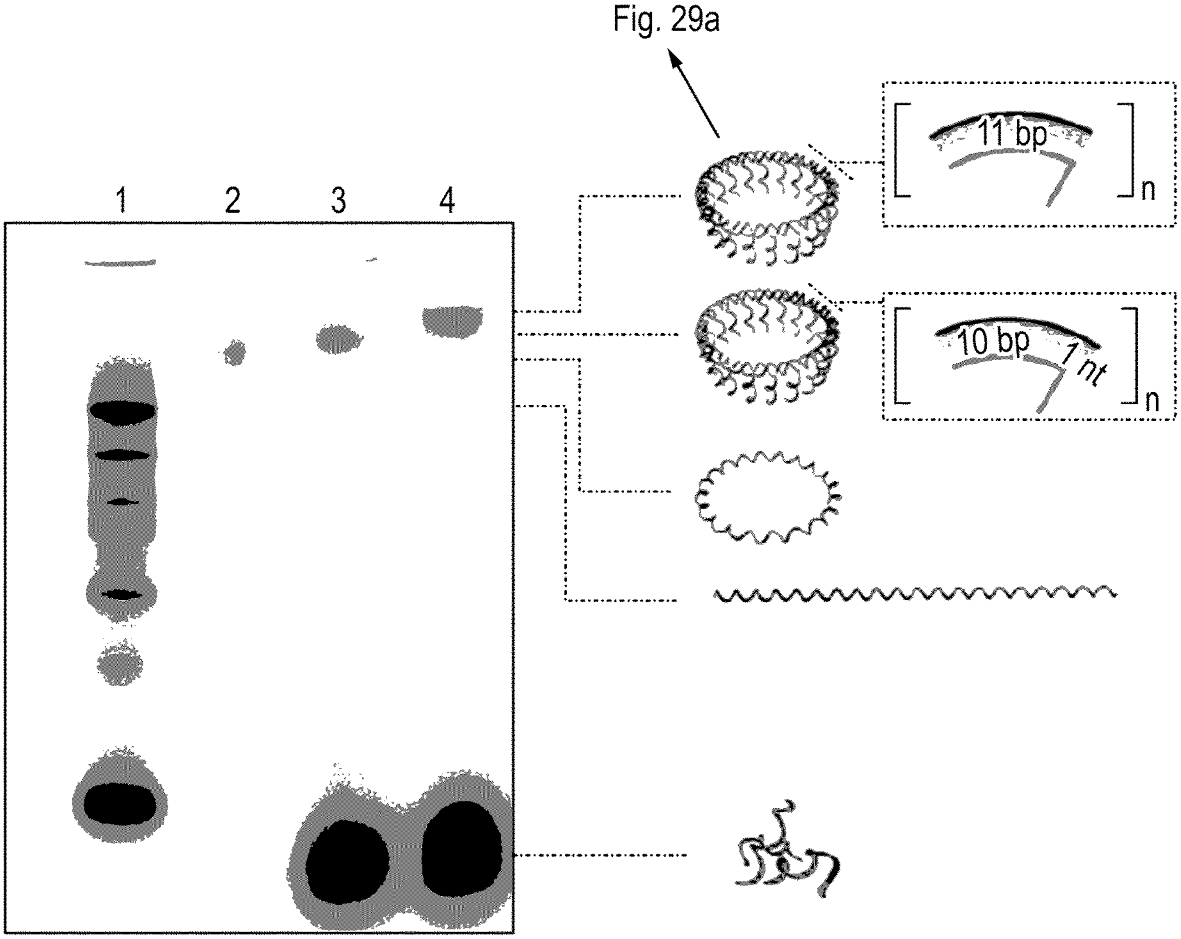
Figure 30:
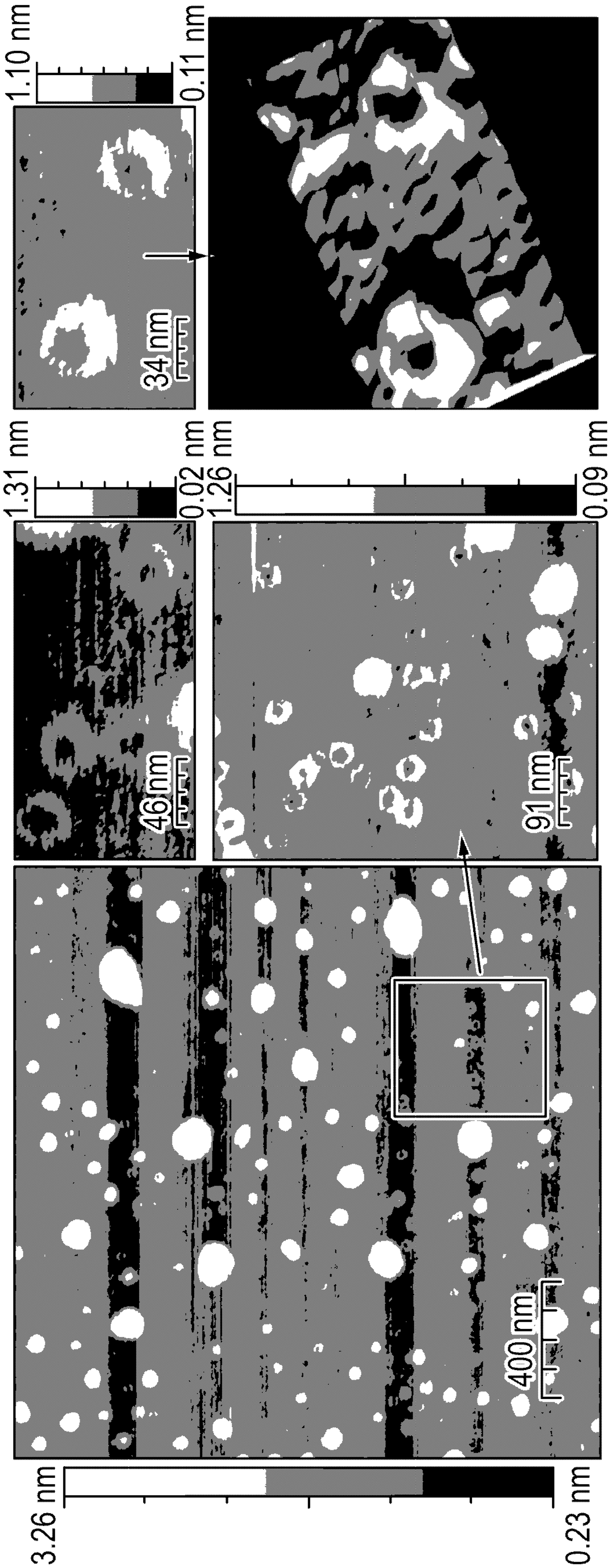
FIG. 30: AFM topography images of $[21^+]_{20}$-DNA nanostructures. Additional AFM images of the $[21^+]_2$-DNA nanostructures without αHL. The images show a homogenous distribution of the DNA nanostructures.
Figure 32B:
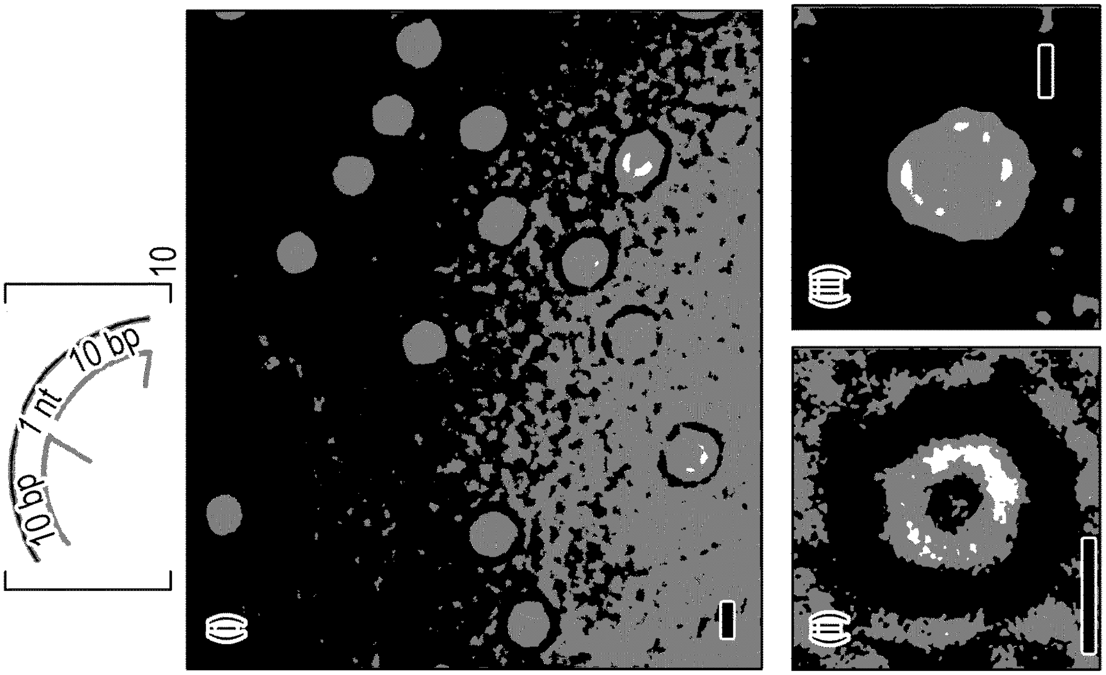
FIG. 32: TEM micrographs of DNA/αHL icosamers based on a, 11 bp, or b, 10.5 bp, per helical turn in the presence of DPhPC liposomes. Hybrid pores were found mainly adhered to the liposomes or on lipid covered areas. Scale bar: a: 50 nm; b: (i) 20 nm, (ii) 10 nm, (iii) 10 nm.
Figure 32A:
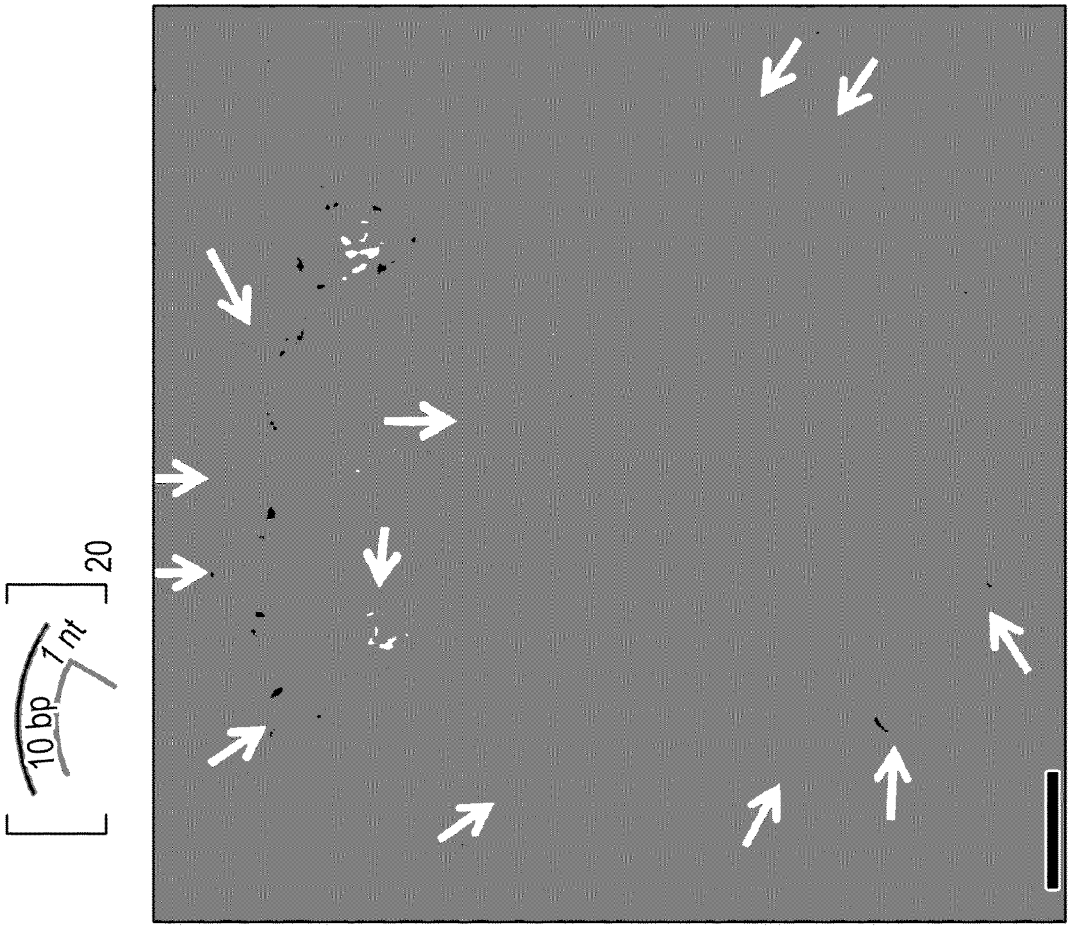
Figures 34A, 34B:
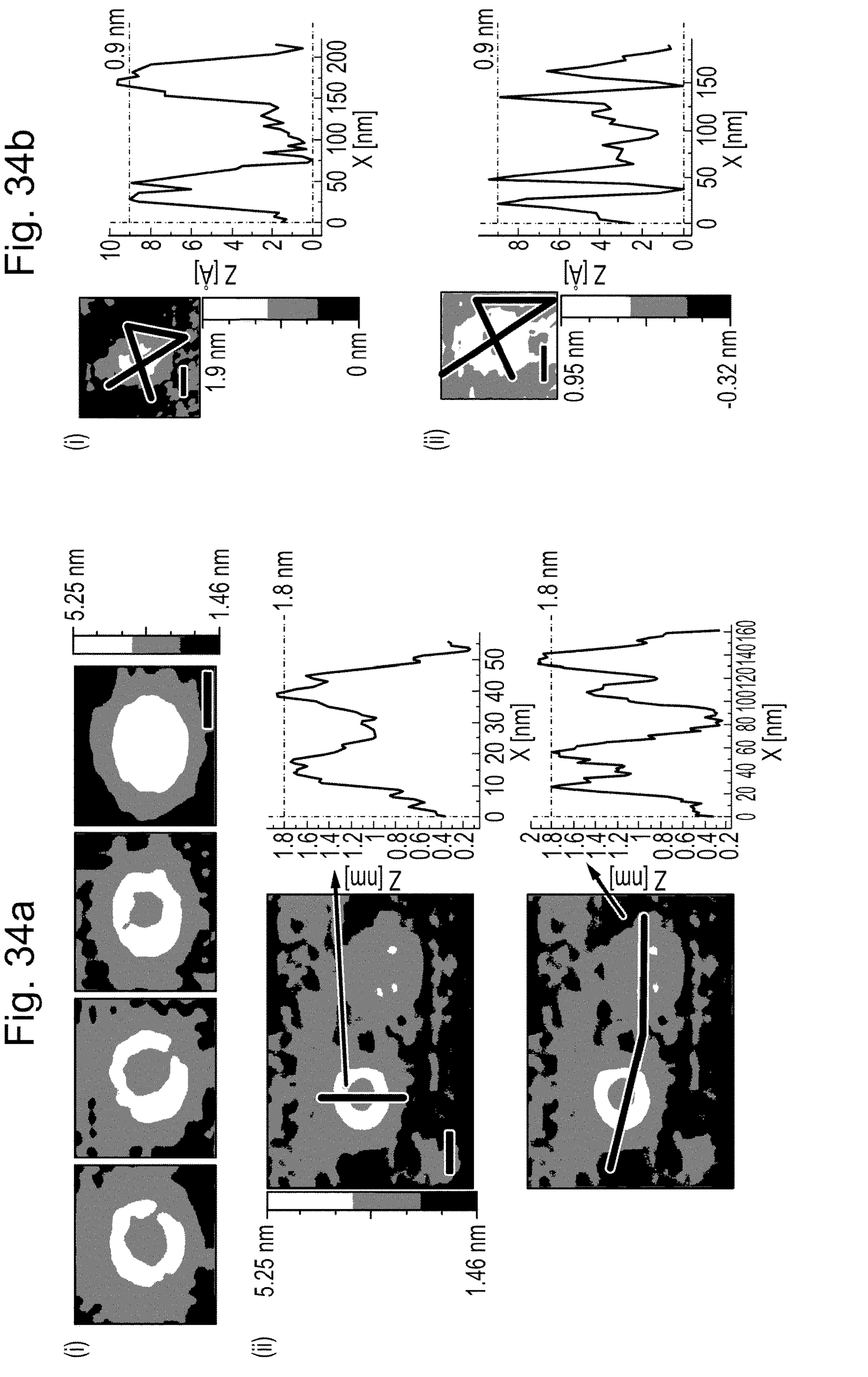
FIG. 34: AFM images of $[21^+]_{20}$-DNA templates with (a) and without (b) αHL monomers. Scale bar is 27 nm and applies to all images.

First we focused on the arrangement of twenty αHL monomers. Since one helical turn in B-DNA consists of 10.5 bp, we examined four different sequence designs for their suitability to align the protruding strands in the same direction. These were either repetitive segments of 11 bp per one helical turn, or 21 bp per two helical turns, with or without an unpaired nucleotide (nt) to compensate for possible tension (FIG. 22G). In other words, the 21-bp long segments comprise two protruding strands each, while the 11 bp-long segments have one protruding strand each. Hence, the total number of segments (n) for a DNA structure based on 21-bp segments is half of that for one based on 11-bp segments to yield a DNA template with the same number of protruding strands. We denoted the DNA structures as $[b^i]_j$, where b represents the number of bp per segment, i the presence (+) or absence (−) of the unpaired nt, and j the number of protruding strands. The stepwise assembled DNA structures (FIG. 22I; FIG. 29B) were of an annular shape with—taking into account the AFM-tip size—a diameter comparable to the theoretical value of ~23 nm (FIG. 22H; FIGS. 29A and 30). In contrast, adding DNA-modified αHL monomers resulted in better-defined circular structures with a 2-fold increase in height compared to the DNA structures alone (FIG. 34). Furthermore, transmission electron microscopy (TEM) images of the constructs in the presence of liposomes showed ring-shaped particles that were predominantly bound to lipid bilayer membranes. In the case of $[11^+]_{20}$- and $[21^+]_{20}$-DNA structures, the diameters were 19.81±1.27 nm (n=13; FIG. 32) and 19.54±1.45 nm (n=96; FIG. 24B(iii)), respectively. K237C-αHL mutants in the absence of the DNA template had a diameter typical for αHL heptamers of 10.11±1.08 nm (n=121; FIG. 24B(i)).

Single-Channel Characterization of αHL Icosamer in Planar Lipid Bilayers (PLBs)

Figure 25A:
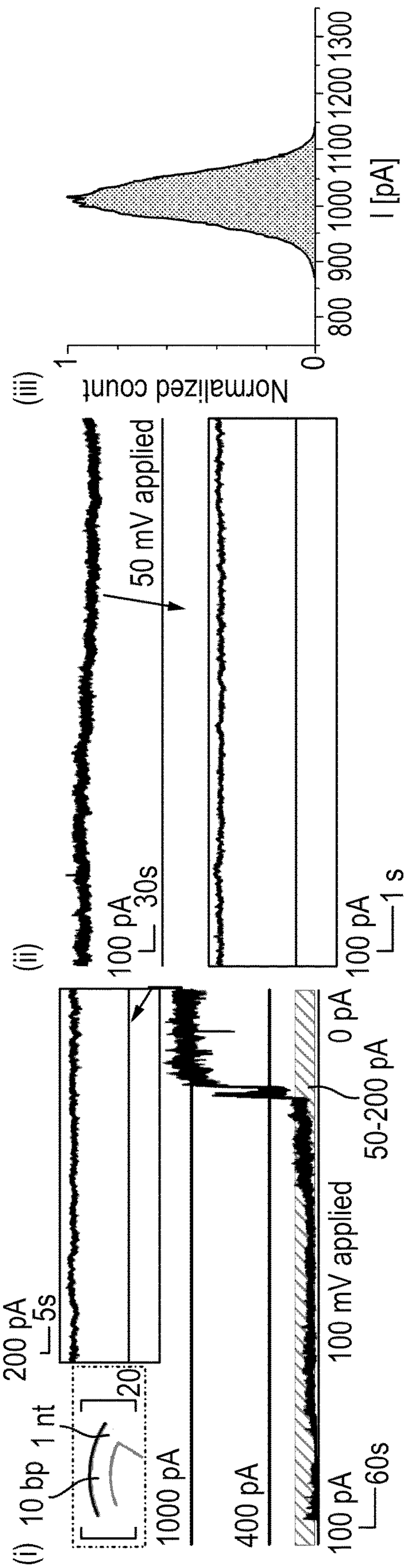
FIG. 25: Electrical recordings of DNA-templated αHL icosamers. (A, i), Stepwise increase in ionic current during the insertion of one $[11^+]_{20}$-based hybrid pore. (ii) Single channel recording after insertion at 50 mV. (iii) All-point histogram of a 1-min-long current trace of an open pore at 100 mV. (B) Insertion trace (i) and single channel recordings at 50 mV (ii) and all-point histogram of a 1-min-long current trace at 100 mV (iii) of an $[21^+]_j$-based icosamer.
Figure 25B:
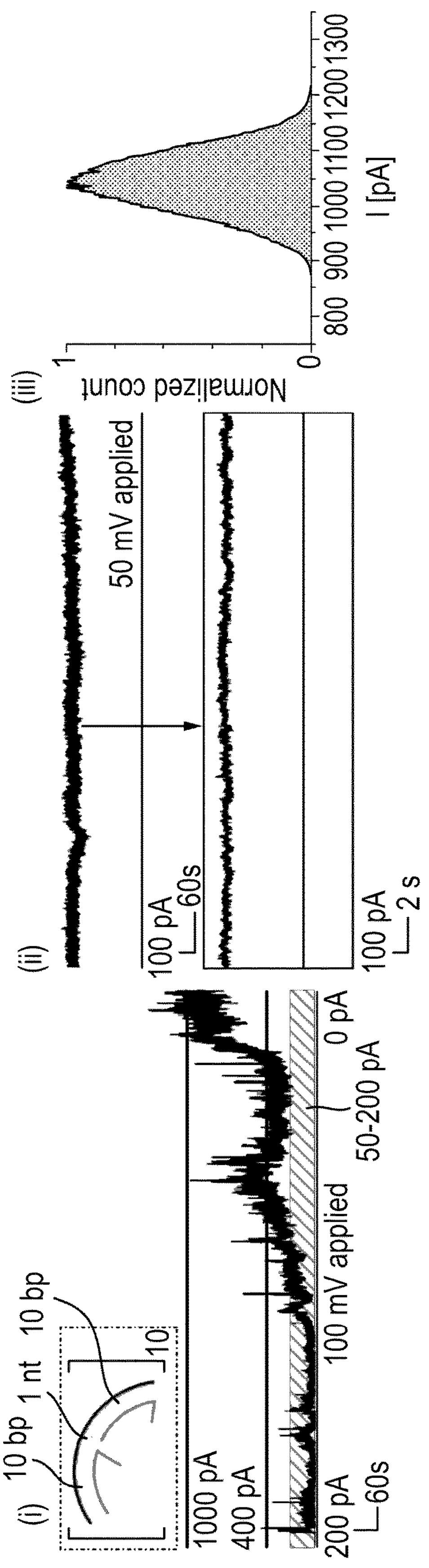
Figure 26B:
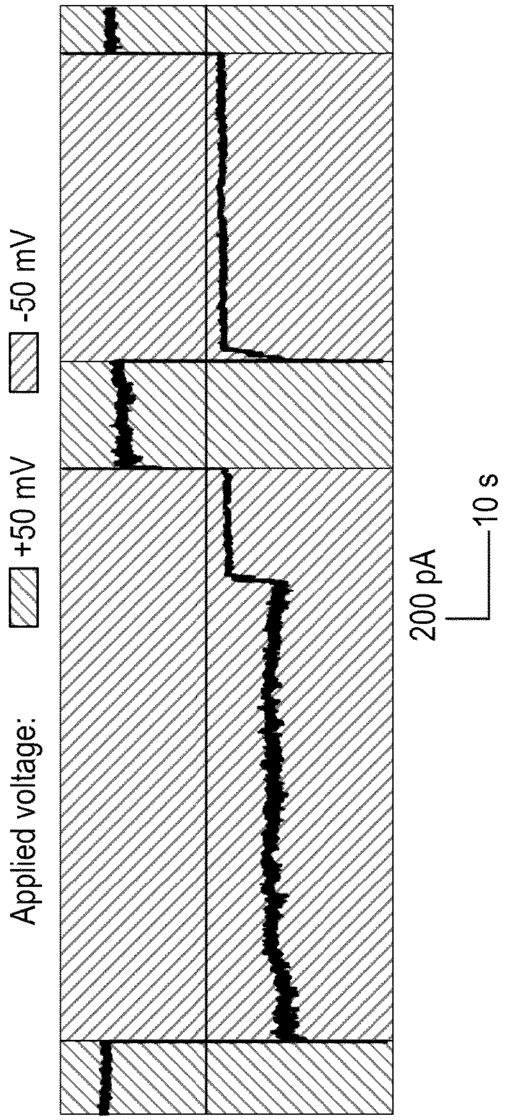
FIG. 26: Blockage of icosameric αHL pore. (A) λ-DNA molecules were added to the trans-side after a purified DNA/αHL hybrid structure was incorporated into a DPhPC bilayer. (B) Electrical recording of a $[21^+]_{20}$-icosameric hybrid pore that is stochastically blocked by a λ-DNA molecule at applied negative potential (−50 mV; shaded in red) and opened at applied positive potential (50 mV; shaded in blue). (C) Current-voltage dependence of an unblocked pore (blue circles) versus a blocked pore (orange triangles).
Figure 26C:
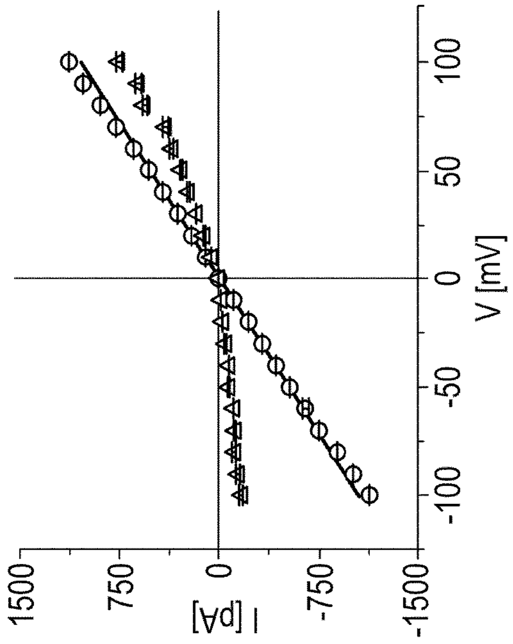
Figure 37:
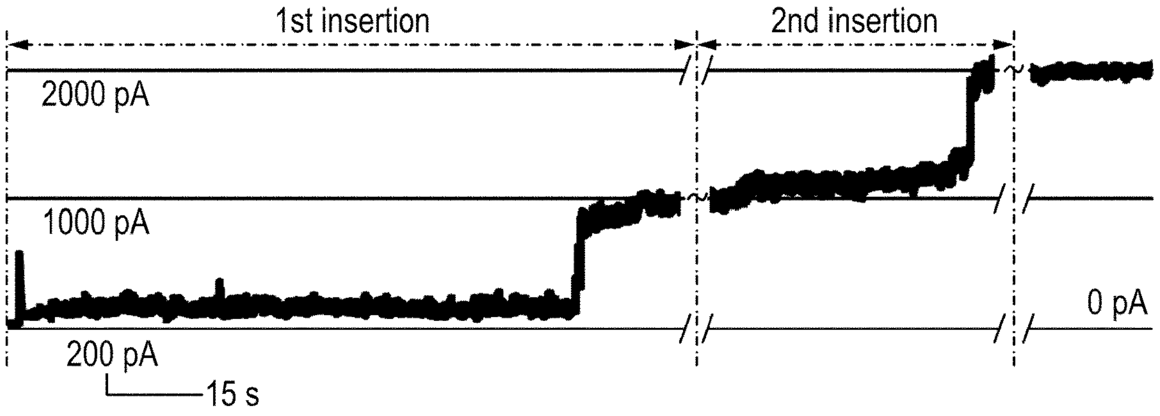
FIG. 37: Typical trace for multiple channel insertions. $[11^+]_{20}$-DNA/αHL hybrid constructs were added to the cis-side of the setup. Each hybrid pore formation features the stepwise insertion.
Figure 38:
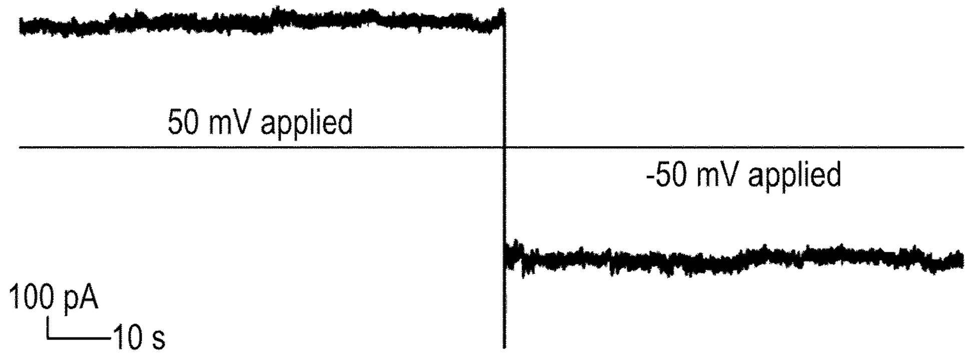
FIG. 38: Representation of current values at positive and negative potential for an open $[21^+]_{20}$-DNA/αHL hybrid pore.
Figure 39A:
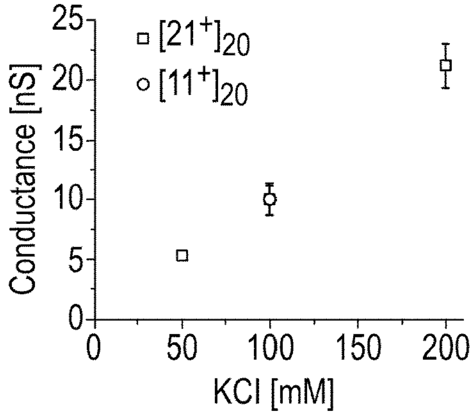
FIG. 39: a, KCl concentration dependence of the conductance of pores assembled on an unpaired nucleotide-containing icosameric DNA template. Single channel recordings of pores with 10.5 bp/turn-based DNA structures at b, 50 mM, and c, 200 mM salt concentration. Purified DNA/protein hybrid structures were incorporated into DPhPC bilayers in 25 mM Tris HCl (pH 7.99), with 50 μM EDTA.
Figure 39B:
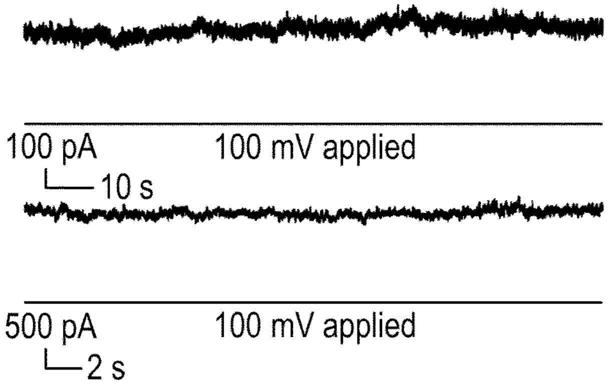

We investigated the functionality of the four different icosameric hybrid constructs using single-channel recordings in 1,2-diphytanoyl-sn-glycero-3-phosphocholine (DPhPC)-based planar lipid bilayers (PLBs). The purified structures were added to the cis-side of the setup in a buffer solution containing 0.1 M KCl. While applying positive voltage, the unpaired-nt containing icosameric constructs inserted into the lipid bilayer with a steady increase in the transmembrane current, starting with conductance fluctuations between 0.5 and 2 nS followed by a first sharp increase to a conductance level of ~4 nS and a subsequent second jump to ~10 nS (FIGS. 25A(i) and B(i); FIG. 37). Eventually, the accompanying fluctuations decreased to 0.2 nS resulting in an open pore that was stable for at least two hours (FIGS. 25A(ii) and B(ii)). We define the four found states as pre-pore, intermediate pore, pre-open pore and open pore, respectively. The open pore was not subject to any closing step and was also unaffected by the salt concentration (FIG. 39). The open pore state of $[11^+]_{20}$- and $[21^+]_{20}$-DNA/αHL hybrid structures was characterized by conductances of 9.98±1.36 nS (n=43) and 10.16±0.94 nS (n=53), respectively, as well as an ohmic I-V response (FIG. 26C, blue circles; FIG. 38). The latter indicates that the DNA template does not influence the conductance for positive and negative potentials, although it may contribute to increased noise (Table 7; FIGS. 25A(iii) and B(iii)).

Figure 35A:
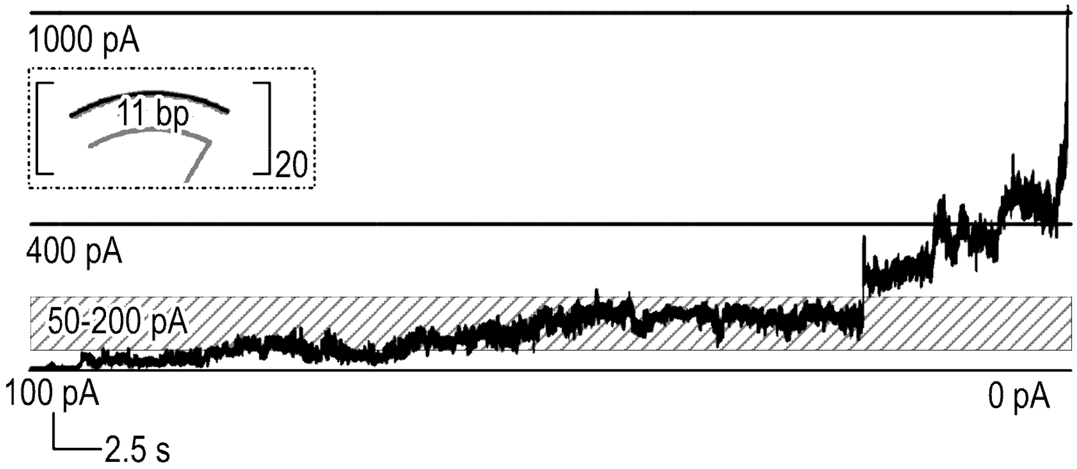
FIG. 35: Electrical recordings of DNA-templated αHL icosamers without unpaired nucleotides. Typical insertion trace for a hybrid pore containing a double-stranded DNA circle based on either a, 11 bp, or b, 10.5 bp, per helical turn. Purified DNA/protein hybrid structures were incorporated into DPhPC bilayers in 0.1 M KCl, 25 mM Tris HCl (pH 7.99) with 50 μM EDTA. A potential of 100 mV was applied to the trans-side, with the cis compartment connected to the ground.
Figure 35B:
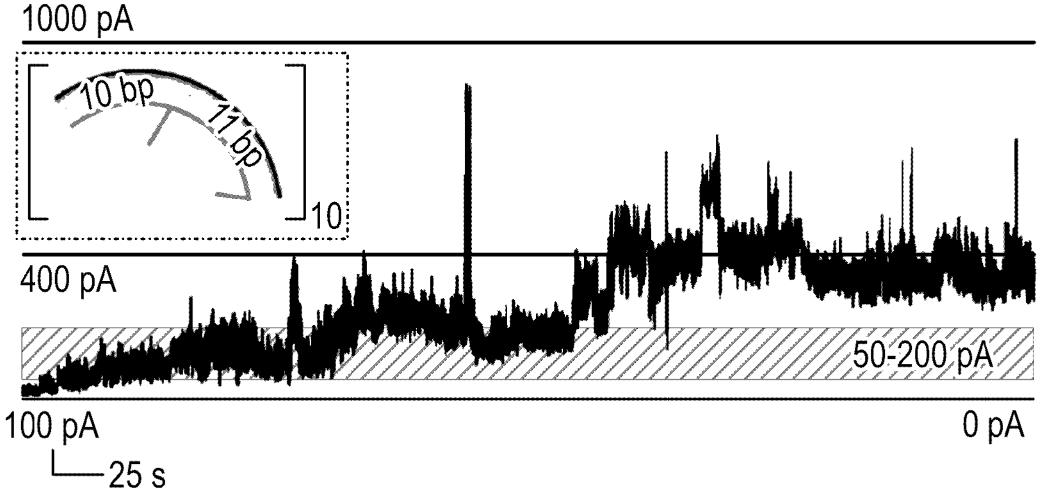

In contrast, the insertion of nt-free hybrid structures involved only the pre-pore and intermediate pore states. In detail, single channel recordings showed that addition of $[11^-]_{20}$-DNA/$(\alpha HL)_{20}$ hybrid structures resulted in a rupture of the lipid bilayer upon opening of the pore (FIG. 35A). Structures with a $[21^-]_{20}$-DNA template were stable for several minutes as an intermediate pore (G=4.48±0.52 nS (n=13 experiments)) (FIG. 35B). The rare opening of these intermediate pores also led to a subsequent collapse of the lipid bilayer at 9.98±0.84 nS (n=3).

Figure 26A:
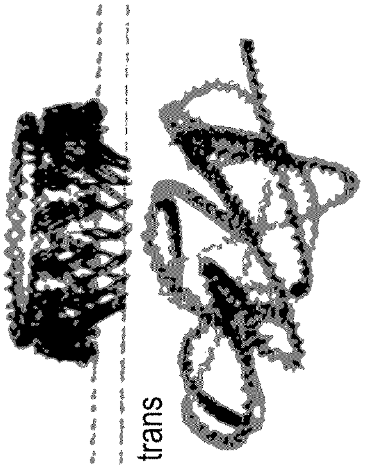
Figure 40:
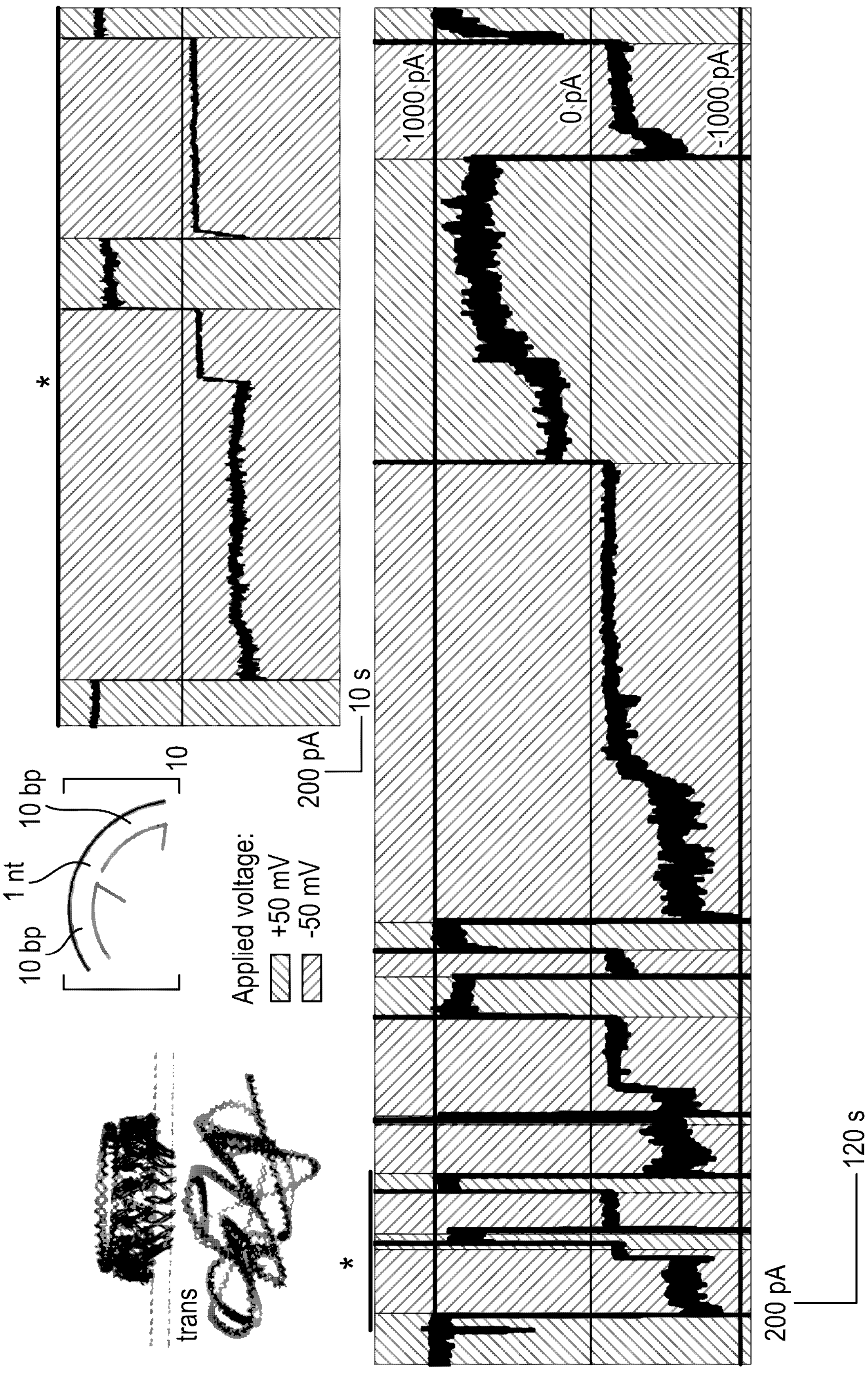
FIG. 40: Electrical recording of a $[21^+]_{20}$-icosameric hybrid pore that is stochastically blocked by the addition of λ-DNA to the trans-side. Extended trace of FIG. 5*b* is shown on the upper right-hand side.
Figures 41A, 41B:
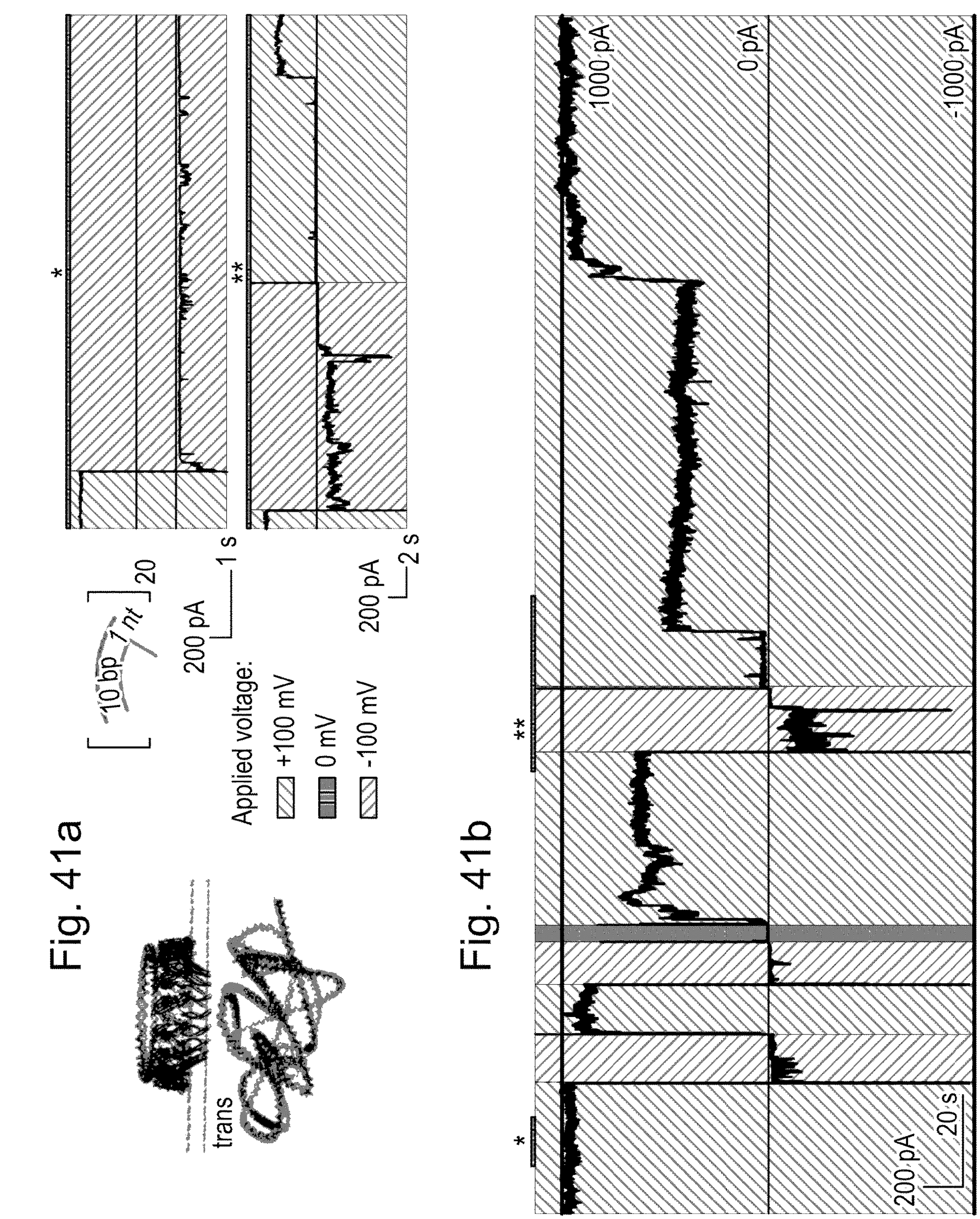
FIG. 41: Blockage of a homo-icosameric αHL pore. a, λ-DNA molecules were added to the trans-side after a purified DNA/αHL hybrid structure was incorporated into a DPhPC bilayer. b, Electrical recording of an icosameric hybrid pore based on $[11^+]_j$-DNA segments at applied positive (+100 mV; shaded in blue) and negative (−100 mV; shaded in red) potential. Magnified sections of the trace (*,**) are shown on the upper right-hand side.
Figure 42:
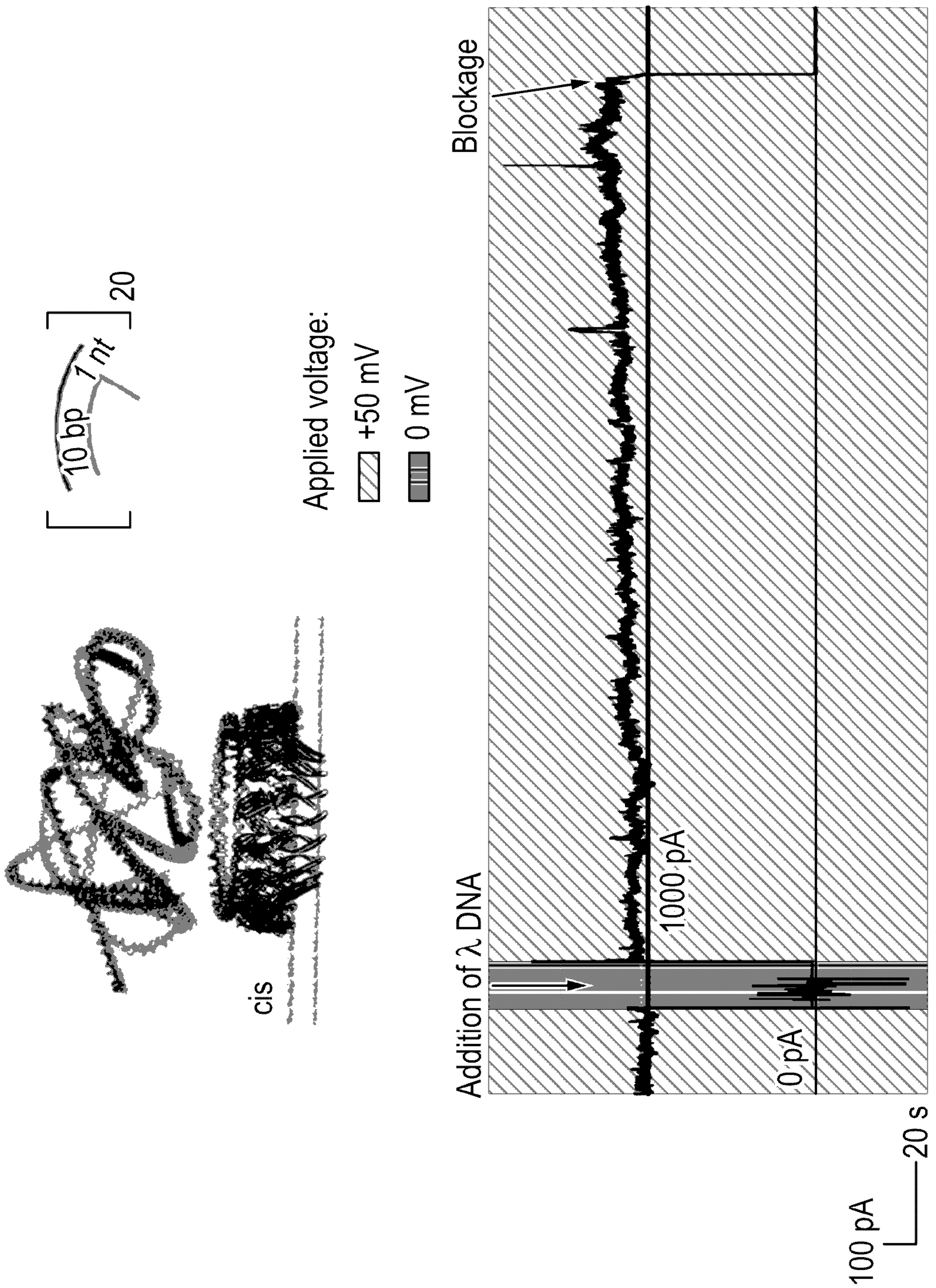
FIG. 42: Electrical recording of blockage of homo-icosameric αHL pore due to λ-DNA addition to the cis-side. 0 mV were applied during the addition of 15.6 fM λ-DNA (shaded in purple). The application of a positive potential (+50 mV; shaded in blue) resulted in a complete blockage of the conductance.

Verification of the pore formation through blockage We further verified the pore formation by blocking the icosameric pores after stable insertion with lambda DNA (λ-DNA). λ-DNA has a radius of gyration of ~530 nm, i.e. 27-fold larger than the outer diameter of the icosamer and, therefore, will block the pore upon its attempt to pass through. We observed complete blockage for $[11^+]_{20}$- and $[21^+]_{20}$-DNA/αHL hybrid structures when λ-DNA was added to the cis- or trans-side of the setup (FIG. 26; FIGS. 40-42). The blockage occurred in a stepwise manner, reflecting the increasing compactness of the λ-DNA molecule as it attempted to pass through the pore. Reversing the direction of the applied potential resulted in the release of the λ-DNA molecule from the pore in a stepwise manner similar to the blockage. The process of closing and opening of the open pore could be repeated multiple times, illustrating the high stability of the channel once the pore is completely inserted into the bilayer.

Functional DNA/αHL Hybrid Structures of Different Diameters

Figure 24C:
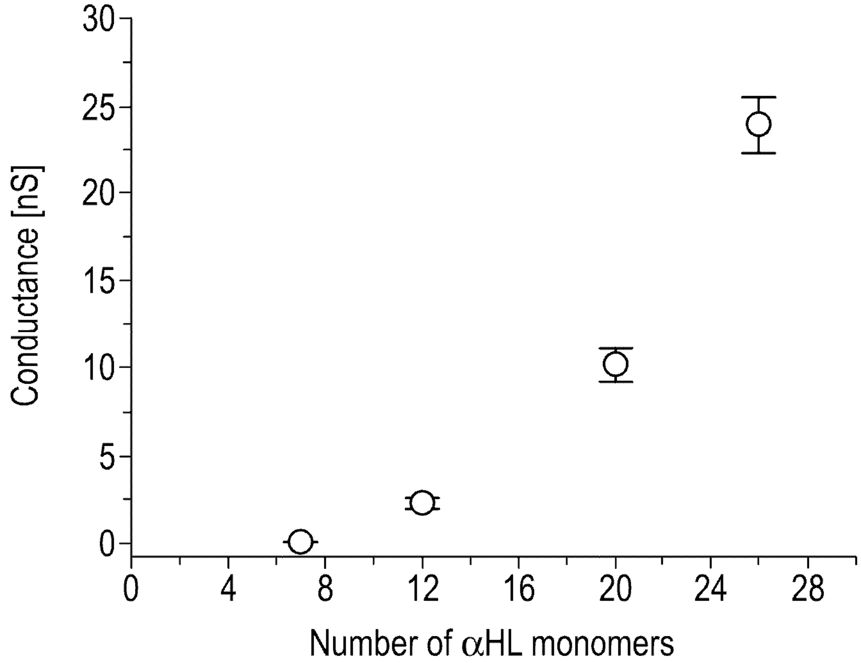
Figure 24D:
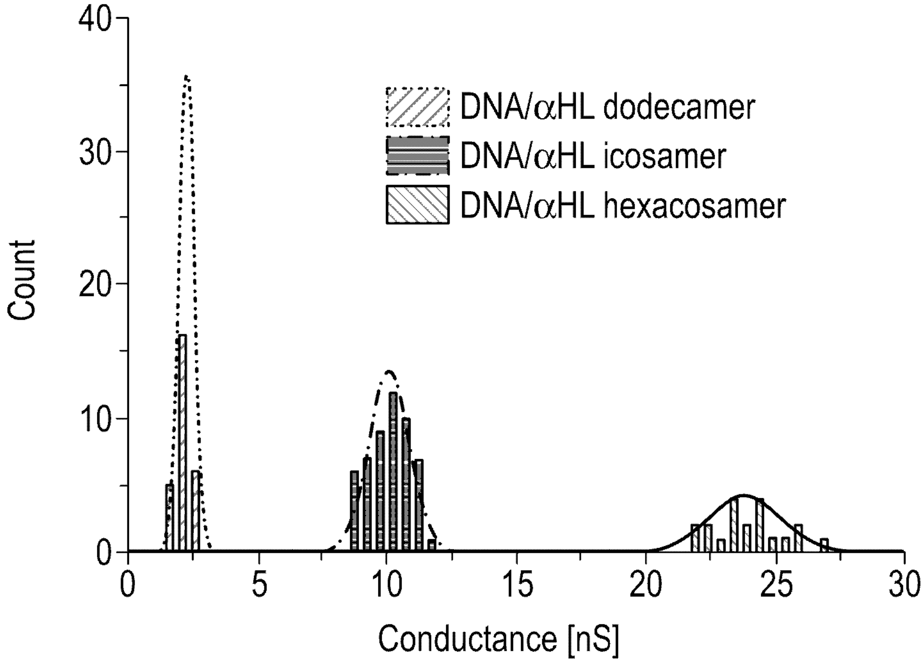
Figures 27A, 27B:
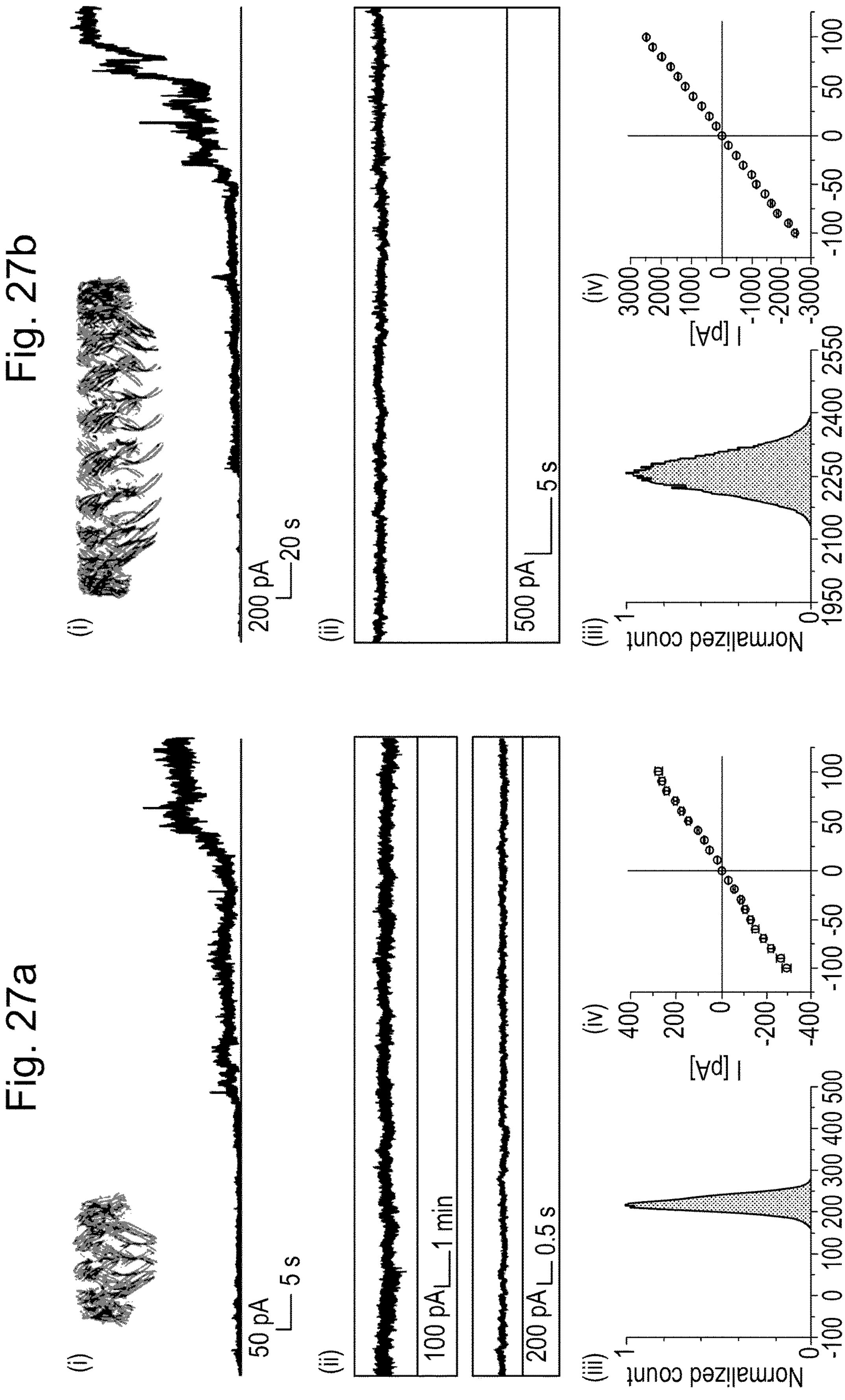
FIG. 27: Electrical recordings of DNA-templated αHL dodecamer and hexacosamer. Typical ionic current recorded for (A) a DNA/αHL dodecamer, and (B) a DNA/αHL hexacosamer, showing their (i) insertion, (ii) stability, (iii) all-point histogram of a 1-min-long current trace of an open pore at 100 mV, and (iv) current-voltage dependence.
Figure 33A:
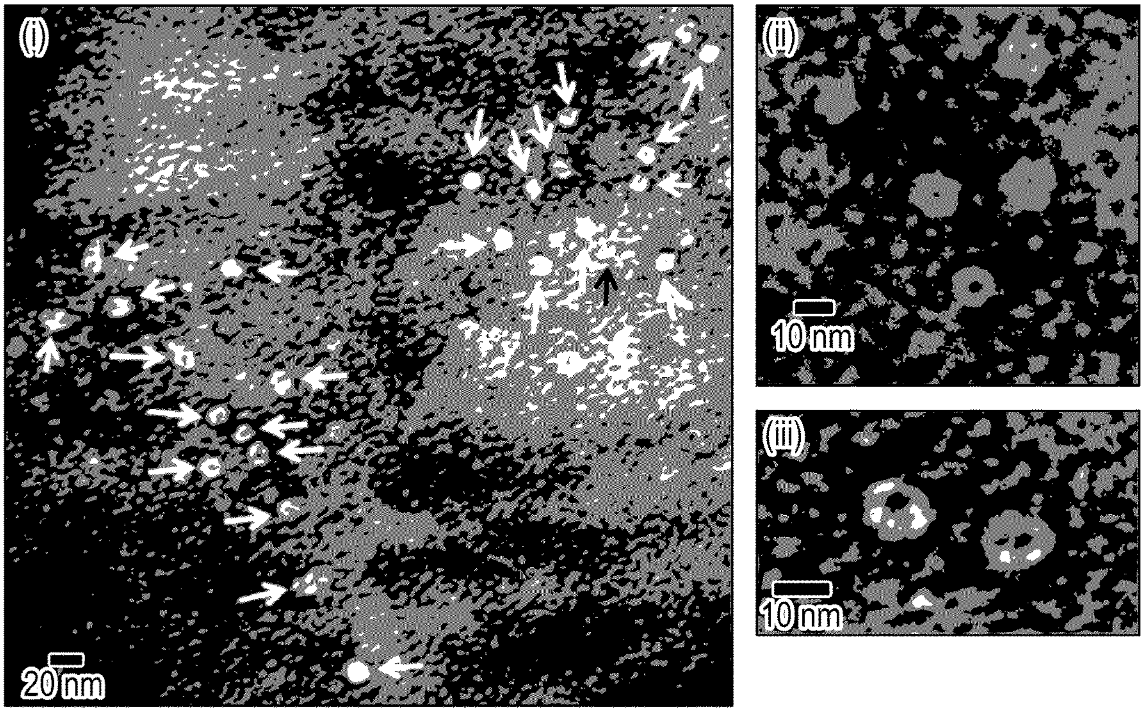
FIG. 33: TEM micrographs of a, DNA/αHL dodecamers, and b, hexacosamers, based on 10.5 bp per helical turn in the presence of DPhPC liposomes. It should be noted that the liposomes could potentially be subject to membrane rupturing upon an increasing number of pore insertions, which would result in lipid bilayer fragments on the TEM grid that include the inserted pores. White and blue arrows indicate the plane and side view of DNA/αHL hybrid pores, respectively.
Figure 33B:
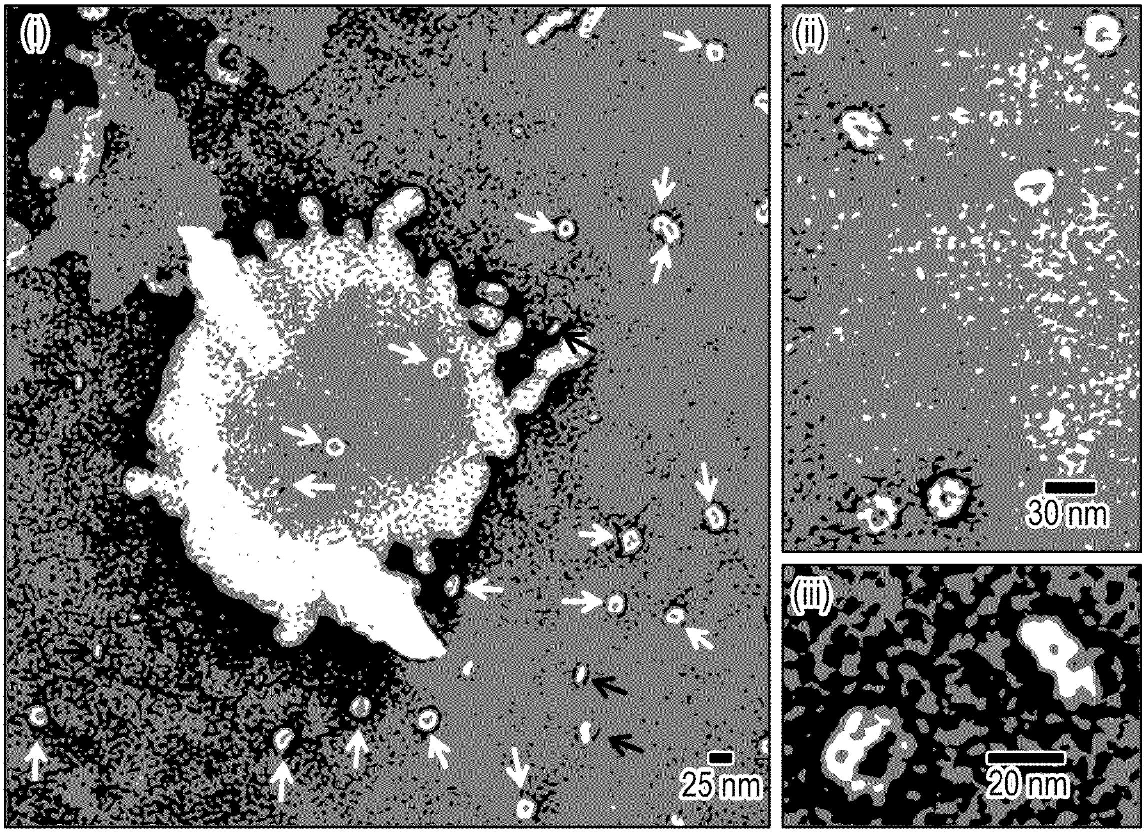

Next we examined the feasibility of our approach to template different numbers of αHL monomers by assembling dodecameric and hexacosameric pores (FIG. 24A) on appropriate $[21^+]_j$-based DNA structures. As observed for the icosamer, these constructs appeared as annular structures on TEM images (FIG. 24B(ii), (iv); FIG. 33). The measured diameters for the dodecamer and hexacosamer were 13.70±1.50 nm (n=164) and 28.42±1.88 nm (n=371), respectively, which are similar to the theoretical values of 13.64 and 29.55 nm, respectively. The last three TEM micrographs in FIG. 24B(iv) show the side view of the hexacosamer found outside the liposomes. These structures have a height of ~10 nm and feature a graded circular shape that resembles the heptameric αHL mushroom-shape. Single-channel recordings in PLBs revealed that the dodecamer and hexacosamer exhibited similar transitions upon pore formation, stability and I-V characteristic response as observed for the icosamer under the same conditions (FIG. 27). An open-pore conductance of 2.28±0.29 nS (n=27 experiments) and 23.96±1.57 nS (n=21 experiments) was found for the dodacemeric and hexacosameric constructs, respectively (FIGS. 24C and D).

Comparison of Wild-Type and DNA-Templated αHL Pore Characteristics

Figure 36A:
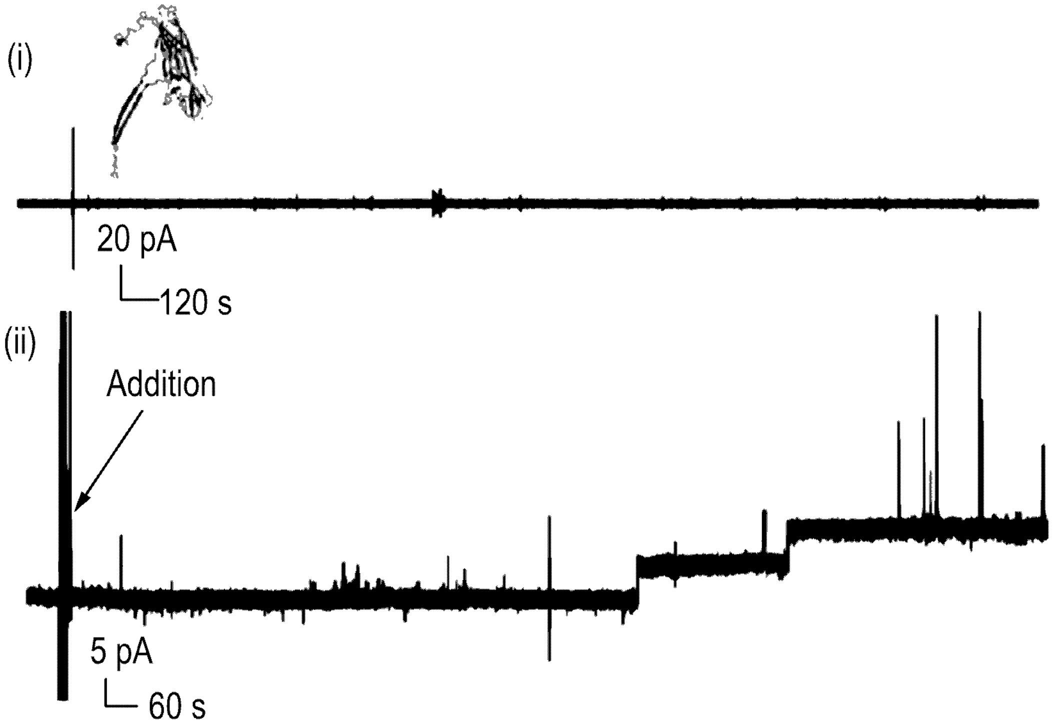
FIG. 36: a, Single channel recordings of DNA-modified K237C-αHL mutants (i) at the same, or (ii) at a 5-fold higher, concentration as used for electrical recordings of the DNA/αHL hybrid structures. b, Typical current trace of DNA templates with twenty $[21^+]_j$-DNA segments at a 5-fold higher concentration than used in DNA/αHL hybrid experiments. Purified proteins (10-kDa MWCO filter device) and DNA structures (30-kDa MWCO filter device) were added to the cis-side of a DPhPC bilayer in 0.1 M KCl buffer containing Tris-EDTA. A potential of 100 mV was applied to the cis-side of the chamber.

The wild-type αHL pore is typically characterized during single-channel recordings by a one-step insertion and a stable open pore conductance of about 0.09 nS. Similarly, the formation of the ssDNA-modified K237C αHLheptameric pore involves only one step (FIG. 36A(ii)). The stable conductance of 0.07 nS is reduced, and accompanied by a higher noise, compared to the wild-type αHL pore (Table 7). Arranging the ssDNA-modified K237C αHL monomers along a DNA template likewise results in highly stable open pores, but compared to the wild-type αHL pore, the traces of the investigated DNA/αHL hybrid pores are characterized by a stepwise insertion and a higher noise. This is likely due to the presence of a flexible highly negatively charged DNA template, and the fact that the αHL monomeric structure is optimized for heptameric oligomerization. For instance, possible missing linkages between the αHL cap domains might result in the destabilization of the hybrid pore, which is accompanied by a fluctuation of the electrical current. We anticipate that engineering the αHL cap regions to increase the interactions between the protomer cap domains would lower the noise. Furthermore, disconnection of the αHL pore from the DNA nanostructure after its complete insertion could potentially reduce the level of noise as well. We plan to investigate both options in follow-up studies. The formation of a membrane-spanning αHL pore requires the initial oligomerization of the monomers. Wild-type αHL monomers typically self-assemble along a lipid membrane. Single-channel recordings of ssDNA-modified K237C αHLmonomers indicate that the duration of the oligomerization depends on the monomer concentration (FIG. 36A). In other words, the higher the number of available monomers along a membrane, the higher the likelihood that the monomers come into contact. For the DNA/αHL hybrid pores, in contrast, the monomers are already in close proximity. This in turn implies that the templated DNA pore will have a higher incorporation yield than the wild-type pore, especially for lower αHL concentrations. This reasoning is supported by our finding that at the same protein concentration used to investigate the DNA/αHL hybrid pores, hardly any pore formation was observed in the absence of a DNA template (FIG. 36A(i)).

Conclusions and Prospects

In summary, we have developed a new approach for assembling functional nanostructures that are composed of both natural polypeptides and artificial DNA domains To our knowledge, this is the first demonstration that more than seven αHL monomers can form a functional pore. The porous αHL/DNA structures offer greater versatility in terms of a potential heteromeric composition along with a high precision for single point modifications. This will enable single molecule experiments of precisely located, multiple reaction partners within the pore. We envision utilizing these pores in a variety of contexts, such as size-dependent sorting of self-assembled nanostructures, and controlled release of therapeutics in drug delivery systems. Furthermore, our approach will facilitate the oligomerization of different pore-forming proteins and their mutants into heteromeric constructs with specific numbers of monomers This will provide detailed biophysical insight into the mechanism of membrane-insertion and oligomerization of pore-forming proteins, and allow for the construction of various novel hybrid pores with defined properties. In addition, the design principles for DNA nanostructures explicitly defined in this work can be applied to arrange diverse monomers into functional proteins, which can potentially be used to construct artificial proteins. Finally, this approach will likely lead to innovative applications of biological nanopores, such as protein sequencing, and single molecule analysis of structures larger than ~4 nm (52), e.g. the in vitro and in vivo study of amyloid formation and assemblies.

Supplementary Information

Sequences Used for the DNA Circle Assembly

TABLE 4

List of DNA sequences used for the assembly of the circular DNA scaffolds. P and $NH_2$ indicate a 5' phosphorylation and a 5' aminolink C6, respectively.

| Name | Sequence (5' to 3') |
|---|---|
| OC01 | P-TTTTTGCCGTATTTTTCCTCGCTTTTTCCTCGCTT TTTCCTCGCTTTTTCCTCGCTTTTTCCTCGCTTTTTC CTCGCTTTTTGCCGTA (SEQ ID NO: 63) |
| OC02 | P-TTTTTCTCGCTTTTTTCCTCGCTTTTTCCTCGCTT TTTCCTCGCTTTTTCCTCGCTTTTTCCTCGCTTTTTC CTCGCTTTTTCTCGCT (SEQ ID NO: 64) |
| OC03 | P-TTTTTGGTGGGTTTTTCCTCGCTTTTTCCTCGCTT TTTGGTGGG (SEQ ID NO: 65) |
| OC04 | P-TTTTTTCCTCCTTTTTACCCCTTTTTCCTCGCTTT TTACCCCTTTTTCCTCGCTTTTTACCCCTTTTTCCTC GCTTTTTCACCC (SEQ ID NO; 66) |
| OC05 | P-TTTTTCCACTCTTTTTACCCCTTTTTCCTCGCTTT TTACCCCTTTTTCCTCGCTTTTTACCCCTTTTTCCTC GCTTTTTCCCGC (SEQ ID NO: 67) |
| OC06 | P-TTTTTCACGTCTTTTTACCCCTTTTTCCTCGCTTT TTCCCCT (SEQ ID NO: 68) |
| OC07 | P-TTTTTTCCTCCTTTTTACCCCTTTTTCCTCGCTTT TTACCCCTTTTTCCTCGCTTTTTACCCCTTTTTCCTC GCTTTTTGCCGA (SEQ ID NO: 69) |
| OC08 | P-TTTTTAGCCGCTTTTTACCCCTTTTTCCTCGCTTT TTACCCCTTTTTCCTCGCTTTTTACCCCTTTTTCCTC GCTTTTTCACCC (SEQ ID NO: 70) |
| OC09 | P-TTTTTCCCACATTTTTACCCCTTTTTCCTCGCTTT TTACCCCTTTTTCCTCGCTTTTTCCCGC (SEQ ID NO: 71) |
| Cap01 | ATTGACCCACCAAAAATACGGC (SEQ ID NO: 72) |
| Cap02 | AAGTAAGCGAGAAAAACCCACC (SEQ ID NO: 73) |
| Cap03 | AGATATACGGCAAAAAAGCGAG (SEQ ID NO: 74) |
| Cap04 | ATTGAGGAGGAAAAAAAGGGGAAAAA (SEQ ID NO: 75) |
| Cap05 | AAGTAGAGTGGAAAAAGGGTGAAAAA (SEQ ID NO: 76) |
| Cap06 | AGATAGACGTGAAAAAGCGGGAAAAA (SEQ ID NO: 77) |
| Cap07 | AAGTAGACGTGAAAAAGGGTGAAAAA (SEQ ID NO: 78) |
| Cap08 | AGTATGCGGCTAAAAATCGGCAAAAA (SEQ ID NO: 79) |
| Cap09 | TATTGTGTGGGAAAAAGGGTGAAAAA (SEQ ID NO: 80) |

TABLE 4-continued

List of DNA sequences used for the assembly of the circular DNA scaffolds. P and $NH_2$ indicate a 5' phosphorylation and a 5' aminolink C6, respectively.

| Name | Sequence (5' to 3') |
|---|---|
| CapComp01 | GCCGTATTTTTGGTGGGTCAAT (SEQ ID NO: 81) |
| CapComp02 | GGTGGGTTTTTCTCGCTTACTT (SEQ ID NO: 82) |
| CapComp03 | CTCGCTTTTTTGCCGTATATCT (SEQ ID NO: 83) |
| CapComp04 | TTTTTCCCCTTTTTTTCCTCCTCAAT (SEQ ID NO: 84) |
| CapComp05 | TTTTTCACCCTTTTTCCACTCTACTT (SEQ ID NO: 85) |
| CapComp06 | TTTTTCCCGCTTTTTCACGTCTATCT (SEQ ID NO: 86) |
| CapComp07 | TTTTTCACCCTTTTTCACGTCTACTT (SEQ ID NO: 87) |
| CapComp08 | TTTTTGCCGATTTTTAGCCGCATACT (SEQ ID NO: 88) |
| CapComp09 | TTTTTCACCCTTTTTCCCACACAATA (SEQ ID NO: 89) |
| IC01a | AAAAAGCGAGTTGTTGTTGTTGAATAA (SEQ ID NO: 90) |
| IC01b | AAAAAGCGAGGTTGTTGTTGTTGAATAA (SEQ ID NO: 91) |
| IC02a | AAAAATACGGTTGTTGTTGTTGAATAA (SEQ ID NO: 92) |
| IC02b | AAAAATACGGCTTGTTGTTGTTGAATAA (SEQ ID NO: 93) |
| IC03a | AAAAAAGCGATTGTTGTTGTTGAATAA (SEQ ID NO: 94) |
| IC03b | AAAAAAGCGAGTTGTTGTTGTTGAATAA (SEQ ID NO: 95) |
| IC04a | AAAAACCCACTTGTTGTTGTTGAATAA (SEQ ID NO: 96) |
| IC04b | AAAAACCCACCTTGTTGTTGTTGAATAA (SEQ ID NO: 97) |
| IC05 | AAAAAGGGGTTTGTTGTTGTTGAATAA (SEQ ID NO: 98) |
| IC06a | AAAAAGCGAGGTTGTTGTTGTTGAATAA (SEQ ID NO: 99) |
| IC06b | AAAAAGCGAGTTGTTGTTGTTGAATAA (SEQ ID NO: 100) |
| IC07a | AAAAAGGAGGATTGTTGTTGTTGAATAA (SEQ ID NO: 101) |
| IC07b | AAAAAGGAGGTTGTTGTTGTTGAATAA (SEQ ID NO: 102) |
| IC08 | AAAAAGGGTGTTGTTGTTGTTGAATAA (SEQ ID NO: 103) |
| IC09 | AAAAAAGGGGTTGTTGTTGTTGAATAA (SEQ ID NO: 104) |

TABLE 4-continued

List of DNA sequences used for the assembly of the circular DNA scaffolds. P and $NH_2$ indicate a 5' phosphorylation and a 5' aminolink C6, respectively.

| Name | Sequence (5' to 3') |
|---|---|
| IC010a | AAAAAGACGTGTTGTTGTTGTTGAATAA (SEQ ID NO: 105) |
| IC010b | AAAAAGACGTTTGTTGTTGTTGAATAA (SEQ ID NO: 106) |
| IC011 | AAAAAGCGGGTTGTTGTTGTTGAATAA (SEQ ID NO: 107) |
| IC012a | AAAAAGAGTGGTTGTTGTTGTTGAATAA (SEQ ID NO: 108) |
| IC012b | AAAAAGAGTGTTGTTGTTGTTGAATAA (SEQ ID NO: 109) |
| IC013 | AAAAATCGGCTTGTTGTTGTTGAATAA (SEQ ID NO: 110) |
| IC014b | AAAAAGCGGCTTGTTGTTGTTGAATAA (SEQ ID NO: 111) |
| IC015 | AAAAAGGGTGTTGTTGTTGTTGAATAA (SEQ ID NO: 112) |
| IC016b | AAAAATGTGGTTGTTGTTGTTGAATAA (SEQ ID NO: 113) |
| ssDNA tail' | $NH_2$-TTATTCAACAACAA (SEQ ID NO: 114) |

TABLE 5

Assignment of the sequences for the different DNA templates.

| DNA structure | DNA sequence: Outer Circle | Cap-L | Cap-C | CapComp | Inner Circle |
|---|---|---|---|---|---|
| Icosamer | | | | | |
| $[11^-]_{20}$ | OC01, OC02, OC03 | Cap01, Cap02 | Cap03 | CapComp01, CapComp02, CapComp03 | IC01b, IC02b, IC03b, IC04b |
| $[11^+]_{20}$ | OC01, OC02, OC03 | Cap01, Cap02 | Cap03 | CapComp01, CapComp02, CapComp03 | IC01a, IC02a, IC03a, IC04a |
| $[21^-]_{20}$ | OC04, OC05, OC06 | Cap04, Cap05 | Cap06 | CapComp04, CapComp05, CapComp06 | IC05, IC06a, IC07a, IC08, IC09, IC10a, IC11, IC12a |
| $[21^+]_{20}$ | OC04, OC05, OC06 | Cap04, Cap05 | Cap06 | CapComp04, CapComp05, CapComp06 | IC05, IC06b, IC07b, IC08, IC09, IC10b, IC11, IC12b |
| Dodecamer | | | | | |
| $[21^+]_{12}$ | OC04, OC06 | Cap04 | Cap07 | CapComp04, CapComp07 | IC05, IC06b, IC07b, IC08, IC09, IC10b |
| Hexacosamer | | | | | |
| $[21^+]_{26}$ | OC06, OC07, OC08, OC09 | Cap04, Cap08, Cap09 | Cap06 | CapComp04, CapComp06, CapComp08, CapComp09 | IC05, IC06b, IC07b, IC09, IC10b, IC11, IC13, IC14b, IC15, IC16b |

Electrical Recordings of the DNA and Protein Components of DNA/αHL Hybrid Pores.

Figure 36B:
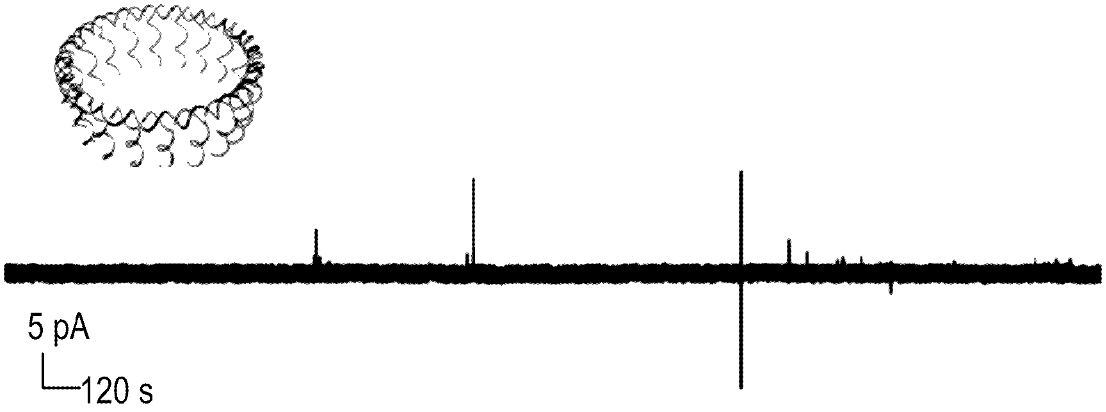

Electrophysiological recordings with DNA-modified K237C mutants resulted in only a few events with an insertion pattern and conductance typical for a heptameric αHL pore (2) (FIG. 36*a*). In experiments where only DNA-templates were added, no lipid-bilayer interactions were observed (FIG. 36*b*).

Overview of observed conductance and noise in planar lipid bilayer experiments. The open pore conductances and noise in PLB recordings for the different hybrid constructs are summarized in Tables 6 and 7, respectively.

TABLE 6

List of the observed open pore conductances for αHL monomers in the presence and absence of a DNA template, during planar lipid bilayer recordings.

| Number of Connected αHL monomers | αHL monomers | DNA template | Conductance in planar lipid bilayer experiments (0.1M KCl solution) | Number of independent insertions used for conductance determination | Number of independent prepared structures used for conductance determination |
|---|---|---|---|---|---|
| 12 | ssDNA-modified K237C mutant | $[21^{+}]_{12}$ | 2.28 ± 0.29 nS | 27 | 3 |
| 20 | ssDNA-modified K237C mutant | $[11^{-}]_{20}$ | No complete insertion | 0 | 3 |
| 20 | ssDNA-modified K237C mutant | $[11^{+}]_{20}$ | 9.98 ± 1.36 nS | 43 | 5 |
| 20 | ssDNA-modified | $[21^{-}]_{20}$ | 9.98 ± 0.84 nS (before rupture of membrane) | 3 | 3 |
| 20 | ssDNA-modified K237C mutant | $[21^{+}]_{20}$ | 10.16 ± 0.94 nS | 53 | 5 |
| 26 | ssDNA-modified K237C mutant | $[21^{+}]_{26}$ | 25.03 ± 2.76 nS | 21 | 5 |
| 1 | ssDNA-modified K237C mutant | — | 0.07 ± 0.03 nS | 18 | 1 |
| 1 | Wild-type | — | 0.09 ± 0.01 nS | 10 | 1 |

TABLE 7

Noise values for αHL monomers in the presence and absence of a DNA template. Electrical recordings were performed in a 0.1M KCl containing buffer solution. The histograms of 500 ms recordings at +100 mV and 0 mV were Gaussian fitted to calculate the noise values (± standard deviation) according to $((\sigma^{0\ mV})^2 + (\sigma^{+100\ mV})^2)^{1/2}$. Ten independent insertions were averaged for the determination of the mean noise values.

| Number of connected αHL monomers | Noise |
|---|---|
| 12 (ssDNA-modified K237C mutant) | 9.50 ± 3.02 |
| 20 (ssDNA-modified K237C mutant) | 22.56 ± 5.75 |
| 26 (ssDNA-modified K237C mutant) | 25.61 ± 6.18 |
| 1 (ssDNA-modified K237C mutant) | 2.38 ± 0.46 |
| 1 (wild type) | 0.40 ± 0.02 |

REFERENCES

1. Bell N. A. W., Keyser U. F. Digitally encoded DNA nanostructures for multiplexed, single-molecule protein sensing with nanopores. Nat. Nanotechnol. 2016; 11:645-651.
2. Quick J., Loman N. J., Duraffour S., Simpson J. T., Severi E., Cowley L., Bore J. A., Koundouno R., Dudas G., Mikhail A. et al. Real-time, portable genome sequencing for Ebola surveillance. Nature. 2016; 530:228-232.
3. Litvinchuk S., Tanaka H., Miyatake T., Pasini D., Tanaka T., Bollot G., Mareda J., Matile S. Synthetic pores with reactive signal amplifiers as artificial tongues. Nat. Mater. 2007; 6:576-580.
4. Manrao E. A., Derrington I. M., Laszlo A. H., Langford K. W., Hopper M. K., Gillgren N., Pavlenok M., Niederweis M., Gundlach J. H. Reading DNA at single-nucleotide resolution with a mutant MspA nanopore and phi29 DNA polymerase. Nat. Biotechnol. 2012; 30:349-353.
5. Banghart M., Borges K., Isacoff E., Trauner D., Kramer R. H. Light-activated ion channels for remote control of neuronal firing. Nat. Neurosci. 2004; 7:1381-1386.
6. Rodriguez-Larrea D., Bayley H. Multistep protein unfolding during nanopore translocation. Nat. Nanotechnol. 2013; 8:288-295.
7. Kong J., Bell N. A. W., Keyser U. F. Quantifying nanomolar protein concentrations using designed DNA carriers and solid-state nanopores. Nano Lett. 2016; 16:3557-3562.
8. Dekker C. Solid-state nanopores. Nat. Nanotechnol. 2007; 2:209-215.
9. Li J., Stein D., McMullan C., Branton D., Aziz M. J., Golovchenko J. A. Ion-beam sculpting at nanometre length scales. Nature. 2011; 412:166-169.
10. Bayley H., Cremer P. S. Stochastic sensors inspired by biology. Nature. 2001; 413:226-230.
11. Kasianowicz J. J., Brandin E., Branton D., Deamer D. W. Characterization of individual polynucleotide molecules using a membrane channel. Proc. Natl. Acad. Sci. U.S.A. 1996; 93:13770-13773.
12. Majd S., Yusko E. C., Billeh Y. N., Macrae M. X., Yang J., Mayer M. Applications of biological pores in nanomedicine, sensing, and nanoelectronics. Curr. Opin. Biotechnol. 2010; 21:439-476.
13. Fahie M. A., Yang B., Mullis M., Holden M. A., Chen M. Selective detection of protein homologues in serum using an OmpG nanopore. Anal. Chem. 2015; 87:11143-11149.
14. Pastoriza-Gallego M., Rabah L., Gibrat G., Thiebot B., Gisou van der Goot F., Auvray L., Betton J.-M., Pelta J. Dynamics of unfolded protein transport through an aerolysin pore. J. Am. Chem. Soc. 2011; 133:2923-2931.
15. Wang S., Haque F., Rychahou P. G., Evers B. M., Guo P. Engineered nanopore of Phi29 DNA-packaging motor for real-time detection of single colon cancer specific antibody in serum. ACS Nano. 2013; 7:9814-9822.
16. Van Meervelt V., Soskine M., Maglia G. Detection of two isomeric binding configurations in a protein-aptamer complex with a biological nanopore. ACS Nano. 2014; 8:12826-12835.
17. Carter J.-M., Hussain S. Robust long-read native DNA sequencing using the ONT CsgG Nanopore system. Wellcome Open Res. 2017; 2:23.
18. Gu L.-Q., Cheley S., Bayley H. Capture of a single molecule in a nanocavity. Science. 2001; 291:636-640.

19. Soskine M., Biesemans A., De Maeyer M., Maglia G. Tuning the size and properties of ClyA nanopores assisted by directed evolution. J. Am. Chem. Soc. 2013; 135: 13456-13463.
20. Montenegro J., Ghadiri M. R., Granja J. R. Ion channel models based on self-assembling cyclic peptide nanotubes. Acc. Chem. Res. 2013; 46:2955-2965.
21. Thomson A. R., Wood C. W., Burton A. J., Bartlett G. J., Sessions R. B., Brady R. L., Woolfson D. N. Computational design of water-soluble α-helical barrels. Science. 2014; 346:485-488.
22. Sakai N., Mareda J., Matile S. Artificial β-Barrels. Acc. Chem. Res. 2008; 41:1354-1365.
23. Geng J., Kim K., Zhang J., Escalada A., Tunuguntla R., Comolli L. R., Allen F. I., Shnyrova A. V., Cho K. R., Munoz D. et al. Stochastic transport through carbon nanotubes in lipid bilayers and live cell membranes. Nature. 2014; 514:612-615.
24. Göpfrich K., Zettl T., Meijering A. E. C., Hernández-Ainsa S., Kocabey S., Liedl T., Keyser U. F. DNA-tile structures induce ionic currents through lipid membranes. Nano Lett. 2015; 15:3134-3138.
25. Göpfrich K., Li C.-Y., Ricci M., Bhamidimarri S. P., Yoo J., Gyenes B., Ohmann A., Winterhalter M., Aksimentiev A., Keyser U. F. Large-conductance transmembrane porin made from DNA origami. ACS Nano. 2016; 10:8207-8214.
26. Krishnan S., Ziegler D., Arnaut V., Martin T. G., Kapsner K., Henneberg K., Bausch A. R., Dietz H., Simmel F. C. Molecular transport through large-diameter DNA nanopores. Nat. Commun. 2016; 7:12787.
27. Langecker M., Arnaut V., Martin T. G., List J., Renner S., Mayer M., Dietz H., Simmel F. C. Synthetic lipid membrane channels formed by designed DNA nanostructures. Science. 2012; 338:932-936.
28. Plesa C., Ananth A. N., Linko V., Gulcher C., Katan A. J., Dietz H., Dekker C. Ionic permeability and mechanical properties of DNA origami nanoplates on solid-state nanopores. ACS Nano. 2014; 8:35-43.
29. Li C.-Y., Hemmig E. A., Kong J., Yoo J., Hernández-Ainsa S., Keyser U. F., Aksimentiev A. Ionic conductivity, structural deformation, and programmable anisotropy of DNA origami in electric field. ACS Nano. 2015; 9:1420-1433.
30. Seifert A., Göpfrich K., Burns J. R., Fertig N., Keyser U. F., Howorka S. Bilayer-spanning DNA nanopores with voltage-switching between open and closed state. ACS Nano. 2014; 9:1117-1126.
31. Burns J. R., Stulz E., Howorka S. Self-assembled DNA nanopores that span lipid bilayers. Nano Lett. 2013; 13:2351-2356.
32. Burns J. R., Göpfrich K., Wood J. W., Thacker V. V., Stulz E., Keyser U. F., Howorka S. Lipid-bilayer-spanning DNA nanopores with a bifunctional porphyrin anchor. Angew. Chem. Int. Ed. 2013; 52:12069-12072.
33. Zhang F., Jiang S., Wu S., Li Y., Mao C., Liu Y., Yan H. Complex wireframe DNA origami nanostructures with multi-arm junction vertices. Nat. Nanotechnol. 2015; 10:779-784.
34. Rothemund P. W. K. Folding DNA to create nanoscale shapes and patterns. Nature. 2006; 440:297-302.
35. Douglas S. M., Dietz H., Liedl T., Högberg B., Graf F., Shih W. M. Self-assembly of DNA into nanoscale three-dimensional shapes. Nature. 2009; 459:414-418.
36. Saccà B., Meyer R., Erkelenz M., Kiko K., Arndt A., Schroeder H., Rabe K. S., Niemeyer C. M. Orthogonal protein decoration of DNA origami. Angew. Chem. Int. Ed. 2010; 49:9378-9383.
37. Yoo J., Aksimentiev A. Molecular dynamics of membrane-spanning DNA channels: conductance mechanism, electro-osmotic transport, and mechanical gating. J. Phys. Chem. Lett. 2015; 6:4680-4687.
38. Mantri S., Sapra T., Cheley S., Sharp T. H., Bayley H. An engineered dimeric protein pore that spans adjacent lipid bilayers. Nat. Commun. 2013; 4:1725.
39. Schindelin J., Arganda-Carreras I., Frise E., Kaynig V., Longair M., Pietzsch T., Preibisch S., Rueden C., Saalfeld S., Schmid B. et al. Fiji: an open-source platform for biological-image analysis. Nat. Methods. 2012; 9:676-682.
40. Horcas I., Fernandez R., Gomez-Rodriguez J. M., Colchero J., Gomez-Herrero J., Baro A. M. WSxM: A software for scanning probe microscopy and a tool for nanotechnology. Rev. Sci. Instrum. 2007; 78:013705.
41. Song L. Z., Hobaugh M. R., Shustak C., Cheley S., Bayley H., Gouaux J. E. Structure of staphylococcal alpha-hemolysin, a heptameric transmembrane pore. Science. 1996; 274:1859-1866.
42. Braha O., Gu L.-Q., Zhou L., Lu X., Cheley S., Bayley H. Simultaneous stochastic sensing of divalent metal ions. Nat. Biotechnol. 2000; 18:1005-1007.
43. Clarke J., Wu H.-C., Jayasinghe L., Patel A., Reid A., Bayley H. Continuous base identification for single-molecule nanopore DNA sequencing. Nat. Nanotechnol. 2009; 4:265-270.
44. Gu L.-Q., Braha O., Conlan S., Cheley S., Bayley H. Stochastic sensing of organic analytes by a pore-forming protein containing a molecular adapter. Nature. 1999; 398:686-690.
45. Harrington L., Alexander L. T., Knapp S., Bayley H. Pim kinase inhibitors evaluated with a single-molecule engineered nanopore sensor. Angew. Chem. Int. Ed. 2015; 54:8154-8159.
46. Rosen C. B., Rodriguez-Larrea D., Bayley H. Single-molecule site-specific detection of protein phosphorylation. Nat. Biotechnol. 2014; 5:807-814.
47. Watson J. D., Crick F. H. Molecular structure of nucleic acids: a structure for deoxyribose nucleic acid. Nature. 1953; 171:737-738.
48. Dlakic M., Park K., Griffith J. D., Harvey S. C., Harrington R. E. The organic crystallizing agent 2-methyl-2,4-pentanediol reduces DNA curvature by means of structural changes in A-tracts. J. Biol. Chem. 1996; 271:17911-17919.
49. Han W., Dlakic M., Zhu Y. J., Lindsay S. M., Harrington R. E. Strained DNA is kinked by low concentrations of Zn2+. Proc. Natl. Acad. Sci. U.S.A. 1997; 94:10565-10570.
50. Sulc P., Romano F., Ouldridge T. E., Rovigatti L., Doye J. P. K., Louis A. A. Sequence-dependent thermodynamics of a coarse-grained DNA model. J. Chem. Phys. 2012; 137:135101.
51. Eddy M. T., Ong T. C., Clark L., Teijido O., van der Wel P. A. C., Garces R., Wagner G., Rostovtseva T., Griffin R. G. Lipid Dynamics and Protein-Lipid Interactions in 2D Crystals Formed with the b-barrel Integral Membrane Protein VDAC1. J. Am. Chem. Soc. 2012; 134:6375-6387.

52. Soskine M., Biesemans A., Maglia G. Single-molecule analyte recognition with ClyA nanopores equipped with internal protein adaptors. J. Am. Chem. Soc. 2015; 137: 5793-5797

S1. Harshman, S., Sugg, N. and Cassidy, P. (1988) Preparation and purification of staphylococcal α-toxin. *Methods Enzymol.,* 165, 3-7.

S2. Menestrina, G. (1986) Ionic channels formed by *Staphylococcus aureus* alpha-toxin: voltage-dependent inhibition by divalent and trivalent cations. *J. Membr. Biol.,* 90, 177-190.

S3. Murzin, A. G., Lesk, A. M. and Chothia, C. (1994) Principles determining the structure of b-sheet barrels in proteins I. A theoretical analysis. *J. Mol. Biol.,* 236, 1369-1381.

S4. Murzin, A. G., Lesk, A. M. and Chothia, C. (1994) Principles determining the structure of b-sheet barrels in proteins II. The observed structures. *J. Mol. Biol.,* 236, 1382-1400.

S5. Liu, W.-M. (1998) Shear numbers of protein β-barrels: definition refinements and statistics. *Journal of Molecular Biology,* 275, 541-545.

S6. Butler, T. Z., Pavlenok, M., Derrington, I. M., Niederweis, M. and Gundlach, J. H. (2008) Single-molecule DNA detection with an engineered MspA protein nanopore. *Proc. Natl. Acad. Sci. U.S.A.,* 105, 20647-20652.

S7. Song, L. Z., Hobaugh, M. R., Shustak, C., Cheley, S., Bayley, H. and Gouaux, J. E. (1996) Structure of staphylococcal alpha-hemolysin, a heptameric transmembrane pore. *Science,* 274, 1859-1866.

S8. Kowalczyk, S. W., Grosberg, A. Y., Rabin, Y. and Dekker, C. (2011) Modeling the conductance and DNA blockade of solid-state nanopores. *Nanotechnology,* 22, 315101.

S9. Pratt, K. W., Koch, W. F., Wu, Y. C. and Berezansky, P. A. (2001) Molality-based primary standards of electrolytic conductivity (IUPAC Technical Report). *Pure Appl. Chem.,* 73, 1783-1793.

S10. Degiacomi, M. T. and Peraro, M. D. (2013) Macromolecular Symmetric Assembly Prediction using Swarm Intellicence Dynamic Modeling. *Structure,* 2, 1097-1106.

S11. Yamashita, D., Sugawara, T., Takeshita, M., Kaneko, J., Kamio, Y., Tanaka, I., Tanaka, Y. and Yao, M. (2014) Molecular basis of transmembrane beta-barrel formation of staphylococcal pore-forming toxins. *Nat. Commun.,* 5, 4897.

S12. Walker, B., Krishnasastry, M., Zorn, L. and Bayley, H. (1992) Assembly of the oligomeric membrane pore formed by staphylococcal alpha-hemolysin examined by truncation mutagenesis. *J. Biol. Chem.,* 267, 21782-21786.

S13. Walker, B., Braha, O., Cheley, S. and Bayley, H. (1995) An intermediate in the assembly of a pore-forming protein trapped with a genetically-engineered switch. *Chem. Biol.,* 2, 99-105.

S14. Stoddart, D., Ayub, M., Höfler, L., Raychaudhuri, P., Klingelhoefer, J. W., Maglia, G., Heron, A. and Bayley, H. (2014) Functional truncated membrane pores. *Proc. Natl. Acad. Sci. U.S.A.,* 111, 2425-2430.

Example 3

An important bottleneck in technologies based on protein nanopores is the inflexibility of the self-assembly of the pore-forming proteins. As a direct consequence, it is currently impossible to reliably make smaller or larger pores than the size that is dictated by the protein itself: a heptameric protein like haemolysin will always assemble into a heptameric pore. A second consequence is that the relative order of these seven subunits cannot be imposed. This limits the development of novel sensors and artificial enzymes that require more than one altered subunit.

To overcome these limitations the ultimate goal was to design and construct a molecular scaffold that can template both the number and the relative order of protein subunits that later form a nanopore. The scaffold made of DNA can be constructed accurately and reproducibly in a single step. It can be modified with proteins or parts of proteins that can be brought together in a nanopore, and it can be detached if required after the correct nanopore has formed.

Design and Synthesis of Building Blocks

We have designed and constructed a molecular scaffold made of DNA that can template both the number and relative order of protein subunits. Our design consists of twelve short single-stranded pieces of DNA that come together into a small ring with twelve arms onto which proteins can be attached. This design has two key advantages over alternative designs. It is more flexible than the larger DNA origami structures based on helix bundles making it much easier to bring together two proteins attached at different binding sites without the need for long and floppy linker molecules. In addition, it does not require an excess amount of the short, protein-modified DNA molecules, of which the majority is incorporated into the scaffold and which may have adverse effects in applications.

The design, construction and analysis of our scaffold is summarised in D1.1 -D1.3. Briefly, we used simulations to verify that our designed scaffold is sufficiently flexible to bring all arms together. In experiments, we have shown that the scaffold can be formed with more than 85% overall yield (based on all DNA molecules), that it is indeed a circle with twelve parts, as designed, and that it has the correct overall mass. Moreover, we have shown that our design can easily be extended to 14, 16 or 18 functional sites.

We have synthesised several different peptides and proteins that can be used to form scaffolded nanopores:

- the α-helical D4 domain in the C-terminal region of Wza (325-359), with a CGG linker at either the N-terminus or the C-terminus
- the β-hairpin of α-haemolysin with a cysteine residue in the loop, both in the up and down configuration
- two mutants of the full-length β-barrel-forming α-haemolysin: N17C and K237C, which can be conjugated to the oligonucleotides that make up our scaffold.

The sequence and synthesis of these peptides is summarised in D1.4.

Assembly of Pore-Forming Peptides onto a Scaffold

We attached the various pore-forming proteins and peptides to the oligonucleotides that make up our DNA scaffold. In the approach taken, all building blocks are first modified separately with the selected peptide through either a permanent or a cleavable linker, and then purified and analysed. This ensures that we can actually scaffolds large numbers of proteins or peptides despite the moderate yield of the reaction between DNA and protein.

The conjugation reaction, purification and analysis are summarised in D2.1-2.2. Briefly, we have shown that our purified peptide-modified DNA can scaffold any number of peptides up to a maximum of twelve (for the smallest scaffold we made) with a high yield.

We studied the nanopores that were formed by the templated peptides and proteins using electrical recordings in planar lipid DPhPC bilayers. We have shown that Wza D4 peptides attached via the N-terminus can form octameric nanopores, and that full-length α-haemolysin N17C can form heptameric pores when attached to a DNA scaffold. We have also shown that our DNA scaffold can stabilise peptide nanopores that are otherwise unstable (Wza).

Moreover, we have shown that the scaffold can be used as a docking site for a variety of molecules, enabling repeated detection or sequencing of an analyte at ultralow concentration, and the in situ assembly of protein complexes near a nanopore sensor.

Formation of Heteromeric Scaffolded Nanopores

First, a new mutant of α-haemolysin (N17C/T145H) is made, expressed and purified. Secondly, these proteins are conjugated to the oligonucleotides of the scaffold, in the same way as with α-haemolysin (N17C) (see D2.1). Finally, by combining these conjugates with appropriate original oligo-N17C conjugates and unmodified oligos, heteromeric pores with a controlled configuration may be formed. This is a promising route to controlled heteromeric pore formation.

D1.1—Design of DNA Scaffold

In designing a DNA scaffold for pore-forming peptides several aspects should be taken into account.

- The scaffold should match the size of the pore that will be formed by the peptides as well as possible, to avoid the use of very long linkers and the possibility that the pore-forming nature of the peptides will be masked by the physico-chemical nature of the DNA scaffold.
- The scaffold should be flexible enough to enable the pore-forming peptides to come together and arrange themselves into a nanopore.
- When using a ring-based scaffold, it is important to consider the number of helical turns in the entire ring and between functionalized nucleotides. Functional groups will point in the same direction with respect to the ring if they are separated by an integer number of helical turns.

Based on the above considerations, we have designed a DNA-ring with twelve arms that can be functionalized with pore-forming peptides (FIG. 1*a*). This scaffold consists only of short oligonucleotides, and lacks a long scaffold strand that is common in DNA origami. Each of the twelve oligos (1-12) (SEQ ID NOs: 15-26, respectively) consists of 43 nucleotides, and is designed to hybridize with four other oligos: two of these hybridized sections form arms and two form stretches of the ring. An adenosine hinge base separates each arm from the main ring and ensures that the arms have sufficient flexibility.

The oligos were optimized to have low melting temperatures of all non-complementary strands and high melting temperatures of (partially) complementary strands (FIG. 10). The design was further optimized to prevent strands 7 and 8 to become trapped in a secondary minimum of hybridization between regions that are not fully complementary, by changing the sequence of strands 7 and 10 (SEQ ID NOs: 21 and 24), to SEQ ID NOs: 27 and 28, respectively. Finally, elongation of strand 11 (11d, SEQ ID NO: 29) and the addition of two oligos (11f and 11g: SEQ ID NOs: 30 and 31) enables the formation of a ring with eleven short and one long arm, which may be useful in characterization of these structures.

D1.3—Scaffold Annealing

The DNA scaffold depicted in FIG. 1*a* can be annealed by mixing stoichiometric amounts of all 12 oligos, to a final concentration of 25 nM-10 uM per strand (tested), in one of the following buffers:

- 0.1 M phosphate buffer, pH 7-8
- 0.1 M Tris-HCl buffer, pH 7.5-8.5
- 1×TAE or 1×TBE buffer, pH 8.3
- 0.1 M ammonium acetate, pH 7
- 0.1 M triethylammonium acetate, pH 7

Addition of 0.3-1.5 M NaCl or KCl improves the annealing yield, addition of mM concentrations of Mg have not had significant effects, presumably because the oligonucleotides stock solutions were prepared in phosphate buffer and magnesium phosphate is poorly soluble. Indeed, when $Mg^{2+}$ was added to the annealing solution, small white precipitates accumulated at the bottom of the tubes. Only in buffers containing large amounts of EDTA, precipitation upon addition of Mg2+ was not observed, but no improvement of the annealing was found. A too low concentration of ions (as for example in 10 mM phosphate buffer) leads to poor annealing.

The oligonucleotides are mixed in a total volume of 25-200 uL and annealed in a PCR machine. A typical annealing protocol is as follows:

- 95° C. for 3 min
- 95° C. to 65° C., over 3 min
- 65° C. to 4° C., over 18 hours
- Keep at 4° C. until use (do not freeze)

The 65° C. to 4° C. step has been shortened to 10 hours and 2 hours without significant effect on the annealing efficiency. An intermediate initial cooling step (95° C. to 80° C. and 80° C. to 65° C.) can be added for the annealing of rings with a long arm (30 nucleotides complementary regions). The annealed rings can be analyzed on 5% acrylamide or 2.5% agarose gels, with 1×TBE running buffer and running at 80-100 V.

D1.4—Peptide Synthesis

Four potential pore-forming peptides have been synthesized, CWza (SEQ ID NO: 1), WzaC (SEQ ID NO: 3), αHL-UP (111-147, T129C) (SEQ ID NO: 9) and αHL-DOWN (SEQ ID NO: 10).

Two peptides are derived from a consensus sequence of the D4 domain (325-359) of outer membrane protein Wza, across all organisms that have this protein. An N- or C-terminal CGG/GGC handle enables coupling of the peptide via its N- or C-terminus, respectively.

Two other peptides are derived from the β-hairpin of *S. aureus* α-haemolysin (111-147). A T129C mutant can be coupled with the trans-side loop of the β-barrel to the DNA scaffold. In another variant the two β-strands have been exchanged, in order to flip the β-hairpins as they hang from the DNA scaffold.

The peptides are synthesized by solid phase peptide synthesis, using Fmoc protected amino acids, on a Rink amide resin, following the protocol outlined below.

Typical scale: 0.25 mmol (all amounts are adjusted to this scale).

Abbreviations

- HBTU=2-(1H-benzotriazol-1-yl)-1,1,3,3-tetramethyluronium hexafluorophosphate
- DIPEA=diisopropyl ethyl amine
- TFA=trifluoroacetic acid
- TIS=triisopropylsilane
- DMB=(1,3)-dimethoxybenzene Preparation

- Weigh 4 eq. (1 mmol) of all amino acids, protected with Fmoc at the amine end and an appropriate protecting group for the side chains (e.g., tBu for Ser, Thr, Tyr; OtBu for Asp, Glu; Trt for Asn, His, Cys and Boc for Lys) in 15 mL Falcon tubes, and store in −20° C.
- Make a 0.45 M HBTU activator solution in DMF. 15.2 g in 80 mL DMF will make about 88 mL 0.45 M HBTU solution. Store in fridge at 4° C. For activation, 3.8 eq. (2.1 mL) of HBTU are needed for every AA.

Weigh 0.25 mmol Rink amide MBHA resin (100-200 mesh; 0.37 mmol/g) in an empty syringe without plunger, with a circular filter fitted at bottom.

Make a 20 g phenol solution in 10 mL EtOH (Kaiser A) and a 0.5 g ninhydrin solution in 10 mL EtOH (Kaiser B). [In literature, often a KCN (aq) in pyridine solution is made as well].

Make a 20% (v/v) piperidine in DMF solution

Peptide Synthesis

Put tube on shaker (720 rpm), attach through valve at bottom to waste container under vacuum. Add Teflon cap with valve connected to DMF bottle.

For every AA carry out the following sequence of steps (typical volumes are 2-3× resin volume, unless specified):

Rinse 6× with DMF, rinse beads from cap and top of tube with glass pipette before opening.

Cleave Fmoc by 20% piperidine (1×1 min, then 1×2 min).

Rinse 6× with DMF, rinse beads from cap and top of tube with glass pipette before opening.

Check for free amines with Kaiser test: take 5 uL sample of resin in DMF, wash 3× with EtOH, add 5 uL Kaiser A and 5 uL Kaiser B, and incubate 5 min at 100° C. Dark blue/black/red (for some AA) coloring of the beads is positive. The dark colour will leak into the solution after a short time.

Activate COOH of Fmoc-AA by adding 2.1 mL 0.45 M HBTU and 0.35 mL DIPEA (8 eq.=2 mmol=2*129.24/0.742=0.35 mL), and shake during 1 min. The activated AA will mostly have a yellow-orange colour.

Rinse resin 1× with DMF, rinse beads from cap and top, drain DMF, close valves, add activated Fmoc-AA-OH to resin and shake for 12 min (make sure that all resin is in contact with the AA, i.e., no white/dry band at bottom of tube).

Drain AA, rinse 6× with DMF, rinse beads from cap and top.

Check for absence of free amines with Kaiser test (minimum 5 minutes is critical): colorless/yellow solution and colorless beads are negative→no free amines, all have reacted to form Fmoc-protected peptide N-terminus.

Proceed with next AA

Finish with free amine for N-terminus, or an amide, depending on needs.

Purification

Rinse resin extensively with EtOH and dry tube under vacuum in desiccator. Weigh for crude mass.

Cleave from resin in TFA cocktail. For 300 mg resin: 5 mL cocktail (TFA:water:TIS:DMB=92.5:2.5:2.5:2.5). Add DMB as scavenger for peptides with Cys and Met.

Add resin to cocktail in 50 mL Falcon tube and shake for 2-3 h.

Evaporate TFA in fume hood by blowing N2 gas into tube, during 10 min.

Precipitate peptide in 40 mL diethyl ether, centrifuge and pour off diethyl ether (keep in case peptide remains soluble in diethyl ether).

Evaporate all ether under N2.

Add MQ water, vortex to disperse most of the peptide, freeze in liquid N2, and lyophilize in freeze dryer Analyse peptide on HPLC & Maldi.

HPLC

Run an analysis of a small sample: dissolve lyophilized sample (from 300 mg) in 200 uL 20/80 acetonitrile/water.

Inject 10 uL into HPLC. Run a gradient from 0-95% 1:1 IPA/Acn, where 0% is water+2% FA.

Detect at 230, 254, 260 nm (Tyrosines).

Collect peaks, and analyse mass (Maldi)

D2.1—Peptide-Oligonucleotide Conjugation

Cysteine-containing peptides and 5'-amino-oligonucleotides are conjugated via one of the following two strategies.

1. SMPEG crosslinker

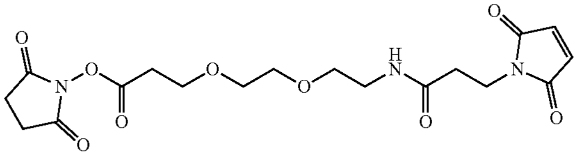

SM(PEG)$_2$
MW 425.39
Spacer Arm 17.5 Å

Typical reaction scale: 10 nmol

Mix 20 uL 500 uM amino-functionalized oligonucleotide in 0.1 M phosphate buffer pH 7.2, with 60 uL 0.1 M phosphate buffer pH 7.2 and 20 uL 10 mg/mL SMPEG2 in DMSO (50× excess linker). Incubate 2 h at room temperature (too long incubation leads to maleimide hydrolysis).

Precipitate oligonucleotide in ethanol: add 10 uL 3 M NaCl and 400 uL icecold 100% ethanol. Leave at −20° C. for 10 min, and spin down at 4° C., 12,000 rcf, 10 min. Discard supernatant and wash precipitate 2× with 70% ethanol.

Dissolve oligonucleotide-PEG-Maleimide in 0.1 M phosphate buffer pH 7.2 and add 20 nmol peptide-SH (reduced using TCEP beads). Incubate overnight at room temperature.

2. PEG-SPDP crosslinker (cleavable)

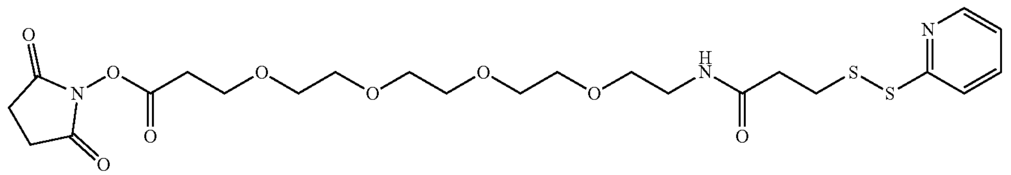

PEG4-SPDP
2-Pyridyldithiol-tetraoxatetradecane-N-hydroxysuccinimide
MW 559.17
Spacer Arm 25.7 Å

Typical reaction scale: 10 nmol

Mix 20 uL 500 uM amino-functionalized oligonucleotide in 0.1 M phosphate buffer pH 7.2, with 60 uL 0.1 M phosphate buffer pH 7.2 and 20 uL 50 mg/mL PEG4-SPDP in DMSO (180× excess linker). Incubate 2 h at room temperature.

Separate modified oligos from excess linker using Spin-Trap desalting columns (3×). Add 0.1 M phosphate buffer to a total volume of 140 uL. Wash columns 5× with 0.4 mL phosphate buffer between each step. Note: ethanol precipitation does not work: pyridyldithiol bond is cleaved in the process.

Add 120 uL 0.17 mg/mL reduced CWza to 70 uL of oligo+linker from previous step and incubate overnight at room temperature.

Conjugates are purified by HPLC, using a C18 reverse phase column, 10 mM triethylammonium borate buffer (pH 8.5) in MilliQ as buffer A, and acetonitrile as buffer B.

A typical elution protocol is as follows:

Binding during 2 min at 96% A, 4% B, 1 mL/min

Gradient from 4% B to 65% B in 10 min, 1 mL/min

Washing at 100% B during 1 min, 1 mL/min

Equilibrate at 96% A and 4% B during 3 min, 1 mL/min.

Unmodified oligonucleotides are eluted around 7.5 minutes, whereas the conjugates are eluted between 9 and 10 minutes after the start of the run. The purified conjugates can be viualized on an AnykD acrylamide gel, with 1×TGS as running buffer, and an applied potential of 150 V.

D2.2—Hybrid Pore Formation

The DNA scaffold depicted in FIG. 1*a* with a predetermined number of pore-forming peptides attached to it can be annealed by mixing stoichiometric amounts of all 12 oligos (with and/or without peptides), to a final concentration of about 250 nM per strand (tested), in 0.1 M phosphate buffer, pH 7.2, with up to 300 mM NaCl added. Addition of DDM (dodecyl-D-mannose) as a surfactant (0.002-0.1%) leads to aggregation of the rings into larger objects and is therefore not recommended. The oligonucleotides are mixed in a total volume of 25-50 uL and annealed in a PCR machine. A typical annealing protocol is as follows:

80° C. 3 min

80° C. to 65° C. in 3 min

65° C. to 4° C. in 10 hours

Keep at 4° C. until use (do not freeze)

The annealed rings can be analyzed on 5% acrylamide or 2.5% agarose gels, with 1×TBE running buffer and running at 80-100 V.

The annealed scaffolds with a predetermined number of pore-forming peptides can be used to create hybrid nanopores in lipid bilayers. Planar lipid bilayer are formed in a circular hole in a teflon film following the procedure described in detail in Gutsman et al., Nature Protocols 10, 188 (2015). Addition of 2-5 nM of rings to the cis compartment, together with 2 uL 1× TGS buffer in a total of 500 uL to aid insertion, can lead to one or more insertions of hybrid pores in DPhPC planar lipid bilayers.

D3.1—Design of Larger DNA Scaffolds

Please refer to D1.1 for the general design principles of the DNA scaffolds.

Figure 43:
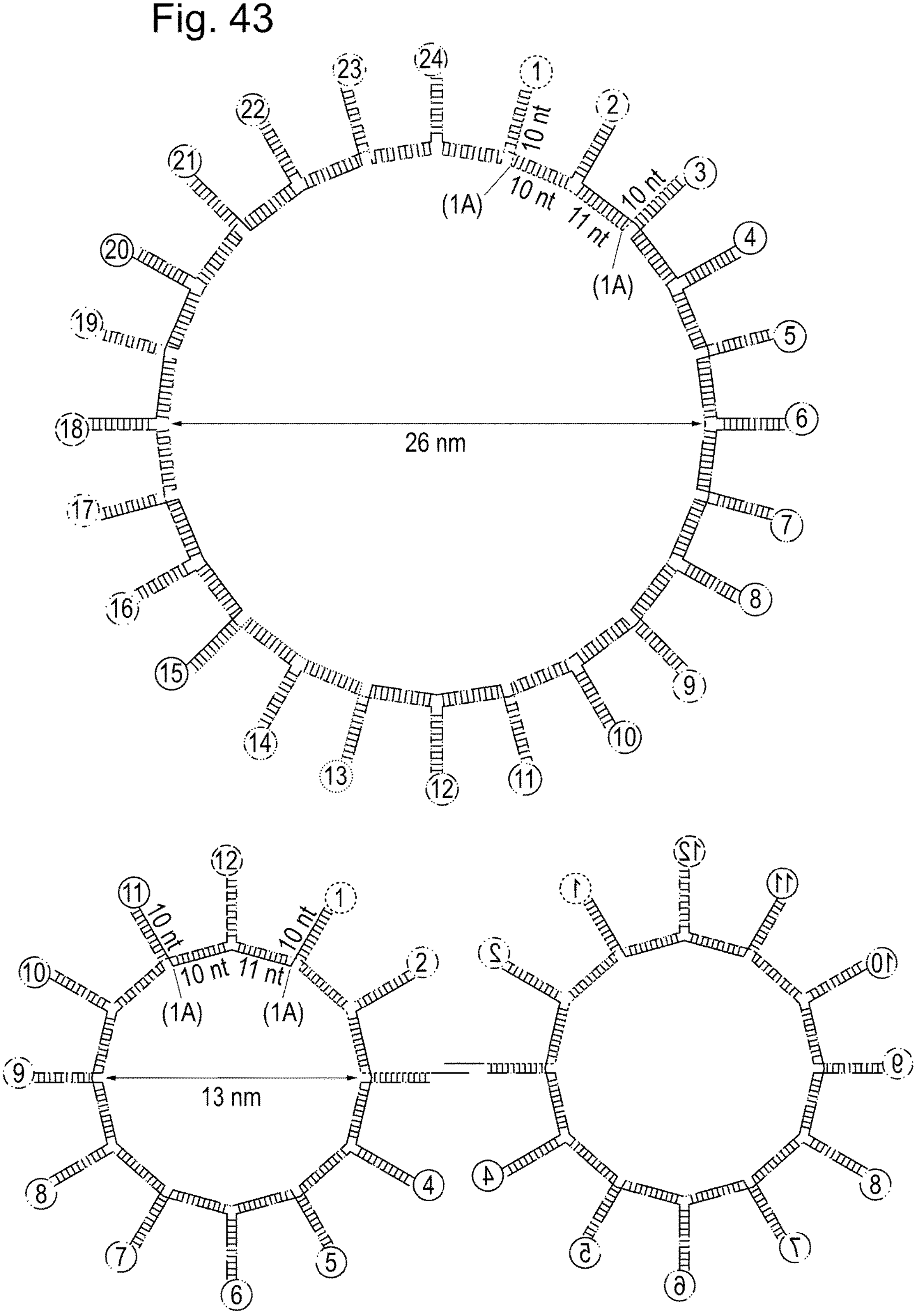
FIG. 43: Design of larger DNA scaffolds. Schematic showing the structure of a large 24-mer DNA scaffold (diameter 26 nm) and the structure of a figure-of-eight shaped scaffold wherein two 12-mer rings are joined together.

Based on the above considerations, we have extended our design of a DNA-ring with twelve arms to rings with 14, 16, 18, 20 and 24 arms, and made a design in which two twelve-arm rings are joined together into a figure-of-eight shape with a total number of sites that can be functionalised with pore-forming peptides of 24 (FIG. 43).

The nucleotide sequences of the 14-mer are 15-20, 22, 23, 27, 28 and 32-35. (Note: sequences 1-10 are the same as sequences 1-10 of the 12-mer ring with improved 7/8 hybridisation (D1.1).)

The nucleotide sequences of the 16-mer are 15-20, 22, 23, 27, 28, 32, 33 and 36-39. (Note: sequences 1-12 are the same as sequences 1-12 of the 14-mer ring above.)

The nucleotide sequences of the 18-mer are 15-20, 22, 23, 27, 28, 32, 33, 36, 37 and 40-43. (Note: sequences 1-14 are the same as sequences 1-14 of the 16-mer ring above.)

The nucleotide sequences of the 20-mer are 15-20, 22, 23, 27, 28, 32, 33, 36, 37, 40, 41 and 44-47. (Note: sequences 1-16 are the same as sequences 1-16 of the 18-mer ring above.)

The nucleotide sequences of the 24-mer are 15-20, 22, 23, 27, 28, 32, 33, 36, 37, 40, 41, 44, 45 and 48-53. (Note: sequences 1-18 are the same as sequences 1-18 of the 20-mer ring above.)

The nucleotide sequences of the double 12-mer are 15-20, 22, 23, 27, 28, 26, 29 and 54. (Note: sequences 1-10 and 12 are the same as sequences 1-10 of the 12-mer ring with improve 7/8 hybridisation (D1.1).)

These oligos were all optimized to have low melting temperatures of all non-complementary strands and high melting temperatures of (partially) complementary strands, as described in D1.1.

For annealing of these oligonucleotides into rings of different sizes the same protocol is used as for the 12-mer rings:

95° C. 3 min

95° C. to 65° C. in 3 min

65° C. to 4° C. in 10 hours

Keep at 4° C. until use (do not freeze)

Figure 44:
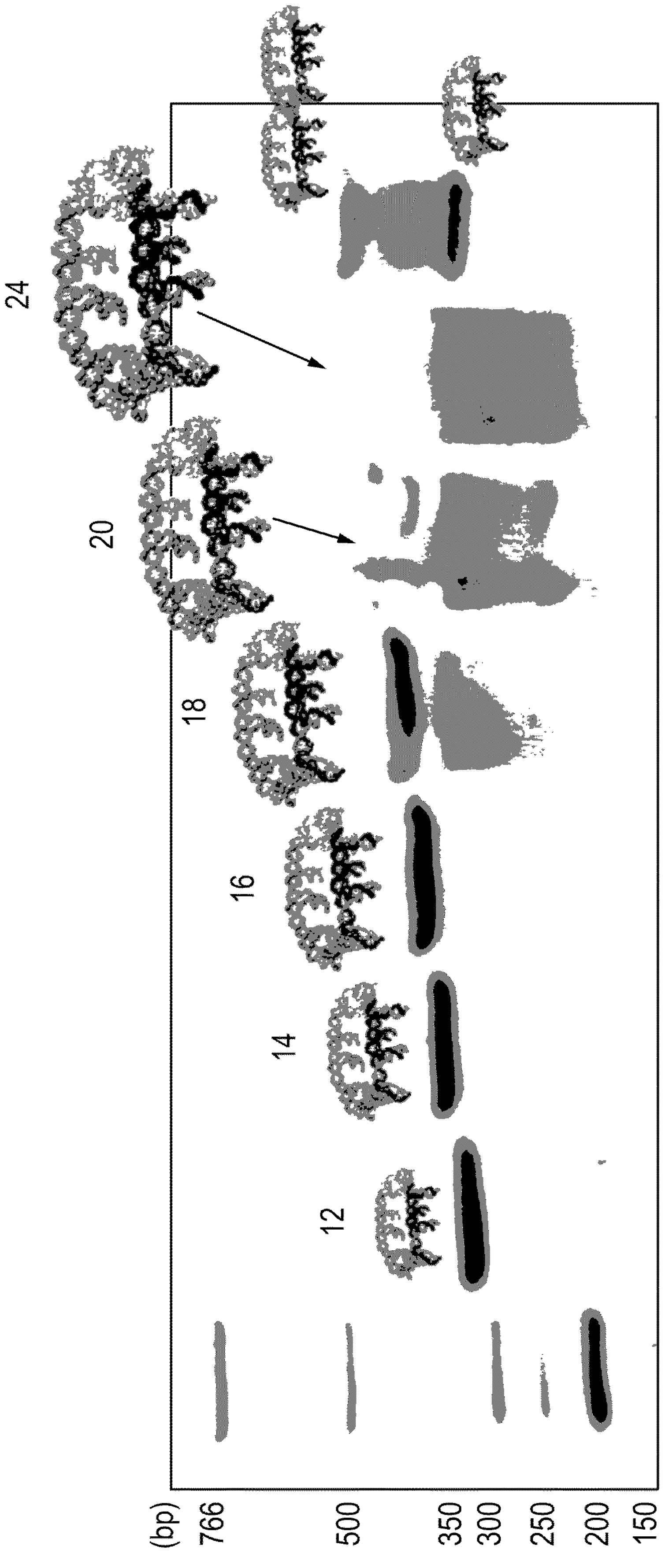
FIG. 44: Purification of larger annealed DNA scaffolds. The annealed rings were analyzed on 2.5% agarose gels, with 1×TBE running buffer, at 80-100 V. Legend: 1. Low MW ladder; 2. 12-mer, annealed in 0.1 M PB+0.5 M NaCl; 3. 14-mer, annealed in 0.1 M PB+0.5 M NaCl; 4. 16-mer, annealed in 0.1 M PB+0.5 M NaCl; 5. 18-mer, annealed in 0.1 M PB+0.5 M NaCl; 6. 20-mer, annealed in 0.1 M PB+0.5 M NaCl; 7. 24-mer, annealed in 0.1 M PB+0.5 M NaCl; 8. Double 12-mer, annealed in 0.1 M PB+0.5 M NaCl.

The annealed rings can be analyzed on 2.5% agarose gels, with 1×TBE running buffer and running at 80-100 V (FIG. 44).

D3.2—Electrophysiology of DNA-Scaffolded Wza and αHL Pores

Figure 45A:
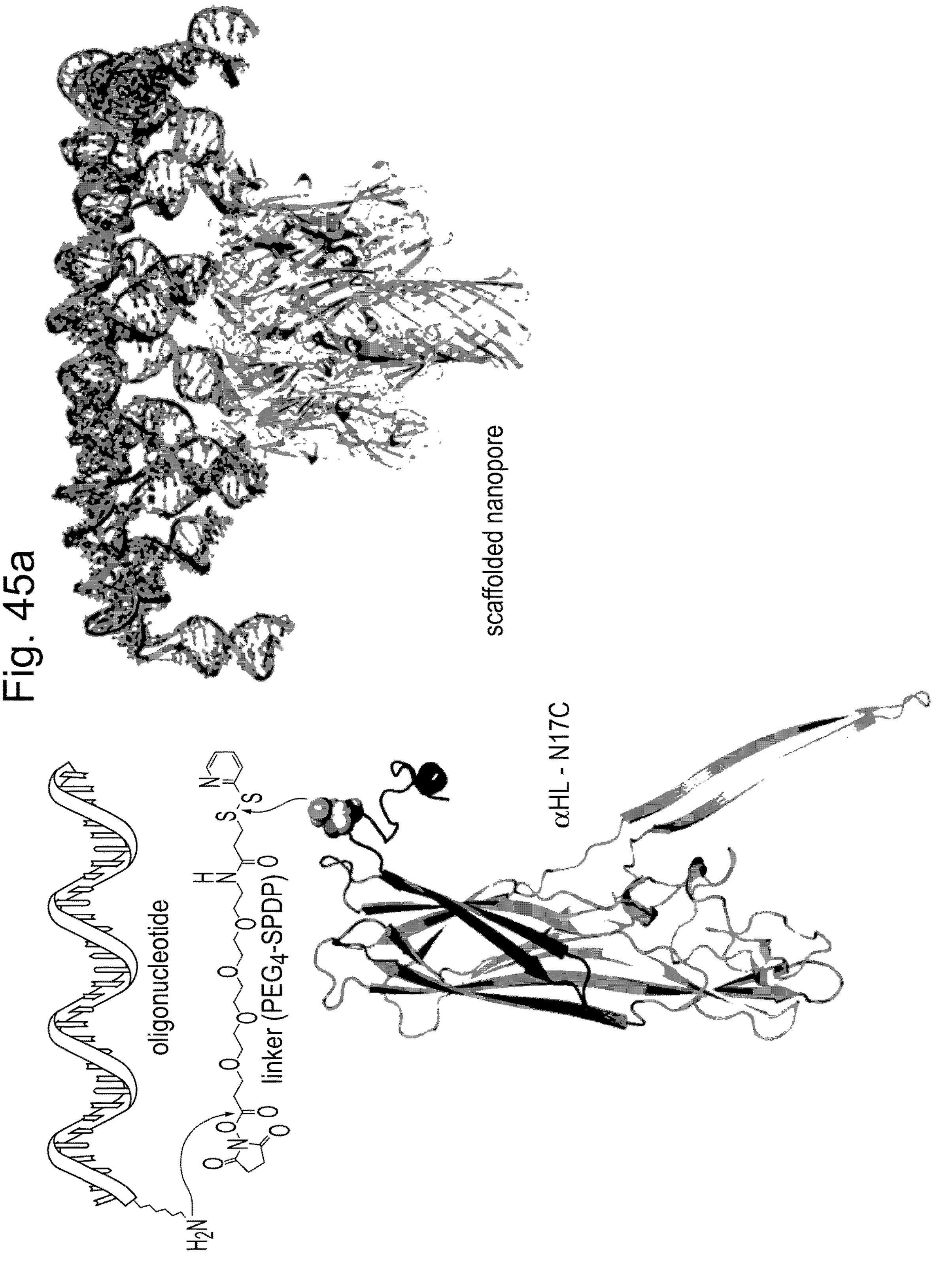
FIG. 45: αHL N17C scaffolding and pore formation. A. Schematic showing linkage of N17C αHL monomer to a nucleic acid through a $PEG_4$-SPDP linker and the formation of the scaffolded αHL pore. B. DNA scaffold linked to αHL N17C monomers were annealed between 50° C. to 4° C., over 8 h. Rings with varying no. of αHL monomers were purified. C. The αHL N17C monomers interact to form heptameric pores that insert into membranes as observed by electrophysiology measurements of pore conductance. D. Electron micrographs showing the scaffolded heptameric αHL N17C pores. E. Conductance analysis and electron micrographs demonstrate that the DNA scaffolds may be used to template 6-mer and 8-mer αHL pores.
Figure 45B:
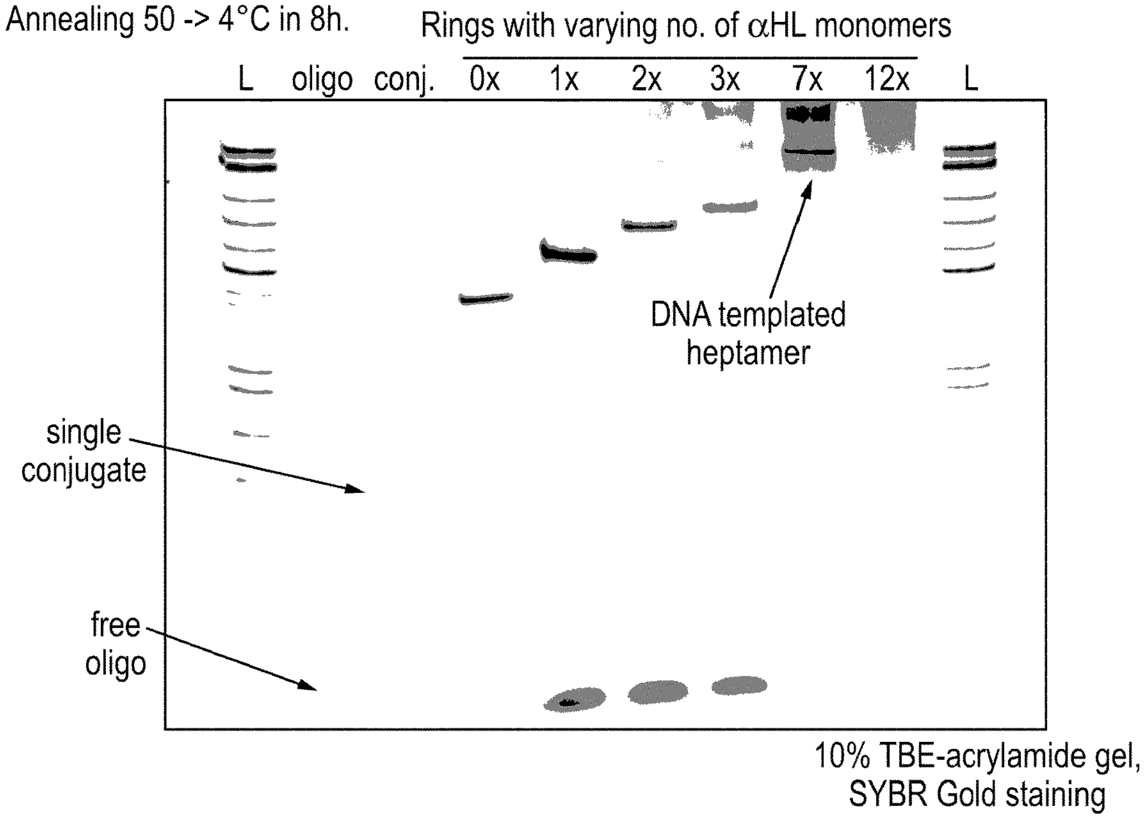

Data showing the formation of pores using scaffold Wza peptides, CWza (SEQ ID NO: 2), WzaC (SEQ ID NO: 4), Wza *E. coli* R376T (SEQ ID NO: 5), KRM consensus Wza (L-state insertion at pos. potentials) (SEQ ID NO: 6), KRM consensus Wza K375C (L-state insertion at pos. potentials) (SEQ ID NO: 7), and KRM consensus Wza Y373C (H-state insertion at pos. potentials) (SEQ ID NO: 8), are shown in FIGS. 3, 11-16.

αHL N17C mutant has been conjugated to DNA scaffolds (FIG. 45A). The oligonucleotide was linked to the N17C mutant via a $PEG_4$ linker with a cleavable disulfide (SS) bond. The resulting conjugates were purified by:

FPLC (anion exchange column),

2× membrane spin filter of collected FPLC peak

1st: 100 kDa, removes heptamers and oligo-heptamers, collect flow through

2nd: 30 kDa, removes free oligos (~13 kDa), collect what is retained in filter

Figure 45C:
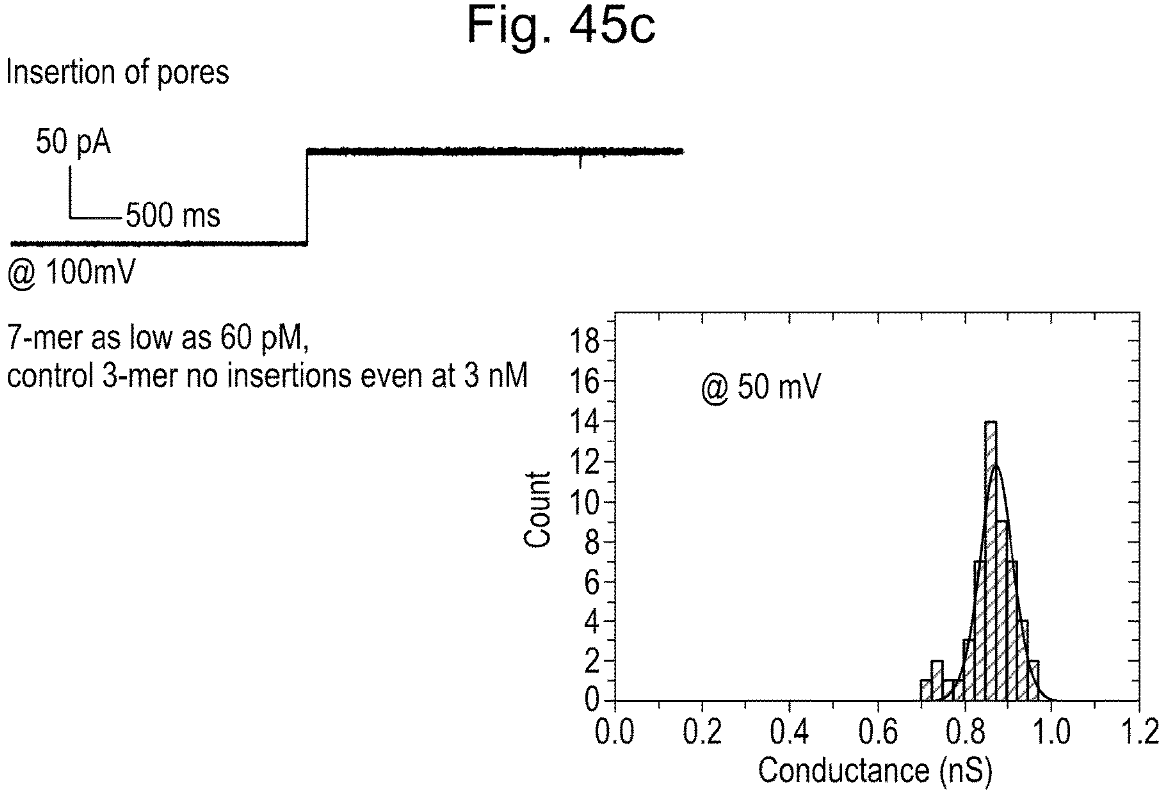
Figure 45D:
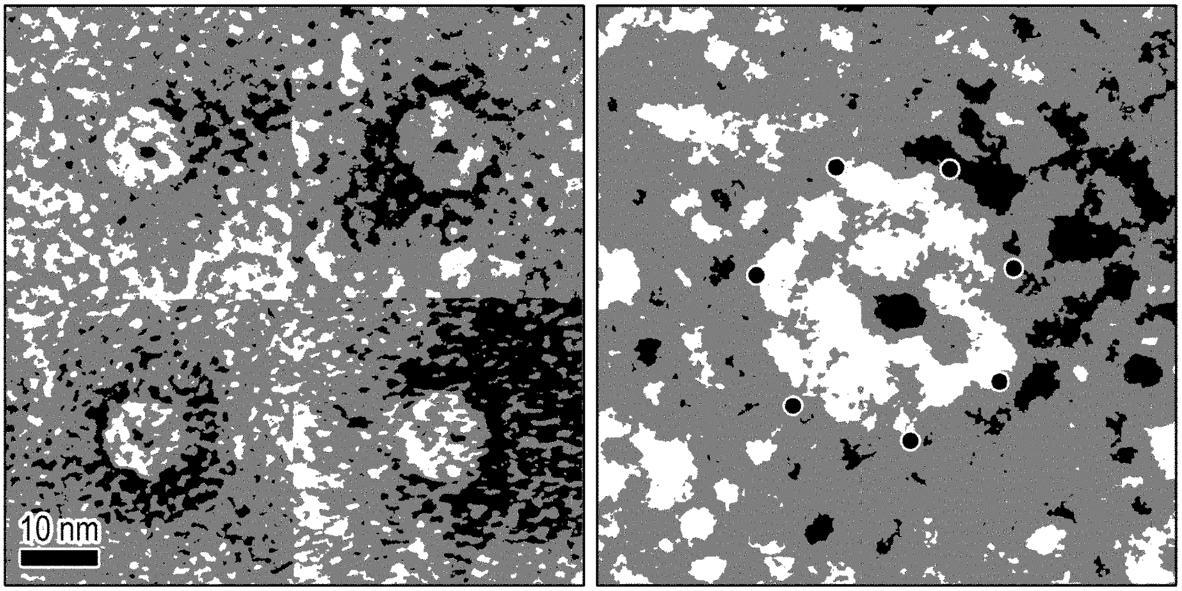
Figure 45E:
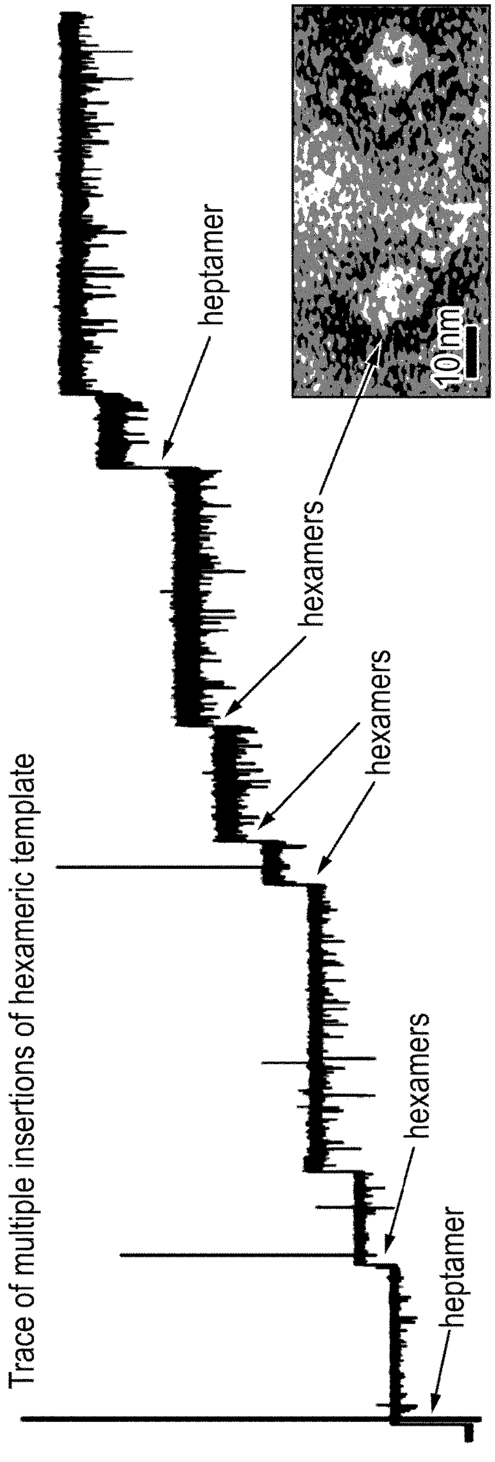
Figure 45F:
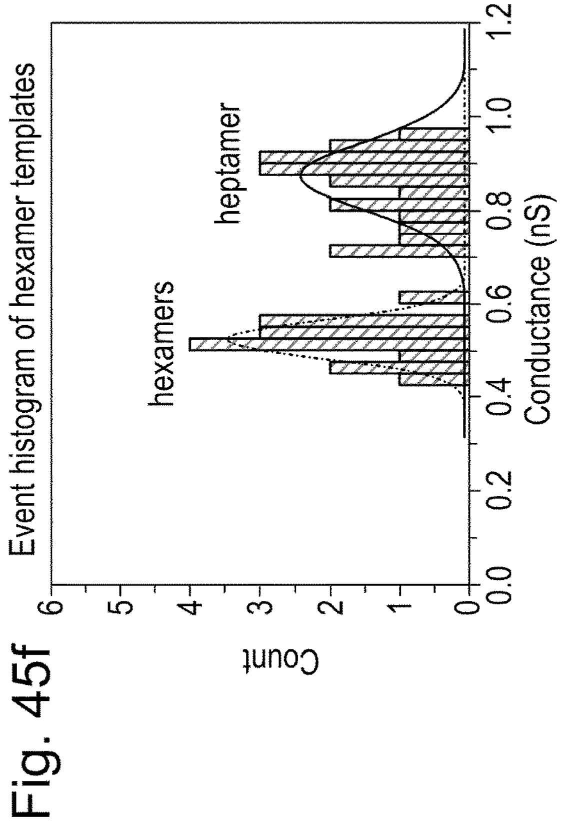
Figure 45G:
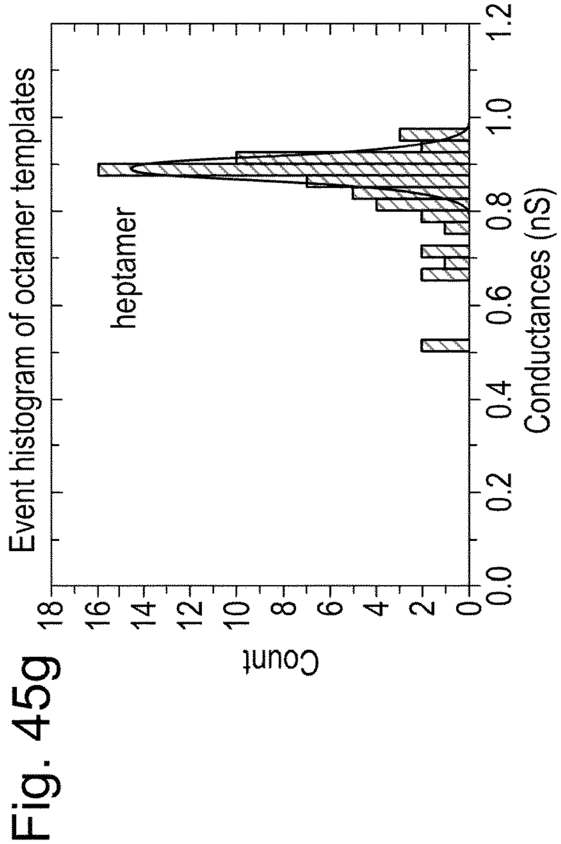
Figure 46A:
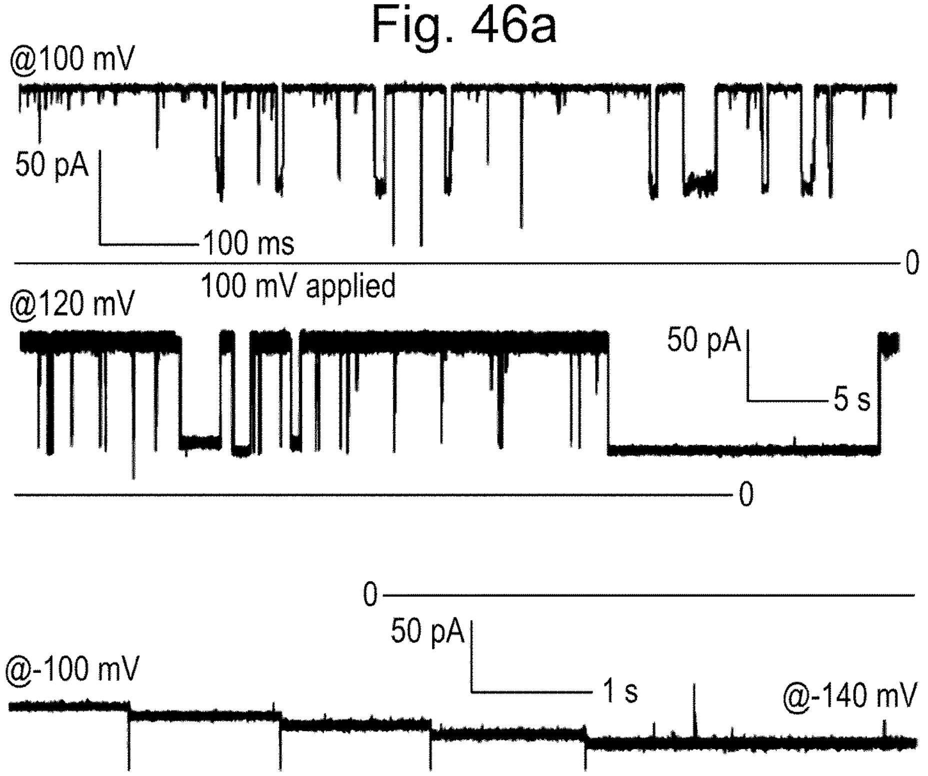
FIG. 46: Analysis of heptameric αHL N17C pore. A. Electrophysiology measurements of pore conductance demonstrate that transient blocking by the DNA scaffold was observed only at positive potentials. B. The DNA scaffold was cleaved by treatment with 10 mM TCEP (tris(2-carboxyethyl)phosphine). (i) Initially, blocking frequency and block time seem to increase. The origami is partially cleaved and has more freedom to move around and block the pore. (ii) After 1 minute, there is no more blocking at all because the origami is fully cleaved and has disappeared into solution. C. Binding of β-cyclodextrin (βCD) to αHL nanopores was observed as blocking of the pore conductance. D. A summary of the kinetics of βCD binding to the templated αHL nanopore is shown.
Figure 46B:
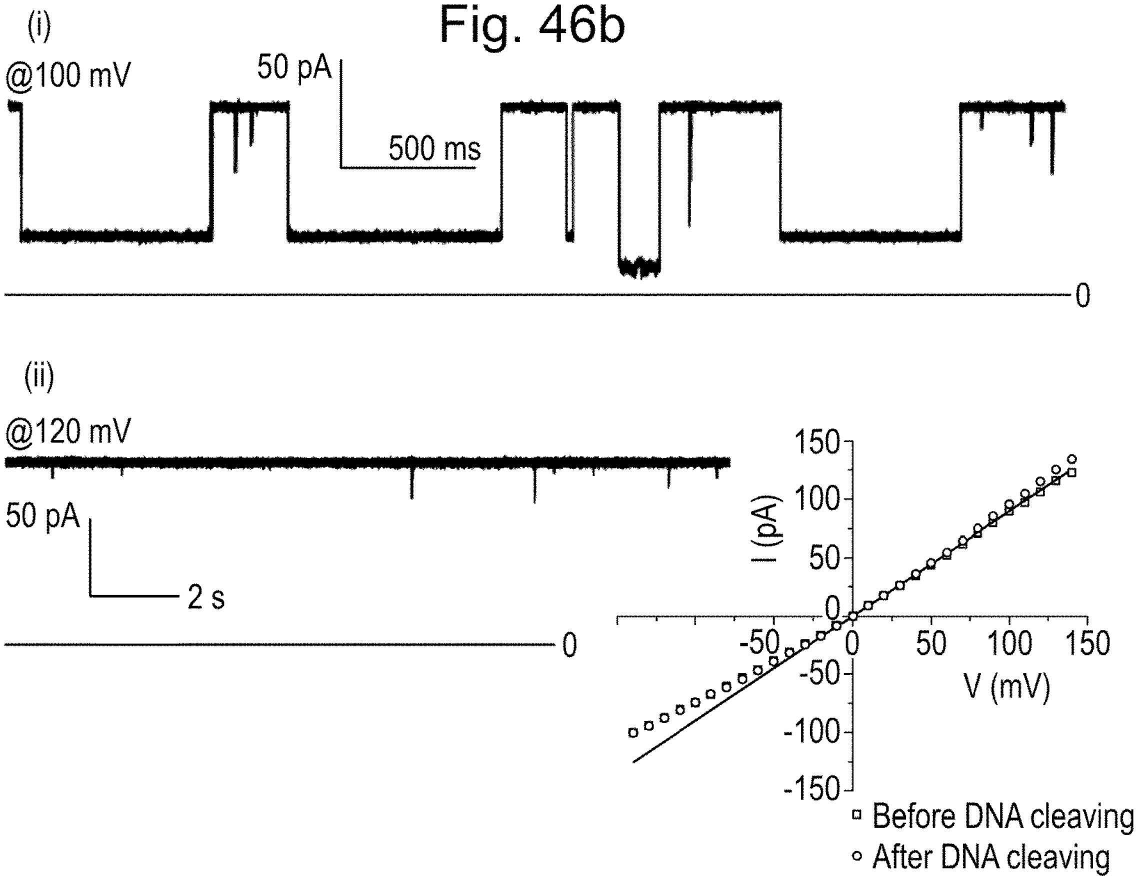
Figure 46C:
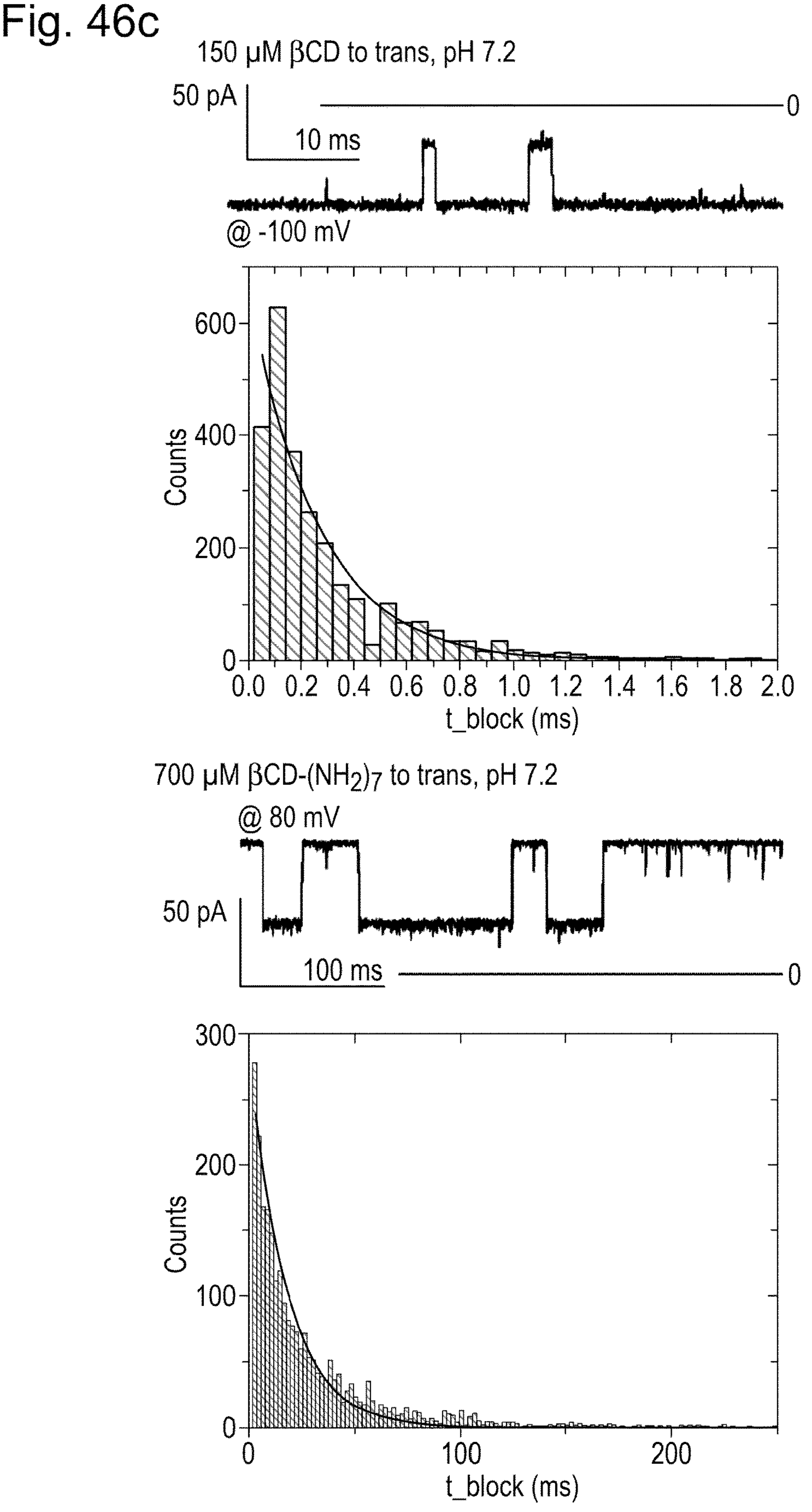
Figure 46D:
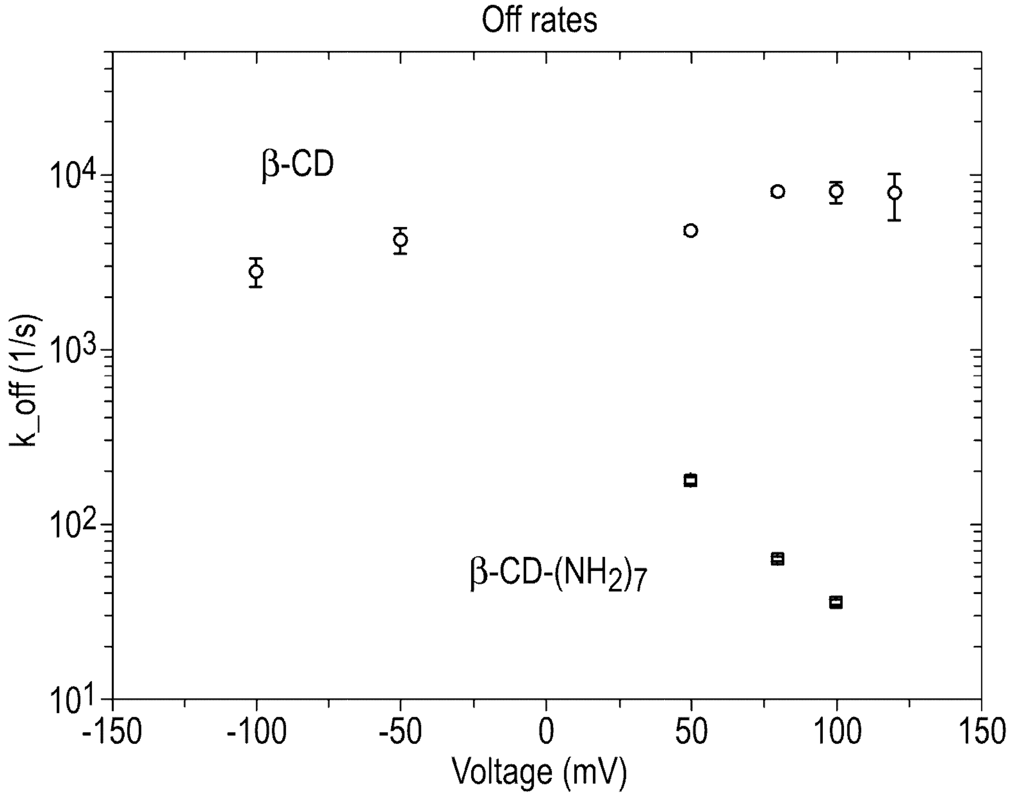
Figure 46D:
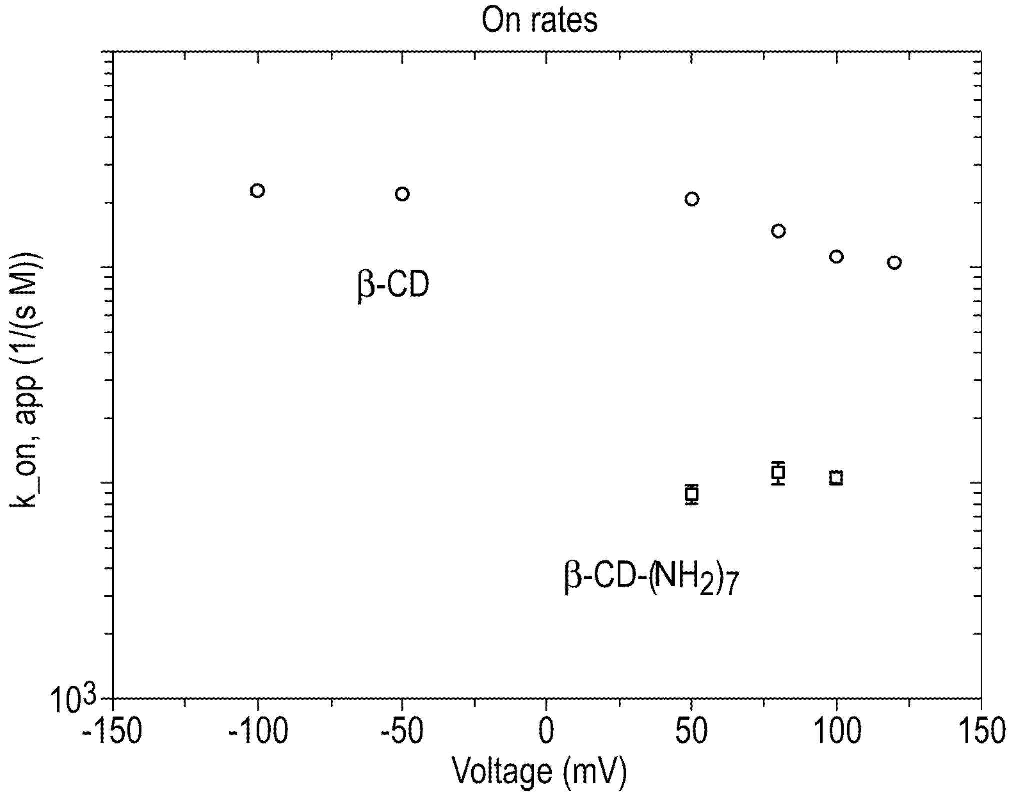

Data showing the purification of the conjugates and annealing of a DNA scaffold linked to αHL N17C is shown in FIGS. 45A and B. Formation of scaffolded αHL N17C pores is shown in FIGS. 45C-E. An analysis of the properties of the scaffolded αHL N17C pores is shown in FIG. 46.

Designing a Proof-of-Concept Double Mutant Barrel

A mutant αHL monomer comprising a T115H or T145H mutation was designed. The mutation was selected such that when the mutant monomer was assembled into the αHL heptameric pore the histidine would project into the pore channel, into the lumen of the β-barrel structure. DNA scaffolded αHL monomers including 5 wild type αHL monomers and 2 T115H mutant αHL monomer ($WT_5(T115H)_2$) were assembled into a heteromeric heptameric pore. The positions of the αHL monomers in the heptameric pore are labelled around the pore as monomers A-G. The positions of the T115H mutant monomers was varied into different configurations, which altered the relative positioning of the mutant histidine residues.

Figure 47A:
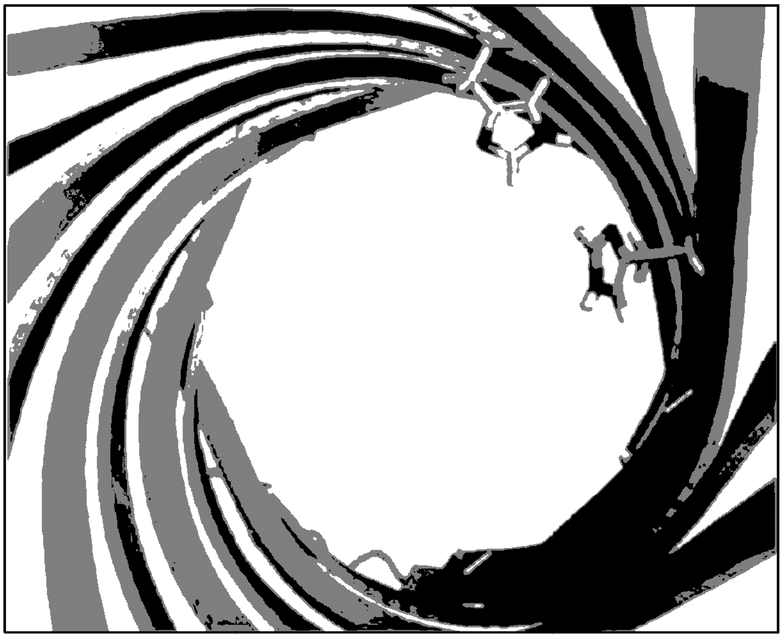
FIG. 47: Scaffolding heteromeric functionalised pores.
FIGS. 47*c*-47f show that binding of gold ($Au^1$) to the ($WT_5$(T115$H)_2$) pores could be detected. Conductance measurements through the pore at different gold concentrations demonstrates gold binding in the pore. The conductance measurements differ for the "AB" and "AD" configurations demonstrating different levels of gold binding in the pore. FIG. $\mathbf{47}_g$ is a schematic showing binding of 2,6-anthracene dicarboxylic acid in the $WT_5(T115H)_2$ "AD" configuration αHL pore.
FIG. 47h is a schematic showing the 2,6-anthracene dicarboxylic acid dimerization reaction.
Figure 47B:
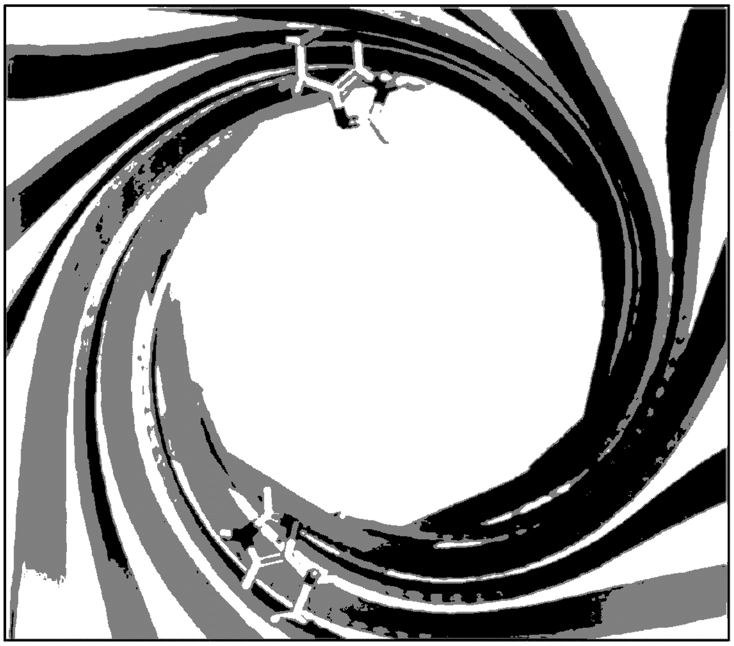
Figure 47C:
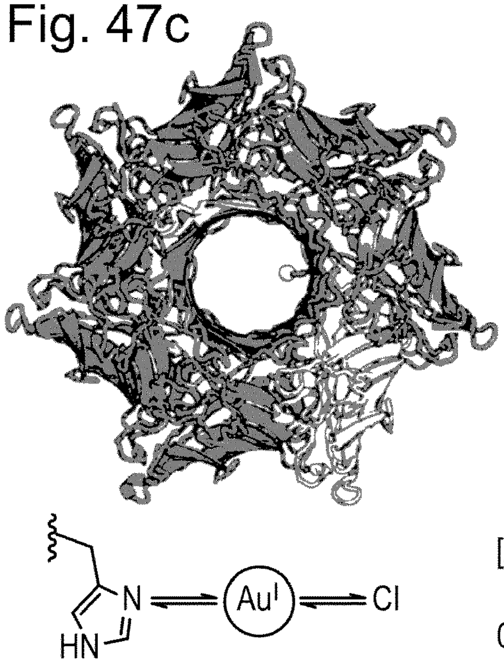
Figure 47D:
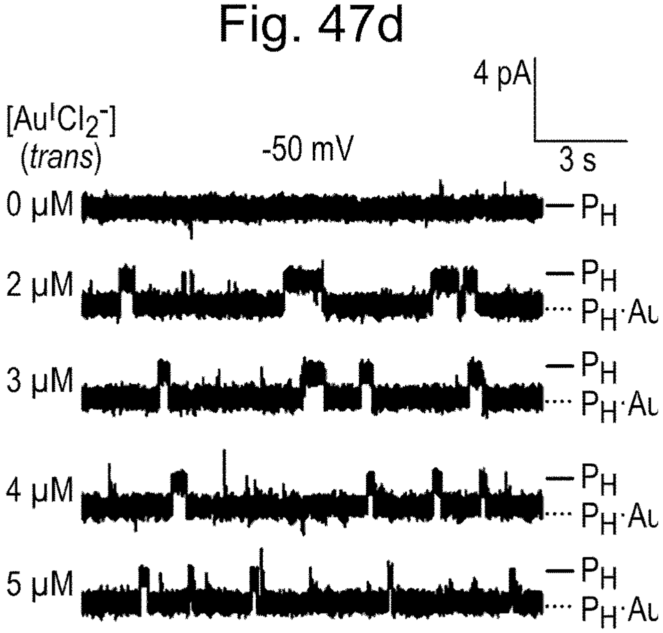
Figure 47E:
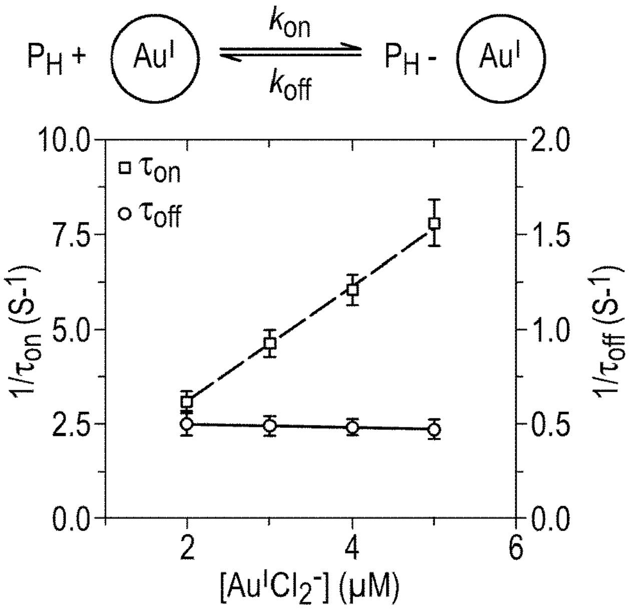
Figure 47F:
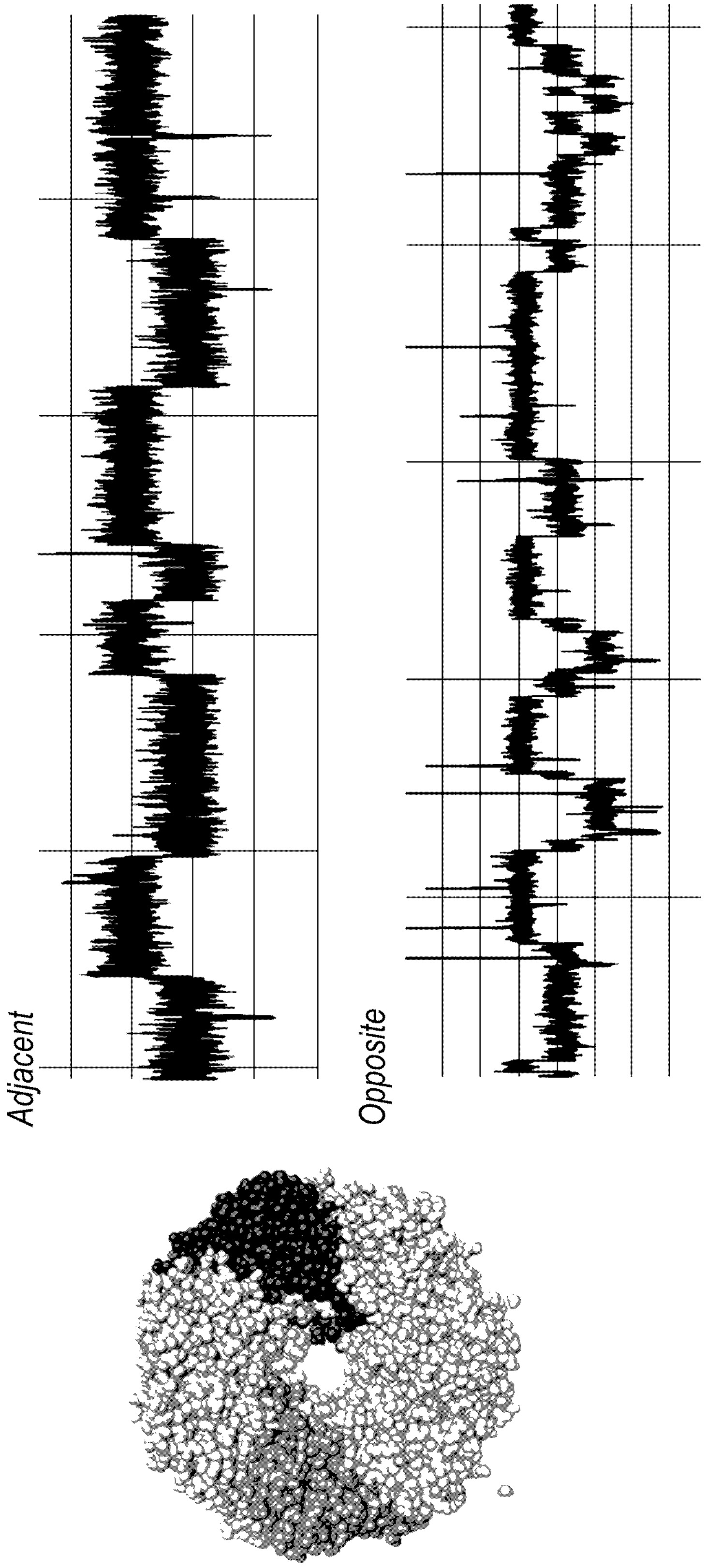

When the T115H monomers were assembled in the "AB" configuration (as shown in FIG. 47*a*), the distance between the two histidine residues (His-His) was 3.8 Å, which allows for the binding of 1 metal ion. When the T115H monomers were assembled in the "AD" configuration (as shown in FIG. 47*b*), His-His=17-19 Å, which allows for the binding of 2 metal ions. FIG. 47*c-f* shows that binding of gold ($Au^I$) to the ($WT_5(T115H)_2$) pores could be detected. It is likely that binding of other transitions metals, particularly those in groups 10-12, such as $Zn^{2+}$, $Cd^{2+}$ or $Ni(NTA)^{2+}$, could also be facilitated by the T115H and T145H mutant αHL monomers.

Figure 47G:
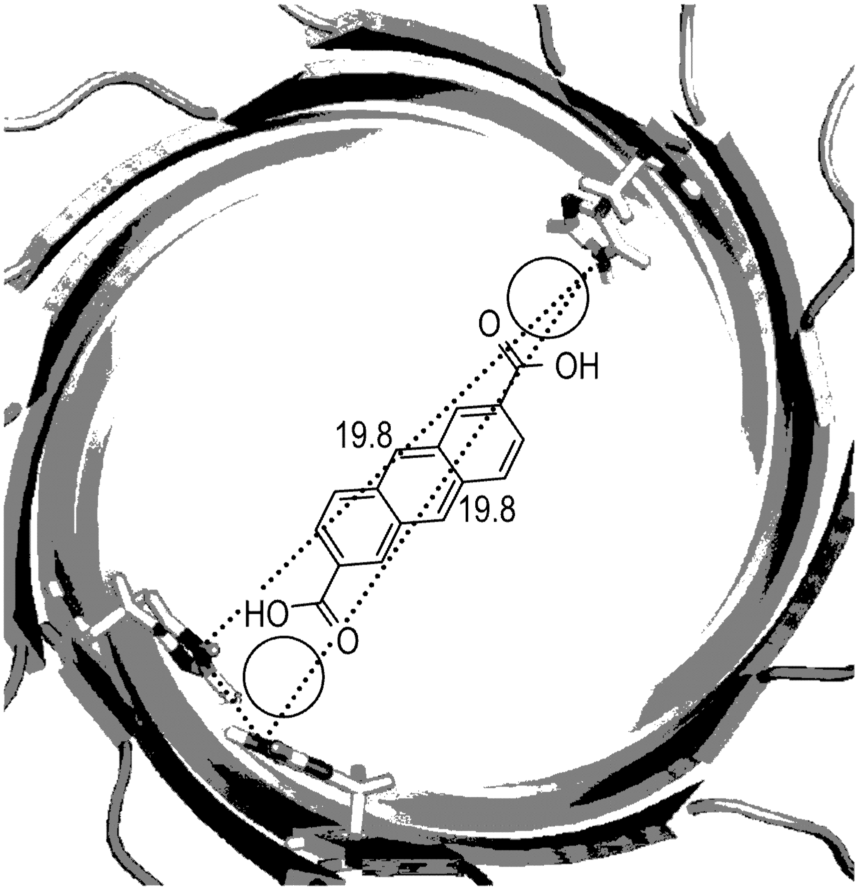
Figure 47H:
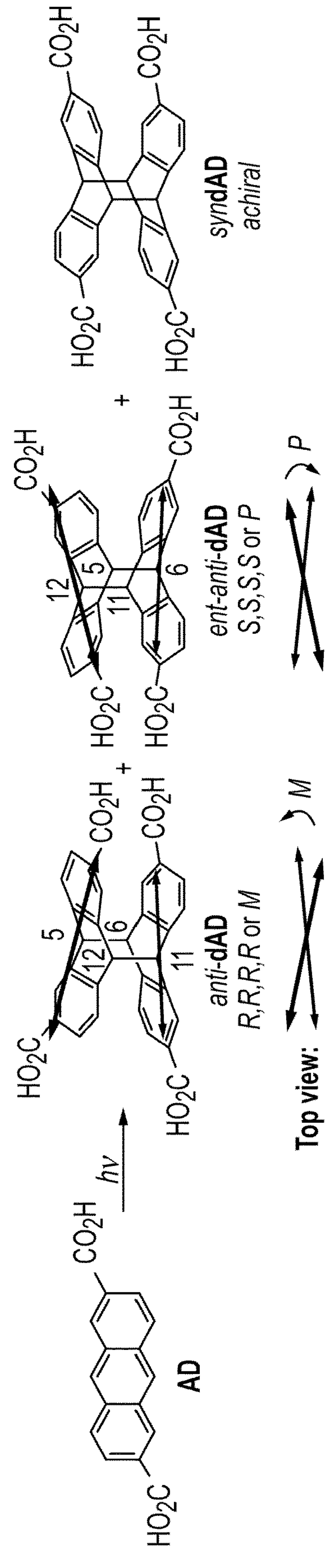

Furthermore, when the T115H mutant αHL monomers are assembled in the "AD" configuration, the distance between the two histidine residues (between 17-19 Å) would allow for the binding of 2 metal ions (such as zinc or gold (Zn, Au)) and tight binding of a rigid 2,6-anthracene dicarboxylic acid molecule (N-N distance 18 Å=2×Zn (1.4 Å)+1× $Anthr-(COOH)_2$ (15 Å)), as shown in FIG. 47*g*. Thus, it may be possible for a dimerization reaction of 2,6-anthracene dicarboxylic acid, such as that shown in FIG. 47*h*, to occur inside the pore.

The invention claimed is:

1. An assembly comprising a nucleic acid scaffold and a plurality of appendages bonded to the scaffold, wherein the appendages form a pore in a layer of amphipathic molecules, and wherein the nucleic acid scaffold comprises a plurality of nucleic acids arranged to form a closed circular structure with protruding arms.

2. The assembly of claim 1, wherein the nucleic acid scaffold comprises double-stranded nucleic acids.

3. The assembly of claim 1, wherein each appendage is bonded to a protruding arm of the nucleic acid scaffold.

4. The assembly of claim 1, wherein each nucleic acid of the nucleic acid scaffold is 10-100 nucleotides in length.

5. The assembly of claim 1, wherein each nucleic acid comprises two central regions that hybridise with the central regions of other nucleic acids in the nucleic acid scaffold and two outer regions that hybridise with the outer regions of other nucleic acids in the nucleic acid scaffold.

6. The assembly of claim 5, wherein each of the appendages is bonded to an outer region of a nucleic acid in the nucleic acid scaffold.

7. The assembly of claim 1, wherein each nucleic acid comprises a first central region that hybridises with a central region of a first nucleic acid in the nucleic acid scaffold; a second central region that hybridises with a central region of a second nucleic acid in the nucleic acid scaffold; a first outer region that hybridises with an outer region of a third nucleic acid in the nucleic acid scaffold; and a second outer region that hybridises with an outer region of a fourth nucleic acid in the nucleic acid scaffold.

8. The assembly of claim 1, wherein the nucleic acid scaffold comprises the same number of protruding arms as nucleic acids.

9. The assembly of claim 1, wherein the nucleic acid scaffold comprises nucleic acids comprising the sequences of SEQ ID NOs: 15-26 or variants thereof, SEQ ID NOs: 15-20, 27, 22, 23, 28, 25 and 26 or variants thereof, SEQ ID NOs: 15-20, 21 or 27, 22, 23, 24 or 28, 29-31 and 26, or variants thereof, SEQ ID NOs: 15-20, 21 or 27, 22, 23, 24 or 28, 29 and 26, or variants thereof; or SEQ ID NOs: 15-20, 21 or 27, 22, 23, 24 or 28, 26, and 59 or variants thereof.

10. The assembly of claim 1, wherein the nucleic acid scaffold comprises nucleic acids comprising the sequences of SEQ ID NOs: 15-20, 21 or 27, 22, 23, 24 or 28 and 32-35, or variants thereof; SEQ ID NOs: 15-20, 21 or 27,22, 23, 24 or 28, 32, 33 and 36-39, or variants thereof; SEQ ID NOs: 15-20, 21 or 27, 22, 23, 24 or 28, 32, 33, 36, 37 and 40-43, or variants thereof; SEQ ID NOs: 15-20, 21 or 27, 22, 23, 24 or 28, 32, 33, 36, 37, 40, 41 and 44-47, or variants thereof; SEQ ID NOs: 15-20, 21 or 27, 22, 23, 24 or 28, 32, 33, 36, 37, 40, 41, 44, 45 and 48-53, or variants thereof; or SEQ ID NOs: 15-20, 21 or 27, 22, 23, 24 or 28, 26, 29 and 54, or variants thereof.

11. The assembly of claim 1, wherein the nucleic acid scaffold comprises (i) a closed circular first nucleic acid strand and (ii) a plurality of second nucleic acid strands, wherein the second nucleic acids strands comprise a first region that hybridises to the first nucleic acid strand and a second region that protrudes from the circular first nucleic acid strand.

12. The assembly of claim 11, wherein each of the appendages is bonded to a third nucleic acid strand, optionally through a linker, wherein the third nucleic acid strand hybridises to the second region of a second nucleic acid strand.

13. The assembly of claim 12, wherein the third nucleic acid strand comprises SEQ ID NO: 114, or variants thereof.

14. The assembly of claim 11, wherein the nucleic acid scaffold comprises:

(a) (i) a first nucleic acid strand comprising sequences having at least 80% sequence identity to SEQ ID NOs: 63-65, or variants thereof, and (ii) a plurality of second nucleic acid strands comprising the sequences of SEQ ID NOs: 91, 93, 95 and 97, or variants thereof;

(b) (i) a first nucleic acid strand comprising sequences having at least 80% sequence identity to SEQ ID NOs: 63-65, or variants thereof, and (ii) a plurality of second nucleic acid strands comprising the sequences of SEQ ID NOs: 90, 92, 94 and 96, or variants thereof;

(c) (i) a first nucleic acid strand comprising sequences having at least 80% sequence identity to SEQ ID NOs: 66-68, or variants thereof, and (ii) a plurality of second nucleic acid strands comprising the sequences of SEQ ID NOs: 98, 99, 101, 103, 104, 105, 107, or variants thereof;

(d) (i) a first nucleic acid strand comprising sequences having at least 80% sequence identity to SEQ ID NOs: 66-68, or variants thereof, and (ii) a plurality of second nucleic acid strands comprising the sequences of SEQ ID NOs: 98, 100, 102, 103, 104, 106, 107 and 109, or variants thereof;

(e) (i) a first nucleic acid strand comprising sequences having at least 80% sequence identity to SEQ ID NOs: 66 and 68, or variants thereof, and (ii) a plurality of second nucleic acid strands comprising the sequences of SEQ ID NOs: 98, 100, 102, 103, 104 and 106, or variants thereof; or (f) (i) a first nucleic acid strand comprising sequences having at least 80% sequence identity to SEQ ID NOs: 68-71, or variants thereof, and (ii) a plurality of second nucleic acid strands comprising the sequences of SEQ ID NOs: 98, 100, 102, 104, 106, 107, 110, 111, 112 and 113, or variants thereof.

15. The assembly of claim 1, wherein the assembly comprises from about 3 to about 100 appendages.

16. The assembly of claim 1, wherein each appendage is covalently bonded to the scaffold, optionally through a flexible linker; optionally wherein each appendage is bonded to the 5' or 3' end of a nucleic acid of the nucleic acid scaffold.

17. The assembly of claim 1, wherein at least one of the appendages comprises a polymer, optionally an amphipathic polymer, optionally an amphipathic polymer selected from the group consisting of a peptide, a polypeptide, a peptidomimetic and a polynucleotide.

18. The assembly of claim 1, wherein at least one of the appendages comprises a peptide or polypeptide that is capable of inserting into a layer of amphipathic molecules.

19. The assembly of claim 1, wherein the appendages comprise polypeptides that form a multimeric complex that forms a pore in a layer of amphipathic molecules.

20. The assembly of claim 1, wherein at least one of the appendages comprises a peptide derived from a protein selected from the group consisting of a bacterial transporter protein, an antimicrobial peptide, a bactericidal peptide, a 3-barrel protein, an a helix barrel protein and a transmembrane protein; optionally wherein at least one of the appendages comprises a peptide derived from a protein selected from the group consisting of Wza, a-hemolysin, cytolysin A, leukocidin, *Mycobacterium smegmatis* porin A (MspA), outer membrane porin F (OmpF), outer membrane porin G (OmpG), outer membrane phospholipase A and *Neisseria* autotransporter lipoprotein (NalP), or variants thereof, or combinations thereof.

21. The assembly of claim 1, wherein each of the appendages comprises a peptide comprising a sequence having at least 80% sequence identity to any one of SEQ ID NOs: 1-10, or variants thereof.

22. The assembly of claim 1, wherein each of the appendages comprises a polypeptide comprising a sequence having at least 80% sequence identity to any one of SEQ ID NOs: 12-14, 117 or 118, or a fragment thereof.

23. A system comprising: (a) a layer of amphipathic molecules; and (b) an assembly comprising a nucleic acid scaffold and a plurality of appendages bonded to the scaffold, wherein the appendages form a pore in the layer of amphipathic molecules, and wherein the nucleic acid scaffold comprises a plurality of nucleic acids arranged to form a closed circular structure with protruding arms.

24. A method of forming a pore in a layer of amphipathic molecules, the method comprising applying an assembly to a layer of amphipathic molecules, wherein the assembly comprises a nucleic acid scaffold and a plurality of appendages bonded to the scaffold, wherein the nucleic acid scaffold comprises a plurality of nucleic acids arranged to form a closed circular structure with protruding arms, and the appendages to interact to form a pore in the layer of amphipathic molecules.

25. A method of detecting and/or characterising a target analyte, comprising:

(a) forming a pore in a layer of amphipathic molecules by applying an assembly to a layer of amphipathic molecules, wherein the assembly comprises a nucleic acid scaffold and a plurality of appendages bonded to the scaffold, wherein the nucleic acid scaffold comprises a plurality of nucleic acids arranged to form a closed circular structure with protruding arms, and the appendages to interact to form a pore in the layer of amphipathic molecules;

(b) contacting the target analyte with the pore; and (c) taking one or more measurements as the target analyte moves through the pore, wherein the measurements are indicative of the presence of and/or one or more characteristics of the target analyte.

26. A kit for characterising a target polynucleotide comprising an assembly of claim 1.

27. An assembly comprising a nucleic acid scaffold and a plurality of appendages bonded to the scaffold, wherein the appendages form a pore in a layer of amphipathic molecules, and wherein the nucleic acid scaffold comprises (i) a closed circular first nucleic acid strand and (ii) a plurality of second nucleic acid strands, wherein the second nucleic acid strands comprise a first region that hybridises to the first nucleic acid strand and a second region that protrudes from the circular first nucleic acid strand.

28. The assembly of claim 27, wherein each of the appendages is bonded to a third nucleic acid strand, optionally through a linker, wherein the third nucleic acid strand hybridises to the second region of a second nucleic acid strand.

29. A system comprising: (a) a layer of amphipathic molecules; and (b) an assembly comprising a nucleic acid scaffold and a plurality of appendages bonded to the scaffold, wherein the appendages form a pore in the layer of amphipathic molecules, and wherein the nucleic acid scaffold comprises (i) a closed circular first nucleic acid strand and (ii) a plurality of second nucleic acid strands, wherein the second nucleic acid strands comprise a first region that hybridises to the first nucleic acid strand and a second region that protrudes from the circular first nucleic acid strand.

30. The system of claim 29, wherein each of the appendages is bonded to a third nucleic acid strand, optionally through a linker, wherein the third nucleic acid strand hybridises to the second region of a second nucleic acid strand.

* * * * *